(12) United States Patent
McCutchen et al.

(10) Patent No.: US 7,622,641 B2
(45) Date of Patent: Nov. 24, 2009

(54) METHODS AND COMPOSITIONS FOR PROVIDING TOLERANCE TO MULTIPLE HERBICIDES

(75) Inventors: Billy Fred McCutchen, College Station, TX (US); Timothy K. Chicoine, St. Charles, IA (US); Jerry M. Green, Landenberg, PA (US); Christine B. Hazel, Port Deposit, MD (US); Jeffrey M. Hegstad, Ankeny, IA (US); James M. Hutchison, Wilmington, DE (US); Donglong Liu, Johnston, IA (US); Albert L. Lu, Newark, DE (US); Kenneth A. Peeples, Wilmington, DE (US); David W. Saunders, Dallas Center, IA (US); Mark D. Vogt, Ankeny, IA (US); James F. H. Wong, Johnston, IA (US)

(73) Assignees: Pioneer Hi-Bred Int'l., Inc., Johnston, IA (US); E.I. du Pont de Nemours and Co., Wilmington, DE (US)

( * ) Notice: Subject to any disclaimer, the term of this patent is extended or adjusted under 35 U.S.C. 154(b) by 425 days.

(21) Appl. No.: 11/507,866

(22) Filed: Aug. 22, 2006

(65) Prior Publication Data

US 2007/0079393 A1 Apr. 5, 2007

Related U.S. Application Data

(60) Provisional application No. 60/710,854, filed on Aug. 24, 2005, provisional application No. 60/817,011, filed on Jun. 28, 2006.

(51) Int. Cl.
*C12N 15/82* (2006.01)
*A01N 27/00* (2006.01)

(52) U.S. Cl. ........................ 800/300; 504/118
(58) Field of Classification Search ................... None
See application file for complete search history.

(56) References Cited

U.S. PATENT DOCUMENTS

| | | |
|---|---|---|
| 4,535,060 A | 8/1985 | Comai |
| 4,769,061 A | 9/1988 | Comai |
| 4,822,146 A | 4/1989 | Yamanobe et al. |
| 4,940,835 A | 7/1990 | Shah et al. |
| 4,971,908 A | 11/1990 | Kishore et al. |
| 5,013,659 A | 5/1991 | Bedbrook et al. |
| 5,084,082 A | 1/1992 | Sebastian |
| 5,089,082 A | 2/1992 | Dreier et al. |
| 5,097,025 A | 3/1992 | Benfey et al. |
| 5,141,870 A | 8/1992 | Bedbrook et al. |
| 5,145,783 A | 9/1992 | Kishore et al. |
| 5,188,642 A | 2/1993 | Shah et al. |
| 5,310,667 A | 5/1994 | Eichholtz et al. |
| 5,312,910 A | 5/1994 | Kishore et al. |
| 5,378,824 A | 1/1995 | Bedbrook et al. |
| 5,463,175 A | 10/1995 | Barry et al. |
| 5,491,288 A | 2/1996 | Chaubet et al. |
| 5,510,471 A | 4/1996 | Lebrun et al. |
| 5,605,011 A | 2/1997 | Bedbrook et al. |
| 5,627,061 A | 5/1997 | Barry et al. |
| 5,633,435 A | 5/1997 | Barry et al. |
| 5,633,448 A | 5/1997 | Lebrun et al. |
| 5,776,760 A | 7/1998 | Barry et al. |
| 5,804,425 A | 9/1998 | Barry et al. |
| 5,821,195 A | 10/1998 | Sandbrink et al. |
| 5,866,775 A | 2/1999 | Eichholtz et al. |
| 5,914,451 A | 6/1999 | Martinell et al. |
| 5,955,646 A | 9/1999 | Gelvin et al. |
| 5,985,793 A | 11/1999 | Sandbrink et al. |
| 6,022,552 A | 2/2000 | Brown et al. |
| 6,072,050 A | 6/2000 | Bowen et al. |
| 6,083,878 A | 7/2000 | Brants et al. |
| 6,130,366 A | 10/2000 | Herrera-Estrella et al. |
| 6,133,199 A | 10/2000 | Soula et al. |
| 6,225,114 B1 | 5/2001 | Eichholtz et al. |

(Continued)

FOREIGN PATENT DOCUMENTS

CN 1772908 5/2006

(Continued)

OTHER PUBLICATIONS

Omirulleh, S., et al., "Activity of a chimeric promoter with the doubled CaMV 35S enhancer element in protoplast-derived cells and transgenic plants in maize," *Plant Mol. Bio.*, 1993, pp. 415-428, vol. 21.

(Continued)

*Primary Examiner*—David H Kruse
(74) *Attorney, Agent, or Firm*—Alston & Bird LLP

(57) ABSTRACT

Methods and compositions are provided related to improved plants that are tolerant to more than one herbicide. Particularly, the invention provides plants that are tolerant of glyphosate and are tolerant to at least one ALS inhibitor, and methods of use thereof. The glyphosate/ALS inhibitor-tolerant plants comprise a polynucleotide that encodes a polypeptide that confers tolerance to glyphosate and a polynucleotide that encodes an ALS inhibitor-tolerant polypeptide. In specific embodiments, a plant of the invention expresses a GAT polypeptide and an HRA polypeptide. Methods to control weeds, improve plant yield, and increase transformation efficiencies are provided.

16 Claims, 9 Drawing Sheets

U.S. PATENT DOCUMENTS

| | | | |
|---|---|---|---|
| 6,239,072 B1 | 5/2001 | Flint et al. | |
| 6,248,876 B1 | 6/2001 | Barry et al. | |
| 6,333,449 B1 | 12/2001 | Michiels et al. | |
| 6,369,001 B1 | 4/2002 | Jimoh | |
| 6,376,754 B1* | 4/2002 | Schillinger et al. | 800/312 |
| 6,448,476 B1 | 9/2002 | Barry | |
| RE37,866 E | 10/2002 | Wright et al. | |
| 6,475,953 B1 | 11/2002 | Ward et al. | |
| 6,500,617 B1 | 12/2002 | Stemmer et al. | |
| 6,500,782 B1 | 12/2002 | Kassebaum | |
| 6,500,783 B1 | 12/2002 | Bryson et al. | |
| 6,603,062 B1 | 8/2003 | Schmidt et al. | |
| 6,803,501 B2 | 10/2004 | Baerson et al. | |
| 6,822,146 B2 | 11/2004 | Gabard et al. | |
| 6,825,400 B2 | 11/2004 | Behr et al. | |
| 6,908,882 B1 | 6/2005 | Becher et al. | |
| 7,018,794 B2 | 3/2006 | Berka et al. | |
| 2002/0146721 A1 | 10/2002 | Berka et al. | |
| 2003/0083480 A1 | 5/2003 | Castle et al. | |
| 2004/0023802 A1 | 2/2004 | Asrar et al. | |
| 2004/0082770 A1 | 4/2004 | Castle et al. | |
| 2005/0113254 A1 | 5/2005 | Ziemer et al. | |
| 2005/0198705 A1 | 9/2005 | Croughan | |
| 2005/0227871 A1 | 10/2005 | Schaetzer et al. | |
| 2005/0233905 A1 | 10/2005 | DeBillot et al. | |
| 2005/0246798 A1 | 11/2005 | Castle et al. | |
| 2005/0266996 A1 | 12/2005 | Krause et al. | |
| 2006/0031962 A1 | 2/2006 | Altier et al. | |
| 2006/0191033 A1 | 8/2006 | Castle et al. | |
| 2006/0200874 A1 | 9/2006 | Castle et al. | |
| 2006/0218663 A1 | 9/2006 | Castle et al. | |
| 2007/0061917 A1 | 3/2007 | McCutchen et al. | |
| 2007/0074303 A1 | 3/2007 | McCutchen et al. | |
| 2007/0130641 A1 | 6/2007 | McCutchen et al. | |
| 2008/0108072 A1 | 5/2008 | Chicoine et al. | |
| 2008/0234130 A1 | 9/2008 | McCutchen et al. | |

FOREIGN PATENT DOCUMENTS

| | | | |
|---|---|---|---|
| EP | 0 730 030 A1 | 9/1996 | |
| WO | WO 97/04103 A2 | 2/1997 | |
| WO | WO 97/04103 A3 | 2/1997 | |
| WO | WO 98/39419 | * | 9/1998 |
| WO | WO 00/09727 A2 | 2/2000 | |
| WO | WO 00/09727 A3 | 2/2000 | |
| WO | WO 00/29596 A1 | 5/2000 | |
| WO | WO 00/66746 A1 | 11/2000 | |
| WO | WO 00/66747 A1 | 11/2000 | |
| WO | WO 01/66704 A2 | 9/2001 | |
| WO | WO 01/66704 A3 | 9/2001 | |
| WO | WO 02/20811 A2 | 3/2002 | |
| WO | WO 02/29113 A2 | 4/2002 | |
| WO | WO 02/36782 A2 | 5/2002 | |
| WO | WO 02/092856 A1 | 11/2002 | |
| WO | WO 03/092360 A2 | 11/2003 | |
| WO | WO 03/092360 A3 | 11/2003 | |
| WO | WO 2005/012515 A2 | 2/2005 | |
| WO | WO 2005/041654 A2 | 5/2005 | |
| WO | WO 2005/107437 A2 | 11/2005 | |

OTHER PUBLICATIONS

Fang, R., et al., "Multiple cis Regulatory Elements for Maximal Expression of the Cauliflower Mosaic Virus 35S Promoter in Transgenic Plants," The *Plant Cell*, 1989, pp. 141-150, vol. 1.

Aono, M., et al., "Paraquat Tolerance of Transgenic Nicotiana Tabacum with Enhanced Activities of Glutathione Reductase and Superoxide Dismutase," *Plant Cell Physiol*, 1995, p. 1687, vol. 36.

Castle, L.A. et al., "Discovery and Directed Evolution of a Glyphosate Tolerance Gene," *Science*, May 21, 2004, pp. 1151-1154, vol. 304.

Datta, S., et al., "Herbicide-resistant Indica Rice Plants from IRRI Breeding Line IR72 After PEG-Medicated Transformation of Protoplasts," *Plant Mol Biol*, 1992, p. 619, vol. 20.

Fang, R-X., et al., "Multiple cis Regulatory elements for Maximal Expression of the Cauliflower Mosaic Virus 35S Promoter in Transgenic Plants," *The Plant Cell*, Jan. 1989, pp. 141-150, vol. 1.

Green, J.M. and J.F. Ulrich, "Response of Corn (*Zea mays* L.) Inbreds and Hybrids to Sulfonylurea Herbicides," *Weed Science*, 1993, pp. 508-516, vol. 41.

Green, J.M., and J.F. Ulrich, "Response of Maize (*Zea Mays*) Inbreds and Hybrids to Rimsulfuron," *Pesticide Science*, 1994, pp. 187-191, vol. 40, No. 3.

Green, J.M., "Differential Tolerance of Corn (*Zea mays*) Inbreds to Four Sulfonylurea Herbicides and Bentazon," *Weed Technology*, 1998, pp. 474-477, vol. 12.

Green, J.M. and C.L. Foy, "Adjuvants, Tools for Enhancing Herbicide Performance," *Weed Biology and Management*, 2003, pp. 375-401, Inderjit (editor), Kluwer Academic Publishers, The Netherlands.

Green, J.M., "Correlation of Corn (*Zea Mays*) Inbred Response to Nicosulfuron and Mesotrione," *Proceedings Weed Science Society of America*, 2004, Abstract No. 13, p. 4, vol. 44.

Hattori, J., et al., "An Acetohydroxy Acid Synthase Mutan t Reveals a Single Site Involved in Multiple Herbicide Resistance," *Mol Gen Genet*, 1995, p. 419, vol. 246.

Keenan, R.J., et al., "DNA Shuffling as a Tool for Protein Crystallization," *PNAS*, Jun. 21, 2005, pp. 8887-8892, vol. 102, No. 25.

Khalil, E.M., et al., "Indoleamine Analogs as Probes of the Substrate Selectivity and Catalytic Mechanism of Serotonin N-Acetyltransferase," *J. Biol. Chem.*, Nov. 13, 1998, pp. 30321-30327, vol. 273, No. 46.

Kinsky, S.C., "Assay, Purification, and Properties of Imidazole Acetylase," *J. Biol. Chem.*, Jan. 1960, pp. 94-98, vol. 235, No. 1.

Kunst, F., et al., "The Complete Genome Sequence of the Gram-positive Bacterium *Bacillus subtilis*," *Nature*, 1997, pp. 249-256, vol. 390.

Kunst, F., et al., "Hyperbolized Protein BSU11000 (*Bacillus subtilis* subsp. Str. 168)," 1997, GenBank Accession No. NP-388981.

Kunst, F., et al., "YITI Protein," EMBL Database Accession No. 006744, Jul. 1, 1997 [Abstract].

Lee, K.Y. et al., "The Molecular Basis of Sulfonylurea Herbicide Resistance in Tobacco," *The EMBO Journal*, 1988, pp. 1241-1248, vol. 7, No. 5.

McCutchen et al., "Interactions of Recombinant and Wild-type Baculoviruses with Classical Insecticides and Pyrethroid-resistant Tobacco Budworm (*Lepidoptera:Noctuidae*)," *J. Econ. Entomol.*, Oct. 1997, pp. 1170-1180, vol. 90, No. 5.

Padgette et al, "New Weed Control Opportunities: Development of Soybeans with a Round UP Ready™" *Herbicide-Resistant Crops*, 1996, pp. 54-84.

Preisler et al., "Statistical Methods to Assessing Responses over Time in Bioassays with Mixtures," *J. Econ. Entomol.* Jun. 1999, pp. 598-603, vol. 92, No. 3.

Retzinger, E. J., Jr. and C.Mallory-Smith, "Classification of Herbicides by Site of Action for Weed Resistance Management Strategies," *Weed Technology*, 1997, pp. 384-393, vol. 11.

Rey, M.W., et al., "Complete Genome Sequence of the Industrial Bacterium *Bacillus licheniformis* and Comparisons with Closely Related *Bacillus* Species," *Genome Biology*, Sep. 13, 2004, R77, vol. 5.

Roche et al., "A *Bacillus subtilis* Chromosome Segment of the 100 Degree to 102 Degree Position Encoding 11 Membrane Proteins," *Microbiology*, 1997, pp. 3309-3312, vol. 143.

Shiota, N. et al., "Herbicide-Resistant Tobacco Plants Expressing the Fused Enzyme Between Rat Cytochrome P4501A1 (CYP1A1) and Yeast NADPH-Cytochrome P450 Oxidoreductase," *Plant Physiol*, 1994, p. 17, vol. 106.

Siehl, D.L., et al., "Evolution of a Microbial Acetyltransferase for Modification of Glyphosate: a Novel Tolerance Strategy," *Pest Manag Sci*, 2005, pp. 235-240, vol. 61.

Simarmata, M., et al., "Inheritance of Glyphosate Resistance in Rigid Ryegrass (*Lolium rigidum*) from California," *Weed Science*, 2005, pp. 615-619, vol. 53.

Vasil, "Phosphinothricin-Resistant Crops," in *Herbicide-Resistant Crops* (Duke, ed.), 1996, pp. 85-91, CRC Press, Boca Raton, FL.

Whittstock, J.C. and A.M. Lesk, "Prediction of Protein Function from Protein Sequence and Structure," *Q. Rev. Biophys*, Aug. 2003, pp. 307-340, vol. 36, No. 3.

ExPASy Sequence Alignment for SEQ ID No. 445-584.

IP.com Prior Art Database, Reference No. IPCOM 000033402D, "Improved Cotton Somatic Embryogenesis and Cell Line Maintenance using Growth Regulator-free Media and D-maltose as Primary Carbon Source".

IP.com Prior Art Database, Reference No. IPCOM 000033403D, "Improved Methods for Transformation of Cotton (*Gossypium* spp.) Using Embryogenic Callus".

IP.com Prior Art Database, Reference No. IPCOM 000033404D, "Improved Methods for Transformation of Cotton (*Gossypium* spp.) Using Embryogenic Cell Suspensions".

Miki, B. and S. McHugh, "Selectable Marker Genes in Transgenic Plants: Applications, Alternatives and Biosafety," *Journal of Biotechnology*, Feb. 5, 2004, pp. 193-232, vol. 107, No. 3.

\* cited by examiner

Fig. 1

35S Enhancer Constructs

| Round | Constructs PHP | Components |
|---|---|---|
| 7th | PHP19288 | ubi prom-ubi intron-GAT4602-pinII |
| 35S 7th | PHP20118 | F1x35S-ubi prom-ubi intron-GAT4602-pinII |
| | PHP20120 | R1x35S-ubi prom-ubi intron-GAT4602-pinII |
| | PHP20122 | F3x35S-ubi prom-ubi intron-GAT4602-pinII |
| | PHP20124 | R3x35S-ubi prom-ubi intron-GAT4602-pinII |

Development of a GAT Selection System

Side-by-side comparison (~ 50 days selection)

METHODS AND COMPOSITIONS FOR PROVIDING TOLERANCE TO MULTIPLE HERBICIDES

CROSS-REFERENCE TO RELATED APPLICATIONS

This application claims priority to U.S. Provisional Application No. 60/710,854, filed on Aug. 24, 2005, and U.S. Provisional Application No. 60/817,011, filed on Jun. 28, 2006, each of which is incorporated by reference in their entirety.

FIELD OF THE INVENTION

This invention is in the field of molecular biology. More specifically, this invention pertains to multiple herbicide tolerances conferred by expression of a sequence that confers tolerance to glyphosate in conjunction with the expression of at least one other herbicide tolerance gene.

BACKGROUND OF THE INVENTION

In the commercial production of crops, it is desirable to easily and quickly eliminate unwanted plants (i.e., "weeds") from a field of crop plants. An ideal treatment would be one which could be applied to an entire field but which would eliminate only the unwanted plants while leaving the crop plants unharmed. One such treatment system would involve the use of crop plants which are tolerant to a herbicide so that when the herbicide was sprayed on a field of herbicide-tolerant crop plants, the crop plants would continue to thrive while non-herbicide-tolerant weeds were killed or severely damaged. Ideally, such treatment systems would take advantage of varying herbicide properties so that weed control could provide the best possible combination of flexibility and economy. For example, individual herbicides have different longevities in the field, and some herbicides persist and are effective for a relatively long time after they are applied to a field while other herbicides are quickly broken down into other and/or non-active compounds. An ideal treatment system would allow the use of different herbicides so that growers could tailor the choice of herbicides for a particular situation.

Crop tolerance to specific herbicides can be conferred by engineering genes into crops which encode appropriate herbicide metabolizing enzymes and/or insensitive herbicide targets. In some cases these enzymes, and the nucleic acids that encode them, originate in a plant. In other cases, they are derived from other organisms, such as microbes. See, e.g., Padgette et al. (1996) "New weed control opportunities: Development of soybeans with a Roundup Ready® gene" and Vasil (1996) "Phosphinothricin-resistant crops," both in *Herbicide-Resistant Crops*, ed. Duke (CRC Press, Boca Raton, Fla.) pp. 54-84 and pp. 85-91. Indeed, transgenic plants have been engineered to express a variety of herbicide tolerance genes from a variety of organisms, including a gene encoding a chimeric protein of rat cytochrome P4507A1 and yeast NADPH-cytochrome P450 oxidoreductase (Shiota et al. (1994) *Plant Physiol.* 106: 17). Other genes that confer tolerance to herbicides include acetohydroxy acid synthase ("AHAS"), mutations in the native sequence have been found to confer resistance to multiple types of herbicides on plants expressing it and has been introduced into a variety of plants (see, e.g., Hattori et al. (1995) *Mol. Gen. Genet.* 246: 419); glutathione reductase and superoxide dismutase (Aono et al. (1995) *Plant Cell Physiol.* 36: 1687); and genes for various phosphotransferases (Datta et al. (1992) *Plant Mol. Biol.* 20: 619).

One herbicide which has been studied extensively is N-phosphonomethylglycine, commonly referred to as glyphosate. Glyphosate is a broad spectrum herbicide that kills both broadleaf and grass-type plants due to inhibition of the enzyme 5-enolpyruvylshikimate-3-phosphate synthase (also referred to as "EPSP synthase" or "EPSPS"), an enzyme which is part of the biosynthetic pathway for the production of aromatic amino acids, hormones, and vitamins. Glyphosate-resistant transgenic plants have been produced which exhibit a commercially viable level of glyphosate resistance due to the introduction of a modified *Agrobacterium* CP4 EPSPS. This modified enzyme is targeted to the chloroplast where, even in the presence of glyphosate, it continues to synthesize EPSP from phosphoenolpyruvic acid ("PEP") and shikimate-3-phosphate. CP4 glyphosate-resistant soybean transgenic plants are presently in commercial use (e.g., as sold by Monsanto under the name "Roundup Ready®").

Other herbicides of interest for commercial crop production include glufosinate (phosphinothricin) and acetolactate synthase (ALS) chemistry such as the sulfonylurea herbicides. Glufosinate is a broad spectrum herbicide which acts on the chloroplast glutamate synthase enzyme. Glufosinate-tolerant transgenic plants have been produced which carry the bar gene from *Streptomyces hygroscopicus*. The enzyme encoded by the bar gene has N-acetylation activity and modifies and detoxifies glufosinate. Glufosinate-tolerant plants are presently in commercial use (e.g., as sold by Bayer under the name "Liberty Link®"). Sulfonylurea herbicides inhibit growth of higher plants by blocking acetolactate synthase (ALS). Plants containing particular mutations in ALS are tolerant to the ALS herbicides including sulfonylureas. Thus, for example, sulfonylurea herbicides such as Synchrony (a mixture of chlorimuron-ethyl plus thifensulfuron-methyl) can be used in conjunction with ALS herbicide-tolerant plants such as the STS® soybean (Synchrony tolerant soybean) variety which contains a trait that enhances the soybean's natural tolerance to soybean sulfonylurea herbicides.

While a number of herbicide-tolerant crop plants are presently commercially available, one issue that has arisen for many commercial herbicides and herbicide/crop combinations is that individual herbicides typically have incomplete spectrum of activity against common weed species. For most individual herbicides which have been in use for some time, populations of herbicide resistant weed species and biotypes have become more prevalent (see, e.g., Tranel and Wright (2002) *Weed Science* 50: 700-712; Owen and Zelaya (2005) *Pest Manag Sci.* 61: 301-311). Transgenic plants which are resistant to more than one herbicide have been described (see, e.g., WO2005/012515). However, improvements in every aspect of crop production, weed control options, extension of residual weed control, and improvement in crop yield are continuously in demand.

Particularly, due to local and regional variation in dominant weed species as well as preferred crop species, a continuing need exists for customized systems of crop protection and weed management which can be adapted to the needs of a particular region, geography, and/or locality. For example, a continuing need exists for methods of crop protection and weed management which can reduce: the number of herbicide applications necessary to control weeds in a field; the amount of herbicide necessary to control weeds in a field; the amount of tilling necessary to produce a crop; and/or programs which delay or prevent the development and/or appearance of herbicide-resistant weeds. A continuing need exists for methods of crop protection and weed management which allow the targeted use of particular herbicide combinations.

SUMMARY OF THE INVENTION

Methods and compositions relating to improved plants that are tolerant to more than one herbicide or class or subclass of herbicides are provided. Compositions include plants that are tolerant to glyphosate as well as at least one other herbicide or class or subclass of herbicide, as well as, methods of use thereof. Additional compositions comprise plants that comprise a polynucleotide encoding a polypeptide that can confer tolerance to glyphosate and a polynucleotide encoding an ALS inhibitor-tolerant polypeptide. In one non-limiting embodiment, compositions comprise a plant expressing a polynucleotide encoding a GAT (glyphosate-N-acetyltransferase) polypeptide and are tolerant to at least one additional herbicide. In some embodiments, a plant of the invention expresses a GAT polypeptide and an HRA polypeptide.

Methods for controlling weeds in an area of cultivation employing the plants of the invention are provided. Further provided are improved methods of transformation.

BRIEF DESCRIPTION OF THE DRAWINGS

FIG. 1 provides examples of constructs having 35S enhancer elements.

DETAILED DESCRIPTION OF THE INVENTION

Figure 2:
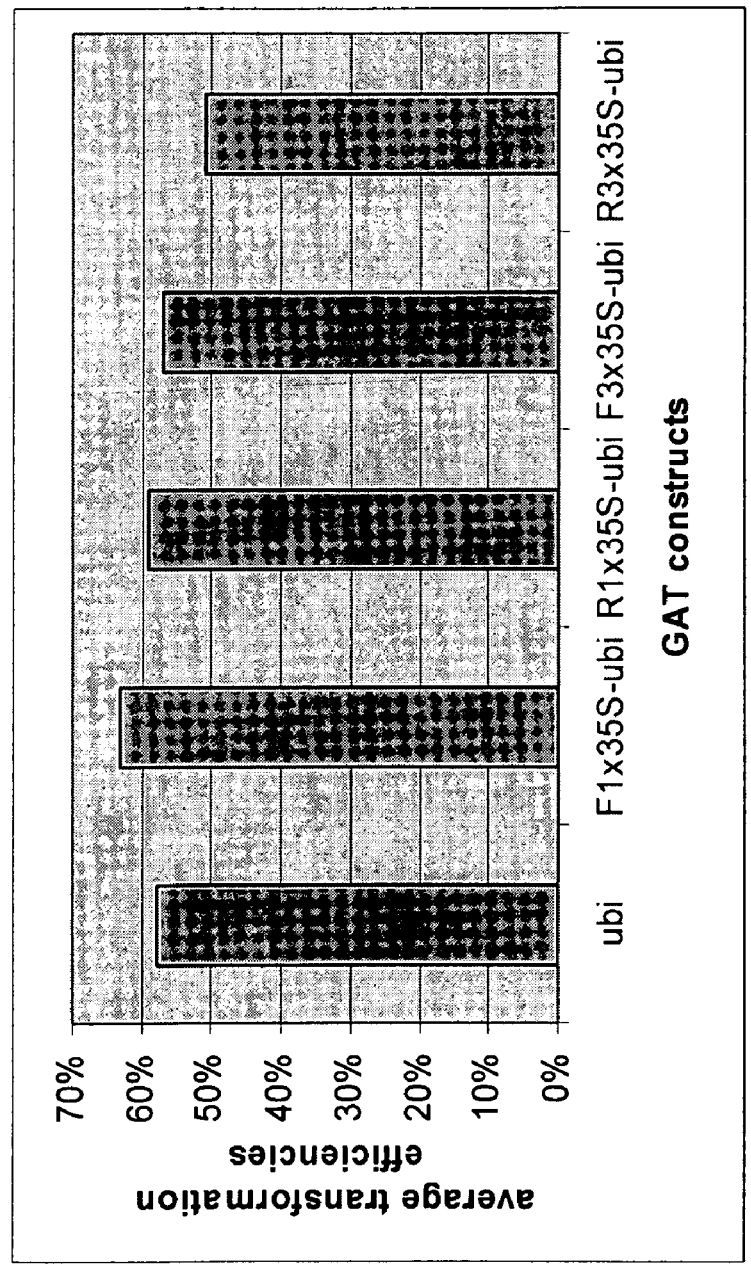
FIG. 2 provides a schematic demonstrating the effect of 35S enhancers on TX efficiency.

The present invention provides methods and compositions for making and using a plant that is tolerant to more than one herbicide or class or subclass of herbicide. In some embodiments, a plant is provided that is tolerant to both glyphosate and at least one other herbicide (or class or subclass of herbicide) or another chemical (or class or subclass of another chemical). Such plants find use, for example, in methods of growing crop plants involving treatment with multiple herbicides. Thus, the invention provides improved plants which tolerate treatment with a herbicide or a combination of herbicides (including a combination of herbicides which act through different modes of action; i.e., application of mixtures having 2, 3, 4, or more modes of herbicide action) or a combination of at least one herbicide and at least one other chemical, including fungicides, insecticides, plant growth regulators and the like. In this manner, the invention provides improved methods of growing crop plants in which weeds are selectively controlled. In one embodiment, the plants of the invention comprise a polynucleotide which encodes a polypeptide that confers tolerance to glyphosate and a polynucleotide encoding an ALS inhibitor-tolerant polypeptide.

As discussed in further detail below, such plants are referred to herein as "glyphosate/ALS inhibitor-tolerant plants."

The plants of the invention display a modified tolerance to herbicides and therefore allow for the application of herbicides at rates that would significantly damage plants and further allow for the application of mixtures of herbicides at lower concentrations than normally applied but which still continue to selectively control weeds. In addition, the glyphosate/ALS inhibitor-tolerant plants of the invention can be used in combination with herbicide blends technology and thereby make the application of chemical pesticides more convenient, economical, and effective for the producer. In the case of the glyphosate/ALS inhibitor-tolerant crops, the blends technology will provide easily formulated crop protection products, of ALS herbicides for example, in a dry granule form that enables delivery of customized mixtures designed to solve specific problems in conjunction with the glyphosate/ALS inhibitor-tolerant crop of the invention. With the addition of robust ALS tolerance afforded by the plants of the invention, the utility of ALS herbicides is further enabled whereby herbicidal crop response is eliminated. These uniquely selective herbicide offerings coupled with glyphosate/ALS inhibitor tolerate crops disclosed herein can now be designed and customized to meet ever-changing weed control needs. This breakthrough now enables a myriad of herbicide blends, including for example ALS inhibitor blends, that can be customized for improved weed management (since ALS inhibitor chemistries have different herbicidal attributes) including increased weed spectrum, the ability to provide specified residual activity, a second mode of action to combat or delay weed resistance (complementing glyphosate, glufosinate or the like), as well as, new offerings that can be designed either or both as pre-emergence or post-emergence. Blends also afford the ability to add or tank mix other agrochemicals at normal, labeled use rates such as additional herbicides with a $3^{rd}$ or $4^{th}$ mechanism of action, to fill spectrum holes or even the ability to include fungicides, insecticides, plant growth regulators and the like thereby saving costs associated with additional applications. As discussed in further detail below, the methods of the invention can be customized for a particular location or region. Improved methods of transformation are also provided.

I. Glyphosate/ALS Inhibitor-Tolerant Plants a. Glyphosate Tolerance

Plants are provided which comprise a polynucleotide which encodes a polypeptide that confers tolerance to glyphosate and a polynucleotide encoding an ALS inhibitor-tolerant polypeptide. Various sequences which confer tolerance to glyphosate can be employed in the methods and compositions of the invention.

In one embodiment, the mechanism of glyphosate resistance is provided by the expression of a polynucleotide having transferase activity. As used herein, a "transferase" polypeptide has the ability to transfer the acetyl group from acetyl CoA to the N of glyphosate, transfer the propionyl group of propionyl CoA to the N of glyphosate, or to catalyze the acetylation of glyphosate analogs and/or glyphosate metabolites, e.g., aminomethylphosphonic acid. Methods to assay for this activity are disclosed, for example, in U.S. Publication No. 2003/0083480, U.S. Publication No. 2004/0082770, and U.S. application Ser. No. 10/835,615, filed Apr. 29, 2004, WO2005/012515, WO2002/36782 and WO2003/092360. In one embodiment, the transferase polypeptide comprises a glyphosate-N-acetyltransferase "GAT" polypeptide.

As used herein, a GAT polypeptide or enzyme comprises a polypeptide which has glyphosate-N-acetyltransferase activity ("GAT" activity), i.e., the ability to catalyze the acetylation of glyphosate. In specific embodiments, a polypeptide having glyphosate-N-acetyltransferase activity can transfer the acetyl group from acetyl CoA to the N of glyphosate. In addition, some GAT polypeptides transfer the propionyl group of propionyl CoA to the N of glyphosate. Some GAT polypeptides are also capable of catalyzing the acetylation of glyphosate analogs and/or glyphosate metabolites, e.g., aminomethylphosphonic acid. GAT polypeptides are characterized by their structural similarity to one another, e.g., in terms of sequence similarity when the GAT polypeptides are aligned with one another. Exemplary GAT polypeptides and the polynucleotides encoding them are known in the art and particularly disclosed, for example, in U.S. application Ser. No. 10/004,357, filed Oct. 29, 2001, U.S. application Ser. No. 10/427,692, filed Apr. 30, 2003, and U.S. application Ser. No. 10/835,615, filed Apr. 29, 2004, each of which is herein incorporated by reference in its entirety. In some embodiments, GAT polypeptides used in creating plants of the invention comprise the amino acid sequence set forth in: SEQ ID NO: 5, 14, 11, 8, 21, 27, 17, 24, 30, 35, 46, 47, 48, 49, 50, 51, 52, 53, 39, 42, 45, or 54. Each of these sequences is also disclosed in U.S. application Ser. No. 10/835,615, filed Apr. 29, 2004. In some embodiments, the corresponding GAT polynucleotides that encode these polypeptides are used; these polynucleotide sequences are set forth in SEQ ID NO: 3, 12, 9, 6, 19, 15, 25, 22, 28, 33, 4, 7, 10, 13, 16, 18, 20, 23, 26, 29, 32, 34, 36, 38, 41, 44, 43, 56, 31, 37, 40, 57, 58, 59, 60, 61, 62, 63, or 64. Each of these sequences is also disclosed in U.S. application Ser. No. 10/835,615, filed Apr. 29, 2004. As discussed in further detail elsewhere herein, the use of fragments and variants of GAT polynucleotides and other known herbicide-tolerance polynucleotides and polypeptides encoded thereby is also encompassed by the present invention.

In specific embodiments, the glyphosate/ALS inhibitor-tolerant plants of the invention express a GAT polypeptide, i.e., a polypeptide having glyphosate-N-acetyltransferase activity wherein the acetyl group from acetyl CoA is transferred to the N of glyphosate. Thus, plants of the invention that have been treated with glyphosate contain the glyphosate metabolite N-acetylglyphosate ("NAG"). Thus, the invention also provides plants that contain NAG as well as a method for producing NAG by treating plants that contain a GAT gene (i.e., that express a GAT polypeptide) with glyphosate. The presence of N-acetylglyphosate can serve as a diagnostic marker for the presence of an active GAT gene in a plant and can be evaluated by methods known in the art, for example, by mass spectrometry or by immunoassay. Generally, the level of NAG in a plant containing a GAT gene that has been treated with glyphosate is correlated with the activity of the GAT gene and the amount of glyphosate with which the plant has been treated.

The plants of the invention can comprise multiple GAT polynucleotides (i.e., at least 1, 2, 3, 4, 5, 6 or more). It is recognized that if multiple GAT polynucleotides are employed, the GAT polynucleotides may encode GAT polypeptides having different kinetic parameters, i.e., a GAT variant having a lower $K_m$ can be combined with one having a higher $k_{cat}$. In some embodiments, the different polynucleotides may be coupled to a chloroplast transit sequence or other signal sequence thereby providing polypeptide expression in different cellular compartments, organelles or secretion of one or more of the polypeptides.

The GAT polypeptide encoded by a GAT polynucleotide may have improved enzymatic activity in comparison to previously identified enzymes. Enzymatic activity can be characterized using the conventional kinetic parameters $k_{cat}$, $K_M$, and $k_{cat}/K_M$. $k_{cat}$ can be thought of as a measure of the rate of acetylation, particularly at high substrate concentrations; $K_M$ is a measure of the affinity of the GAT enzyme for its substrates (e.g., acetyl CoA, propionyl CoA and glyphosate); and $k_{cat}/K_M$ is a measure of catalytic efficiency that takes both substrate affinity and catalytic rate into account. $k_{cat}/K_M$ is particularly important in the situation where the concentration of a substrate is at least partially rate-limiting. In general, a GAT with a higher $k_{cat}$ or $k_{cat}/K_M$ is a more efficient catalyst than another GAT with lower $k_{cat}$ or $k_{cat}/K_M$. A GAT with a lower $K_M$ is a more efficient catalyst than another GAT with a higher $K_M$. Thus, to determine whether one GAT is more effective than another, one can compare kinetic parameters for the two enzymes. The relative importance of $k_{cat}$, $k_{cat}/K_M$ and $K_M$ will vary depending upon the context in which the GAT will be expected to function, e.g., the anticipated effective concentration of glyphosate relative to the $K_M$ for glyphosate. GAT activity can also be characterized in terms of any of a number of functional characteristics, including but not limited to stability, susceptibility to inhibition, or activation by other molecules.

Thus, for example, the GAT polypeptide may have a lower $K_M$ for glyphosate than previously identified enzymes, for example, less than 1 mM, 0.9 mM, 0.8 mM, 0.7 mM, 0.6 mM, 0.5 mM, 0.4 mM, 0.3 mM, 0.2 mM, 0.1 mM, 0.05 mM, or less. The GAT polypeptide may have a higher $k_{cat}$ for glyphosate than previously identified enzymes, for example, a $k_{cat}$ of at least 500 min$^{-1}$, 1000 min$^{-1}$, 1100 min$^{-1}$, 1200 min$^{-1}$, 1250 min$^{-1}$, 1300 min$^{-1}$, 1400 min$^{-1}$, 1500 min$^{-1}$, 1600 min$^{-1}$, 1700 min$^{-1}$, 1800 min$^{-1}$, 1900 min$^{-1}$, or 2000 min$^{-1}$ or higher. GAT polypeptides for use in the invention may have a higher $k_{cat}/K_M$ for glyphosate than previously identified enzymes, for example, a $k_{cat}/K_M$ of at least 1000 mM$^{-1}$min$^{-1}$, 2000 mM$^{-1}$min$^{-1}$, 3000 mM$^{-1}$min$^{-}$, 4000 mM$^{-1}$min$^{-1}$, 5000 mM$^{-1}$min$^{-1}$, 6000 mM$^{-1}$min$^{-1}$, 7000 mM$^{-1}$min$^{-1}$, or 8000 mM$^{-1}$min$^{-1}$, or higher. The activity of GAT enzymes is affected by, for example, pH and salt concentration; appropriate assay methods and conditions are known in the art (see, e.g., WO2005012515). Such improved enzymes may find particular use in methods of growing a crop in a field where the use of a particular herbicide or combination of herbicides and/or other agricultural chemicals would result in damage to the plant if the enzymatic activity (i.e., $k_{cat}$, $K_M$, or $k_{cat}/K_M$) were lower.

Glyphosate-tolerant plants can also be produced by modifying the plant to increase the capacity to produce a higher level of 5-enolpyruvylshikimate-3-phosphate synthase (EPSPS) as more fully described in U.S. Pat. Nos. 6,248,876; 5,627,061; 5,804,425; 5,633,435; 5,145,783; 4,971,908; 5,312,910; 5,188,642; 4,940,835; 5,866,775; 6,225,114; 6,130,366; 5,310,667; 4,535,060; 4,769,061; 5,633,448; 5,510,471; U.S. Pat. No. Re. 36,449; U.S. Pat. No. RE 37,287 E; and U.S. Pat. No. 5,491,288; and international publications WO 97/04103; WO 00/66746; WO 01/66704; and WO 00/66747, which are incorporated herein by reference in their entireties for all purposes. Glyphosate resistance can also be imparted to plants that express a gene that encodes a glyphosate oxido-reductase enzyme as described more fully in U.S. Pat. Nos. 5,776,760 and 5,463,175, which are incorporated herein by reference in their entireties for all purposes. Additionally, glyphosate tolerant plants can be generated through the selection of naturally occurring mutations that impart tolerance to glyphosate.

It is recognized that the methods and compositions of the invention can employ any combination of sequences (i.e., sequences that act via the same or different modes) that confer tolerance to glyphosate known in the art to produce plants and plant explants with superior glyphosate resistance.

b. Acetolactate Synthase (ALS) Inhibitor Tolerance

Glyphosate/ALS inhibitor-tolerant plants are provided which comprise a polynucleotide which encodes a polypeptide that confers tolerance to glyphosate and further comprise a polynucleotide encoding an acetolactate synthase (ALS) inhibitor-tolerant polypeptide. As used herein, an "ALS inhibitor-tolerant polypeptide" comprises any polypeptide which when expressed in a plant confers tolerance to at least one ALS inhibitor. A variety of ALS inhibitors are known and include, for example, sulfonylurea, imidazolinone, triazolopyrimidines, pryimidinyoxy(thio)benzoates, and/or sulfonylaminocarbonyltriazolinone herbicide. Additional ALS inhibitors are known and are disclosed elsewhere herein. It is known in the art that ALS mutations fall into different classes with regard to tolerance to sulfonylureas, imidazolinones, triazolopyrimidines, and pyrimidinyl(thio)benzoates, including mutations having the following characteristics: (1) broad tolerance to all four of these groups; (2) tolerance to imidazolinones and pyrimidinyl(thio)benzoates; (3) tolerance to sulfonylureas and triazolopyrimidines; and (4) tolerance to sulfonylureas and imidazolinones.

Various ALS inhibitor-tolerant polypeptides can be employed. In some embodiments, the ALS inhibitor-tolerant polynucleotides contain at least one nucleotide mutation resulting in one amino acid change in the ALS polypeptide. In specific embodiments, the change occurs in one of seven substantially conserved regions of acetolactate synthase. See, for example, Hattori et al. (1995) *Molecular Genetics and Genomes* 246:419-425; Lee et al. (1998) *EMBO Journal* 7:1241-1248; Mazur et al. (1989) *Ann. Rev. Plant Phys.* 40:441-470; and U.S. Pat. No. 5,605,011, each of which is incorporated by reference in their entirety. The ALS inhibitor-tolerant polypeptide can be encoded by, for example, the SuRA or SuRB locus of ALS. In specific embodiments, the ALS inhibitor-tolerant polypeptide comprises the C3 ALS mutant, the HRA ALS mutant, the S4 mutant or the S4/HRA mutant or any combination thereof. Different mutations in ALS are known to confer tolerance to different herbicides and groups (and/or subgroups) of herbicides; see, e.g., Tranel and Wright (2002) *Weed Science* 50:700-712. See also, U.S. Pat. Nos. 5,605,011, 5,378,824, 5,141,870, and 5,013,659, each of which is herein incorporated by reference in their entirety. See also, SEQ ID NO:65 comprising a soybean HRA sequence; SEQ ID NO:66 comprising a maize HRA sequence; SEQ ID NO:67 comprising an *Arabidopsis* HRA sequence; and SEQ ID NO:86 comprising an HRA sequence used in cotton. The HRA mutation in ALS finds particular use in one embodiment of the invention. The mutation results in the production of an acetolactate synthase polypeptide which is resistant to at least one ALS inhibitor chemistry in comparison to the wild-type protein. For example, a plant expressing an ALS inhibitor-tolerant polypeptide may be tolerant of a dose of sulfonylurea, imidazolinone, triazolopyrimidines, pryimidinyloxy(thio)benzoates, and/or sulfonylaminocarbonyltriazolinone herbicide that is at least 2, 3, 4, 5, 6, 7, 8, 9, 10, 15, 20, 25, 30, 35, 40, 50, 70, 80, 100, 125, 150, 200, 500, or 1000 times higher than a dose of the herbicide that would cause damage to an appropriate control plant. In some embodiments, an ALS inhibitor-tolerant polypeptide comprises a number of mutations. Additionally, plants having an ALS inhibitor polypeptide can be generated through the selection of naturally occurring mutations that impart tolerance to glyphosate.

In some embodiments, the ALS inhibitor-tolerant polypeptide confers tolerance to sulfonylurea and imidazolinone herbicides. Sulfonylurea and imidazolinone herbicides inhibit growth of higher plants by blocking acetolactate synthase (ALS), also known as, acetohydroxy acid synthase (AHAS). For example, plants containing particular mutations in ALS (e.g., the S4 and/or HRA mutations) are tolerant to sulfonylurea herbicides. The production of sulfonylurea-tolerant plants and imidazolinone-tolerant plants is described more fully in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference in their entireties for all purposes. In specific embodiments, the ALS inhibitor-tolerant polypeptide comprises a sulfonamide-tolerant acetolactate synthase (otherwise known as a sulfonamide-tolerant acetohydroxy acid synthase) or an imidazolinone-tolerant acetolactate synthase (otherwise known as an imidazolinone-tolerant acetohydroxy acid synthase).

A plant of the invention that comprises at least one sequence which confers tolerance to glyphosate and at least one sequence which confers tolerance to an ALS inhibitor is referred to herein as a "glyphosate/ALS inhibitor-tolerant plant." A plant of the invention that contains at least one GAT polypeptide and at least one HRA polypeptide is referred to herein as a "GAT-HRA plant."

c. Additional Herbicide Tolerance

In some embodiments, plants are provided having enhanced tolerance to glyphosate and at least one ALS inhibitor herbicide, as well as, tolerance to at least one additional herbicide. In specific embodiments, tolerance to the additional herbicide is due to the expression of at least one polypeptide imparting tolerance to the additional herbicide. In some embodiments, a composition of the invention (e.g., a plant) may comprise two, three, four, five, six, seven, or more traits which confer tolerance to at least one herbicide, so that a plant of the invention may be tolerant to at least two, three, four, five, six, or seven or more different types of herbicides. Thus, a plant of the invention that is tolerant to more than two different herbicides may be tolerant to herbicides that have different modes of action and/or different sites of action. In some embodiments, all of these traits are transgenic traits, while in other embodiments, at least one of these traits is not transgenic.

In some of these embodiments, each herbicide tolerance gene confers tolerance to a different herbicide or class or subclass of herbicides. In some of these embodiments, at least two of the herbicide tolerance genes confer tolerance to the same herbicide or to members of the same class or subclass of herbicides. Accordingly, further provided are plants having a polynucleotide that encodes a polypeptide which can confer tolerance to glyphosate and a polynucleotide that encodes an ALS inhibitor-tolerant polypeptide can further comprise at least one additional herbicide-tolerance polynucleotide which when expressed imparts tolerance to an additional herbicide. Such additional herbicides, include but are not limited to, an acetyl Co—A carboxylase inhibitor such as quizalofop-P-ethyl, a synthetic auxin such as quinclorac, a protoporphyrinogen oxidase (PPO) inhibitor herbicide (such as sulfentrazone), a pigment synthesis inhibitor herbicide such as a hydroxyphenylpyruvate dioxygenase inhibitor (e.g., mesotrione or sulcotrione), a phosphinothricin acetyltransferase or a phytoene desaturase inhibitor like diflufenican or pigment synthesis inhibitor. It is understood that the invention is not bound by the mechanism of action of a herbicide, so long as the goal of the invention (i.e., herbicide tolerance to glyphosate and at least on ALS inhibitor) is achieved. Additional herbicides of interest are disclosed elsewhere herein.

In some embodiments, the compositions of the invention further comprise polypeptides conferring tolerance to herbicides which inhibit the enzyme glutamine synthase, such as phosphinothricin or glufosinate (e.g., the bar gene or pat gene). Glutamine synthetase (GS) appears to be an essential enzyme necessary for the development and life of most plant cells, and inhibitors of GS are toxic to plant cells. Glufosinate herbicides have been developed based on the toxic effect due to the inhibition of GS in plants. These herbicides are non-selective; that is, they inhibit growth of all the different species of plants present. The development of plants containing an exogenous phosphinothricin acetyltransferase is described in U.S. Pat. Nos. 5,969,213; 5,489,520; 5,550,318; 5,874,265; 5,919,675; 5,561,236; 5,648,477; 5,646,024; 6,177,616; and 5,879,903, which are incorporated herein by reference in their entireties for all purposes. Mutated phosphinothricin acetyltransferase having this activity are also disclosed.

In still other embodiments, the compositions of the invention further comprise polypeptides conferring tolerance to herbicides which inhibit protox (protoporphyrinogen oxidase). Protox is necessary for the production of chlorophyll, which is necessary for all plant survival. The protox enzyme serves as the target for a variety of herbicidal compounds. These herbicides also inhibit growth of all the different species of plants present. The development of plants containing altered protox activity which are resistant to these herbicides are described in U.S. Pat. Nos. 6,288,306; 6,282,837; and 5,767,373; and international publication WO 01/12825, which are incorporated herein by reference in their entireties for all purposes.

In still other embodiments, compositions of the invention may comprise polypeptides involving other modes of herbicide resistance. For example, hydroxyphenylpyruvatedioxygenases are enzymes that catalyze the reaction in which para-hydroxyphenylpyruvate (HPP) is transformed into homogentisate. Molecules which inhibit this enzyme and which bind to the enzyme in order to inhibit transformation of the HPP into homogentisate are useful as herbicides. Plants more resistant to certain herbicides are described in U.S. Pat. Nos. 6,245,968; 6,268,549; and 6,069,115; and international publication WO 99/23886, which are incorporated herein by reference in their entireties for all purposes. Mutated hydroxyphenylpyruvatedioxygenase having this activity are also disclosed.

d. Fragments and Variants of Sequences that Confer Herbicide Tolerance

Depending on the context, "fragment" refers to a portion of the polynucleotide or a portion of the amino acid sequence and hence protein encoded thereby. Fragments of a polynucleotide may encode protein fragments that retain the biological activity of the original protein and hence confer tolerance to a herbicide. Thus, fragments of a nucleotide sequence may range from at least about 20 nucleotides, about 50 nucleotides, about 100 nucleotides, and up to the full-length polynucleotide encoding a herbicide-tolerance polypeptide.

A fragment of a herbicide-tolerance polynucleotide that encodes a biologically active portion of a herbicide-tolerance polypeptide will encode at least 15, 25, 30, 50, 100, 150, 200, or 250 contiguous amino acids, or up to the total number of amino acids present in a full-length herbicide-tolerance polypeptide. A biologically active portion of a herbicide-tolerance polypeptide can be prepared by isolating a portion of a herbicide-tolerance polynucleotide, expressing the encoded portion of the herbicide-tolerance polypeptide (e.g., by recombinant expression in vitro), and assessing the activity of the encoded portion of the herbicide-tolerance polypeptide. Polynucleotides that are fragments of a herbicide-tolerance polynucleotide comprise at least 16, 20, 50, 75, 100, 150, 200, 250, 300, 350, 400, 450, 500, 550, 600, 650, 700, 800, 900, 1,000, 1,100, 1,200, 1,300, or 1,400 contiguous nucleotides, or up to the number of nucleotides present in a full-length herbicide-tolerance polynucleotide.

The term "variants" refers to substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally-occurring nucleotide sequence or amino acid sequence, respectively. For polynucleotides, conservative variants include those sequences that, because of the degeneracy of the genetic code, encode the amino acid sequence of a herbicide-tolerance polypeptide. Naturally occurring allelic variants such as these can be identified with the use of well-known molecular biology techniques, as, for example, with polymerase chain reaction (PCR) and hybridization techniques. Variant polynucleotides also include synthetically derived polynucleotides, such as those generated, for example, by using site-directed mutagenesis or "shuffling." Generally, variants of a particular polynucleotide have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

Variants of a particular polynucleotide (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from a native and/or original protein by deletion (so-called truncation) of one or more amino acids at the N-terminal and/or C-terminal end of the protein; deletion and/or addition of one or more amino acids at one or more internal sites in the protein; or substitution of one or more amino acids at one or more sites in the protein. Variant proteins encompassed by the present invention are biologically active, that is they continue to possess the desired herbicide-tolerance activity as described herein. Biologically active variants of a herbicide-tolerance polypeptide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a herbicide-tolerance polypeptide may differ from that polypeptide by as few as 1-15 amino acid residues, as few as 1-10, such as 6-10, as few as 5, as few as 4, 3, 2, or even 1 amino acid residue. Variant herbicide-tolerance polypeptides, as well as polynucleotides encoding these variants, are known in the art.

Herbicide-tolerance polypeptides may be altered in various ways including amino acid substitutions, deletions, truncations, and insertions. Methods for such manipulations are generally known in the art. For example, amino acid sequence variants and fragments of herbicide-tolerance polypeptides can be prepared by mutations in the encoding polynucleotide. Methods for mutagenesis and polynucleotide alterations are well known in the art. See, for example, Kunkel (1985) *Proc. Natl. Acad. Sci. USA* 82: 488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be made. One skilled in the art will appreciate that the activity of a herbicide-tolerance polypeptide can be evaluated by routine screening assays. That is, the activity can be evaluated by determining whether a transgenic plant has an increased tolerance to a herbicide, for example, as illustrated in working Example 1, or with an in vitro assay, such as the production of N-acetylglyphosphate from glyphosate by a GAT polypeptide (see, e.g., WO 02/36782).

Variant polynucleotides and polypeptides also encompass sequences and proteins derived from a mutagenic and recombinogenic procedure such as DNA shuffling. With such a procedure, one or more different herbicide-tolerance polypeptide coding sequences can be manipulated to create a new herbicide-tolerance polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a herbicide-tolerance polypeptide and other known genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91: 10747-10751; Stemmer (1994) *Nature* 370: 389-391; Crameri et al. (1997) *Nature Biotech.* 15: 436-438; Moore et al. (1997) *J. Mol. Biol.* 272: 336-347; Zhang et al. (1997) *Proc. Natl. Acad. Sci. USA* 94: 4504-4509; Crameri et al. (1998) *Nature* 391: 288-291; and U.S. Pat. Nos. 5,605,793 and 5,837,458.

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4: 11-17; the local alignment algorithm of Smith et al. (1981) *Adv. Appl. Math.* 2:482; the global alignment algorithm of Needleman and Wunsch (1970) *J. Mol. Biol.* 48: 443-453; the search-for-local alignment method of Pearson and Lipman (1988) *Proc. Natl. Acad. Sci.* 85: 2444-2448; the algorithm of Karlin and Altschul (1990) *Proc. Natl. Acad. Sci. USA* 87: 2264-2268, modified as in Karlin and Altschul (1993) *Proc. Natl. Acad. Sci. USA* 90: 5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73: 237-244 (1988); Higgins et al. (1989) *CABIOS* 5: 151-153; Corpet et al. (1988) *Nucleic Acids Res.* 16:10881-90; Huang et al. (1992) *CABIOS* 8: 155-65; and Pearson et al. (1994) *Meth. Mol. Biol.* 24: 307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. BLAST software is publicly available on the NCBI website. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89: 10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to be limited to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. Thus, polynucleotides also encompass all forms of sequences including, but not limited to, single-stranded forms, double-stranded forms, hairpins, stem-and-loop structures, and the like.

e. Herbicide Tolerance

A "herbicide" is a chemical that causes temporary or permanent injury to a plant. Non-limiting examples of herbicides that can be employed in the various methods and compositions of the invention are discussed in further detail elsewhere herein. A herbicide may be incorporated into the plant, or it may act on the plant without being incorporated into the plant or its cells. An "active ingredient" is the chemical in a herbicide formulation primarily responsible for its phytotoxicity and which is identified as the active ingredient on the product label. Product label information is available from the U.S. Environmental Protection Agency and is updated online at the url oaspub.epa.gov/pestlabl/ppls.own; product label information is also available online at the url www.cdms.net. The term "acid equivalent" expresses the rate or quantity as the herbicidally active parent acid. For example, 2,4-D acid is often formulated in the form of a sodium or amine salt or an ester as the active ingredient in formulated products. The active acid equivalent per gallon of a widely used ester formulation is 3.8 lb a.e./gallon (about 0.454 kg a.e./L), while the active ingredient per gallon is 6.0 lb ai/gallon (about 0.717 kg ai/L). As used herein, an "agricultural chemical" is any chemical used in the context of agriculture.

"Herbicide-tolerant" or "tolerant" or "crop tolerance" in the context of herbicide or other chemical treatment as used herein means that a plant or other organism treated with a particular herbicide or class or subclass of herbicide or other chemical or class or subclass of other chemical will show no significant damage or less damage following that treatment in comparison to an appropriate control plant. A plant may be naturally tolerant to a particular herbicide or chemical, or a plant may be herbicide-tolerant as a result of human intervention such as, for example, breeding or genetic engineering. An "herbicide-tolerance polypeptide" is a polypeptide that confers herbicide tolerance on a plant or other organism expressing it (i.e., that makes a plant or other organism herbicide-tolerant), and an "herbicide-tolerance polynucleotide" is a polynucleotide that encodes a herbicide-tolerance polypeptide. For example, a sulfonylurea tolerant polypeptide is one that confers tolerance to sulfonylurea herbicides on a plant or other organism that expresses it, an imidazolinone tolerant polypeptide is one that confers tolerance to imidazolinone herbicides on a plant or other organism that expresses it; and a glyphosate tolerant polypeptide is one that confers tolerance to glyphosate on a plant or other organism that expresses it.

Thus, a plant is tolerant to a herbicide or other chemical if it shows damage in comparison to an appropriate control plant that is less than the damage exhibited by the control plant by at least 5%, 10%, 15%, 20%, 25%, 30%, 35%, 40%, 45%, 50%, 55%, 60%, 65%, 70%, 75%, 80%, 90%, 100%, 150%, 200%, 250%, 300%, 400%, 500%, 600%, 700%, 800%, 900%, or 1000% or more. In this manner, a plant that is tolerant to a herbicide or other chemical shows "improved tolerance" in comparison to an appropriate control plant. Damage resulting from herbicide or other chemical treatment is assessed by evaluating any parameter of plant growth or well-being deemed suitable by one of skill in the art. Damage can be assessed by visual inspection and/or by statistical analysis of suitable parameters of individual plants or of a group of plants. Thus, damage may be assessed by evaluating, for example, parameters such as plant height, plant weight, leaf color, leaf length, flowering, fertility, silking, yield, seed production, and the like. Damage may also be assessed by evaluating the time elapsed to a particular stage of development (e.g., silking, flowering, or pollen shed) or the time elapsed until a plant has recovered from treatment with a particular chemical and/or herbicide.

In making such assessments, particular values may be assigned to particular degrees of damage so that statistical analysis or quantitative comparisons may be made. The use of ranges of values to describe particular degrees of damage is known in the art, and any suitable range or scale may be used. For example, herbicide injury scores (also called tolerance scores) can be assigned as illustrated in Example 1 using the scale set forth in Table 7. In this scale, a rating of 9 indicates that a herbicide treatment had no effect on a crop, i.e., that no crop reduction or injury was observed following the herbicide treatment. Thus, in this scale, a rating of 9 indicates that the crop exhibited no damage from the herbicide and therefore that the crop is tolerant to the herbicide. As indicated above, herbicide tolerance is also indicated by other ratings in this scale where an appropriate control plant exhibits a lower score on the scale, or where a group of appropriate control plants exhibits a statistically lower score in response to a herbicide treatment than a group of subject plants.

Damage caused by a herbicide or other chemical can be assessed at various times after a plant has been treated with a herbicide. Often, damage is assessed at about the time that the control plant exhibits maximum damage. Sometimes, damage is assessed after a period of time in which a control plant that was not treated with herbicide or other chemical has measurably grown and/or developed in comparison to the size or stage at which the treatment was administered. Damage can be assessed at various times, for example, at 12 hours or at 1, 2, 3, 4, 5, 6, 7, 8, 9, 10, 11, 12, 13, 14 days, or three weeks, four weeks, or longer after the test plant was treated with herbicide. Any time of assessment is suitable as long as it permits detection of a difference in response to a treatment of test and control plants.

A herbicide does not "significantly damage" a plant when it either has no effect on a plant or when it has some effect on a plant from which the plant later recovers, or when it has an effect which is detrimental but which is offset, for example, by the impact of the particular herbicide on weeds. Thus, for example, a crop plant is not "significantly damaged by" a herbicide or other treatment if it exhibits less than 50%, 40%, 30%, 25%, 20%, 15%, 10%, 9%, 8%, 7%, 6%, 5%, 4%, 3%, 2%, or 1% decrease in at least one suitable parameter that is indicative of plant health and/or productivity in comparison to an appropriate control plant (e.g., an untreated crop plant). Suitable parameters that are indicative of plant health and/or productivity include, for example, plant height, plant weight, leaf length, time elapsed to a particular stage of development, flowering, yield, seed production, and the like. The evaluation of a parameter can be by visual inspection and/or by statistical analysis of any suitable parameter. Comparison may be made by visual inspection and/or by statistical analysis. Accordingly, a crop plant is not "significantly damaged by" a herbicide or other treatment if it exhibits a decrease in at least one parameter but that decrease is temporary in nature and the plant recovers fully within 1 week, 2 weeks, 3 weeks, 4 weeks, or 6 weeks.

Conversely, a plant is significantly damaged by a herbicide or other treatment if it exhibits more than a 50%, 60%, 70%, 80%, 90%, 100%, 110%, 120%, 150%, 170% decrease in at least one suitable parameter that is indicative of plant health and/or productivity in comparison to an appropriate control plant (e.g., an untreated weed of the same species). Thus, a plant is significantly damaged if it exhibits a decrease in at least one parameter and the plant does not recover fully within 1 week, 2 weeks, 3 weeks, 4 weeks, or 6 weeks.

Damage resulting from a herbicide or other chemical treatment of a plant can be assessed by visual inspection by one of skill in the art and can be evaluated by statistical analysis of suitable parameters. The plant being evaluated is referred to as the "test plant." Typically, an appropriate control plant is one that expresses the same herbicide-tolerance polypeptide(s) as the plant being evaluated for herbicide tolerance (i.e., the "test plant") but that has not been treated with herbicide. For example, in evaluating a herbicide-tolerant plant of the invention that confers tolerance to glyphosate and an ALS inhibitor, an appropriate control plant would be a plant that expresses each of these sequence but is not treated with the herbicide. In some circumstances, the control plant is one that that has been subjected to the same herbicide treatment as the plant being evaluated (i.e., the test plant) but that does not express the enzyme intended to provide tolerance to the herbicide of interest in the test plant. One of skill in the art will be able to design, perform, and evaluate a suitable controlled experiment to assess the herbicide tolerance of a plant of interest, including the selection of appropriate test plants, control plants, and treatments.

Thus, as used herein, a "test plant or plant cell" is one in which genetic alteration has been effected as to at least one gene of interest, or is a plant or plant cell which is descended from a plant or cell so altered and which comprises the alteration. A genetic alteration may be introduced into the plant by breeding or by transformation. "Genetic alteration" is intended to mean a gene or mutation thereof which confers a phenotype on the plant that differs from the phenotype of a plant that does not contain the genetic alteration.

A "control" or "control plant" or "control plant cell" provides a reference point for measuring changes in phenotype of the subject plant or plant cell, and may be any suitable plant or plant cell. A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell which is genetically identical to the subject plant or plant cell but which is not exposed to the same treatment (e.g., herbicide treatment) as the subject plant or plant cell; (e) the subject plant or plant cell itself, under conditions in which the gene of interest is not expressed; or (f) the subject plant or plant cell itself, under conditions in which it has not been exposed to a particular treatment such as, for example, a herbicide or combination of herbicides and/or other chemicals. In some instances, an appropriate control plant or control plant cell may have a different genotype from the subject plant or plant cell but may share the herbicide-sensitive characteristics of the starting material for the genetic alteration(s) which resulted in the subject plant or cell (see, e.g., Green (1998) *Weed Technology* 12: 474-477; Green and Ulrich (1993) *Weed Science* 41: 508-516). In some instances, an appropriate control maize plant comprises a NK603 event (Nielson et al. (2004) *European Food Research and Technology* 219:421-427 and Ridley et al. (2002) *Journal of Agriculture and Food Chemistry* 50: 7235-7243), an elite stiff stalk inbred plant, a P3162 plant (Pioneer Hi-Bred International), a 39T66 plant (Pioneer Hi-Bred International), or a 34M91 plant (Pioneer Hi-Bred International). In some instances, an appropriate control soybean plant is a "Jack" soybean plant (Illinois Foundation Seed, Champaign, Ill.).

Plants of the invention express a polypeptide that confers tolerance to glyphosate and at least one other polypeptide that confers tolerance to an ALS inhibitor. A plant of the invention shows at least one improved property relative to an appropriate control plant, such as, for example, improved herbicide tolerance, reduced lodging, increased height, reduced time to maturity, and improved yield. A plant has an improved property when it exhibits a statistically significant difference from an appropriate control plant wherein that difference is in a direction that represents an improvement over the control plant. For example, a plant has an improved property when it exhibits an increase in yield that is statistically significant in comparison to a control plant, and/or when it exhibits a decrease in damage resulting from treatment with a herbicide. Techniques for such assessments are known in the art. Any suitable statistical analysis may be used, such as, for example, an ANOVA (available as a commercial package from SAS Institute, Inc., 100 SAS Campus Drive, Cary, N.C.).

f. Plants

As used herein, the term "plant" includes plant cells, plant protoplasts, plant cell tissue cultures from which plants can be regenerated, plant calli, plant clumps, explants, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides. Thus, the invention provides transgenic seeds produced by the plants of the invention.

The present invention may be used for transformation of any plant species, including, but not limited to, monocots and dicots. Examples of plant species of interest include, but are not limited to, corn (*Zea mays*, also referred to herein as "maize"), *Brassica* spp. (e.g., *B. napus, B. rapa, B. juncea*), particularly those *Brassica* species useful as sources of seed oil (also referred to as "canola"), flax (*Linum* spp.), alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, fruits, ornamentals (flowers), sugar cane, conifers, *Arabidopsis*.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Any tree can also be employed. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Hardwood trees can also be employed including ash, aspen, beech, basswood, birch, black cherry, black walnut, buckeye, American chestnut, cottonwood, dogwood, elm, hackberry, hickory, holly, locust, magnolia, maple, oak, poplar, red alder, redbud, royal paulownia, sassafras, sweetgum, sycamore, tupelo, willow, yellow-poplar.

In specific embodiments, plants of the present invention are crop plants (for example, corn (also referred to as "maize"), alfalfa, sunflower, *Brassica*, soybean, cotton, safflower, peanut, sorghum, wheat, millet, tobacco, etc.).

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Other plants of interest include Turfgrasses such as, for example, turfgrasses from the genus *Poa, Agrostis, Festuca, Lolium*, and *Zoysia*. Additional turfgrasses can come from the subfamily Panicoideae. Turfgrasses can further include, but are not limited to, Blue gramma (*Bouteloua gracilis* (H.B.K.) Lag. Ex Griffiths); Buffalograss (*Buchloe dactyloids* (Nutt.)

Engelm.); Slender creeping red fescue (*Festuca rubra* ssp. *Litoralis*); Red fescue (*Festuca rubra*); Colonial bentgrass (*Agrostis tenuis* Sibth.); Creeping bentgrass (*Agrostis palustris* Huds.); Fairway wheatgrass (*Agropyron cristatum* (L.) Gaertn.); Hard fescue (*Festuca longifolia* Thuill.); Kentucky bluegrass (*Poa pratensis* L.); Perennial ryegrass (*Lolium perenne* L.); Rough bluegrass (*Poa trivialis* L.); Sideoats grama (*Bouteloua curtipendula* Michx. Torr.); Smooth bromegrass (*Bromus inermis* Leyss.); Tall fescue (*Festuca arundinacea* Schreb.); Annual bluegrass (*Poa annua* L.); Annual ryegrass (*Lolium multiflorum* Lam.); Redtop (*Agrostis alba* L.); Japanese lawn grass (*Zoysia japonica*); bermudagrass (*Cynodon dactylon; Cynodon* spp. L.C. Rich; *Cynodon transvaalensis*); Seashore paspalum (*Paspalum vaginatum* Swartz); Zoysiagrass (*Zoysia* spp. Willd; *Zoysia japonica* and *Z. matrella* var. *matrella*); Bahiagrass (*Paspalum notatum* Flugge); Carpetgrass (*Axonopus affinis* Chase); Centipedegrass (*Eremochloa ophiuroides* Munro Hack.); Kikuyugrass (*Pennisetum clandesinum* Hochst Ex Chiov); Browntop bent (*Agrostis tenuis* also known as *A. capillaris*); Velvet bent (*Agrostis canina*); Perennial ryegrass (*Lolium perenne*); and, St. Augustinegrass (*Stenotaphrum secundatum* Walt. Kuntze). Additional grasses of interest include switchgrass (*Panicum virgatum*).

g. Stacking of Traits and Additional Traits of Interest

In some embodiments, the polynucleotide conferring the glyphosate tolerance and the ALS inhibitor tolerance in the plants of the invention are engineered into a molecular stack. In other embodiments, the molecular stack further comprises at least one additional polynucleotide that confers tolerance to a $3^{rd}$ herbicide. Such sequences are disclosed elsewhere in herein. In one embodiment, the sequence confers tolerance to glufosinate, and 2 in a specific embodiment, the sequence comprises pat.

In other embodiments, the glyphosate/ALS inhibitor-tolerant plants of the invention comprise one or more trait of interest, and in more specific embodiments, the plant is stacked with any combination of polynucleotide sequences of interest in order to create plants with a desired combination of traits. A trait, as used herein, refers to the phenotype derived from a particular sequence or groups of sequences. For example, herbicide-tolerance polynucleotides may be stacked with any other polynucleotides encoding polypeptides having pesticidal and/or insecticidal activity, such as *Bacillus thuringiensis* toxic proteins (described in U.S. Pat. Nos. 5,366,892; 5,747,450; 5,737,514; 5,723,756; 5,593,881; Geiser et al. (1986) *Gene* 48: 109; Lee et al. (2003) *Appl. Environ. Microbiol.* 69: 4648-4657 (Vip3A); Galitzky et al. (2001) *Acta Crystallogr. D. Biol. Crystallogr.* 57:1101-1109 (Cry3Bb1); and Herman et al. (2004) *J. Agric. Food Chem.* 52: 2726-2734 (Cry1F)), lectins (Van Damme et al. (1994) *Plant Mol. Biol.* 24: 825, pentin (described in U.S. Pat. No. 5,981,722), and the like. The combinations generated can also include multiple copies of any one of the polynucleotides of interest.

In some embodiments, herbicide-tolerance polynucleotides of the glyphosate/ALS inhibitor-tolerant plants (i.e., such as plant comprising GAT and HRA) may be stacked with other herbicide-tolerance traits to create a transgenic plant of the invention with further improved properties. Other herbicide-tolerance polynucleotides that could be used in such embodiments include those conferring tolerance to glyphosate or to ALS inhibitors by other modes of action, such as, for example, a gene that encodes a glyphosate oxido-reductase enzyme as described more fully in U.S. Pat. Nos. 5,776,760 and 5,463,175. Other traits that could be combined with herbicide-tolerance polynucleotides of the glyphosate/ALS inhibitor-tolerant plants (i.e., such as GAT and HRA sequence) include those derived from polynucleotides that confer on the plant the capacity to produce a higher level of 5-enolpyruvylshikimate-3-phosphate synthase (EPSPS), for example, as more fully described in U.S. Pat. Nos. 6,248,876 B1; 5,627,061; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; U.S. Pat. No. Re. 36,449; U.S. Pat. Nos. RE 37,287 E; and 5,491,288; and international publications WO 97/04103; WO 00/66746; WO 01/66704; and WO 00/66747. Other traits that could be combined with herbicide-tolerance polynucleotides of the glyphosate/ALS inhibitor-tolerant plants (i.e., such as GAT and HRA sequences) include those conferring tolerance to sulfonylurea and/or imidazolinone, for example, as described more fully in U.S. Pat. Nos. 5,605, 011; 5,013,659; 5,141,870; 5,767,361; 5,731,180; 5,304,732; 4,761,373; 5,331,107; 5,928,937; and 5,378,824; and international publication WO 96/33270.

In some embodiments, herbicide-tolerance polynucleotides of the glyphosate/ALS inhibitor-tolerant plants (i.e., such as GAT and HRA sequence) may be stacked with, for example, hydroxyphenylpyruvatedioxygenases which are enzymes that catalyze the reaction in which para-hydroxyphenylpyruvate (HPP) is transformed into homogentisate. Molecules which inhibit this enzyme and which bind to the enzyme in order to inhibit transformation of the HPP into homogentisate are useful as herbicides. Traits conferring tolerance to such herbicides in plants are described in U.S. Pat. Nos. 6,245,968 B1; 6,268,549; and 6,069,115; and international publication WO 99/23886. Other examples of suitable herbicide-tolerance traits that could be stacked with herbicide-tolerance polynucleotides of the glyphosate/ALS inhibitor-tolerant plants (i.e., such GAT and HRA sequences) include aryloxyalkanoate dioxygenase polynucleotides (which reportedly confer tolerance to 2,4-D and other phenoxy auxin herbicides as well as to aryloxyphenoxypropionate herbicides as described, for example, in WO2005/107437) and dicamba-tolerance polynucleotides as described, for example, in Herman et al. (2005) *J. Biol. Chem.* 280: 24759-24767.

Other examples of herbicide-tolerance traits that could be combined with herbicide-tolerance polynucleotides of the glyphosate/ALS inhibitor-tolerant plants (i.e., GAT and HRA plants) include those conferred by polynucleotides encoding an exogenous phosphinothricin acetyltransferase, as described in U.S. Pat. Nos. 5,969,213; 5,489,520; 5,550,318; 5,874,265; 5,919,675; 5,561,236; 5,648,477; 5,646,024; 6,177,616; and 5,879,903. Plants containing an exogenous phosphinothricin acetyltransferase can exhibit improved tolerance to glufosinate herbicides, which inhibit the enzyme glutamine synthase. Other examples of herbicide-tolerance traits that could be combined with the herbicide-tolerance polynucleotides of the glyphosate/ALS inhibitor-tolerant plants (i.e., GAT and HRA plants) include those conferred by polynucleotides conferring altered protoporphyrinogen oxidase (protox) activity, as described in U.S. Pat. Nos. 6,288, 306 B1; 6,282,837 B1; and 5,767,373; and international publication WO 01/12825. Plants containing such polynucleotides can exhibit improved tolerance to any of a variety of herbicides which target the protox enzyme (also referred to as "protox inhibitors").

Other examples of herbicide-tolerance traits that could be combined with herbicide-tolerance polynucleotides of the glyphosate/ALS inhibitor-tolerant plants (i.e., GAT and HRA plants) include those conferring tolerance to at least one herbicide in a plant such as, for example, a maize plant or horseweed. Herbicide-tolerant weeds are known in the art, as are plants that vary in their tolerance to particular herbicides. See, e.g., Green and Williams (2004) "Correlation of Corn (*Zea mays*) Inbred Response to Nicosulfuron and Mesotrione," poster presented at the WSSA Annual Meeting in Kansas City, Mo., Feb. 9-12, 2004; Green (1998) *Weed Technology* 12: 474-477; Green and Ulrich (1993) *Weed Science* 41: 508-516. The trait(s) responsible for these tolerances can be combined by breeding or via other methods with herbicide-tolerance polynucleotides of the glyphosate/ALS inhibitor-tolerant plants (i.e., GAT and HRA plants) to provide a plant of the invention as well as methods of use thereof.

In this manner, the invention provides plants that are more tolerant to glyphosate and other ALS inhibitor chemistries and also provides plants that are more tolerant to the herbicide for which each of the traits discussed above confers tolerance. Accordingly, the invention provides methods for growing a crop (i.e., for selectively controlling weeds in an area of cultivation) that comprise treating an area of interest (e.g., a field or area of cultivation) with at least one herbicide to which the plant of the invention is tolerant, such as for example, glyphosate, an ALS inhibitor chemistry, a mixture of ALS inhibitor chemistries, or a mixture of glyphosate and ALS inhibitor chemistry. In some embodiments, methods of the invention further comprise treatment with additional herbicides to which the plant of the invention is tolerant. In such embodiments, generally the methods of the invention permit selective control of weeds without significantly damaging the crop. As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc), a greenhouse, a growth chamber, etc.

Herbicide-tolerant traits can also be combined with at least one other trait to produce plants of the present invention that further comprise a variety of desired trait combinations including, but not limited to, traits desirable for animal feed such as high oil content (e.g., U.S. Pat. No. 6,232,529); balanced amino acid content (e.g., hordothionins (U.S. Pat. Nos. 5,990,389; 5,885,801; 5,885,802; and 5,703,409; U.S. Pat. No. 5,850,016); barley high lysine (Williamson et al. (1987) *Eur. J. Biochem.* 165: 99-106; and WO 98/20122) and high methionine proteins (Pedersen et al. (1986) *J. Biol. Chem.* 261: 6279; Kirihara et al. (1988) *Gene* 71: 359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference. Desired trait combinations also include LLNC (low linolenic acid content; see, e.g., Dyer et al. (2002) *Appl. Microbiol. Biotechnol.* 59: 224-230) and OLCH (high oleic acid content; see, e.g., Fernandez-Moya et al. (2005) *J. Agric. Food Chem.* 53: 5326-5330).

Herbicide-tolerant traits of interest can also be combined with other desirable traits such as, for example, fumonisim detoxification genes (U.S. Pat. No. 5,792,931), avirulence and disease resistance genes (Jones et al. (1994) *Science* 266: 789; Martin et al. (1993) *Science* 262: 1432; Mindrinos et al. (1994) *Cell* 78: 1089), and traits desirable for processing or process products such as modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine herbicide-tolerant polynucleotides with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

In another embodiment, the herbicide-tolerant traits of interest can also be combined with the Rcg1 sequence or biologically active variant or fragment thereof. The Rcg1 sequence is an anthracnose stalk rot resistance gene in corn. See, for example, U.S. patent application Ser. No. 11/397, 153, 11/397,275, and 11/397,247, each of which is herein incorporated by reference.

These stacked combinations can be created by any method including, but not limited to, breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like. Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48: 109); and the like.

Genes encoding disease resistance traits include detoxification genes, such as against fumonosin (U.S. Pat. No. 5,792,931); avirulence (avr) and disease resistance (R) genes (Jones et al. (1994) *Science* 266: 789; Martin et al. (1993) *Science* 262: 1432; and Mindrinos et al. (1994) *Cell* 78: 1089); and the like.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxybutryrate synthase), and acetoacetyl-CoA reductase (see Schubert et al. (1988) *J. Bacteriol.* 170: 5837-5847) facilitate expression of polyhydroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

II. Polynucleotide Constructs

In specific embodiments, one or more of the herbicide-tolerant polynucleotides employed in the methods and compositions can be provided in an expression cassette for expression in the plant or other organism of interest. The cassette will include 5' and 3' regulatory sequences operably linked to a herbicide-tolerance polynucleotide. "Operably linked" is intended to mean a functional linkage between two or more elements. For example, an operable linkage between a polynucleotide of interest and a regulatory sequence (e.g., a promoter) is functional link that allows for expression of the polynucleotide of interest. Operably linked elements may be contiguous or non-contiguous. When used to refer to the joining of two protein coding regions, by "operably linked" is intended that the coding regions are in the same reading frame. When used to refer to the effect of an enhancer, "operably linked" indicates that the enhancer increases the expression of a particular polynucleotide or polynucleotides of interest. Where the polynucleotide or polynucleotides of interest encode a polypeptide, the encoded polypeptide is produced at a higher level.

The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the herbicide-tolerance polynucleotide to be under the transcriptional regulation of the regulatory regions. The expression cassette may additionally contain other genes, including other selectable marker genes. Where a cassette contains more than one polynucleotide, the polynucleotides in the cassette may be transcribed in the same direction or in different directions (also called "divergent" transcription).

An expression cassette comprising a herbicide-tolerance polynucleotide will include in the 5'-3' direction of transcription a transcriptional and translational initiation region (i.e., a promoter), a herbicide-tolerance polynucleotide (e.g., a GAT polynucleotide, a ALS inhibitor-tolerant polynucleotide, an HRA polynucleotide, or any combination thereof, etc.), and a transcriptional and translational termination region (i.e., termination region) functional in plants or the other organism of interest. Accordingly, plants having such expression cassettes are also provided. The regulatory regions (i.e., promoters, transcriptional regulatory regions, and translational termination regions) and/or the herbicide-tolerance polynucleotide may be native (i.e., analogous) to the host cell or to each other. Alternatively, the regulatory regions and/or the herbicide-tolerance polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same (i.e., analogous) species, one or both are substantially modified from their original form and/or genomic locus, or the promoter is not the native promoter for the operably linked polynucleotide.

While it may be optimal to express polynucleotides using heterologous promoters, native promoter sequences may be used. Such constructs can change expression levels and/or expression patterns of the encoded polypeptide in the plant or plant cell. Expression levels and/or expression patterns of the encoded polypeptide may also be changed as a result of an additional regulatory element that is part of the construct, such as, for example, an enhancer. Thus, the phenotype of the plant or cell can be altered even though a native promoter is used.

The termination region may be native with the transcriptional initiation region, may be native with the operably linked herbicide-tolerance polynucleotide of interest, may be native with the plant host, or may be derived from another source (i.e., foreign or heterologous) to the promoter, the herbicide-tolerance polynucleotide of interest, the plant host, or any combination thereof. Convenient termination regions are available from the Ti-plasmid of *A. tumefaciens*, such as the octopine synthase and nopaline synthase termination regions, or can be obtained from plant genes such as the *Solanum tuberosum* proteinase inhibitor II gene. See also Guerineau et al. (1991) *Mol. Gen. Genet.* 262: 141-144; Proudfoot (1991) *Cell* 64: 671-674; Sanfacon et al. (1991) *Genes Dev.* 5: 141-149; Mogen et al. (1990) *Plant Cell* 2: 1261-1272; Munroe et al. (1990) *Gene* 91: 151-158; Ballas et al. (1989) *Nucleic Acids Res.* 17: 7891-7903; and Joshi et al. (1987) *Nucleic Acids Res.* 15: 9627-9639.

A number of promoters can be used in the practice of the invention, including the native promoter of the polynucleotide sequence of interest. The promoters can be selected based on the desired outcome. The polynucleotides of interest can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313: 810-812); rice actin (McElroy et al. (1990) *Plant Cell* 2: 163-171); the maize actin promoter; the ubiquitin promoter (see, e.g., Christensen et al. (1989) *Plant Mol. Biol.* 12: 619-632; Christensen et al. (1992) *Plant Mol. Biol.* 18: 675-689; Callis et al. (1995) *Genetics* 139: 921-39); pEMU (Last et al. (1991) *Theor. Appl. Genet.* 81: 581-588); MAS (Velten et al. (1984) *EMBO J.* 3: 2723-2730); ALS promoter (U.S. Pat. No. 5,659,026), and the like. Other constitutive promoters include, for example, those described in U.S. Pat. Nos. 5,608,149; 5,608,144; 5,604,121; 5,569,597; 5,466,785; 5,399,680; 5,268,463; 5,608,142; and 6,177,611. Some promoters show improved expression when they are used in conjunction with a native 5' untranslated region and/or other elements such as, for example, an intron. For example, the maize ubiquitin promoter is often placed upstream of a polynucleotide of interest along with at least a portion of the 5' untranslated region of the ubiquitin gene, including the first intron of the maize ubiquitin gene.

Chemical-regulated promoters can be used to modulate the expression of a gene in a plant through the application of an exogenous chemical regulator. Depending upon the objective, the promoter may be a chemical-inducible promoter for which application of the chemical induces gene expression or the promoter may be a chemical-repressible promoter for which application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88: 10421-10425 and McNellis et al. (1998) *Plant J.* 14(2): 247-257) and tetracycline-inducible and tetracycline-repressible promoters (see, for example, Gatz et al. (1991) *Mol. Gen. Genet.* 227: 229-237, and U.S. Pat. Nos. 5,814,618 and 5,789,156), herein incorporated by reference.

Tissue-preferred promoters can be utilized to target enhanced herbicide-tolerance polypeptide expression within a particular plant tissue. Tissue-preferred promoters include Yamamoto et al. (1997) *Plant J.* 12(2): 255-265; Kawamata et al. (1997) *Plant Cell Physiol.* 38(7): 792-803; Hansen et al. (1997) *Mol. Gen Genet.* 254(3): 337-343; Russell et al. (1997) *Transgenic Res.* 6(2): 157-168; Rinehart et al. (1996) *Plant Physiol.* 112(3):1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20: 181-196; Orozco et al. (1993) *Plant Mol Biol.* 23(6): 1129-1138; Matsuoka et al. (1993) *Proc Natl. Acad. Sci. USA* 90(20): 9586-9590; and Guevara-Garcia et al. (1993) Plant J. 4(3): 495-505. Such promoters can be modified, if necessary, for weak expression.

Leaf-preferred promoters are known in the art. See, for example, Yamamoto et al. (1997) *Plant J.* 12(2): 255-265; Kwon et al. (1994) *Plant Physiol.* 105: 357-67; Yamamoto et al. (1994) *Plant Cell Physiol.* 35(5): 773-778; Gotor et al. (1993) *Plant J.* 3: 509-18; Orozco et al. (1993) *Plant Mol. Biol.* 23(6): 1129-1138; and Matsuoka et al. (1993) *Proc. Natl. Acad. Sci. USA* 90(20): 9586-9590.

Root-preferred promoters are known and can be selected from the many available from the literature or isolated de novo from various compatible species. See, for example, Hire et al. (1992) *Plant Mol. Biol.* 20(2): 207-218 (soybean root-specific glutamine synthetase gene); Keller and Baumgartner (1991) *Plant Cell* 3(10): 1051-1061 (root-specific control element in the GRP 1.8 gene of French bean); Sanger et al. (1990) *Plant Mol. Biol.* 14(3): 433-443 (root-specific promoter of the mannopine synthase (MAS) gene of *Agrobacterium tumefaciens*); and Miao et al. (1991) *Plant Cell* 3(1): 11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1): 69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.*

29(4): 759-772); and rolB promoter (Capana et al. (1994) *Plant Mol. Biol.* 25(4): 681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10: 108, herein incorporated by reference. Such seed-preferred promoters include, but are not limited to, Cim1 (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is an endosperm-specific promoter. Globulin 1 (Glb-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, Globulin 1, etc. See also WO 00/12733, where seed-preferred promoters from end1 and end2 genes are disclosed; herein incorporated by reference.

Additional promoters of interest include the SCP1 promoter (U.S. Pat. No. 6,072,050), the HB2 promoter (U.S. Pat. No. 6,177,611) and the SAMS promoter (US20030226166 and SEQ ID NO: 87 and biologically active variants and fragments thereof); each of which is herein incorporated by reference. In addition, as discussed elsewhere herein, various enhancers can be used with these promoters including, for example, the ubiquitin intron (i.e, the maize ubiquitin intron 1 (see, for example, NCBI sequence S94464), the omega enhancer or the omega prime enhancer (Gallie et al. (1989) *Molecular Biology of RNA* ed. Cech (Liss, N.Y.) 237-256 and Gallie et al. *Gene* (1987) 60:217-25), or the 35S enhancer; each of which is incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85: 610-9 and Fetter et al. (2004) *Plant Cell* 16: 215-28), cyan florescent protein (CYP) (Bolte et al. (2004) *J. Cell Science* 117: 943-54 and Kato et al. (2002) *Plant Physiol* 129: 913-42), and yellow fluorescent protein (PhiYFP from Evrogen, see, Bolte et al. (2004) *J. Cell Science* 117: 943-54). For additional selectable markers, see generally, Yarranton (1992) *Curr. Opin. Biotech.* 3: 506-511; Christopherson et al. (1992) *Proc. Natl. Acad. Sci. USA* 89: 6314-6318; Yao et al. (1992) *Cell* 71: 63-72; Reznikoff (1992) *Mol. Microbiol.* 6: 2419-2422; Barkley et al. (1980) in *The Operon*, pp. 177-220; Hu et al. (1987) *Cell* 48: 555-566; Brown et al. (1987) *Cell* 49: 603-612; Figge et al. (1988) *Cell* 52: 713-722; Deuschle et al. (1989) *Proc. Natl. Acad. Aci. USA* 86: 5400-5404; Fuerst et al. (1989) *Proc. Natl. Acad. Sci. USA* 86: 2549-2553; Deuschle et al. (1990) *Science* 248: 480-483; Gossen (1993) Ph.D. Thesis, University of Heidelberg; Reines et al. (1993) *Proc. Natl. Acad. Sci. USA* 90: 1917-1921; Labow et al. (1990) *Mol. Cell. Biol.* 10: 3343-3356; Zambretti et al. (1992) *Proc. Natl. Acad. Sci. USA* 89: 3952-3956; Baim et al. (1991) *Proc. Natl. Acad. Sci. USA* 88: 5072-5076; Wyborski et al. (1991) *Nucleic Acids Res.* 19: 4647-4653; Hillenand-Wissman (1989) *Topics Mol. Struc. Biol.* 10: 143-162; Degenkolb et al. (1991) *Antimicrob. Agents Chemother.* 35: 1591-1595; Kleinschnidt et al. (1988) *Biochemistry* 27: 1094-1104; Bonin (1993) Ph.D. Thesis, University of Heidelberg; Gossen et al. (1992) *Proc. Natl. Acad. Sci. USA* 89: 5547-5551; Oliva et al. (1992) *Antimicrob. Agents Chemother.* 36: 913-919; Hlavka et al. (1985) *Handbook of Experimental Pharmacology*, Vol. 78 (Springer-Verlag, Berlin); Gill et al. (1988) *Nature* 334: 721-724. Such disclosures are herein incorporated by reference. The above list of selectable marker genes is not meant to be limiting. Any selectable marker gene can be used in the present invention, including the GAT gene and/or HRA gene.

Methods are known in the art of increasing the expression level of a polypeptide of the invention in a plant or plant cell, for example, by inserting into the polypeptide coding sequence one or two G/C-rich codons (such as GCG or GCT) immediately adjacent to and downstream of the initiating methionine ATG codon. Where appropriate, the polynucleotides may be optimized for increased expression in the transformed plant. That is, the polynucleotides can be synthesized substituting in the polypeptide coding sequence one or more codons which are less frequently utilized in plants for codons encoding the same amino acid(s) which are more frequently utilized in plants, and introducing the modified coding sequence into a plant or plant cell and expressing the modified coding sequence. See, for example, Campbell and Gowri (1990) *Plant Physiol.* 92: 1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17: 477-498, herein incorporated by reference. Embodiments comprising such modifications are also a feature of the invention.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures. "Enhancers" such as the CaMV 35S enhancer may also be used (see, e.g., Benfey et al. (1990) *EMBO J.* 9: 1685-96), or other enhancers may be used. For example, the sequence set forth in SEQ ID NO: 1, 72, 79, 84, 85, 88, or 89 or a biologically active variant or fragment thereof can be used. See, also, U.S. Utility application Ser. No. 11/508,045, entitled "Methods and Compositions for the Expression of a Polynucleotide of Interest", filed concurrently herewith, and herein incorporated by reference in its entirety. The term "promoter" is intended to mean a regulatory region of DNA comprising a transcriptional initiation region, which in some embodiments, comprises a TATA box capable of directing RNA polymerase II to initiate RNA synthesis at the appropriate transcription initiation site for a particular coding sequence. The promoter can further be operably linked to additional regulatory elements that influence transcription, including, but not limited to, introns, 5' untranslated regions, and enhancer elements. As used herein, an "enhancer sequence," "enhancer domain," "enhancer element," or "enhancer," when operably linked to an appropriate promoter, will modulate the level of transcription of an operably linked polynucleotide of interest. Biologically active fragments and variants of the enhancer domain may retain the biological activity of modulating (increase or decrease) the level of transcription when operably linked to an appropriate promoter.

Fragments of a polynucleotide for the enhancer domain or a promoter may range from at least about 50 nucleotides, about 100 nucleotides, about 150 nucleotides, about 200 nucleotides, about 250 nucleotides, about 300 nucleotides, about 350 nucleotides, about 400 nucleotides, about 450 nucleotides, about 500 nucleotides, and up to the full-length nucleotide sequence of the invention for the enhancer domain of the invention. In other embodiments, a fragment of the enhancer domain comprises a length of about 50 to about 100, 100 to about 150, 150 to about 200, 200 to about 250, about 250 to about 300, about 300 to about 350, about 350 to about 400, about 400 to about 450, about 450 to about 500, about 500 to about 535 nucleotides. Generally, variants of a particular polynucleotides of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotides as determined by sequence alignment programs and parameters described elsewhere herein. A biologically active variant of an enhancer or a promoter may differ from that sequence by as few as 1-15 nucleic acid residues, as few as 1-10, such as 6-10, as few as 10, 9, 8, 7, 6, 5, 4, 3, 2, or even 1 nucleic acid residue. Such active variants and fragments will continue to modulate transcription.

Multiple copies of the enhancer domain or active variants and fragments thereof can be operably linked to a promoter. In specific embodiment, the chimeric transcriptional regulatory control region comprises at least 1, 2, 3, 4, 5, 6, 7 or more copies of the enhancer domain. In further embodiments, the enhancer domain employed does not comprise the sequence set forth in SEQ ID NO:5. In addition, the enhancer can be orientated in either orientation (i.e., sense or reverse).

The distance between the promoter and the enhancer domain can vary, so long as the chimeric transcriptional regulatory region continues to direct transcription of the operably linked polynucleotide of interest in the desired manner. For example, an enhancer domain can be positioned at least about 10000 to about 15000, about 10000 to about a 9000, about 9000 to about 8000, about 8000 to about 7000, about 7000 to about 6000, about 6000 to about 5000, about 5000 to about 4000, about 4000 to about 3000, about 3000 to about 2000, about 2000 to about 1000, about 1000 to about 500, about 500 to about 250, about 250 to immediately adjacent to the promoter. It is further recognized that one or more copies of the enhancer can be placed upstream (5') of the promoter or alternatively, one or more copies of the enhancer can be located 3' to the promoter. In specific embodiments, when located 3' of the promoter, the enhancer is downstream of the terminator region. In still further embodiments, one or more of the enhancers can be arranged either in the 5' or 3' orientation (as shown in SEQ ID NO: 1 or 72) or in the 3' to 5' orientation.

If multiple enhancers are employed, the enhancers can be positioned in the construct with respect to the promoter such that the desired affect on expression is achieved. For example, the enhances can be immediately adjacent to each other or at least between 1 to 100, 100 to 300, 300 to 500, 500 to 1000 nucleotides apart.

It is further recognized that the enhancer employed in the invention can be positioned in a DNA construct between and operably linked to a first and a second promoter. In such embodiments, the enhancer allows for a modulation in expression of both the first and the second promoters from a divergent direction. Exemplary, but non-limiting, examples of such DNA constructs comprise in the 5' to 3' or 3' to 5' orientation: a first polynucleotide of interest operably linked to a first promoter, operably linked to at least one copy of an enhancer of the invention, operably linked to a second promoter, operably linked to a second polynucleotide of interest. In specific embodiments, the enhancer sequence is heterologous to the first and the second enhancer sequence. In other embodiments, the first promoter is operably linked to a polynucleotide encoding an ALS inhibitor and the second promoter is operably linked to a polynucleotide encoding a polypeptide that confers tolerance to glyphosate. Such polynucleotides are disclosed elsewhere herein.

The expression cassette may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86: 6126-6130); potyvirus leaders, for example, TEV leader (Tobacco Etch Virus) (Gallie et al. (1995) *Gene* 165(2): 233-238), MDMV leader (Maize Dwarf Mosaic Virus) (*Virology* 154: 9-20), and human immunoglobulin heavy-chain binding protein (BiP) (Macejak et al. (1991) *Nature* 353: 90-94); untranslated leader from the coat protein mRNA of alfalfa mosaic virus (AMV RNA 4) (Jobling et al. (1987) *Nature* 325: 622-625); tobacco mosaic virus leader (TMV) (Gallie et al. (1989) in *Molecular Biology of RNA*, ed. Cech (Liss, N.Y.), pp. 237-256); and maize chlorotic mottle virus leader (MCMV) (Lommel et al. (1991) *Virology* 81: 382-385). See also, Della-Cioppa et al. (1987) *Plant Physiol.* 84: 965-968.

In preparing the expression cassette, the various polynucleotide fragments may be manipulated, so as to provide for sequences to be in the proper orientation and, as appropriate, in the proper reading frame. Toward this end, adapters or linkers may be employed to join the fragments or other manipulations may be involved to provide for convenient restriction sites, removal of superfluous material such as the removal of restriction sites, or the like. For this purpose, in vitro mutagenesis, primer repair, restriction, annealing, resubstitutions, e.g., transitions and transversions, may be involved. Standard recombinant DNA and molecular cloning techniques used herein are well known in the art and are described more fully, for example, in Sambrook et al. (1989) *Molecular Cloning: A Laboratory Manual* (Cold Spring Harbor Laboratory Press, Cold Spring Harbor) (also known as "Maniatis").

In some embodiments, the polynucleotide of interest is targeted to the chloroplast for expression. In this manner, where the polynucleotide of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9: 104-126; Clark et al. (1989) *J. Biol. Chem.* 264: 17544-17550; Della-Cioppa et al. (1987) *Plant Physiol.* 84: 965-968; Romer et al. (1993) *Biochem. Biophys. Res. Commun.* 196: 1414-1421; and Shah et al. (1986) *Science* 233: 478-481.

Chloroplast targeting sequences are known in the art and include the chloroplast small subunit of ribulose-1,5-bisphosphate carboxylase (Rubisco) (de Castro Silva Filho et al. (1996) *Plant Mol. Biol.* 30: 769-780; Schnell et al. (1991) *J. Biol. Chem.* 266(5): 3335-3342); 5-(enolpyruvyl)shikimate-3-phosphate synthase (EPSPS) (Archer et al. (1990) *J. Bioenerg Biomemb.* 22(6): 789-810); tryptophan synthase (Zhao et al. (1995) *J. Biol. Chem.* 270(11): 6081-6087); plastocyanin (Lawrence et al. (1997) *J. Biol. Chem.* 272(33): 20357-20363); chorismate synthase (Schmidt et al. (1993) *J. Biol. Chem.* 268(36): 27447-27457); and the light harvesting chlorophyll a/b binding protein (LHBP) (Lamppa et al. (1988) *J. Biol. Chem.* 263: 14996-14999). See also Von Heijne et al. (1991) *Plant Mol. Biol. Rep.* 9: 104-126; Clark et al. (1989) *J. Biol. Chem.* 264: 17544-17550; Della-Cioppa et al. (1987) *Plant Physiol.* 84: 965-968; Romer et al. (1993) *Biochem. Biophys. Res. Commun.* 196: 1414-1421; and Shah et al. (1986) Science 233: 478-481.

Methods for transformation of chloroplasts are known in the art. See, for example, Svab et al. (1990) *Proc. Natl. Acad. Sci. USA* 87: 8526-8530; Svab and Maliga (1993) *Proc. Natl. Acad. Sci. USA* 90: 913-917; Svab and Maliga (1993) *EMBO J.* 12: 601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91: 7301-7305.

The polynucleotides of interest to be targeted to the chloroplast may be optimized for expression in the chloroplast to account for differences in codon usage between the plant nucleus and this organelle. In this manner, the polynucleotide of interest may be synthesized using chloroplast-preferred codons. See, for example, U.S. Pat. No. 5,380,831, herein incorporated by reference.

"Gene" refers to a polynucleotide that expresses a specific protein, generally including regulatory sequences preceding (5' non-coding sequences) and following (3' non-coding sequences) the coding sequence (i.e., the portion of the sequence that encodes the specific protein). "Native gene" refers to a gene as found in nature, generally with its own regulatory sequences. A "transgene" is a gene that has been introduced into the genome by a transformation procedure. Accordingly, a "transgenic plant" is a plant that contains a transgene, whether the transgene was introduced into that particular plant by transformation or by breeding; thus, descendants of an originally-transformed plant are encompassed by the definition.

III. Methods of Introducing

The plants of the invention are generated by introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods, virus-mediated methods, and breeding.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell (i.e., monocot or dicot) targeted for transformation. Suitable methods of introducing polypeptides and polynucleotides into plant cells include microinjection (Crossway et al. (1986) *Biotechniques* 4: 320-334), electroporation (Riggs et al. (1986) *Proc. Natl. Acad. Sci. USA* 83: 5602-5606, *Agrobacterium*-mediated transformation (U.S. Pat. No. 5,563,055 and U.S. Pat. No. 5,981,840), direct gene transfer (Paszkowski et al. (1984) *EMBO J.* 3: 2717-2722), and ballistic particle acceleration (see, for example, U.S. Pat. No. 4,945,050; U.S. Pat. No. 5,879,918; U.S. Pat. Nos. 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6: 923-926); and Lec1 transformation (WO 00/28058). Also see Weissinger et al. (1988) *Ann. Rev. Genet.* 22: 421-477; Sanford et al. (1987) *Particulate Science and Technology* 5: 27-37 (onion); Christou et al. (1988) *Plant Physiol.* 87: 671-674 (soybean); McCabe et al. (1988) *Bio/Technology* 6: 923-926 (soybean); Finer and McMullen (1991) In Vitro *Cell Dev. Biol.* 27P: 175-182 (soybean); Singh et al. (1998) *Theor. Appl. Genet.* 96:319-324 (soybean); Datta et al. (1990) *Biotechnology* 8: 736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91: 440-444 (maize); Fromm et al. (1990) *Biotechnology* 8: 833-839 (maize); protocols published electronically by "IP.com" under the permanent publication identifiers IPCOM000033402D, IPCOM000033402D, and IPCOM000033402D and available at the "IP.com" website (cotton); Hooykaas-Van Slogteren et al. (1984) *Nature* (London) 311: 763-764; U.S. Pat. No. 5,736,369 (cereals); Bytebier et al. (1987) *Proc. Natl. Acad. Sci. USA* 84: 5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9: 415-418 and Kaeppler et al. (1992) *Theor. Appl. Genet.* 84: 560-566 (whisker-mediated transformation); D'Halluin et al. (1992) *Plant Cell* 4: 1495-1505 (electroporation); Li et al. (1993) *Plant Cell Reports* 12: 250-255 and Christou and Ford (1995) *Annals of Botany* 75: 407-413 (rice); Osjoda et al. (1996) *Nature Biotechnology* 14: 745-750 (maize via *Agrobacterium tumefaciens*); all of which are herein incorporated by reference.

In specific embodiments, herbicide-tolerance or other desirable sequences can be provided to a plant using a variety of transient transformation methods. Such transient transformation methods include, but are not limited to, the introduction of the polypeptide or variants and fragments thereof directly into the plant or the introduction of a transcript into the plant. Such methods include, for example, microinjection or particle bombardment. See, for example, Crossway et al. (1986) *Mol Gen. Genet.* 202: 179-185; Nomura et al. (1986) *Plant Sci.* 44: 53-58; Hepler et al. (1994) *Proc. Natl. Acad. Sci.* 91: 2176-2180 and Hush et al. (1994) *The Journal of Cell Science* 107: 775-784, all of which are herein incorporated by reference. Alternatively, a herbicide-tolerance polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use particles coated with polyethylimine (PEI; Sigma #P3143).

In other embodiments, polynucleotides may be introduced into plants by contacting plants with a virus or viral nucleic acids. Generally, such methods involve incorporating a nucleotide construct within a viral DNA or RNA molecule. It is recognized that a polypeptide of interest may be initially synthesized as part of a viral polyprotein, which later may be processed by proteolysis in vivo or in vitro to produce the desired recombinant protein. Further, it is recognized that useful promoters may include promoters utilized for transcription by viral RNA polymerases. Methods for introducing polynucleotides into plants and expressing a polypeptide encoded thereby, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5: 209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, a polynucleotide can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5: 81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

In specific embodiments, a polypeptide or the polynucleotide of interest is introduced into the plant cell. Subsequently, a plant cell having the introduced sequence of the invention is selected using methods known to those of skill in the art such as, but not limited to, Southern blot analysis, DNA sequencing, PCR analysis, or phenotypic analysis. A plant or plant part altered or modified by the foregoing embodiments is grown under plant forming conditions for a time sufficient to modulate the concentration and/or activity of polypeptides in the plant. Plant forming conditions are well known in the art and discussed briefly elsewhere herein.

It is also recognized that the level and/or activity of a polypeptide of interest may be modulated by employing a polynucleotide that is not capable of directing, in a transformed plant, the expression of a protein or an RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such nucleotide constructs and methods of use are known in the art. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96: 8774-8778; herein incorporated by reference.

It is therefore recognized that methods of the present invention do not depend on the incorporation of the entire polynucleotide into the genome, only that the plant or cell thereof is altered as a result of the introduction of the polynucleotide into a cell. In one embodiment of the invention, the genome may be altered following the introduction of the polynucleotide into a cell. For example, the polynucleotide, or any part thereof, may incorporate into the genome of the plant. Alterations to the genome of the present invention include, but are not limited to, additions, deletions, and substitutions of nucleotides into the genome. While the methods of the present invention do not depend on additions, deletions, and substitutions of any particular number of nucleotides, it is recognized that such additions, deletions, or substitutions comprises at least one nucleotide.

Plants of the invention may be produced by any suitable method, including breeding. Plant breeding can be used to introduce desired characteristics (e.g., a stably incorporated transgene or a genetic variant or genetic alteration of interest) into a particular plant line of interest, and can be performed in any of several different ways. Pedigree breeding starts with the crossing of two genotypes, such as an elite line of interest and one other elite inbred line having one or more desirable characteristics (i.e., having stably incorporated a polynucleotide of interest, having a modulated activity and/or level of the polypeptide of interest, etc.) which complements the elite plant line of interest. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection is practiced: F1→F2; F2→F3; F3→F4; F4→F$_5$, etc. After a sufficient amount of inbreeding, successive filial generations will serve to increase seed of the developed inbred. In specific embodiments, the inbred line comprises homozygous alleles at about 95% or more of its loci. Various techniques known in the art can be used to facilitate and accelerate the breeding (e.g., backcrossing) process, including, for example, the use of a greenhouse or growth chamber with accelerated day/night cycles, the analysis of molecular markers to identify desirable progeny, and the like.

In addition to being used to create a backcross conversion, backcrossing can also be used in combination with pedigree breeding to modify an elite line of interest and a hybrid that is made using the modified elite line. As discussed previously, backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2.

Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, an embodiment of this invention is a method of making a backcross conversion of an inbred line of interest comprising the steps of crossing a plant from the inbred line of interest with a donor plant comprising at least one mutant gene or transgene conferring a desired trait (e.g., herbicide tolerance), selecting an F1 progeny plant comprising the mutant gene or transgene conferring the desired trait, and backcrossing the selected F1 progeny plant to a plant of the inbred line of interest. This method may further comprise the step of obtaining a molecular marker profile of the inbred line of interest and using the molecular marker profile to select for a progeny plant with the desired trait and the molecular marker profile of the inbred line of interest. In the same manner, this method may be used to produce an F1 hybrid seed by adding a final step of crossing the desired trait conversion of the inbred line of interest with a different plant to make F1 hybrid seed comprising a mutant gene or transgene conferring the desired trait.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross-pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation breeding is one of many methods that could be used to introduce new traits into an elite line. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation such as X-rays, Gamma rays (e.g., cobalt 60 or cesium 137), neutrons, (product of nuclear fission of uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in "Principals of Cultivar Development" Fehr, 1993 Macmillan Publishing Company the disclosure of which is incorporated herein by reference. In addition, mutations created in other lines may be used to produce a backcross conversion of elite lines that comprises such mutations.

IV. Methods of Modulating Expression

In some embodiments, the activity and/or level of the polypeptide is modulated (i.e., increased or decreased). An increase in the level and/or activity of the polypeptide can be achieved by providing the polypeptide to the plant. As discussed elsewhere herein, many methods are known the art for providing a polypeptide to a plant including, but not limited to, direct introduction of the polypeptide into the plant, introducing into the plant (transiently or stably) a polynucleotide construct encoding a polypeptide having the desired activity. It is also recognized that the methods of the invention may employ a polynucleotide that is not capable of directing, in the transformed plant, the expression of a protein or an RNA. Thus, the level and/or activity of a polypeptide may be modulated by altering the gene encoding the polypeptide or its promoter. See, e.g., Kmiec, U.S. Pat. No. 5,565,350; Zarling et al., PCT/US93/03868. Therefore mutagenized plants that carry mutations in genes, where the mutations increase expression of the gene or increase the activity of the encoded polypeptide are provided.

In other embodiments, the activity and/or level of a polypeptide is reduced or eliminated by introducing into a plant a polynucleotide that inhibits the level or activity of the polypeptide. The polynucleotide may inhibit the expression of the polypeptide directly, by preventing translation of the corresponding messenger RNA, or indirectly, by encoding a polypeptide that inhibits the transcription or translation of a gene encoding the protein. Methods for inhibiting or eliminating the expression of a gene in a plant are well known in the art, and any such method may be used in the present invention to inhibit the expression of a gene in a plant. In other embodiments of the invention, the activity of a polypeptide is reduced or eliminated by transforming a plant cell with a sequence encoding a polypeptide that inhibits the activity of the polypeptide. In other embodiments, the activity of a polypeptide may be reduced or eliminated by disrupting the gene encoding the polypeptide. The invention encompasses mutagenized plants that carry mutations in genes of interest, where the mutations reduce expression of the gene or inhibit the activity of the encoded polypeptide.

Reduction of the activity of specific genes (also known as gene silencing or gene suppression) is desirable for several aspects of genetic engineering in plants. Many techniques for gene silencing are well known to one of skill in the art, including, but not limited to, antisense technology (see, e.g., Sheehy et al. (1988) *Proc. Natl. Acad. Sci. USA* 85: 8805-8809; and U.S. Pat. Nos. 5,107,065; 5,453,566; and 5,759,829); cosuppression (e.g., Taylor (1997) *Plant Cell* 9: 1245; Jorgensen (1990) *Trends Biotech.* 8(12): 340-344; Flavell (1994) *Proc. Natl. Acad. Sci. USA* 91: 3490-3496; Finnegan et al. (1994) *Bio/Technology* 12: 883-888; and Neuhuber et al. (1994) *Mol. Gen. Genet.* 244: 230-241); RNA interference (Napoli et al. (1990) *Plant Cell* 2: 279-289; U.S. Pat. No. 5,034,323; Sharp (1999) *Genes Dev.* 13: 139-141; Zamore et al. (2000) *Cell* 101: 25-33; and Montgomery et al. (1998) *Proc. Natl. Acad. Sci. USA* 95: 15502-15507), virus-induced gene silencing (Burton et al. (2000) *Plant Cell* 12: 691-705; and Baulcombe (1999) *Curr. Op. Plant Bio.* 2: 109-113); target-RNA-specific ribozymes (Haseloff et al. (1988) *Nature* 334: 585-591); hairpin structures (Smith et al. (2000) *Nature* 407: 319-320; WO 99/53050; WO 02/00904; WO 98/53083; Chuang and Meyerowitz (2000) *Proc. Natl. Acad. Sci. USA* 97: 4985-4990; Stoutjesdijk et al. (2002) *Plant Physiol.* 129: 1723-1731; Waterhouse and Helliwell (2003) *Nat. Rev. Genet.* 4: 29-38; Pandolfini et al. *BMC Biotechnology* 3: 7, U.S. Patent Publication No. 20030175965; Panstruga et al. (2003) *Mol. Biol. Rep.* 30: 135-140; Wesley et al. (2001) *Plant J.* 27: 581-590; Wang and Waterhouse (2001) *Curr. Opin. Plant Biol.* 5: 146-150; U.S. Patent Publication No. 20030180945; and WO 02/00904, all of which are herein incorporated by reference); ribozymes (Steinecke et al. (1992) *EMBO J.* 11: 1525; and Perriman et al. (1993) *Antisense Res. Dev.* 3: 253); oligonucleotide-mediated targeted modification (e.g., WO 03/076574 and WO 99/25853); Zn-finger targeted molecules (e.g., WO 01/52620; WO 03/048345; and WO 00/42219); transposon tagging (Maes et al. (1999) *Trends Plant Sci.* 4: 90-96; Dharmapuri and Sonti (1999) *FEMS Microbiol. Lett.* 179: 53-59; Meissner et al. (2000) *Plant J.* 22: 265-274; Phogat et al. (2000) *J. Biosci.* 25: 57-63; Walbot (2000) *Curr. Opin. Plant Biol.* 2: 103-107; Gai et al. (2000) *Nucleic Acids Res.* 28: 94-96; Fitzmaurice et al. (1999) *Genetics* 153: 1919-1928; Bensen et al. (1995) *Plant Cell* 7: 75-84; Mena et al. (1996) *Science* 274: 1537-1540; and U.S. Pat. No. 5,962,764); each of which is herein incorporated by reference; and other methods or combinations of the above methods known to those of skill in the art.

It is recognized that antisense constructions complementary to at least a portion of the messenger RNA (mRNA) for a polynucleotide of interest can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having at least 70%, optimally 80%, more optimally 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, 300, 400, 450, 500, 550, or greater may be used.

Polynucleotides may also be used in the sense orientation to suppress the expression of endogenous genes in plants. Methods for suppressing gene expression in plants using polynucleotides in the sense orientation are known in the art. The methods generally involve transforming plants with a DNA construct comprising a promoter that drives expression in a plant operably linked to at least a portion of a polynucleotide that corresponds to the transcript of the endogenous gene. Typically, such a nucleotide sequence has substantial sequence identity to the sequence of the transcript of the endogenous gene, generally greater than about 65%, 85%, or 95% sequence identity. See, U.S. Pat. Nos. 5,283,184 and 5,034,323; herein incorporated by reference. Thus, many methods may be used to reduce or eliminate the activity of a polypeptide. More than one method may be used to reduce the activity of a single polypeptide. In addition, combinations of methods may be employed to reduce or eliminate the activity of a polypeptide.

In one embodiment, the expression level of a polypeptide may be measured directly, for example, by assaying for the level of the polynucleotide or polypeptide or a known metabolite in the plant (e.g., by assaying for the level of N-acetylglyphosate ("NAG") in a plant containing a GAT gene), or indirectly, for example, by evaluating the plant containing it for the trait to be conferred by the polypeptide, e.g., herbicide resistance.

V. Methods of Controlling Weeds

Methods are provided for controlling weeds in an area of cultivation, preventing the development or the appearance of herbicide resistant weeds in an area of cultivation, producing a crop, and increasing crop safety. The term "controlling," and derivations thereof, for example, as in "controlling weeds" refers to one or more of inhibiting the growth, germination, reproduction, and/or proliferation of; and/or killing, removing, destroying, or otherwise diminishing the occurrence and/or activity of a weed.

The glyphosate/ALS inhibitor plants of the invention display a modified tolerance to herbicides and therefore allow for the application of one or more herbicides at rates that would significantly damage control plants and further allow for the application of combinations of herbicides at lower concentrations than normally applied which still continue to selectively control weeds. In addition, the glyphosate/ALS inhibitor-tolerant plants of the invention can be used in combination with herbicide blends technology and thereby make the application of chemical pesticides more convenient, economical, and effective for the producer.

The methods of the invention comprise planting the area of cultivation with glyphosate/ALS inhibitor-tolerant crop seeds or plants of the invention, and in specific embodiments, applying to any crop, crop part, weed or area of cultivation thereof an effective amount of a herbicide of interest. It is recognized that the herbicide can be applied before or after the crop is planted in the area of cultivation. Such herbicide applications can include an application of glyphosate, an ALS inhibitor chemistry, or any combination thereof. In specific embodiments, a mixture of ALS inhibitor chemistry in combination with glyphosate is applied to the glyphosate/ALS inhibitor-tolerant plant, wherein the effective concentration of at least two of the ALS inhibitor chemistries would significantly damage an appropriate control plant. In one non-limiting embodiment, the herbicide comprises at least one of a sulfonylaminocarbonyltriazolinone; a triazolopyrimidine; a pyrimidinyl(thio)benzoate; an imidazolinone; a triazine; and/or a phosphinic acid.

In another non-limiting embodiment, the combination of herbicides comprises glyphosate, imazapyr, chlorimuron-ethyl, quizalofop, and fomesafen, wherein said effective amount is tolerated by the crop and controls weeds. As disclosed elsewhere herein, any effective amount of these herbicides can be applied. In specific embodiments, this combination of herbicides comprises an effective amount of glyphosate comprising about 1110 to about 1130 g ai/hectare; an effective amount of imazapyr comprising about 7.5 to about 27.5 g ai/hectare; an effective amount of chlorimuron-ethyl comprising about 7.5 to about 27.5 g ai/hectare; an effective amount of quizalofop comprising about 50 to about 70 g ai/hectare; and, an effective amount of fomesafen comprising about 240 to about 260 g ai/hectare.

In other embodiments, at least a combination of two herbicides are applied, wherein the combination does not include glyphosate. In other embodiments, at least one ALS inhibitor and glyphosate is applied to the plant. More details regarding the various herbicide combinations that can be employed in the methods of the invention are discussed elsewhere herein.

In one embodiment, the method of controlling weeds comprises planting the area with a glyphosate/ALS inhibitor-tolerant crop seeds or plant and applying to the crop, crop part, seed of said crop or the area under cultivation, an effective amount of a herbicide, wherein said effective amount comprises i) an amount that is not tolerated by a first control crop when applied to the first control crop, crop part, seed or the area of cultivation, wherein said first control crop expresses a first polynucleotide that confers tolerance to glyphosate and does not express a second polynucleotide that encodes an ALS inhibitor-tolerant polypeptide;

ii) an amount that is not tolerated by a second control crop when applied to the second crop, crop part, seed or the area of cultivation, wherein said second control crop expresses the second polynucleotide and does not express the first polynucleotide; and, iii) an amount that is tolerated when applied to the glyphosate/ALS inhibitor-tolerant crop, crop part, seed, or the area of cultivation thereof. The herbicide can comprise a combination of herbicides that either includes or does not include glyphosate. In specific embodiments, the combination of herbicides comprises ALS inhibitor chemistries as discussed in further detail below.

In another embodiment, the method of controlling weeds comprises planting the area with a glyphosate/ALS inhibitor-tolerant crop seeds or plant and applying to the crop, crop part, seed of said crop or the area under cultivation, an effective amount of a herbicide, wherein said effective amount comprises a level that is above the recommended label use rate for the crop, wherein said effective amount is tolerated when applied to the glyphosate/ALS inhibitor-tolerant crop, crop part, seed, or the area of cultivation thereof. The herbicide applied can comprise a combination of herbicides that either includes or does not include glyphosate. In specific embodiments, the combination of herbicides comprises at least one ALS inhibitor chemistries as discussed in further detail below. Further herbicides and combinations thereof that can be employed in the various methods of the invention are discussed in further detail below.

In another non-limiting embodiment, the herbicide applied in any method disclosed herein does not comprise glyphosate, chlorimuron-methyl, rimsulfuron, tribenuron-methyl or thifensufuron-methyl.

a. Types of Herbicides

Any herbicide can be applied to the glyphosate/ALS inhibitor-tolerant crop, crop part, or the area of cultivation containing said crop plant. Classifications of herbicides (i.e., the grouping of herbicides into classes and subclasses) is well-known in the art and includes classifications by HRAC (Herbicide Resistance Action Committee) and WSSA (the Weed Science Society of America) (see also, Retzinger and Mallory-Smith (1997) *Weed Technology* 11: 384-393). An abbreviated version of the HRAC classification (with notes regarding the corresponding WSSA group) is set forth below in Table 1.

Herbicides can be classified by their mode of action and/or site of action and can also be classified by the time at which they are applied (e.g., preemergent or postemergent), by the method of application (e.g., foliar application or soil application), or by how they are taken up by or affect the plant. For example, thifensulfuron-methyl and tribenuron-methyl are applied to the foliage of a crop (e.g., maize) and are generally metabolized there, while rimsulfuron and chlorimuron-ethyl are generally taken up through both the roots and foliage of a plant. "Mode of action" generally refers to the metabolic or physiological process within the plant that the herbicide inhibits or otherwise impairs, whereas "site of action" generally refers to the physical location or biochemical site within the plant where the herbicide acts or directly interacts. Herbicides can be classified in various ways, including by mode of action and/or site of action (see, e.g., Table 1).

Often, a herbicide-tolerance gene that confers tolerance to a particular herbicide or other chemical on a plant expressing it will also confer tolerance to other herbicides or chemicals in the same class or subclass, for example, a class or subclass set forth in Table 1. Thus, in some embodiments of the invention, a transgenic plant of the invention is tolerant to more than one herbicide or chemical in the same class or subclass, such as, for example, an inhibitor of PPO, a sulfonylurea, or a synthetic auxin.

Typically, the plants of the present invention can tolerate treatment with different types of herbicides (i.e., herbicides having different modes of action and/or different sites of action) as well as with higher amounts of herbicides than previously known plants, thereby permitting improved weed management strategies that are recommended in order to reduce the incidence and prevalence of herbicide-tolerant weeds. Specific herbicide combinations can be employed to effectively control weeds.

The invention thereby provides a transgenic crop plant which can be selected for use in crop production based on the prevalence of herbicide-tolerant weed species in the area where the transgenic crop is to be grown. Methods are known in the art for assessing the herbicide tolerance of various weed species. Weed management techniques are also known in the art, such as for example, crop rotation using a crop that is tolerant to a herbicide to which the local weed species are not tolerant. A number of entities monitor and publicly report the incidence and characteristics of herbicide-tolerant weeds, including the Herbicide Resistance Action Committee (HRAC), the Weed Science Society of America, and various state agencies (see, e.g., see, for example, herbicide tolerance scores for various broadleaf weeds from the 2004 Illinois Agricultural Pest Management Handbook), and one of skill in the art would be able to use this information to determine which crop and herbicide combinations should be used in a particular location.

These entities also publish advice and guidelines for preventing the development and/or appearance of and controlling the spread of herbicide tolerant weeds (see, e.g., Owen and Hartzler (2004), 2005 *Herbicide Manual for Agricultural Professionals*, Pub. WC 92 Revised (Iowa State University Extension, Iowa State University of Science and Technology, Ames, Iowa); *Weed Control for Corn, Soybeans, and Sorghum*, Chapter 2 of "2004 Illinois Agricultural Pest Management Handbook" (University of Illinois Extension, University of Illinois at Urbana-Champaign, Ill.)); *Weed Control Guide for Field Crops*, MSU Extension Bulletin E434 (Michigan State University, East Lansing, Mich.)).

TABLE 1

Abbreviated version of HRAC Herbicide Classification

I. ALS Inhibitors (WSSA Group 2)
   A. Sulfonylureas
      1. Azimsulfuron
      2. Chlorimuron-ethyl
      3. Metsulfuron-methyl
      4. Nicosulfuron
      5. Rimsulfuron
      6. Sulfometuron-methyl
      7. Thifensulfuron-methyl
      8. Tribenuron-methyl
      9. Amidosulfuron
      10. Bensulfuron-methyl
      11. Chlorsulfuron
      12. Cinosulfuron

TABLE 1-continued

Abbreviated version of HRAC Herbicide Classification

13. Cyclosulfamuron
    14. Ethametsulfuron-methyl
    15. Ethoxysulfuron
    16. Flazasulfuron
    17. Flupyrsulfuron-methyl
    18. Foramsulfuron
    19. Imazosulfuron
    20. Iodosulfuron-methyl
    21. Mesosulfuron-methyl
    22. Oxasulfuron
    23. Primisulfuron-methyl
    24. Prosulfuron
    25. Pyrazosulfuron-ethyl
    26. Sulfosulfuron
    27. Triasulfuron
    28. Trifloxysulfuron
    29. Triflusulfuron-methyl
    30. Tritosulfuron
    31. Halosulfuron-methyl
    32. Flucetosulfuron
  B. Sulfonylaminocarbonyltriazolinones
    1. Flucarbazone
    2. Procarbazone
  C. Triazolopyrimidines
    1. Cloransulam-methyl
    2. Flumetsulam
    3. Diclosulam
    4. Florasulam
    5. Metosulam
    6. Penoxsulam
    7. Pyroxsulam
  D. Pyrimidinyloxy(thio)benzoates
    1. Bispyribac
    2. Pyriftalid
    3. Pyribenzoxim
    4. Pyrithiobac
    5. Pyriminobac-methyl
  E. Imidazolinones
    1. Imazapyr
    2. Imazethapyr
    3. Imazaquin
    4. Imazapic
    5. Imazamethabenz-methyl
    6. Imazamox
II. Other Herbicides - Active Ingredients/
Additional Modes of Action
  A. Inhibitors of Acetyl CoA carboxylase
    (ACCase) (WSSA Group 1)
    1. Aryloxyphenoxypropionates ('FOPs')
      a. Quizalofop-P-ethyl
      b. Diclofop-methyl
      c. Clodinafop-propargyl
      d. Fenoxaprop-P-ethyl
      e. Fluazifop-P-butyl
      f. Propaquizafop
      g. Haloxyfop-P-methyl
      h. Cyhalofop-butyl
      i. Quizalofop-P-ethyl
    2. Cyclohexanediones ('DIMs')
      a. Alloxydim
      b. Butroxydim
      c. Clethodim
      d. Cycloxydim
      e. Sethoxydim
      f. Tepraloxydim
      g. Tralkoxydim
  B. Inhibitors of Photosystem II - HRAC
    Group C1/WSSA Group 5
    1. Triazines
      a. Ametryne
      b. Atrazine
      c. Cyanazine
      d. Desmetryne
      e. Dimethametryne
      f. Prometon
      g. Prometryne
      h. Propazine
      i. Simazine
      j. Simetryne
      k. Terbumeton
      l. Terbuthylazine
      m. Terbutryne
      n. Trietazine
    2. Triazinones
      a. Hexazinone
      b. Metribuzin
      c. Metamitron
    3. Triazolinone
      a. Amicarbazone
    4. Uracils
      a. Bromacil
      b. Lenacil
      c. Terbacil
    5. Pyridazinones
      a. Pyrazon
    6. Phenyl carbamates
      a. Desmedipham
      b. Phenmedipham
  C. Inhibitors of Photosystem II - HRAC
    Group C2/WSSA Group 7
    1. Ureas
      a. Fluometuron
      b. Linuron
      c. Chlorobromuron
      d. Chlorotoluron
      e. Chloroxuron
      f. Dimefuron
      g. Diuron
      h. Ethidimuron
      i. Fenuron
      j. Isoproturon
      k. Isouron
      l. Methabenzthiazuron
      m. Metobromuron
      n. Metoxuron
      o. Monolinuron
      p. Neburon
      q. Siduron
      r. Tebuthiuron
    2. Amides
      a. Propanil
      b. Pentanochlor
  D. Inhibitors of Photosystem II - HRAC
    Group C3/WSSA Group 6
    1. Nitriles
      a. Bromofenoxim
      b. Bromoxynil
      c. Ioxynil
    2. Benzothiadiazinone (Bentazon)
      a. Bentazon
    3. Phenylpyridazines
      a. Pyridate
      b. Pyridafol
  E. Photosystem-I-electron diversion
    (Bipyridyliums) (WSSA Group 22)
    1. Diquat
    2. Paraquat
  F. Inhibitors of PPO (protoporphyrinogen
    oxidase) (WSSA Group 14)
    1. Diphenylethers
      a. Acifluorfen-Na
      b. Bifenox
      c. Chlomethoxyfen
      d. Fluoroglycofen-ethyl
      e. Fomesafen
      f. Halosafen
      g. Lactofen
      h. Oxyfluorfen
    2. Phenylpyrazoles
      a. Fluazolate
      b. Pyraflufen-ethyl TABLE 1-continued Abbreviated version of HRAC Herbicide Classification 3. N-phenylphthalimides
  a. Cinidon-ethyl
  b. Flumioxazin
  c. Flumiclorac-pentyl
4. Thiadiazoles
  a. Fluthiacet-methyl
  b. Thidiazimin
5. Oxadiazoles
  a. Oxadiazon
  b. Oxadiargyl
6. Triazolinones
  a. Carfentrazone-ethyl
  b. Sulfentrazone
7. Oxazolidinediones
  a. Pentoxazone
8. Pyrimidindiones
  a. Benzfendizone
  b. Butafenicil
9. Others
  a. Pyrazogyl
  b. Profluazol
G. Bleaching: Inhibition of carotenoid biosynthesis at the phytoene desaturase step (PDS) (WSSA Group 12)
  1. Pyridazinones
    a. Norflurazon
  2. Pyridinecarboxamides
    a. Diflufenican
    b. Picolinafen
  3. Others
    a. Beflubutamid
    b. Fluridone
    c. Flurochloridone
    d. Flurtamone
H. Bleaching: Inhibition of 4-hydroxyphenyl-pyruvate-dioxygenase (4-HPPD) (WSSA Group 28)
  1. Triketones
    a. Mesotrione
    b. Sulcotrione
  2. Isoxazoles
    a. Isoxachlortole
    b. Isoxaflutole
  3. Pyrazoles
    a. Benzofenap
    b. Pyrazoxyfen
    c. Pyrazolynate
  4. Others
    a. Benzobicyclon
I. Bleaching: Inhibition of carotenoid biosynthesis (unknown target) (WSSA Group 11 and 13)
  1. Triazoles (WSSA Group 11)
    a. Amitrole
  2. Isoxazolidinones (WSSA Group 13)
    a. Clomazone
  3. Ureas
    a. Fluometuron
  3. Diphenylether
    a. Aclonifen
J. Inhibition of EPSP Synthase
  1. Glycines (WSSA Group 9)
    a. Glyphosate
    b. Sulfosate
K. Inhibition of glutamine synthetase
  1. Phosphinic Acids
    a. Glufosinate-ammonium
    b. Bialaphos
L. Inhibition of DHP (dihydropteroate) synthase (WSSA Group 18)
  1. Carbamates
    a. Asulam
M. Microtubule Assembly Inhibition (WSSA Group 3)
  1. Dinitroanilines
    a. Benfluralin
    b. Butralin c. Dinitramine
  d. Ethalfluralin
  e. Oryzalin
  f. Pendimethalin
  g. Trifluralin
2. Phosphoroamidates
  a. Amiprophos-methyl
  b. Butamiphos
3. Pyridines
  a. Dithiopyr
  b. Thiazopyr
4. Benzamides
  a. Pronamide
  b. Tebutam
5. Benzenedicarboxylic acids
  a. Chlorthal-dimethyl
N. Inhibition of mitosis/microtubule organization WSSA Group 23)
  1. Carbamates
    a. Chlorpropham
    b. Propham
    c. Carbetamide
O. Inhibition of cell division (Inhibition of very long chain fatty acids as proposed mechanism; WSSA Group 15)
  1. Chloroacetamides
    a. Acetochlor
    b. Alachlor
    c. Butachlor
    d. Dimethachlor
    e. Dimethanamid
    f. Metazachlor
    g. Metolachlor
    h. Pethoxamid
    i. Pretilachlor
    j. Propachlor
    k. Propisochlor
    l. Thenylchlor
  2. Acetamides
    a. Diphenamid
    b. Napropamide
    c. Naproanilide
  3. Oxyacetamides
    a. Flufenacet
    b. Mefenacet
  4. Tetrazolinones
    a. Fentrazamide
  5. Others
    a. Anilofos
    b. Cafenstrole
    c. Indanofan
    d. Piperophos
P. Inhibition of cell wall (cellulose) synthesis
  1. Nitriles (WSSA Group 20)
    a. Dichlobenil
    b. Chlorthiamid
  2. Benzamides (isoxaben (WSSA Group 21))
    a. Isoxaben
  3. Triazolocarboxamides (flupoxam)
    a. Flupoxam
Q. Uncoupling (membrane disruption): (WSSA Group 24)
  1. Dinitrophenols
    a. DNOC
    b. Dinoseb
    c. Dinoterb
R. Inhibition of Lipid Synthesis by other than ACC inhibition
  1. Thiocarbamates (WSSA Group 8)
    a. Butylate
    b. Cycloate
    c. Dimepiperate
    d. EPTC
    e. Esprocarb
    f. Molinate

TABLE 1-continued

Abbreviated version of HRAC Herbicide Classification

- g. Orbencarb
- h. Pebulate
- i. Prosulfocarb
- j. Benthiocarb
- k. Tiocarbazil
- l. Triallate
- m. Vernolate
2. Phosphorodithioates
    - a. Bensulide
3. Benzofurans
    - a. Benfuresate
    - b. Ethofumesate
4. Halogenated alkanoic acids (WSSA Group 26)
    - a. TCA
    - b. Dalapon
    - c. Flupropanate
S. Synthetic auxins (IAA-like) (WSSA Group 4)
  1. Phenoxycarboxylic acids
      - a. Clomeprop
      - b. 2,4-D
      - c. Mecoprop
  2. Benzoic acids
      - a. Dicamba
      - b. Chloramben
      - c. TBA
  3. Pyridine carboxylic acids
      - a. Clopyralid
      - b. Fluroxypyr
      - c. Picloram
      - d. Tricyclopyr
  4. Quinoline carboxylic acids
      - a. Quinclorac
      - b. Quinmerac
  5. Others (benazolin-ethyl)
      - a. Benazolin-ethyl
T. Inhibition of Auxin Transport
  1. Phthalamates; semicarbazones (WSSA Group 19)
      - a. Naptalam
      - b. Diflufenzopyr-Na
U. Other Mechanism of Action
  1. Arylaminopropionic acids
      - a. Flamprop-M-methyl/-isopropyl
  2. Pyrazolium
      - a. Difenzoquat
  3. Organoarsenicals
      - a. DSMA
      - b. MSMA
  4. Others
      - a. Bromobutide
      - b. Cinmethylin
      - c. Cumyluron
      - d. Dazomet
      - e. Daimuron-methyl
      - f. Dimuron
      - g. Etobenzanid

TABLE 1-continued

Abbreviated version of HRAC Herbicide Classification

- h. Fosamine
- i. Metam
- j. Oxaziclomefone
- k. Oleic acid
- l. Pelargonic acid
- m. Pyributicarb In one embodiment, one ALS inhibitor or at least two ALS inhibitors are applied to the glyphosate/ALS inhibitor-tolerant crop or area of cultivation. In one non-limiting embodiment, the combination of ALS herbicides does not include glyphosate. The ALS inhibitor can be applied at any effective rate that selectively controls weeds and does not significantly damage the crop. In specific embodiments, at least one ALS inhibitor is applied at a level that would significantly damage an appropriate control plant. In other embodiments, at least one ALS inhibitor is applied above the recommended label use rate for the crop. In still other embodiments, a mixture of ALS inhibitors is applied at a lower rate than the recommended use rate and weeds continue to be selectively controlled. Herbicides that inhibit acetolactate synthase (also known as acetohydroxy acid synthase) and are therefore useful in the methods of the invention include sulfonylureas as listed in Table 1, including agriculturally suitable salts (e.g., sodium salts) thereof; sulfonylaminocarbonyltriazolinones as listed in Table 1, including agriculturally suitable salts (e.g., sodium salts) thereof; triazolopyrimidines as listed in Table 1, including agriculturally suitable salts (e.g., sodium salts) thereof; pyrimidinyloxy(thio)benzoates as listed in Table 1, including agriculturally suitable salts (e.g., sodium salts) thereof; and imidazolinones as listed in Table 1, including agriculturally suitable salts (e.g., sodium salts) there. In some embodiments, methods of the invention comprise the use of a sulfonylurea which is not chlorimuron-ethyl, chlorsulfuron, rimsulfuron, thifensulfuron-methyl, or tribenuron-methyl.

In still further methods, glyphosate, in combination with another herbicide of interest, can be applied to the glyphosate/ALS inhibitor-tolerant plants or their area of cultivation. Non-limiting examples of glyphosate formations are set forth in Table 2. In specific embodiments, the glyphosate is in the form of a salt, such as, ammonium, isopropylammonium, potassium, sodium (including sesquisodium) or trimesium (alternatively named sulfosate). In still further embodiments, a mixture of a synergistically effective amount of a combination of glyphosate and an ALS inhibitor (such as a sulfonylurea) is applied to the glyphosate/ALS inhibitor-tolerant plants or their area of cultivation.

TABLE 2

Glyphosate formulations comparisons.

| Herbicide by Registered Trademark | Manufacturer | Salt | Active ingredient per gallon | Acid equivalent per gallon | Apply: fl oz/ acre | Acid equivalent per acre |
|---|---|---|---|---|---|---|
| Roundup Original | Monsanto | Isopropylamine | 4 | 3 | 32 | 0.750 |
| Roundup Original II | Monsanto | Isopropylamine | 4 | 3 | 32 | 0.750 |
| Roundup Original MAX | Monsanto | Potassium | 5.5 | 4.5 | 22 | 0.773 |
| Roundup UltraMax | Monsanto | Isopropylamine | 5 | 3.68 | 26 | 0.748 |
| Roundup UltraMax II | Monsanto | Potassium | 5.5 | 4.5 | 22 | 0.773 |
| Roundup Weathermax | Monsanto | Potassium | 5.5 | 4.5 | 22 | 0.773 |

TABLE 2-continued

Glyphosate formulations comparisons.

| Herbicide by Registered Trademark | Manufacturer | Salt | Active ingredient per gallon | Acid equivalent per gallon | Apply: fl oz/ acre | Acid equivalent per acre |
|---|---|---|---|---|---|---|
| Touchdown | Syngenta | Diammomium | 3.7 | 3 | 32 | 0.750 |
| Touchdown HiTech | Syngenta | Potassium | 6.16 | 5 | 20 | 0.781 |
| Touchdown Total | Syngenta | Potassium | 5.14 | 4.17 | 24 | 0.782 |
| Durango | Dow AgroSciences | Isopropylamine | 5.4 | 4 | 24 | 0.750 |
| Glyphomax | Dow AgroSciences | Isopropylamine | 4 | 3 | 32 | 0.750 |
| Glyphomax Plus | Dow AgroSciences | Isopropylamine | 4 | 3 | 32 | 0.750 |
| Glyphomax XRT | Dow AgroSciences | Isopropylamine | 4 | 3 | 32 | 0.750 |
| Gly Star Plus | Albaugh/Agri Star | Isopropylamine | 4 | 3 | 32 | 0.750 |
| Gly Star 5 | Albaugh/Agri Star | Isopropylamine | 5.4 | 4 | 24 | 0.750 |
| Gly Star Original | Albaugh/Agri Star | Isopropylamine | 4 | 3 | 32 | 0.750 |
| Gly-Flo | Micro Flo | Isopropylamine | 4 | 3 | 32 | 0.750 |
| Credit | Nufarm | Isopropylamine | 4 | 3 | 32 | 0.750 |
| Credit Extra | Nufarm | Isopropylamine | 4 | 3 | 32 | 0.750 |
| Credit Duo | Nufarm | Isopro + monoamm. | 4 | 3 | 32 | 0.750 |
| Credit Duo Extra | Nufarm | Isopro + monoamm. | 4 | 3 | 32 | 0.750 |
| Extra Credit 5 | Nufarm | Isopropylamine | 5 | 3.68 | 26 | 0.748 |
| Cornerstone | Agriliance | Isopropylamine | 4 | 3 | 32 | 0.750 |
| Cornerstone Plus | Agriliance | Isopropylamine | 4 | 3 | 32 | 0.750 |
| Glyfos | Cheminova | Isopropylamine | 4 | 3 | 32 | 0.750 |
| Glyfos X-TRA | Cheminova | Isopropylamine | 4 | 3 | 32 | 0.750 |
| Rattler | Helena | Isopropylamine | 4 | 3 | 32 | 0.750 |
| Rattler Plus | Helena | Isopropylamine | 4 | 3 | 32 | 0.750 |
| Mirage | UAP | Isopropylamine | 4 | 3 | 32 | 0.750 |
| Mirage Plus | UAP | Isopropylamine | 4 | 3 | 32 | 0.750 |
| Glyphosate 41% | Helm Agro USA | Isopropylamine | 4 | 3 | 32 | 0.750 |
| Buccaneer | Tenkoz | Isopropylamine | 4 | 3 | 32 | 0.750 |
| Buccaneer Plus | Tenkoz | Isopropylamine | 4 | 3 | 32 | 0.750 |
| Honcho | Monsanto | Isopropylamine | 4 | 3 | 32 | 0.750 |
| Honcho Plus | Monsanto | Isopropylamine | 4 | 3 | 32 | 0.750 |
| Gly-4 | Univ. Crop Prot. Alli. | Isopropylamine | 4 | 3 | 32 | 0.750 |
| Gly-4 Plus | Univ. Crop Prot. Alli. | Isopropylamine | 4 | 3 | 32 | 0.750 |
| ClearOut 41 | Chemical Products Tech. | Isopropylamine | 4 | 3 | 32 | 0.750 |
| ClearOut 41 Plus | Chemical Products Tech. | Isopropylamine | 4 | 3 | 32 | 0.750 |
| Spitfire | Control Soultions | Isopropylamine | 4 | 3 | 32 | 0.750 |
| Spitfire Plus | Control Soultions | Isopropylamine | 4 | 3 | 32 | 0.750 |
| Glyphosate 4 | FarmerSaver.com | Isopropylamine | 4 | 3 | 32 | 0.750 |
| FS Glyphosate Plus | Growmark | Isopropylamine | 4 | 3 | 32 | 0.750 |
| Glyphosate Original | Griffin, LLC. | Isopropylamine | 4 | 3 | 32 | 0.750 |

Thus, in some embodiments, a transgenic plant of the invention is used in a method of growing a glyphosate/ALS inhibitor-tolerant crop by the application of herbicides to which the plant is tolerant. In this manner, treatment with a combination of one of more herbicides which include, but are not limited to: acetochlor, acifluorfen and its sodium salt, aclonifen, acrolein (2-propenal), alachlor, alloxydim, ametryn, amicarbazone, amidosulfuron, aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clethodim, clodinafop-propargyl, clomazone, clomeprop, clopyralid, clopyralid-olamine, cloransulam-methyl, CUH-35 (2-methoxyethyl 2-[[[4-chloro-2-fluoro-5-[(1-methyl-2-propynyl)oxy]phenyl](3-fluoro-benzoyl)amino] carbonyl]-1-cyclohexene-1-carboxylate), cumyluron, cyanazine, cycloate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethofumesate, ethoxyfen, ethoxysulfuron, etobenzanid, fenoxaprop-ethyl, fenoxaprop-P-ethyl, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glyphosate and its salts such as ammonium, isopropylammonium, potassium, sodium (including sesquisodium) and trimesium (alternatively named sulfosate), halosulfuron-methyl, haloxyfop-etotyl, haloxyfop-methyl, hexazinone, HOK-201 (N-(2,4-difluorophenyl)-1,5-dihydro-N-(1-methylethyl)-5-oxo-1-[(tetrahydro-2H-pyran-2-yl)methyl]-4H-1,2,4-triazole-4-carboxamide), imazamethabenz-methyl, imazamox, imazapic, imazapyr, imazaquin, imazaquin-ammonium, imazethapyr, imazethapyr-ammonium, imazosulfuron, indanofan, iodosulfuron-methyl, ioxynil, ioxynil octanoate, ioxynil-sodium, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, methabenzthiazuron, methylarsonic acid and its calcium, monoammonium, monosodium and disodium salts, methyldymron, metobenzuron, metobromuron, metolachlor, S-metholachlor, metosulam, metoxuron, metribuzin, metsulfuron-methyl, molinate, monolinuron, naproanilide, napropamide, naptalam, neburon, nicosulfuron, norflurazon, orbencarb, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxyamid, phenmedipham, picloram, picloram-potassium, picolinafen, pinoxaden, piperofos, pretilachlor, primisulfuron-methyl, prodiamine, profoxydim, prometon, prometryn, propachlor, propanil, propaquizafop, propazine, propham, propisochlor, propoxycarbazone, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxsulam, quinclorac, quinmerac, quinoclamine, quizalofop-ethyl, quizalofop-P-ethyl, quizalofop-P-tefuryl, rimsulfuron, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terburneton, terbuthylazine, terbutryn, thenylchlor, thiazopyr, thiencarbazone, thifensulfuron-methyl, thiobencarb, tiocarbazil, topramezone, tralkoxydim, tri-allate, triasulfuron, triaziflam, tribenuron-methyl, triclopyr, triclopyr-butotyl, triclopyr-triethylammonium, tridiphane, trietazine, trifloxysulfuron, trifluralin, triflusulfuron-methyl, tritosulfuron and vemolate.

Other suitable herbicides and agricultural chemicals are known in the art, such as, for example, those described in WO 2005/041654. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub. Combinations of various herbicides can result in a greater-than-additive (i.e., synergistic) effect on weeds and/or a less-than-additive effect (i.e. safening) on crops or other desirable plants. In certain instances, combinations of glyphosate with other herbicides having a similar spectrum of control but a different mode of action will be particularly advantageous for preventing the development of resistant weeds. Herbicidally effective amounts of any particular herbicide can be easily determined by one skilled in the art through simple experimentation.

Herbicides may be classified into groups and/or subgroups as described herein above with reference to their mode of action, or they may be classified into groups and/or subgroups in accordance with their chemical structure.

Sulfonamide herbicides have as an essential molecular structure feature a sulfonamide moiety (—S(O)$_2$NH—). As referred to herein, sulfonamide herbicides particularly comprise sulfonylurea herbicides, sulfonylaminocarbonyltriazolinone herbicides and triazolopyrimidine herbicides. In sulfonylurea herbicides the sulfonamide moiety is a component in a sulfonylurea bridge (—S(O)$_2$NHC(O)NH(R)—). In sulfonylurea herbicides the sulfonyl end of the sulfonylurea bridge is connected either directly or by way of an oxygen atom or an optionally substituted amino or methylene group to a typically substituted cyclic or acyclic group. At the opposite end of the sulfonylurea bridge, the amino group, which may have a substituent such as methyl (R being CH$_3$) instead of hydrogen, is connected to a heterocyclic group, typically a symmetric pyrimidine or triazine ring, having one or two substituents such as methyl, ethyl, trifluoromethyl, methoxy, ethoxy, methylamino, dimethylamino, ethylamino and the halogens. In sulfonylaminocarbonyltriazolinone herbicides, the sulfonamide moiety is a component is a sulfonylaminocarbonyl bridge (—S(O)$_2$NHC(O)—). In sulfonylaminocarbonyltriazolinone herbicides the sulfonyl end of the sulfonylaminocarbonyl bridge is typically connected to substituted phenyl ring. At the opposite end of the sulfonylaminocarbonyl bridge, the carbonyl is connected to the 1-position of a triazolinone ring, which is typically substituted with groups such as alkyl and alkoxy. In triazolopyrimidine herbicides the sulfonyl end of the sulfonamide moiety is connected to the 2-position of a substituted [1,2,4]triazolopyrimidine ring system and the amino end of the sulfonamide moiety is connected to a substituted aryl, typically phenyl, group or alternatively the amino end of the sulfonamide moiety is connected to the 2-position of a substituted [1,2,4]triazolopyrimidine ring system and the sulfonyl end of the sulfonamide moiety is connected to a substituted aryl, typically pyridinyl, group.

Representative of the sulfonylurea herbicides useful in the present invention are those of the formula:

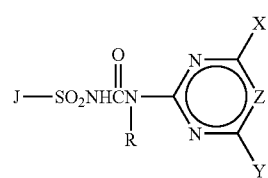

wherein:

J is selected from the group consisting of

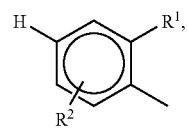

J-1

-continued

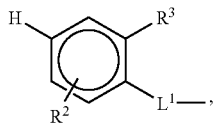
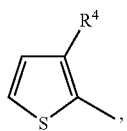
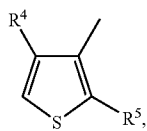
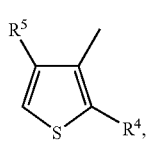
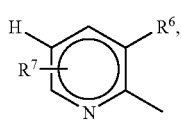
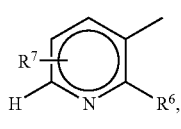
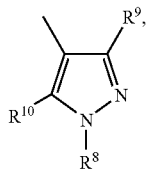
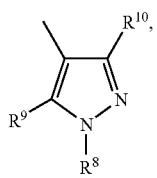
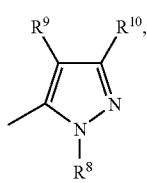
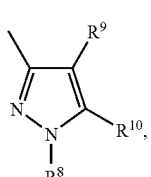

J-2
J-3
J-4
J-5
J-6
J-7
J-8
J-9
J-10
J-11

-continued

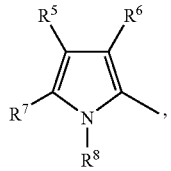
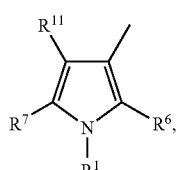

and

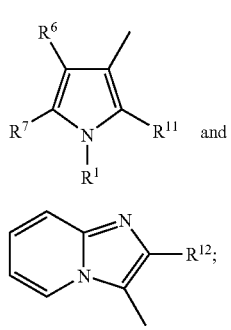
; or

J-12
J-13
J-14
J-15

J is $R^{13}SO_2N(CH_3)$—;

R is H or $CH_3$;

$R^1$ is F, Cl, Br, $NO_2$, $C_1$-$C_4$ alkyl, $C_1$-$C_4$ haloalkyl, $C_3$-$C_4$ cycloalkyl, $C_2$-$C_4$ haloalkenyl, $C_1$-$C_4$ alkoxy, $C_1$-$C_4$ haloalkoxy, $C_2$-$C_4$ alkoxyalkoxy, $CO_2R^{14}$, $C(O)NR^{15}R^{16}$, $SO_2NR^{17}R^{18}$, $S(O)_nR^{19}$, $C(O)R^{20}$, $CH_2CN$ or L;

$R^2$ is H, F, Cl, Br, I, CN, $CH_3$, $OCH_3$, $SCH_3$, $CF_3$ or $OCF_2H$;

$R^3$ is Cl, $NO_2$, $CO_2CH_3$, $CO_2CH_2CH_3$, $C(O)CH_3$, $C(O)CH_2CH_3$, C(O)-cyclopropyl, $SO_2N(CH_3)_2$, $SO_2CH_3$, $SO_2CH_2CH_3$, $OCH_3$ or $OCH_2CH_3$;

$R^4$ is $C_1$-$C_3$ alkyl, $C_1$-$C_2$ haloalkyl, $C_1$-$C_2$ alkoxy, $C_2$-$C_4$ haloalkenyl, F, Cl, Br, $NO_2$, $CO_2R^{14}$, $C(O)NR^{15}R^{16}$, $SO_2NR^{17}R^{18}$, $S(O)_nR^{19}$, $C(O)R^{20}$ or L;

$R^5$ is H, F, Cl, Br or $CH_3$;

$R^6$ is $C_1$-$C_3$ alkyl optionally substituted with 0-3 F, 0-1 Cl and 0-1 $C_3$-$C_4$ alkoxyacetyloxy, or $R^6$ is $C_1$-$C_2$ alkoxy, $C_2$-$C_4$ haloalkenyl, F, Cl, Br, $CO_2R^{14}$, $C(O)NR^{15}R^{16}$, $SO_2NR^{17}R^{18}$, $S(O)$, $R^{19}$, $C(O)R^{20}$ or L;

$R^7$ is H, F, Cl, $CH_3$ or $CF_3$;

$R^8$ is H, $C_1$-$C_3$ alkyl or pyridinyl;

$R^9$ is $C_1$-$C_3$ alkyl, $C_1$-$C_2$ alkoxy, F, Cl, Br, $NO_2$, $CO_2R^{14}$, $SO_2NR^{17}R^{18}$, $S(O)_nR^{19}$, $OCF_2H$, $C(O)R^{20}$, $C_2$-$C_4$ haloalkenyl or L;

$R^{10}$ is H, Cl, F, Br, $C_1$-$C_3$ alkyl or $C_1$-$C_2$ alkoxy;

$R^{11}$ is H, $C_1$-$C_3$ alkyl, $C_1$-$C_2$ alkoxy, $C_2$-$C_4$ haloalkenyl, F, Cl, Br, $CO_2R^{14}$, $C(O)NR^{15}R^{16}$, $SO_2NR^{17}R^{18}$, $S(O)_nR^{19}$, $C(O)R^{20}$ or L;

$R^{12}$ is halogen, $C_1$-$C_4$ alkyl or $C_1$-$C_3$ alkylsulfonyl;

$R^{13}$ is $C_1$-$C_4$ alkyl;

$R^{14}$ is allyl, propargyl or oxetan-3-yl; or $R^{14}$ is $C_1$-$C_3$ alkyl optionally substituted by at least one member independently selected from halogen, $C_1$-$C_2$ alkoxy and CN;

$R^{15}$ is H, $C_1$-$C_3$ alkyl or $C_1$-$C_2$ alkoxy;

$R^{16}$ is $C_1$-$C_2$ alkyl;

$R^{17}$ is H, $C_1$-$C_3$ alkyl, $C_1$-$C_2$ alkoxy, allyl or cyclopropyl;

$R^{18}$ is H or $C_1$-$C_3$ alkyl;
$R^{19}$ is $C_1$-$C_3$ alkyl, $C_1$-$C_3$ haloalkyl, allyl or propargyl;
$R^{20}$ is $C_1$-$C_4$ alkyl, $C_1$-$C_4$ haloalkyl or $C_3$-$C_5$ cycloalkyl optionally substituted by halogen;
n is 0, 1 or 2;
L is

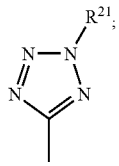

$L^1$ is $CH_2$, NH or O;
$R^{21}$ is H or $C_1$-$C_3$ alkyl;
X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino or di($C_1$-$C_3$ alkyl)amino;
Y is H, $C_1$-$C_4$ alkyl, $C_1$-$C_4$ alkoxy, $C_1$-$C_4$ haloalkoxy, $C_1$-$C_4$ alkylthio, $C_1$-$C_4$ haloalkylthio, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_2$-$C_5$ alkylsulfinylalkyl, $C_2$-$C_5$ alkylsulfonylalkyl, $C_1$-$C_4$ haloalkyl, $C_2$-$C_4$ alkynyl, $C_3$-$C_5$ cycloalkyl, azido or cyano; and
Z is CH or N;
provided that (i) when one or both of X and Y is $C_1$ haloalkoxy, then Z is CH; and (ii) when X is halogen, then Z is CH and Y is $OCH_3$, $OCH_2CH_3$, $N(OCH_3)CH_3$, $NHCH_3$, $N(CH_3)_2$ or $OCF_2H$. Of note is the present single liquid herbicide composition comprising one or more sulfonylureas of Formula I wherein when $R^6$ is alkyl, said alkyl is unsubstituted.

Representative of the triazolopyrimidine herbicides contemplated for use in this invention are those of the formula:

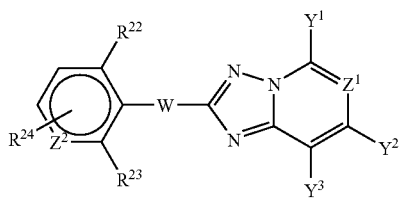

wherein:
$R^{22}$ and $R^{23}$ each independently halogen, nitro, $C_1$-$C_4$ alkyl, $C_1$-$C_4$ haloalkyl, $C_1$-$C_4$ alkoxy, $C_1$-$C_4$ haloalkoxy or $C_2$-$C_3$ alkoxycarbonyl;
$R^{24}$ is H, halogen, $C_1$-$C_2$ alkyl or $C_1$-$C_2$ alkoxy;
W is —NHS(O)$_2$— or —S(O)$_2$NH—;
$Y^1$ is H, $C_1$-$C_2$ alkyl or $C_1$-$C_2$ alkoxy;
$Y^2$ is H, F, Cl, Br, $C_1$-$C_2$ alkyl or $C_1$-$C_2$ alkoxy;
$Y^3$ is H, F or methoxy;
$Z^1$ is CH or N; and
$Z^2$ is CH or N;
provided that at least one of $Y^1$ and $Y^2$ is other than H.

In the above Markush description of representative triazolopyrimidine herbicides, when W is —NHS(O)$_2$— the sulfonyl end of the sulfonamide moiety is connected to the [1,2,4]triazolopyrimidine ring system, and when W is —S(O)$_2$ NH— the amino end of the sulfonamide moiety is connected to the [1,2,4]triazolopyrimidine ring system.

In the above recitations, the term "alkyl", used either alone or in compound words such as "alkylthio" or "haloalkyl" includes straight-chain or branched alkyl, such as, methyl, ethyl, n-propyl, i-propyl, or the different butyl isomers. "Cycloalkyl" includes, for example, cyclopropyl, cyclobutyl and cyclopentyl. "Alkenyl" includes straight-chain or branched alkenes such as ethenyl, 1-propenyl, 2-propenyl, and the different butenyl isomers. "Alkenyl" also includes polyenes such as 1,2-propadienyl and 2,4-butadienyl. "Alkynyl" includes straight-chain or branched alkynes such as ethynyl, 1-propynyl, 2-propynyl and the different butynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkenyloxy" includes straight-chain or branched alkenyloxy moieties. Examples of "alkenyloxy" include $H_2C=CHCH_2O$, $(CH_3)CH=CHCH_2O$ and $CH_2=CHCH_2CH_2O$. "Alkynyloxy" includes straight-chain or branched alkynyloxy moieties. Examples of "alkynyloxy" include $HC\equiv CCH_2O$ and $CH_3C\equiv CCH_2O$. "Alkylthio" includes branched or straight-chain alkylthio moieties such as methylthio, ethylthio, and the different propylthio isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$; "alkylsulfinylalkyl" and "alkylsulfonyl-alkyl" include the corresponding sulfoxides and sulfones, respectively. Other substituents such as "alkylamino", "dialkylamino" are defined analogously.

The total number of carbon atoms in a substituent group is indicated by the "$C_i$-$C_j$" prefix where i and j are numbers from 1 to 5. For example, $C_1$-$C_4$ alkyl designates methyl through butyl, including the various isomers. As further examples, $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkoxy", "haloalkylthio", and the like, are defined analogously to the term "haloalkyl". Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$.

The following sulfonylurea herbicides illustrate the sulfonylureas useful for this invention: amidosulfuron (N-[[[[(4,6-dimethoxy-2-pyrimdinyl)amino]carbonyl]amino]-sulfonyl]-N-methylmethanesulfonamide), azimsulfuron (N-[[[(4,6-dimethoxy-2-pyrimidinyl)amino]carbonyl]-1-methyl-4-(2-methyl-2H-tetrazol-5-yl)-1H-pyrazole-5-sulfonamide), bensulfuron-methyl (methyl 2-[[[[[(4,6-dimethoxy-2-pyrimidinyl)amino]carbonyl]amino]sulfonyl]methyl]benzoate), chlorimuron-ethyl (ethyl 2-[[[[(4-chloro-6-methoxy-2-pyrimidinyl)amino]carbonyl]amino]sulfonyl]-benzoate), chlorsulfuron (2-chloro-N-[[(4-methoxy-6-methyl-1,3,5-triazin-2-yl)amino]-carbonyl]benzenesulfonamide), cinosulfuron (N-[[(4,6-dimethoxy-1,3,5-triazin-2-yl)amino]carbonyl]-2-(2-methoxyethoxy)benzenesulfonamide), cyclosulfamuron (N-[[[2-(cyclopropylcarbonyl)phenyl]amino]sulfonyl]-N$^1$-(4,6-dimethoxypyrimidin-2-yl)urea), ethametsulfuron-methyl (methyl 2-[[[[[4-ethoxy-6-(methylamino)-1,3,5-triazin-2-yl]amino]carbonyl]amino]sulfonyl]benzoate), ethoxysulfuron (2-ethoxyphenyl [[(4,6-dimethoxy-2-pyrimidinyl)amino]carbonyl]sulfamate), flazasulfuron (N-[[(4,6-dimethoxy-2-pyrimidinyl)amino]carbonyl]-3-(trifluoromethyl)-2-pyridinesulfonamide), flucetosulfuron (1-[3-[[[[(4,6-dimethoxy-2-pyrimidinyl)amino]carbonyl]amino]sulfonyl]-2-pyridinyl]-2-fluoropropyl methoxyacetate), flupyrsulfuron-methyl (methyl 2-[[[[(4,6-dimethoxy-2-pyrimidinyl)amino]carbonyl]amino]sulfonyl]-6-(trifluoromethyl)-3-pyridinecarboxylate), foramsulfuron (2-[[[[(4,6-dimethoxy-2-pyrimidinyl)amino]carbonyl]amino]sulfonyl]-4-(formylamino)-N,N-dimethylbenzamide), halosulfuron-methyl(methyl 3-chloro-5-[[[[(4,6-dimethoxy-2-pyrimidinyl)amino]-carbonyl]amino]sulfonyl]-1-methyl-1H-pyrazole-4-carboxylate), imazosulfuron (2-chloro-N-[[(4,6-dimethoxy-2-pyrimidinyl)amino]carbonyl]imidazo[1,2-a]pyridine-3-sulfonamide), iodosulfuron-methyl (methyl 4-iodo-2-[[[[(4-methoxy-6-methyl-1,3,5-triazin-2-yl)amino]carbonyl]amino]sulfonyl]benzoate), mesosulfuron-methyl (methyl 2-[[[[(4,6-dimethoxy-2-pyrimidinyl)amino]carbonyl]amino]sulfonyl]-4-[[(methylsulfonyl)-amino]methyl]benzoate), metsulfuron-methyl (methyl 2-[[[[(4-methoxy-6-methyl-1,3,5-triazin-2-yl)amino]carbonyl]amino]sulfonyl]benzoate), nicosulfuron (2-[[[[(4,6-dimethoxy-2-pyrimidinyl)amino]carbonyl]amino]sulfonyl]-N,N-dimethyl-3-pyridinecarboxamide), oxasulfuron (3-oxetanyl 2-[[[[(4,6-dimethyl-2-pyrimidinyl)-amino]carbonyl]amino]sulfonyl]benzoate), primisulfuron-methyl (methyl 2-[[[[[4,6-bis(trifluoromethoxy)-2-pyrimidinyl]amino]carbonyl]amino]sulfonyl]benzoate), prosulfuron (N-[[(4-methoxy-6-methyl-1,3,5-triazin-2-yl)amino]carbonyl]-2-(3,3,3-trifluoropropyl)benzenesulfonamide), pyrazosulfuron-ethyl (ethyl 5-[[[[(4,6-dimethoxy-2-pyrimidinyl)amino]carbonyl]amino]sulfonyl]-1-methyl-1H-pyrazole-4-carboxylate), rimsulfuron (N-[[(4,6-dimethoxy-2-pyrimidinyl)amino]carbonyl]-3-(ethylsulfonyl)-2-pyridinesulfonamide), sulfometuron-methyl (methyl-2-[[[[(4,6-dimethyl-2-pyrimidinyl)amino]carbonyl]amino]sulfonyl]-benzoate), sulfosulfuron (N-[[(4,6-dimethoxy-2-pyrimidinyl)amino]carbonyl]-2-(ethylsulfonyl)imidazo[1,2-a]pyridine-3-sulfonamide), thifensulfuron-methyl (methyl 3-[[[[(4-methoxy-6-methyl-1,3,5-triazin-2-yl)amino]carbonyl]amino]sulfonyl]-2-thiophenecarboxylate), triasulfuron (2-(2-chloroethoxy)-N-[[(4-methoxy-6-methyl-1,3,5-triazin-2-yl)amino]carbonyl]benzenesulfonamide), tribenuron-methyl (methyl 2-[[[[N-(4-methoxy-6-methyl-1,3,5-triazin-2-yl)-N-methylamino]carbonyl]-amino]sulfonyl]benzoate), trifloxysulfuron (N-[[(4,6-dimethoxy-2-pyrimidinyl)amino]-carbonyl]-3-(2,2,2-trifluoroethoxy)-2-pyridinesulfonamide), triflusulfuron-methyl (methyl 2-[[[[[4-dimethylamino)-6-(2,2,2-trifluoroethoxy)-1,3,5-triazin-2-yl]amino]carbonyl]amino]sulfonyl]-3-methylbenzoate) and tritosulfuron (N-[[[4-methoxy-6-(trifluoromethyl)-1,3,5-triazin-2-yl]amino]carbonyl]-2-(trifluoromethyl)benzene-sulfonamide).

The following triazolopyrimidine herbicides illustrate the triazolopyrimidines useful for this invention: cloransulam-methyl (methyl 3-chloro-2-[[(5-ethoxy-7-fluoro-[1,2,4]triazolo [1,5-c]pyrimidin-2-yl)sulfonyl]amino]benzoate, diclosulam (N-(2,6-dichlorophenyl)-5-ethoxy-7-fluoro[1,2,4]triazolo[1,5-c]pyrimidine-2-sulfonamide, florasulam (N-(2,6-difluorophenyl)-8-fluoro-5-methoxy[1,2,4]triazolo[1,5-c]pyrimidine-2-sulfonamide), flumetsulam (N-(2,6-difluorophenyl)-5-methyl[1,2,4]triazolo[1,5-a]pyrimidine-2-sulfonamide), metosulam (N-(2,6-dichloro-3-methylphenyl)-5,7-dimethoxy[1,2,4]triazolo[1,5-a]pyrimidine-2-sulfonamide), penoxsulam (2-(2,2-difluoroethoxy)-N-(5,8-dimethoxy[1,2,4]triazolo[1,5-c]pyrimidin-2-yl)-6-(trifluoromethyl)benzenesulfonamide) and pyroxsulam (N-(5,7-dimethoxy[1,2,4]triazolo[1,5-a]pyrimidin-2-yl)-2-methoxy-4-(trifluoromethyl)-3-pyridinesulfonamide).

The following sulfonylaminocarbonyltriazolinone herbicides illustrate the sulfonylaminocarbonyltriazolinones useful for this invention: flucarbazone (4,5-dihydro-3-methoxy-4-methyl-5-oxo-N-[[2-(trifluoromethoxy)phenyl]sulfonyl]-1H-1,2,4-triazole-1-carboxamide) and procarbazone (methyl 2-[[[(4,5-dihydro-4-methyl-5-oxo-3-propoxy-1H-1,2,4-triazol-1-yl)carbonyl]amino]sulfonyl]benzoate).

Additional herbicides include phenmedipham, triazolinones, and the herbicides disclosed in WO2006/012981, herein incorporated by reference in its entirety.

The methods further comprise applying to the crop and the weeds in the field a sufficient amount of at least one herbicide to which the crop seeds or plants is tolerant, such as, for example, glyphosate, a hydroxyphenylpyruvatedioxygenase inhibitor (e.g., mesotrione or sulcotrione), a phytoene desaturase inhibitor (e.g., diflufenican), a pigment synthesis inhibitor, sulfonamide, imidazolinone, bialaphos, phosphinothricin, azafenidin, butafenacil, sulfosate, glufosinate, triazolopyrimidine, pyrimidinyloxy(thio)benzoate, or sulonylaminocarbonyltriazolinone, an acetyl Co—A carboxylase inhibitor such as quizalofop-P-ethyl, a synthetic auxin such as quinclorac, or a protox inhibitor to control the weeds without significantly damaging the crop plants.

b. Effective Amount of a Herbicide

Generally, the effective amount of herbicide applied to the field is sufficient to selectively control the weeds without significantly affecting the crop. "Weed" as used herein refers to a plant which is not desirable in a particular area. Conversely, a "crop plant" as used herein refers to a plant which is desired in a particular area, such as, for example, a soybean plant. Thus, in some embodiments, a weed is a non-crop plant or a non-crop species, while in some embodiments, a weed is a crop species which is sought to be eliminated from a particular area, such as, for example, an inferior and/or non-transgenic maize plant in a field planted with transgenic maize, or a soybean plant in a field planted with corn. Weeds can be either classified into two major groups: monocots and dicots.

Many plant species can be controlled (i.e., killed or damaged) by the herbicides described herein. Accordingly, the methods of the invention are useful in controlling these plant species where they are undesirable (i.e., where they are weeds). These plant species include crop plants as well as species commonly considered weeds, including but not limited to species such as: blackgrass (*Alopecurus myosuroides*), giant foxtail (*Setaria faberi*), large crabgrass (*Digitaria sanguinalis*), Surinam grass (*Brachiaria decumbens*), wild oat (*Avena fatua*), common cocklebur (*Xanthium pensylvanicum*), common lambsquarters (*Chenopodium album*), morning glory (*Ipomoea coccinea*), pigweed (*Amaranthus* spp.), velvetleaf (*Abutilion theophrasti*), common barnyardgrass (*Echinochloa crus-galli*), bermudagrass (*Cynodon dactylon*), downy brome (*Bromus tectorum*), goosegrass (*Eleusine indica*), green foxtail (*Setaria viridis*), Italian ryegrass (*Lo-*

*lium multiflorum*), Johnsongrass (*Sorghum halepense*), lesser canarygrass (*Phalaris minor*), windgrass (*Apera spicaventi*), wooly cupgrass (*Erichloa villosa*), yellow nutsedge (*Cyperus esculentus*), common chickweed (*Stellaria media*), common ragweed (*Ambrosia artemisuifolia*), *Kochia scoparia*, horseweed (*Conyza canadensis*), rigid ryegrass (*Lolium rigidum*), goosegrass (*Eleucine indica*), hairy fleabane (*Conyza bonariensis*), buckhorn plantain (*Plantago lanceolata*), tropical spiderwort (*Commelina benghalensis*), field bindweed (*Convolvulus arvensis*), purple nutsedge (*Cyperus rotundus*), redvine (*Brunnichia ovata*), hemp sesbania (*Sesbania exaltata*), sicklepod (*Senna obtusifolia*), Texas blueweed (*Helianthus ciliaris*), and Devil's claws (*Proboscidea louisianica*). In other embodiments, the weed comprises a herbicide-resistant ryegrass, for example, a glyphosate resistant ryegrass, a paraquat resistant ryegrass, a ACCase-inhibitor resistant ryegrass, and a non-selective herbicide resistant ryegrass. In some embodiments, the undesired plants are proximate the crop plants.

As used herein, by "selectively controlled" is intended that the majority of weeds in an area of cultivation are significantly damaged or killed, while if crop plants are also present in the field, the majority of the crop plants are not significantly damaged. Thus, a method is considered to selectively control weeds when at least 55%, 60%, 65%, 70%, 75%, 80%, 85%, 90%, 95%, or more of the weeds are significantly damaged or killed, while if crop plants are also present in the field, less than 45%, 40%, 35%, 30%, 25%, 20%, 15%, 10%, 5%, or 1% of the crop plants are significantly damaged or killed.

In some embodiments, a glyphosate/ALS inhibitor-tolerant plant of the invention is not significantly damaged by treatment with a particular herbicide applied to that plant at a dose equivalent to a rate of at least 0.5, 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 150, 170, 200, 300, 400, 500, 600, 700, 800, 800, 1000, 2000, 3000, 4000, 5000 or more grams or ounces (1 ounce=29.57 ml) of active ingredient or commercial product or herbicide formulation per acre or per hectare, whereas an appropriate control plant is significantly damaged by the same treatment.

In specific embodiments, an effective amount of an ALS inhibitor herbicide comprises at least about 0.1, 1, 5, 10, 25, 50, 75, 100, 150, 200, 250, 300, 350, 400, 450, 500, 600, 700, 750, 800, 850, 900, 950, 1000, 2000, 3000, 4000, 5000, or more grams or ounces (1 ounce=29.57 ml) of active ingredient per hectare. In other embodiments, an effective amount of an ALS inhibitor comprises at least about 0.1-50, about 25-75, about 50-100, about 100-110, about 110-120, about 120-130, about 130-140, about 140-150, about 150-200, about 200-500, about 500-600, about 600-800, about 800-1000, or greater grams or ounces (1 ounce=29.57 ml) of active ingredient per hectare. Any ALS inhibitor, for example, those listed in Table 1 can be applied at these levels.

In other embodiments, an effective amount of a sulfonylurea comprises at least 0.1, 1, 5, 10, 25, 50, 75, 100, 150, 200, 250, 300, 350, 400, 450, 500, 600, 700, 800, 900, 1000, 5000 or more grams or ounces (1 ounce=29.57 ml) of active ingredient per hectare. In other embodiments, an effective amount of a sulfonylurea comprises at least about 0.1-50, about 25-75, about 50-100, about 100-110, about 110-120, about 120-130, about 130-140, about 140-150, about 150-160, about 160-170, about 170-180, about 190-200, about 200-250, about 250-300, about 300-350, about 350-400, about 400-450, about 450-500, about 500-550, about 550-600, about 600-650, about 650-700, about 700-800, about 800-900, about 900-1000, about 1000-2000, or more grams or ounces (1 ounce=29.57 ml) of active ingredient per hectare. Representative sulfonylureas that can be applied at this level are set forth in Table 1.

In other embodiments, an effective amount of a sulfonylaminocarbonyltriazolinones, triazolopyrimidines, pyrimidinyloxy(thio)benzoates, and imidazolinones can comprise at least about 0.1, 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1500, 1550, 1600, 1650, 1700, 1800, 1850, 1900, 1950, 2000, 2500, 3500, 4000, 4500, 5000 or greater grams or ounces (1 ounce=29.57 ml) active ingredient per hectare. In other embodiments, an effective amount of a sulfonyluminocarbonyltriazolines, triazolopyrimidines, pyrimidinyloxy(thio) benzoates, or imidazolinones comprises at least about 0.1-50, about 25-75, about 50-100, about 100-110, about 110-120, about 120-130, about 130-140, about 140-150, about 150-160, about 160-170, about 170-180, about 190-200, about 200-250, about 250-300, about 300-350, about 350-400, about 400-450, about 450-500, about 500-550, about 550-600, about 600-650, about 650-700, about 700-800, about 800-900, about 900-1000, about 1000-2000, or more grams or ounces (1 ounce=29.57 ml) active ingredient per hectare.

Additional ranges of the effective amounts of herbicides can be found, for example, in various publications from University Extension services. See, for example, Bernards et al. (2006) *Guide for Weed Management in Nebraska* (www.ianrpubs.url.edu/sendlt/ec130); Regher et al. (2005) *Chemical Weed Control for Fields Crops, Pastures, Rangeland, and Noncropland*, Kansas State University Agricultural Extension Station and Corporate Extension Service; Zollinger et al. (2006) *North Dakota Weed Control Guide*, North Dakota Extension Service, and the Iowa State University Extension at www.weeds.iastate.edu, each of which is herein incorporated by reference.

In some embodiments of the invention, glyphosate is applied to an area of cultivation and/or to at least one plant in an area of cultivation at rates between 8 and 32 ounces of acid equivalent per acre, or at rates between 10, 12, 14, 16, 18, 20, 22, 24, 26, 28, and 30 ounces of acid equivalent per acre at the lower end of the range of application and between 12, 14, 16, 18, 20, 22, 24, 26, 28, 30, and 32 ounces of acid equivalent per acre at the higher end of the range of application (1 ounce=29.57 ml). In other embodiments, glyphosate is applied at least at 1, 5, 10, 20, 30, 40, 50, 60, 70, 80, 90 or greater ounce of active ingredient per hectare (1 ounce=29.57 ml). In some embodiments of the invention, a sulfonylurea herbicide is applied to a field and/or to at least one plant in a field at rates between 0.04 and 1.0 ounces of active ingredient per acre, or at rates between 0.1, 0.2, 0.4, 0.6, and 0.8 ounces of active ingredient per acre at the lower end of the range of application and between 0.2, 0.4, 0.6, 0.8, and 1.0 ounces of active ingredient per acre at the higher end of the range of application. (1 ounce=29.57 ml)

As is known in the art, glyphosate herbicides as a class contain the same active ingredient, but the active ingredient is present as one of a number of different salts and/or formulations. However, herbicides known to inhibit ALS vary in their active ingredient as well as their chemical formulations. One of skill in the art is familiar with the determination of the amount of active ingredient and/or acid equivalent present in a particular volume and/or weight of herbicide preparation.

In some embodiments, an ALS inhibitor herbicide is employed. Rates at which the ALS inhibitor herbicide is applied to the crop, crop part, seed or area of cultivation can be any of the rates disclosed herein. In specific embodiments, the rate for the ALS inhibitor herbicide is about 0.1 to about 5000 g ai/hectare, about 0.5 to about 300 g ai/hectare, or about 1 to about 150 g ai/hectare.

Generally, a particular herbicide is applied to a particular field (and any plants growing in it) no more than 1, 2, 3, 4, 5, 6, 7, or 8 times a year, or no more than 1, 2, 3, 4, or 5 times per growing season.

By "treated with a combination of" or "applying a combination of" herbicides to a crop, area of cultivation or field" is intended that a particular field, crop or weed is treated with each of the herbicides and/or chemicals indicated to be part of the combination so that desired effect is achieved, i.e., so that weeds are selectively controlled while the crop is not significantly damaged. In some embodiments, weeds which are susceptible to each of the herbicides exhibit damage from treatment with each of the herbicides which is additive or synergistic. The application of each herbicide and/or chemical may be simultaneous or the applications may be at different times, so long as the desired effect is achieved. Furthermore, the application can occur prior to the planting of the crop.

The proportions of herbicides used in the methods of the invention with other herbicidal active ingredients in herbicidal compositions are generally in the ratio of 5000:1 to 1:5000, 1000:1 to 1:1000, 100:1 to 1:100, 10:1 to 1:10 or 5:1 to 1:5 by weight. The optimum ratios can be easily determined by those skilled in the art based on the weed control spectrum desired. Moreover, any combinations of ranges of the various herbicides disclosed in Table 3 can also be applied in the methods of the invention.

Thus, in some embodiments, the invention provides improved methods for selectively controlling weeds in a field wherein the total herbicide application may be less than 90%, 85%, 80%, 75%, 70%, 65%, 60%, 55%, 50%, 45%, 40%, 35%, 30%, 25%, 20%, 15%, 10%, 5%, or 1% of that used in other methods. Similarly, in some embodiments, the amount of a particular herbicide used for selectively controlling weeds in a field may be less than 90%, 85%, 80%, 75%, 70%, 65%, 60%, 55%, 50%, 45%, 40%, 35%, 30%, 25%, 20%, 15%, 10%, 5%, or 1% of the amount of that particular herbicide that would be used in other methods, i.e., methods not utilizing a plant of the invention.

In some embodiments, a glyphosate/ALS inhibitor-tolerant plant of the invention benefits from a synergistic effect wherein the herbicide tolerance conferred by a polypeptide that confers resistance to glyphosate (i.e., GAT) and at least an ALS inhibitor-tolerant polypeptide is greater than expected from simply combining the herbicide tolerance conferred by each gene separately to a transgenic plant containing them individually. See, e.g., McCutchen et al. (1997) *J. Econ. Entomol.* 90: 1170-1180; Priesler et al. (1999) *J. Econ. Entomol.* 92: 598-603. As used herein, the terms "synergy," "synergistic," "synergistically" and derivations thereof, such as in a "synergistic effect" or a "synergistic herbicide combination" or a "synergistic herbicide composition" refer to circumstances under which the biological activity of a combination of herbicides, such as at least a first herbicide and a second herbicide, is greater than the sum of the biological activities of the individual herbicides. Synergy, expressed in terms of a "Synergy Index (SI)," generally can be determined by the method described by F. C. Kull, et al., *Applied Microbiology* 9, 538 (1961). See also Colby S. R., "Calculating Synergistic and Antagonistic Responses of Herbicide Combinations," *Weeds* 15, 20-22 (1967).

In other instances, the herbicide tolerance conferred on a glyphosate/ALS inhibitor-tolerant plant of the invention is additive; that is, the herbicide tolerance profile conferred by the herbicide tolerance genes is what would be expected from simply combining the herbicide tolerance conferred by each gene separately to a transgenic plant containing them individually. Additive and/or synergistic activity for two or more herbicides against key weed species will increase the overall effectiveness and/or reduce the actual amount of active ingredient(s) needed to control said weeds. Where such synergy is observed, the plant of the invention may display tolerance to a higher dose or rate of herbicide and/or the plant may display tolerance to additional herbicides or other chemicals beyond those to which it would be expected to display tolerance. For example, a plant containing a GAT gene and an HRA gene may show tolerance to organophosphate compounds such as insecticides and/or inhibitors of 4-hydroxyphenylpyruvate dioxygenase.

Thus, for example, glyphosate/ALS inhibitor-tolerant plants of the invention can exhibit greater than expected tolerance to various herbicides, including but not limited to glyphosate, ALS inhibitor chemistries, and sulfonylurea herbicides. The glyphosate/ALS inhibitor-tolerant plants of the invention may show tolerance to a particular herbicide or herbicide combination that is at least 1%, 2%, 3%, 4%, 5%, 6%, 7%, 8%, 9%, 10%, 12%, 15%, 17%, 20%, 22%, 25%, 27%, 30%, 35%, 40%, 45%, 50%, 55%, 60%, 65%, 70%, 80%, 90%, 100%, 125%, 150%, 175%, 200%, 300%, 400%, or 500% or more higher than the tolerance of an appropriate control plant that contains only a single herbicide tolerance gene which confers tolerance to the same herbicide or herbicide combination. Thus, glyphosate/ALS inhibitor-tolerant plants of the invention may show decreased damage from the same dose of herbicide in comparison to an appropriate control plant, or they may show the same degree of damage in response to a much higher dose of herbicide than the control plant. Accordingly, in specific embodiments, a particular herbicide used for selectively containing weeds in a field is more than 1%, 5%, 10%, 15%, 20%, 25%, 30%, 35%, 40%, 45%, 50%, 60%, 70%, 80%, 90%, 100% or greater than the amount of that particular herbicide that would be used in other methods, i.e., methods not utilizing a plant of the invention.

In the same manner, in some embodiments, a glyphosate/ALS inhibitor-tolerant plant of the invention shows improved tolerance to a particular formulation of a herbicide active ingredient in comparison to an appropriate control plant. Herbicides are sold commercially as formulations which typically include other ingredients in addition to the herbicide active ingredient; these ingredients are often intended to enhance the efficacy of the active ingredient. Such other ingredients can include, for example, safeners and adjuvants (see, e.g., Green and Foy (2003) "Adjuvants: Tools for Enhancing Herbicide Performance," in *Weed Biology and Management*, ed. Inderjit (Kluwer Academic Publishers, The Netherlands)). Thus, a glyphosate/ALS inhibitor-tolerant plant of the invention can show tolerance to a particular formulation of a herbicide (e.g., a particular commercially available herbicide product) that is at least 1%, 2%, 3%, 4%, 5%, 6%, 7%, 8%, 9%, 10%, 12%, 15%, 17%, 20%, 22%, 25%, 27%, 30%, 35%, 40%, 45%, 50%, 55%, 60%, 65%, 70%, 80%, 90%, 100%, 125%, 150%, 175%, 200%, 300%, 400%, 500%, 600%, 700%, 800%, 900%, 1000%, 1100%, 1200%, 1300%, 1400%, 1500%, 1600%, 1700%, 1800%, 1900%, or 2000% or more higher than the tolerance of an appropriate control plant that contains only a single herbicide tolerance gene which confers tolerance to the same herbicide formulation.

In some embodiments, a glyphosate/ALS inhibitor-tolerant plant of the invention shows improved tolerance to a herbicide or herbicide class to which the at least one other herbicide tolerance gene confers tolerance as well as improved tolerance to at least one other herbicide or chemical which has a different mechanism or basis of action than either glyphosate or the herbicide corresponding to said at least one other herbicide tolerance gene. This surprising benefit of the invention finds use in methods of growing crops that comprise treatment with various combinations of chemicals, including, for example, other chemicals used for growing crops. Thus, for example, a glyphosate/ALS inhibitor-tolerant maize plant of the invention (i.e., a GAT/HRA plant) may also show improved tolerance to chlorpyrifos, a systemic organophosphate insecticide which interferes with the ability of maize to metabolize herbicide via interference with the cytochrome P450 gene. Thus, the invention also provides a transgenic plant comprising a sequence that confers tolerance to glyphosate (i.e., a GAT gene) and a sulfonylurea herbicide tolerance gene which shows improved tolerance to chemicals which affect the cytochrome P450 gene, and methods of use thereof. In some embodiments, glyphosate/ALS inhibitor-tolerant plants of the invention comprising, for example, a GAT gene and a sulfonylurea herbicide tolerance gene also show improved tolerance to dicamba. In these embodiments, the improved tolerance to dicamba may be evident in the presence of glyphosate and a sulfonylurea herbicide.

In other methods, a herbicide combination is applied over a glyphosate/ALS inhibitor-tolerant plant of the invention, where the herbicide combination produces either an additive or a synergistic effect for controlling weeds. Such combinations of herbicides can allow the application rate to be reduced, a broader spectrum of undesired vegetation to be controlled, improved control of the undesired vegetation with fewer applications, more rapid onset of the herbicidal activity, or more prolonged herbicidal activity.

An "additive herbicidal composition" has a herbicidal activity that is about equal to the observed activities of the individual components. A "synergistic herbicidal combination" has a herbicidal activity higher than what can be expected based on the observed activities of the individual components when used alone. Accordingly, the presently disclosed subject matter provides a synergistic herbicide combination, wherein the degree of weed control of the mixture exceeds the sum of control of the individual herbicides. In some embodiments, the degree of weed control of the mixture exceeds the sum of control of the individual herbicides by any statistically significant amount including, for example, about 1% to 5%, about 5% to about 10%, about 10% to about 20%, about 20% to about 30%, about 30% to 40%, about 40% to about 50%, about 50% to about 60%, about 60% to about 70%, about 70% to about 80%, about 80% to about 90%, about 90% to about 100%, about 100% to 120% or greater. Further, a "synergistically effective amount" of a herbicide refers to the amount of one herbicide necessary to elicit a synergistic effect in another herbicide present in the herbicide composition. Thus, the term "synergist," and derivations thereof, refer to a substance that enhances the activity of an active ingredient (ai), i.e., a substance in a formulation from which a biological effect is obtained, for example, a herbicide.

Accordingly, in some embodiments, the presently disclosed subject matter provides a method for controlling weeds in an area of cultivation. In some embodiments, the method comprises: (a) planting the area with crop seeds or crop plants, wherein the crop seeds or crop plants comprise: (i) a first polynucleotide encoding a polypeptide that can confer tolerance to glyphosate operably linked to a promoter active in the crop seeds or crop plants; and (ii) a second polynucleotide encoding an ALS inhibitor-tolerant polypeptide operable linked to a promoter active in the crop seeds or crop plants; and (b) applying to the weed, the crop plants, a crop part, the area of cultivation, or a combination thereof, an effective amount of a herbicide composition comprising at least one of a synergistically effective amount of glyphosate and a synergistically effective amount of an ALS inhibitor (for example, but not limited to, a sulfonylurea herbicide), or agriculturally suitable salts thereof, wherein at least one of: (i) the synergistically effective amount of the glyphosate is lower than an amount of glyphosate required to control the weeds in the absence of the sulfonylurea herbicide; (ii) the synergistically effective amount of the ALS inhibitor herbicide is lower than an amount of the ALS inhibitor required to control the weeds in the absence of glyphosate; and (iii) combinations thereof; and wherein the effective amount of the herbicide composition is tolerated by the crop seeds or crop plants and controls the weeds in the area of cultivation.

As described in more detail hereinabove, in some embodiments, the first polynucleotide encodes a glyphosate-N-acetyltransferase. More particularly, in some embodiments, the first polynucleotide encodes a glyphosate-tolerant 5-enolpyruvylshikimate-3-phosphate synthase or a glyphosate-tolerant glyphosate oxido-reductase. Further, as also described in more detail hereinabove, the ALS inhibitor-tolerant polypeptide comprises a mutated acetolactate synthase polypeptide. In some embodiments, the mutated acetolactate synthase polypeptide comprises HRA.

In some embodiments, the herbicide composition used in the presently disclosed method for controlling weeds comprises a synergistically effective amount of glyphosate and a sulfonylurea herbicide. In further embodiments, the presently disclosed synergistic herbicide composition comprises glyphosate and a sulfonylurea herbicide selected from the group consisting of metsulfuron-methyl, chlorsulfuron, and triasulfuron.

In particular embodiments, the synergistic herbicide combination further comprises an adjuvant such as, for example, an ammonium sulfate-based adjuvant, e.g., ADD-UP® (Wenkem S. A., Halfway House, Midrand, South Africa). In additional embodiments, the presently disclosed synergistic herbicide compositions comprise an additional herbicide, for example, an effective amount of a pyrimidinyloxy(thio)benzoate herbicide. In some embodiments, the pyrimidinyloxy (thio)benzoate herbicide comprises bispyribac, e.g., (VELOCITY®, Valent U.S.A. Corp., Walnut Creek, Calif., United States of America), or an agriculturally suitable salt thereof.

In some embodiments of the presently disclosed method for controlling undesired plants, the glyphosate is applied pre-emergence, post-emergence or pre- and post-emergence to the undesired plants or plant crops; and the ALS inhibitor herbicide (i.e., the sulfonylurea herbicide) is applied pre-emergence, post-emergence or pre- and post-emergence to the undesired plants or plant crops. In other embodiments, the glyphosate and the ALS inhibitor herbicide (i.e., the sulfonylurea herbicide) are applied together or are applied separately. In yet other embodiments, the synergistic herbicide composition is applied, e.g. step (b) above, at least once prior to planting the crop(s) of interest, e.g., step (a) above.

While the glyphosate/ALS inhibitor-tolerant plants of the invention are tolerant to many herbicides, they are not tolerant to several herbicides, such as, for example, dinitroaniline, ACCase, and chloracetamide herbicides. Thus, methods of the invention that comprise the control of weeds may also make use of these treatments to control glyphosate/ALS inhibitor-tolerant plants, such as, for example, "volunteer"

glyphosate/ALS inhibitor-tolerant plants crops that arise in a field that has been planted or replanted with a different crop.

Weeds that can be difficult to control with glyphosate alone in fields where a crop is grown (such as, for example, a soybean crop) include but are not limited to the following: horseweed (e.g., *Conyza canadensis*); rigid ryegrass (e.g., *Lolium rigidum*); goosegrass (e.g., *Eleusine indica*); Italian ryegrass (e.g., *Lolium multiflorum*); hairy fleabane (e.g., *Conyza bonariensis*); buckhorn plantain (e.g., *Plantago lanceolata*); common ragweed (e.g., *Ambrosia artemisifolia*); morning glory (e.g., *Ipomoea* spp.); waterhemp (e.g., *Amaranthus* spp.); field bindweed (e.g., *Convolvulus arvensis*); yellow nutsedge (e.g., *Cyperus esculentus*); common lambsquarters (e.g., *Chenopodium album*); wild buckwheat (e.g., *Polygonium convolvulus*); velvetleaf (e.g., *Abutilon theophrasti*); kochia (e.g., *Kochia scoparia*); and Asiatic dayflower (e.g., *Commelina* spp.). In areas where such weeds are found, the glyphosate/ALS inhibitor-tolerant plants of the invention (GAT-HRA plants) are particularly useful in allowing the treatment of a field (and therefore any crop growing in the field) with combinations of herbicides that would cause unacceptable damage to crop plants that did not contain both of these polynucleotides. Plants of the invention that are tolerant to glyphosate and other herbicides such as, for example, sulfonylurea, imidazolinone, triazolopyrimidine, pyrimidinyl(thio)benzoate, and/or sulfonylaminocarbonyltriazolinone herbicides in addition to being tolerant to at least one other herbicide with a different mode of action or site of action are particularly useful in situations where weeds are tolerant to at least two of the same herbicides to which the plants are tolerant. In this manner, plants of the invention make possible improved control of weeds that are tolerant to more than one herbicide.

For example, some commonly used treatments for weed control in fields where current commercial crops (including, for example, soybeans) are grown include glyphosate and, optionally, 2,4-D; this combination, however, has some disadvantages. Particularly, there are weed species that it does not control well and it also does not work well for weed control in cold weather. Another commonly used treatment for weed control in soybean fields is the sulfonylurea herbicide chlorimuron-ethyl, which has significant residual activity in the soil and thus maintains selective pressure on all later-emerging weed species, creating a favorable environment for the growth and spread of sulfonylurea-resistant weeds. However, the glyphosate/ALS inhibitor-tolerant plants (i.e., GAT-HRA plants of the invention), including glyphosate/ALS inhibitor-tolerant soybean plants (i.e., GAT-HRA soybean plants), can be treated with herbicides (e.g., chlorimuron-ethyl) and combinations of herbicides that would cause unacceptable damage to standard plant varieties. Thus, for example, fields containing the glyphosate/ALS inhibitor-tolerant soybean plant (i.e., GAT-HRA soybean plants) can be treated with sulfonylurea, imidazolinone, triazolopyrimidines, pyrimidiny(thio)benzoates, and/or sulfonylaminocarbonyltriazonlinone such as the sulfonylurea chlorimuron-ethyl, either alone or in combination with other herbicides. For example, fields containing soybean plants of the invention can be treated with a combination of glyphosate and tribenuron-methyl (available commercially as Express®). This combination has several advantages for weed control under some circumstances, including the use of herbicides with different modes of action and the use of herbicides having a relatively short period of residual activity in the soil. A herbicide having a relatively short period of residual activity is desirable, for example, in situations where it is important to reduce selective pressure that would favor the growth of herbicide-tolerant weeds. Of course, in any particular situation where weed control is required, other considerations may be more important, such as, for example, the need to prevent the development of and/or appearance of weeds in a field prior to planting a crop by using a herbicide with a relatively long period of residual activity. The glyphosate/ALS inhibitor-tolerant soybean plants can also be treated with herbicide combinations that include at least one of nicosulfuron, metsulfuron-methyl, tribenuron-methyl, thifensulfuron-methyl, and/or rimsulfuron. Treatments that include both tribenuron-methyl and thifensulfuron-methyl may be particularly useful.

Other commonly used treatments for weed control in fields where current commercial varieties of crops (including, for example, soybeans) are grown include the sulfonylurea herbicide thifensulfuron-methyl (available commercially as Harmony GT®). However, one disadvantage of thifensulfuron-methyl is that the higher application rates required for consistent weed control often cause injury to a crop growing in the same field. The glyphosate/ALS inhibitor-tolerant plants of the invention, including soybean plants, can be treated with a combination of glyphosate and thifensulfuron-methyl, which has the advantage of using herbicides with different modes of action. Thus, weeds that are resistant to either herbicide alone are controlled by the combination of the two herbicides, and the glyphosate/ALS inhibitor-tolerant plants of the invention are not significantly damaged by the treatment.

Other herbicides which are used for weed control in fields where current commercial varieties of crops (including, for example, soybeans) are grown are the triazolopyrimidine herbicide cloransulam-methyl (available commercially as FirstRate®) and the imidazolinone herbicide imazaquin (available commercially as Sceptor®). When these herbicides are used individually they may provide only marginal control of weeds. However, fields containing the glyphosate/ALS inhibitor-tolerant plants of the invention, including soybean plants, can be treated, for example, with a combination of glyphosate (e.g., Roundup® (glyphosate isopropylamine salt)), imazapyr (currently available commercially as Arsenal®), chlorimuron-ethyl (currently available commercially as Classic®), quizalofop-P-ethyl (currently available commercially as Assure II®), and fomesafen (currently available commercially as Flexstar®). This combination has the advantage of using herbicides with different modes of action. Thus, weeds that are tolerant to just one or several of these herbicides are controlled by the combination of the five herbicides, and the glyphosate/ALS inhibitor-tolerant plants of the invention are not significantly damaged by treatment with this herbicide combination. This combination provides an extremely broad spectrum of protection against the type of herbicide-tolerant weeds that might be expected to arise and spread under current weed control practices.

Fields containing the glyphosate/ALS inhibitor-tolerant plants of the invention (i.e., GAT/HRA plants), including soybean plants, may also be treated, for example, with a combination of herbicides including glyphosate, rimsulfuron, and dicamba or mesotrione. This combination may be particularly useful in controlling weeds which have developed some tolerance to herbicides which inhibit ALS. Another combination of herbicides which may be particularly useful for weed control includes glyphosate and at least one of the following: metsulfuron-methyl (commercially available as Ally®), imazapyr (commercially available as Arsenal®), imazethapyr, imazaquin, and sulfentrazone. It is understood that any of the combinations discussed above or elsewhere herein may also be used to treat areas in combination with any other herbicide or agricultural chemical.

Some commonly-used treatments for weed control in fields where current commercial crops (including, for example, maize) are grown include glyphosate (currently available commercially as Roundup®), rimsulfuron (currently available commercially as Resolve® or Matrix®), dicamba (commercially available as Clarity®), atrazine, and mesotrione (commercially available as Callisto®). These herbicides are sometimes used individually due to poor crop tolerance to multiple herbicides. Unfortunately, when used individually, each of these herbicides has significant disadvantages. Particularly, the incidence of weeds that are tolerant to individual herbicides continues to increase, rendering glyphosate less effective than desired in some situations. Rimsulfuron provides better weed control at high doses which can cause injury to a crop, and alternatives such as dicamba are often more expensive than other commonly-used herbicides. However, glyphosate/ALS inhibitor-tolerant plants (i.e., GAT-HRA plants) of the invention, including glyphosate/ALS inhibitor-tolerant maize plants, can be treated with herbicides and combinations of herbicides that would cause unacceptable damage to standard plant varieties, including combinations of herbicides that comprise rimsulfuron and/or dicamba. Other suitable combinations of herbicides for use with glyphosate/ALS inhibitor-tolerant plants of the invention include glyphosate, sulfonylurea, imidazolinone, triazolopyrimidine, pryimidinyloxy(thio)benzoates, and/or sulfonylaminocarbonyltriazonlinone herbicides, including, for example, and at least one of the following: metsulfuron-methyl, tribenuron-methyl, chlorimuron-ethyl, imazethapyr, imazapyr, and imazaquin.

For example, glyphosate/ALS inhibitor-tolerant maize plants (i.e. GAT/HRA plants) can be treated with a combination of glyphosate and rimsulfuron, or a combination or rimsulfuron and at least one other herbicide. Glyphosate/ALS inhibitor plants (i.e., GAT-HRA plants) can also be treated with a combination of glyphosate, rimsulfuron, and dicamba, or a combination of glyphosate, rimsulfuron, and at least one other herbicide. In some embodiments, the at least one other herbicide has a different mode of action than both glyphosate and rimsulfuron. The combination of glyphosate, rimsulfuron, and dicamba has the advantage that these herbicides have different modes of action and short residual activity, which decreases the risk of incidence and spread of herbicide-tolerant weeds.

Some commonly-used treatments for weed control in fields where current commercial crops (including, for example, cotton) are grown include glyphosate (currently available commercially as Roundup®), chlorimuron-ethyl, tribenuron-methyl, rimsulfuron (currently available commercially as Resolve® or Matrix®), imazethapyr, imazapyr, and imazaquin. Unfortunately, when used individually, each of these herbicides has significant disadvantages. Particularly, the incidence of weeds that are tolerant to individual herbicides continues to increase, rendering each individual herbicide less effective than desired in some situations. However, glyphosate/ALS inhibitor-tolerant plants of the invention, including cotton plants, can be treated with a combination of herbicides that would cause unacceptable damage to standard plant varieties, including combinations of herbicides that include at least one of those mentioned above.

c. Methods of Herbicide Application

In the methods of the invention, a herbicide may be formulated and applied to an area of interest such as, for example, a field or area of cultivation, in any suitable manner. A herbicide may be applied to a field in any form, such as, for example, in a liquid spray or as solid powder or granules. In specific embodiments, the herbicide or combination of herbicides that are employed in the methods comprise a tankmix or a premix. A herbicide may also be formulated, for example, as a "homogenous granule blend" produced using blends technology (see, e.g., U.S. Pat. No. 6,022,552, entitled "Uniform Mixtures of Pesticide Granules"). The blends technology of U.S. Pat. No. 6,022,552 produces a nonsegregating blend (i.e., a "homogenous granule blend") of formulated crop protection chemicals in a dry granule form that enables delivery of customized mixtures designed to solve specific problems. A homogenous granule blend can be shipped, handled, subsampled, and applied in the same manner as traditional premix products where multiple active ingredients are formulated into the same granule.

Briefly, a "homogenous granule blend" is prepared by mixing together at least two extruded formulated granule products. In some embodiments, each granule product comprises a registered formulation containing a single active ingredient which is, for example, a herbicide, a fungicide, and/or an insecticide. The uniformity (homogeneity) of a "homogenous granule blend" can be optimized by controlling the relative sizes and size distributions of the granules used in the blend. The diameter of extruded granules is controlled by the size of the holes in the extruder die, and a centrifugal sifting process may be used to obtain a population of extruded granules with a desired length distribution (see, e.g., U.S. Pat. No. 6,270,025).

A homogenous granule blend is considered to be "homogenous" when it can be subsampled into appropriately sized aliquots and the composition of each aliquot will meet the required assay specifications. To demonstrate homogeneity, a large sample of the homogenous granule blend is prepared and is then subsampled into aliquots of greater than the minimum statistical sample size (see Example 4).

In non-limiting embodiments, the glyphosate/ALS inhibitor-tolerant plant (i.e., a GAT-HRA plant), including a soybean plant, can be treated with herbicides (e.g., chlorimuron-ethyl and combinations of other herbicides that without the glyphosate/ALS inhibitor-tolerant crop would have caused unacceptable crop response to plant varieties without the glyphosate/ALS inhibitor genetics). Thus, for example, fields planted with and containing glyphosate/ALS inhibitor-tolerant soybean, corn or cotton varieties (i.e., GAT/HRA plants) can be treated with sulfonylurea, imidazolinone, triazolopyrimidine, pyrimidinyl(thio)benzoate, and/or sulfonylaminocarbonyltriazonlinone herbicides, either alone or in combination with other herbicides. Since ALS inhibitor chemistries have different herbicidal attributes, blends of ALS plus other chemistries will provide superior weed management strategies including varying and increased weed spectrum, the ability to provide specified residual activity (SU/ALS inhibitor chemistry with residual activity leads to improved foliar activity which leads to a wider window between glyphosate applications, as well as, an added period of control if weather conditions prohibit timely application).

Blends also afford the ability to add other agrochemicals at normal, labeled use rates such as additional herbicides (a $3^{rd}/4^{th}$ mechanism of action), fungicides, insecticides, plant growth regulators and the like thereby saving costs associated with additional applications.

Any herbicide formulation applied over the glyphosate/ALS inhibitor-tolerant plant can be prepared as a "tank-mix" composition. In such embodiments, each ingredient or a combination of ingredients can be stored separately from one another. The ingredients can then be mixed with one another prior to application. Typically, such mixing occurs shortly before application. In a tank-mix process, each ingredient, before mixing, typically is present in water or a suitable organic solvent. For additional guidance regarding the art of formulation, see T. S. Woods, "The Formulator's Toolbox—Product Forms for Modern Agriculture" *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; and Hance et al., *Weed Control Handbook*, 8th Ed., Blackwell Scientific Publications, Oxford, 1989, each of which is incorporated herein by reference in their entirety.

The methods of the invention further allow for the development of herbicide combinations to be used in with the glyphosate/ALS inhibitor-tolerant plants. In such methods, the environmental conditions in an area of cultivation are evaluated. Environmental conditions that can be evaluated include, but are not limited to, ground and surface water pollution concerns, intended use of the crop, crop tolerance, soil residuals, weeds present in area of cultivation, soil texture, pH of soil, amount of organic matter in soil, application equipment, and tillage practices. Upon the evaluation of the environmental conditions, an effective amount of a combination of herbicides can be applied to the crop, crop part, seed of the crop or area of cultivation.

d. Timing of Herbicide Application

In some embodiments, the herbicide applied to the glyphosate/ALS inhibitor-tolerant plants of the invention serves to prevent the initiation of growth of susceptible weeds and/or serve to cause damage to weeds that are growing in the area of interest. In some embodiments, the herbicide or herbicide mixture exert these effects on weeds affecting crops that are subsequently planted in the area of interest (i.e., field or area of cultivation). In the methods of the invention, the application of the herbicide combination need not occur at the same time. So long as the field in which the crop is planted contains detectable amounts of the first herbicide and the second herbicide is applied at some time during the period in which the crop is in the area of cultivation, the crop is considered to have been treated with a mixture of herbicides according to the invention. Thus, methods of the invention encompass applications of herbicide which are "preemergent," "postemergent," "preplant incorporation" and/or which involve seed treatment prior to planting.

In one embodiment, methods are provided for coating seeds. The methods comprise coating a seed with an effective amount of a herbicide or a combination of herbicides (as disclosed elsewhere herein). The seeds can then be planted in an area of cultivation. Further provided are seeds having a coating comprising an effective amount of a herbicide or a combination of herbicides (as disclosed elsewhere herein).

"Preemergent" refers to a herbicide which is applied to an area of interest (e.g., a field or area of cultivation) before a plant emerges visibly from the soil. "Postemergent" refers to a herbicide which is applied to an area after a plant emerges visibly from the soil. In some instances, the terms "preemergent" and "postemergent" are used with reference to a weed in an area of interest, and in some instances these terms are used with reference to a crop plant in an area of interest. When used with reference to a weed, these terms may apply to only a particular type of weed or species of weed that is present or believed to be present in the area of interest. While any herbicide may be applied in a preemergent and/or postemergent treatment, some herbicides are known to be more effective in controlling a weed or weeds when applied either preemergence or postemergence. For example, rimsulfuron has both preemergence and postemergence activity, while other herbicides have predominately preemergence (metolachlor) or postemergence (glyphosate) activity. These properties of particular herbicides are known in the art and are readily determined by one of skill in the art. Further, one of skill in the art would readily be able to select appropriate herbicides and application times for use with the transgenic plants of the invention and/or on areas in which transgenic plants of the invention are to be planted. "Preplant incorporation" involves the incorporation of compounds into the soil prior to planting.

Thus, the invention provides improved methods of growing a crop and/or controlling weeds such as, for example, "pre-planting burn down," wherein an area is treated with herbicides prior to planting the crop of interest in order to better control weeds. The invention also provides methods of growing a crop and/or controlling weeds which are "no-till" or "low-till" (also referred to as "reduced tillage"). In such methods, the soil is not cultivated or is cultivated less frequently during the growing cycle in comparison to traditional methods; these methods can save costs that would otherwise be incurred due to additional cultivation, including labor and fuel costs.

The methods of the invention encompass the use of simultaneous and/or sequential applications of multiple classes of herbicides. In some embodiments, the methods of the invention involve treating a plant of the invention and/or an area of interest (e.g., a field or area of cultivation) and/or weed with just one herbicide or other chemical such as, for example, a sulfonylurea herbicide.

The time at which a herbicide is applied to an area of interest (and any plants therein) may be important in optimizing weed control. The time at which a herbicide is applied may be determined with reference to the size of plants and/or the stage of growth and/or development of plants in the area of interest, e.g., crop plants or weeds growing in the area. The stages of growth and/or development of plants are known in the art. For example, soybean plants normally progress through vegetative growth stages known as $V_E$ (emergence), $V_C$ (cotyledon), $V_1$ (unifoliate), and $V_2$ to $V_N$. Soybeans then switch to the reproductive growth phase in response to photoperiod cues; reproductive stages include $R_1$ (beginning bloom), $R_2$ (full bloom), $R_3$ (beginning pod), $R_4$ (full pod), $R_5$ (beginning seed), $R_6$ (full seed), $R_7$ (beginning maturity), and $R_8$ (full maturity). Corn plants normally progress through the following vegetative stages VE (emergence); V1 (first leaf); V2 (second leaf); V3 (third leaf); V(n) (Nth/leaf); and VT (tasseling). Progression of maize through the reproductive phase is as follows: R1 (silking); R2 (blistering); R3 (milk); R4 (dough); R5 (dent); and R6 (physiological maturity). Cotton plants normally progress through $V_E$ (emergence), $V_C$ (cotyledon), $V_1$ (first true leaf), and $V_2$ to $V_N$. Then, reproductive stages beginning around $V_{14}$ include $R_1$ (beginning bloom), $R_2$ (full bloom), $R_3$ (beginning boll), $R_4$ (cutout, boll development), $R_5$ (beginning maturity, first opened boll), $R_6$ (maturity, 50% opened boll), and $R_7$ (full maturity, 80-90% open bolls). Thus, for example, the time at which a herbicide or other chemical is applied to an area of interest in which plants are growing may be the time at which some or all of the plants in a particular area have reached at least a particular size and/or stage of growth and/or development, or the time at which some or all of the plants in a particular area have not yet reached a particular size and/or stage of growth and/or development.

In some embodiments, the glyphosate/ALS inhibitor-tolerant plants of the invention show improved tolerance to postemergence herbicide treatments. For example, plants of the invention may be tolerant to higher doses of herbicide, tolerant to a broader range of herbicides (i.e., tolerance to more ALS inhibitor chemistries), and/or may be tolerant to doses of herbicide applied at earlier or later times of development in comparison to an appropriate control plant. For example, in some embodiments, the glyphosate/ALS inhibitor-tolerant plants of the invention show an increased resistance to morphological defects that are known to result from treatment at particular stages of development. Thus, for example, a phenomenon known as "ear pinch" often results when maize plants are treated with herbicide at a stage later than V5, V6, V7, V8, V9, V10, V11, V12, V13, or a later stage, whereas the glyphosate/ALS inhibitor-tolerant plants of the invention show a decreased incidence of "ear pinch" when treated at the same stage. Thus, the glyphosate/ALS inhibitor-tolerant plants of the invention find use in methods involving herbicide treatments at later stages of development than were previously feasible. Thus, plants of the invention may be treated with a particular herbicide that causes morphological defects in a control plant treated at the same stage of development, but the glyphosate/ALS inhibitor-tolerant plants of the invention will not be significantly damaged by the same treatment.

Different chemicals such as herbicides have different "residual" effects, i.e., different amounts of time for which treatment with the chemical or herbicide continues to have an effect on plants growing in the treated area. Such effects may be desirable or undesirable, depending on the desired future purpose of the treated area (e.g., field or area of cultivation). Thus, a crop rotation scheme may be chosen based on residual effects from treatments that will be used for each crop and their effect on the crop that will subsequently be grown in the same area. One of skill in the art is familiar with techniques that can be used to evaluate the residual effect of a herbicide; for example, generally, glyphosate has very little or no soil residual activity, while herbicides that act to inhibit ALS vary in their residual activity levels. Residual activities for various herbicides are known in the art, and are also known to vary with various environmental factors such as, for example, soil moisture levels, temperature, pH, and soil composition (texture and organic matter). The glyphosate/ALS inhibitor-tolerant plants of the invention find particular use in methods of growing a crop where improved tolerance to residual activity of a herbicide is beneficial.

For example, in one embodiment, the glyphosate/ALS inhibitor-tolerant plants of the invention have an improved tolerance to glyphosate as well as to ALS inhibitor chemistries (such as sulfonylurea herbicides) when applied individually, and further provide improved tolerance to combinations of herbicides such as glyphosate and/or ALS inhibitor chemistries. Moreover, the transgenic plants of the invention provide improved tolerance to treatment with additional chemicals commonly used on crops in conjunction with herbicide treatments, such as safeners, adjuvants such as ammonium sulfonate and crop oil concentrate, and the like.

e. Safeners and Adjuvants

The term "safener" refers to a substance that when added to a herbicide formulation eliminates or reduces the phytotoxic effects of the herbicide to certain crops. One of ordinary skill in the art would appreciate that the choice of safener depends, in part, on the crop plant of interest and the particular herbicide or combination of herbicides included in the synergistic herbicide composition. Exemplary safeners suitable for use with the presently disclosed herbicide compositions include, but are not limited to, those disclosed in U.S. Pat. Nos. 4,808,208; 5,502,025; 6,124,240 and U.S. Patent Application Publication Nos. 2006/0148647; 2006/0030485; 2005/0233904; 2005/0049145; 2004/0224849; 2004/0224848; 2004/0224844; 2004/0157737; 2004/0018940; 2003/0171220; 2003/0130120; 2003/0078167, the disclosures of which are incorporated herein by reference in their entirety. The methods of the invention can involve the use of herbicides in combination with herbicide safeners such as benoxacor, BCS (1-bromo-4-[(chloromethyl)sulfonyl]benzene), cloquintocet-mexyl, cyometrinil, dichlormid, 2-(dichloromethyl)-2-methyl-1,3-dioxolane (MG 191), fenchlorazole-ethyl, fenclorim, flurazole, fluxofenim, furilazole, isoxadifen-ethyl, mefenpyr-diethyl, methoxyphenone ((4-methoxy-3-methylphenyl)(3-methylphenyl)-methanone), naphthalic anhydride (1,8-naphthalic anhydride) and oxabetrinil to increase crop safety. Antidotally effective amounts of the herbicide safeners can be applied at the same time as the compounds of this invention, or applied as seed treatments. Therefore an aspect of the present invention relates to the use of a mixture comprising glyphosate, at least one other herbicide, and an antidotally effective amount of a herbicide safener.

Seed treatment is particularly useful for selective weed control, because it physically restricts antidoting to the crop plants. Therefore a particularly useful embodiment of the present invention is a method for selectively controlling the growth of weeds in a field comprising treating the seed from which the crop is grown with an antidotally effective amount of safener and treating the field with an effective amount of herbicide to control weeds. Antidotally effective amounts of safeners can be easily determined by one skilled in the art through simple experimentation. An antidotally effective amount of a safener is present where a desired plant is treated with the safener so that the effect of a herbicide on the plant is decreased in comparison to the effect of the herbicide on a plant that was not treated with the safener; generally, an antidotally effective amount of safener prevents damage or severe damage to the plant treated with the safener. One of skill in the art is capable of determining whether the use of a safener is appropriate and determining the dose at which a safener should be administered to a crop.

In specific embodiments, the herbicide or herbicide combination applied to the plant of the invention acts as a safener. In this embodiment, a first herbicide or a herbicide mixture is applied at an antidotally effect amount to the plant. Accordingly, a method for controlling weeds in an area of cultivation is provided. The method comprises planting the area with crop seeds or plants which comprise a first polynucleotide encoding a polypeptide that can confer tolerance to glyphosate operably linked to a promoter active in a plant; and, a second polynucleotide encoding an ALS inhibitor-tolerant polypeptide operably linked to a promoter active in a plant. A combination of herbicides comprising at least an effective amount of a first and a second herbicide is applied to the crop, crop part, weed or area of cultivation thereof. The effective amount of the herbicide combination controls weeds; and, the effective amount of the first herbicide is not tolerated by the crop when applied alone when compared to a control crop that has not been exposed to the first herbicide; and, the effective amount of the second herbicide is sufficient to produce a safening effect, wherein the safening effect provides an increase in crop tolerance upon the application of the first and the second herbicide when compared to the crop tolerance when the first herbicide is applied alone.

In specific embodiments, the combination of safening herbicides comprises a first ALS inhibitor and a second ALS inhibitor. In other embodiments, the safening effect is achieved by applying an effective amount of a combination of glyphosate and at least one ALS inhibitor chemistry. In still other embodiments, a safening affect is achieved when the glyphosate/ALS inhibitor-tolerant crops, crop part, crop seed, weed, or area of cultivation is treated with at least one herbicide from the sulfonylurea family of chemistries in combination with at least one herbicide from the ALS family of chemistries (such as, for example, an imidazolinone).

Such mixtures provides increased crop tolerance (i.e., a decrease in herbicidal injury). This method allows for increased application rates of the chemistries post or pre-treatment. Such methods find use for increased control of unwanted or undesired vegetation. In still other embodiments, a safening affect is achieved when the glyphosate/ALS inhibitor-tolerant crops, crop part, crop seed, weed, or area of cultivation is treated with at least one herbicide from the sulfonylurea family of chemistry in combination with at least one herbicide from the imidazolinone family. This method provides increased crop tolerance (i.e., a decrease in herbicidal injury). In specific embodiments, the sulfonylurea comprises rimsulfuron and the imidazolinone comprises imazethapyr. In other embodiments, glyphosate is also applied to the crop, crop part, or area of cultivation.

As used herein, an "adjuvant" is any material added to a spray solution or formulation to modify the action of an agricultural chemical or the physical properties of the spray solution. See, for example, Green and Foy (2003) "Adjuvants: Tools for Enhancing Herbicide Performance," in *Weed Biology and Management*, ed. Inderjit (Kluwer Academic Publishers, The Netherlands). Adjuvants can be categorized or subclassified as activators, acidifiers, buffers, additives, adherents, antiflocculants, antifoamers, defoamers, antifreezes, attractants, basic blends, chelating agents, cleaners, colorants or dyes, compatibility agents, cosolvents, couplers, crop oil concentrates, deposition agents, detergents, dispersants, drift control agents, emulsifiers, evaporation reducers, extenders, fertilizers, foam markers, formulants, inerts, humectants, methylated seed oils, high load COCs, polymers, modified vegetable oils, penetrators, repellants, petroleum oil concentrates, preservatives, rainfast agents, retention aids, solubilizers, surfactants, spreaders, stickers, spreader stickers, synergists, thickeners, translocation aids, uv protectants, vegetable oils, water conditioners, and wetting agents.

f. Additional Agricultural Chemicals

In addition, methods of the invention can comprise the use of a herbicide or a mixture of herbicides, as well as, one or more other insecticides, fungicides, nematocides, bactericides, acaricides, growth regulators, chemosterilants, semiochemicals, repellents, attractants, pheromones, feeding stimulants or other biologically active compounds or entomopathogenic bacteria, virus, or fungi to form a multi-component mixture giving an even broader spectrum of agricultural protection. Examples of such agricultural protectants which can be used in methods of the invention include: insecticides such as abamectin, acephate, acetamiprid, amidoflumet (S-1955), avermectin, azadirachtin, azinphos-methyl, bifenthrin, bifenazate, buprofezin, carbofuran, cartap, chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyriprole, pyriproxyfen, rotenone, ryanodine, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron; fungicides such as fungicides such as acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazole, iprobenfos, iprodione, iprovalicarb, isoconazole, isoprothiolane, kasugamycin, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neo-aszoin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pryazophos, pyrifenox, pyrimethanil, pyrifenox, pyrolnitrine, pyroquilon, quinconazole, quinoxyfen, quintozene, silthiofam, simeconazole, spiroxamine, streptomycin, sulfur, tebuconazole, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, triticonazole, uniconazole, validamycin, vinclozolin, zineb, ziram, and zoxamide; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *Aizawai, Bacillus thuringiensis* subsp. *Kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV. The weight ratios of these various mixing partners to other compositions (e.g., herbicides) used in the methods of the invention typically are between 100:1 and 1:100, or between 30:1 and 1:30, between 10:1 and 1:10, or between 4:1 and 1:4.

The present invention also pertains to a composition comprising a biologically effective amount of a herbicide of interest or a mixture of herbicides, and an effective amount of at least one additional biologically active compound or agent and can further comprise at least one of a surfactant, a solid diluent or a liquid diluent. Examples of such biologically active compounds or agents are: insecticides such as abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenyl-amino)-4H-imidazol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), flumorf/flumorlin (SYP-L190), fluoxastrobin (HEC 5725), fluquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metomino-strobin/fenominostrobin (SSF-126), metrafenone (AC375839), myclobutanil, neoasozin (ferric methane-arsonate), nicobifen (BAS 510), orysastrobin, oxadixyl, penconazole, pencycuron, probenazole, prochloraz, propamocarb, propiconazole, proquinazid (DPX-KQ926), prothioconazole (JAU 6476), pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *Aizawai, Bacillus thuringiensis* subsp. *Kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV. Methods of the invention may also comprise the use of plants genetically transformed to express proteins toxic to invertebrate pests (such as *Bacillus thuringiensis* delta-endotoxins). In such embodiments, the effect of exogenously applied invertebrate pest control compounds may be synergistic with the expressed toxin proteins.

General references for these agricultural protectants include *The Pesticide Manual, 13th Edition*, C. D. S. Tomlin, Ed., British Crop Protection Council, Farnham, Surrey, U.K., 2003 and *The BioPesticide Manual, $2^{nd}$ Edition*, L. G. Copping, Ed., British Crop Protection Council, Farnham, Surrey, U.K., 2001.

In certain instances, combinations with other invertebrate pest control compounds or agents having a similar spectrum of control but a different mode of action will be particularly advantageous for resistance management. Thus, compositions of the present invention can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound of this invention can also provide a broader spectrum of plant protection and be advantageous for resistance management.

Thus, methods of the invention employ a herbicide or herbicide combination and may further comprise the use of insecticides and/or fungicides, and/or other agricultural chemicals such as fertilizers. The use of such combined treatments of the invention can broaden the spectrum of activity against additional weed species and suppress the proliferation of any resistant biotypes.

Methods of the invention can further comprise the use of plant growth regulators such as aviglycine, N-(phenylmethyl)-1H-purin-6-amine, ethephon, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

VI. Use as Selectable Markers and Methods of Transformation

In some embodiments of the invention, a construct of the invention comprising a GAT polynucleotide or an ALS inhibitor-tolerant polypeptide functions as a selectable marker, e.g., in a plant, bacteria, actinomycete, yeast, algae or other fungi. For example, an organism that has been transformed with a vector including a GAT polynucleotide can be selected based on its ability to grow in the presence of glyphosate. Alternatively, an organism that has been transformed with a vector comprising an ALS-inhibitor-tolerant polynucleotide can be selected based on its ability to grown in the presence of an ALS inhibitor. In some embodiments of the invention, a construct of the invention comprising a GAT polynucleotide and another herbicide-tolerance polynucleotide (i.e., an polynucleotide encoding an ALS inhibitor-tolerant polypeptide, a polynucleotide encoding an HRA polypeptide, etc.) functions as a selectable marker, e.g., in a plant, bacteria, actinomycete, yeast, algae or other fungi. For example, an organism that has been transformed with a vector including a GAT polynucleotide and another herbicide-tolerance polynucleotide can be selected based on its ability to grow in the presence of glyphosate and the appropriate other herbicide. As demonstrated in Example 10 and FIG. 7, such methods of selection allow one to evaluate expression of any polynucleotide of interest at, for example, early stages in the transformation process in order to identify potential problems with expression. While any polynucleotide of interest can be employed, in specific embodiments, an insecticidal gene is used.

A construct of the invention comprising a GAT polynucleotide and/or a polynucleotide encoding an ALS inhibitor-tolerant polypeptide may exhibit a very high transformation efficiency, such as an efficiency of at least 20%, 30%, 40%, 50%, or 60% or higher. In this manner, improved methods of transformation are provided. Moreover, when a construct of the invention comprises a GAT polynucleotide and/or ALS inhibitor-tolerant polynucleotide, the transformants that are obtained may exhibit a very high frequency of tolerance to glyphosate or ALS inhibitor, so that, for example, at least 20%, 30%, 40%, 50%, 60%, 70%, 80%, 90%, or 100% of the transformants are tolerant to glyphosate and/or an ALS inhibitor. As used herein "transformation efficacy" is defined as the percentage of the T0 events that were resistant to a specific concentration of selection agent, such as glyphosate and/or an ALS inhibitor chemistry. When a construct of the invention comprises a GAT polynucleotide and/or ALS inhibitor-tolerant polynucleotide operably linked to an enhancer such as, for example, a 35S enhancer, the transformants that are obtained may exhibit a very high frequency of tolerance to glyphosate and/or ALS inhibitor, so that for example, at least 20%, 30%, 40%, 50%, 60%, 70%, 80%, 90%, or 100% of the transformants are tolerant to glyphosate or ALS inhibitor. In addition, when a construct of the invention comprises a GAT polynucleotide and/or an ALS inhibitor-tolerant polynucleotide, the frequency of transformation events in which only a single copy of the construct is inserted into the genome may be as high as at least 35%, 40%, 50%, 60%, 70%, 80%, 90%, or higher. When a construct of the invention comprises a GAT polynucleotide and/or ALS inhibitor-tolerant polynucleotide operably linked to an enhancer such as, for example, a 35S enhancer, the frequency of transformation events in which only a single copy of the construct is inserted into the genome may be as high as at least 35%, 40%, 50%, 60%, 70%, 80%, 90%, or higher. In this manner, the invention also provides improved methods of transformation. It is recognized that when an enhancer is employed in the construct (such as $S^{35}$ enhancer) multiple copies could be used, including 1, 2, 3, 4, 5, 6 or more. In such methods, the transformants may be selected using glyphosate and/or an ALS inhibitor, or they may be selected using another compound, such as another herbicide for which the transformed construct contains a tolerance trait.

VII. Kits

The invention further provides a kit comprising at least one nucleic acid construct which comprises a polynucleotide which encodes a polypeptide that can confer glyphosate tolerance and/or a polynucleotide encoding an ALS inhibitor-tolerant polypeptide for use in creating a glyphosate/ALS inhibitor plant of the invention. In specific embodiments, the kit can comprise a polynucleotide encoding GAT or the kit can comprise a polynucleotide encoding GAT and a polynucleotide encoding an ALS inhibitor-tolerant polynucleotide (i.e., HRA). In some aspects a construct of the invention will comprise a T-DNA sequence. The construct can optionally include a regulatory sequence (e.g., a promoter) operably linked to the polynucleotide conferring glyphosate resistance, where the promoter is heterologous with respect to the polynucleotide and effective to cause sufficient expression of the encoded polypeptide to enhance the glyphosate tolerance of a plant cell transformed with the nucleic acid construct.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

EXPERIMENTAL

Example 1

GAT-HRA Maize Plants are Tolerant of Various Herbicides and Agricultural Chemicals For *Agrobacterium*-mediated transformation of maize with an expression cassette containing a GAT polynucleotide (SEQ ID NO:4) and an HRA polynucleotide (SEQ ID NO:66) operably linked to a constitutive promoter, the method of Zhao is employed (U.S. Pat. No. 5,981,840, and PCT patent publication WO98/32326; the contents of which are hereby incorporated by reference). Expression cassettes were made that comprised a GAT polynucleotide and an HRA polynucleotide. In some expression cassettes, the GAT and HRA polynucleotides were operably linked to at least one copy of a 35S enhancer [SEQ ID NO:72]. In some expression cassettes, the GAT and HRA polynucleotides were operably linked to two or three copies of the 35S enhancer of SEQ ID NO:1. In some expression cassettes, the GAT polynucleotide was operably linked to a ubiquitin promoter and the HRA polynucleotide was operably linked to the native maize acetolactate synthase (ALS) promoter.

Briefly, immature embryos are isolated from maize and the embryos contacted with a suspension of *Agrobacterium*, where the bacteria are capable of transferring the GAT and HRA sequence to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

Evaluation of Herbicide Tolerance

GAT-HRA maize plants were evaluated for tolerance to glyphosate and other herbicides. One protocol used in this evaluation was as follows. At the V2 stage (Ritchie and Hanway (1982), "How a corn plant develops" *Spec. Rep.* 48. (Coop. Ext. Ser., Iowa State Univ., Ames, Iowa)), plant heights were measured and herbicides were applied by spray application. Ten to fourteen days after the spray application, the transgenic plants were evaluated for injury symptoms and measured for plant height again in order to determine plant growth rates. In one series of tests, GAT-HRA maize and control plants were treated (postemergence) with one of the following herbicides: tribenuron (as Express®, at application rates of 0 and 200 grams active ingredient per hectare (g ai/ha)); chlorimuron (as Classic®, at 0 and 200 g ai/ha); imazapyr (as Arsenal®, at 0 and 200 g ai/ha); metsulfuron-methyl (as Ally®, at 0.5 oz ai/ac (36.9 ml ai/ha) or 35 g ai/ha). For each treatment, the GAT-HRA maize showed no significant damage from the treatment, while the control maize was severely damaged or killed.

GAT-HRA maize plants were also treated with various other herbicides and combinations of herbicides as well as other agricultural chemicals, including: glyphosate (as WeatherMax®, at an application rate of 64.4 oz ai/ac (4.7 L ai/ha)); rimsulfuron (as Matrix®, at an application rate of 1.9 oz ai/ac (140 ml ai/ha)); sulfometuron-methyl (as Oust®, at an application rate of 4.5 oz ai/ac (332 ml ai/ha)); Basis® (a combination of rimsulfuron and thifensulfuron-methyl, at an application rate of 1.4 oz ai/ac (103 ml ai/ha)); and chlorpyrifos (as Lorsban®, at an application rate of 14.4 oz ai/ac (1.06 L ai/ha)). Plants were then evaluated at various times after treatment, such as 10 or 14 days after treatment. Tolerant plants were those which showed little or no damage following treatment with a herbicide or herbicide combination. This evaluation identified GAT-HRA plants which were tolerant to multiple sulfonylurea and glyphosate chemistries. GAT-HRA plants did not exhibit any significant differences in growth or seed set (i.e., yield) in comparison to control plants. Leaf samples were taken from GAT-HRA plants and used in quantitative PCR analysis and other analyses to determine the number and arrangement of copies of the GAT and HRA polynucleotides that had been integrated into the plant genome.

Other protocols for evaluation included treatment with imidazolinone herbicides, such as the commercial herbicide Lightning® (a combination of imazapyr and imazethapyr), which was applied to GAT-HRA maize at the V2 leaf stage at four times the field label rate (250 g ai/ha). Plants were evaluated fourteen days after the herbicide application, and four of the six transgenic events tested showed no symptoms of injury from the herbicide. Another protocol for evaluation included treatment with imidazolinone herbicides as well as sulfonylurea and glyphosate herbicides. In these tests, GAT-HRA maize was treated with various combinations of Lightning® (imazapyr and imazethapyr), Basis® (rimsulfuron and thifensulfuron-methyl) and WeatherMAX® (glyphosate potassium salt). These herbicides were applied at the V2 stage as follows: Lightning® at twice the field label rate (1.8 oz ai/ac (133 ml ai/ha)), Basis® at twice the field label rate (0.5 oz ai/ac (36.9 ml ai/ha)) and WeatherMax® at four times the field label rate (43 oz ai/ac). Fourteen days after the treatment application, the plants were evaluated. Plants containing eleven of the twelve transgenic events showed no herbicide injury symptoms. "Field label rate" refers to the application rate specified on the product label. Where the application rate for a particular situation is a range of rates, as used herein, the term "field label rate" indicates the upper end of that range. Product label information for pesticides is available from the U.S. Environmental Protection Agency and is updated online at the url oaspub.epa.gov/pestlabl/ppls.own; product label information is also available online at the url www.cdms.net.

Further tests confirmed that the multiple herbicide tolerance of these GAT-HRA maize plants was stably inherited. T1 seed was harvested from 20 transgenic T0 plants that showed excellent herbicide tolerance in greenhouse evaluations. As is known in the art, the tolerance of plants to herbicide can vary with the environment, and herbicide treatments in a greenhouse environment can have a greater impact on treated plants than herbicide treatments in the field. Accordingly, the T1 seed was further evaluated under field conditions. T1 plants were sprayed at the V4 leaf stage with four different herbicide treatment combinations including sulfonylurea and glyphosate herbicides. In some tests, a transgenic control line was used that was known to be tolerant of glyphosate but susceptible to other herbicides. The tested T1 plants also showed excellent herbicide tolerance under field conditions, confirming the stable inheritance of the herbicide tolerance.

Evaluation of Tolerance to Range of Herbicides

GAT-HRA maize plants were then evaluated to determine whether they were also tolerant to other herbicides. A test of both preemergent and postemergent herbicide application was conducted. Specifically, seven corn seeds of each line to be evaluated were planted 1 cm deep in 5.5 inch square plastic containers of Tama silt loam soil. Treatments described in Tables 3 and 4 were applied before any watering. A week after emergence, seedlings were thinned so that each container had two uniform plants. Corn seedlings were watered and fertilized for rapid growth and grown with a 16-h light photoperiod. When the natural light intensity fell below 500 $\mu E/m^2/s$, it was supplemented by metal halide lights with 160 $\mu E/m^2/s$ photosynthetically active radiation. Temperature was maintained at 28±2° C. during the day and 22±2° C. at night. Relative humidity generally ranged from 50 to 90%.

The studies of preemergence herbicide application used commercial herbicide formulations. Spray mixtures were prepared using deionized water at room temperature and were stirred for at least 15 minutes. Treatments were sprayed 1 to 2 h after preparation. All treatments were applied in a spray volume of 374 L/ha with a flat fan nozzle at 51 cm with spray pressure set at 138 kPa with a high pH, basic blend adjuvant to ensure solubilization. Plants were visually evaluated for injury and fresh shoots were weighed 4 weeks after treatment (results shown in Table 1). Crop injury was also estimated visually on a scale ranging from 0% to 100%, where 0% signifies no injury and 100% signifies plant death. Results are shown in Table 3 and are expressed as the mean of four replications.

TABLE 3

Preemergence Effect of 34 ALS Herbicides on Fresh Weight of GAT-HRA and Parent Inbred Corn

| ALS Inhibitor Class | Herbicide Treatment* | patent elite stiff stalk inbred Fresh Weight (g) | Heterozygous GAT-HRA Fresh Weight (g) |
|---|---|---|---|
| Untreated | | 36.7 | 47.0 |
| Imidazolinone | 200 g/ha Imazamethabenz-methyl | 36.2 | 48.5 |
| | 200 g/ha Imazethapyr | 24.4 | 50.0 |
| | 200 g/ha Imazamox | 0.8 | 47.5 |
| | 200 g/ha Imazapyr | 0.3 | 44.2 |
| | 200 g/ha Imazaquin | 1.5 | 45.4 |
| Pyrimidinylthiobenzoate | 200 g/ha Pyriminobac methyl | 30.4 | 39.9 |
| | 200 g/ha Pyrithiobac Na$^+$ | 0.0 | 48.6 |
| Sulfonylaminocarbonyltriazolinone | 200 g/ha Flucarbazone Na$^+$ | 0.0 | 48.8 |
| | 200 g/ha Propoxycarbazone Na$^+$ | 0.6 | 46.7 |
| Sulfonylurea | 200 g/ha Amidosulfuron | 14.2 | 47.7 |
| | 200 g/ha Azimsulfuron | 0.0 | 49.1 |
| | 200 g/ha Bensulfuron-methyl | 28.4 | 39.9 |
| | 200 g/ha Chlorimuron-ethyl | 9.3 | 39.4 |
| | 200 g/ha Chlorsulfuron | 0.0 | 48.4 |
| | 200 g/ha Ethametsulfuron-methyl | 1.6 | 50.1 |
| | 200 g/ha Ethoxysulfuron | 28.1 | 40.0 |
| | 200 g/ha Flupyrsulfuron-methyl Na$^+$ | 23.6 | 45.8 |
| | 200 g/ha Foramsulfuron | 30.6 | 39.1 |
| | 200 g/ha Halosulfuron-methyl | 28.9 | 40.1 |
| | 200 g/ha Iodosulfuron-methyl Na$^+$ | 24.4 | 52.5 |
| | 200 g/ha Metsulfuron-methyl | 0.0 | 41.1 |
| | 200 g/ha Nicosulfuron | 33.6 | 50.3 |
| | 200 g/ha Primisulfuron-methyl | 19.5 | 37.9 |
| | 200 g/ha Prosulfuron | 20.9 | 43.3 |
| | 200 g/ha Rimsulfuron | 29.8 | 45.3 |
| | 200 g/ha Sulfometuron-methyl | 0.0 | 47.3 |
| | 200 g/ha Sulfosulfuron | 1.0 | 50.6 |
| | 200 g/ha Thifensulfuron-methyl | 15.2 | 36.0 |
| | 200 g/ha Triasulfuron | 14.1 | 47.7 |
| | 200 g/ha Tribenuron-methyl | 32.1 | 46.8 |
| | 200 g/ha Trifloxysulfuron Na$^+$ | 0.0 | 50.8 |
| | 200 g/ha Triflusulfuron-methyl | 26.3 | 53.5 |
| Triazolopyrimidine | 200 g/ha Chloransulam-methyl | 5.5 | 44.9 |
| | 200 g/ha Flumetsulam | 24.6 | 39.1 |

TABLE 4

Preemergence Effect of 34 ALS Herbicides on Visual Injury to GAT-HRA and Parent Inbred Corn

| ALS Class | Herbicide Treatment* | Patent elite stiff stalk inbred % Visual Injury | Heterozygous GAT-HRA % Visual Injury |
|---|---|---|---|
| Imidazolinone | 200 g/ha Imazamethabenz-methyl | 61 | 15 |
| | 200 g/ha Imazethapyr | 69 | 20 |
| | 200 g/ha Imazamox | 99 | 13 |
| | 200 g/ha Imazapyr | 99 | 30 |
| | 200 g/ha Imazaquin | 99 | 28 |
| Pyrimidinylthiobenzoate | 200 g/ha Pyriminobac-methyl | 83 | 20 |
| | 200 g/ha Pyrithiobac Na$^+$ | 100 | 0 |
| Sulfonylaminocarbonyltriazolinone | 200 g/ha Flucarbazone Na$^+$ | 100 | 40 |
| | 200 g/ha Propoxycarbazone Na$^+$ | 100 | 100 |
| Sulfonylurea | 200 g/ha Amidosulfuron | 97 | 25 |
| | 200 g/ha Azimsulfuron | 100 | 40 |
| | 200 g/ha Bensulfuron-methyl | 23 | 10 |
| | 200 g/ha Chlorimuron-ethyl | 100 | 10 |
| | 200 g/ha Chlorsulfuron | 100 | 33 |
| | 200 g/ha Ethametsulfuron-methyl | 100 | 88 |
| | 200 g/ha Ethoxysulfuron | 63 | 25 |
| | 200 g/ha Flupyrsulfuron-methyl Na$^+$ | 87 | 90 |
| | 200 g/ha Foramsulfuron | 5 | 7 |
| | 200 g/ha Halosulfuron-methyl | 30 | 15 |
| | 200 g/ha Iodosulfuron-methyl Na$^+$ | 92 | 5 |

TABLE 4-continued

Preemergence Effect of 34 ALS Herbicides on Visual Injury to GAT-HRA and Parent Inbred Corn

| ALS Class | Herbicide Treatment* | Patent elite stiff stalk inbred % Visual Injury | Heterozygous GAT-HRA |
|---|---|---|---|
| | 200 g/ha Metsulfuron-methyl | 100 | 0 |
| | 200 g/ha Nicosulfuron | 43 | 0 |
| | 200 g/ha Primisulfuron-methyl | 68 | 7 |
| | 200 g/ha Prosulfuron | 68 | 9 |
| | 200 g/ha Rimsulfuron | 74 | 0 |
| | 200 g/ha Sulfometuron-methyl | 100 | 6 |
| | 200 g/ha Sulfosulfuron | 100 | 18 |
| | 200 g/ha Thifensulfuron-methyl | 88 | 3 |
| | 200 g/ha Triasulfuron | 89 | 12 |
| | 200 g/ha Tribenuron-methyl | 66 | 25 |
| | 200 g/ha Trifloxysulfuron Na$^+$ | 100 | 0 |
| | 200 g/ha Triflusulfuron-methyl | 100 | 5 |
| Triazolopyrimidine | 200 g/ha Chloransulam-methyl | 3 | 3 |
| | 200 g/ha Flumetsulam | 13 | 13 |

The studies of postemergence herbicide application also used commercial herbicide formulations. Specifically, four corn seeds of each line to be evaluated were planted 1 cm deep in 5.5 inch square plastic containers of synthetic growth medium. Very young transgenic seedlings were pretreated with glyphosate to eliminate segregants which were sensitive to glyphosate. Plants injured by the glyphosate treatment were removed and containers were thinned to two uniform plants each. Extra containers were planted so that only containers with two uniform and uninjured plants were used in the experiment. Corn seedlings were watered and fertilized for rapid growth and grown with a 16-h light photoperiod. When the natural light intensity fell below 500 $\mu E/m^2/s$, it was supplemented by metal halide lights with 160 $\mu E/m^2/s$ photosynthetically active radiation. Temperature was maintained at 28±2° C. during the day and 22±2° C. at night. Relative humidity generally ranged from 50 to 90%.

Postemergence studies used commercial herbicide formulations and were applied two weeks after planting. Spray mixtures of herbicides were prepared using deionized water at room temperature and were stirred for at least 15 minutes. Treatments were sprayed 1 to 2 h after preparation. All ALS herbicide treatments were applied in a spray volume of 374 L/ha with a flat fan nozzle at 51 cm with spray pressure set at 138 kPa and included a high pH, basic blend adjuvant to ensure solubilization and foliar penetration. Glyphosate and glufosinate herbicide preparations included adjuvant systems in their commercial formulations to ensure high foliar activity. Fresh shoots were weighed 2 weeks after treatment (data shown in Table 5), and plants were visually evaluated for injury on a scale from 0% to 100% on which 0% indicates no injury and 100% indicates plant death (data shown in Table 6). Results are expressed in Tables 5 and 6 as the mean of four replications.

TABLE 5

Postemergence Effect of 34 ALS Herbicides on Fresh Weight of GAT-HRA and Parent Inbred Corn

| ALS Class | Herbicide Treatment* | Parent elite stiff stalk inbred Fresh Weight (g) | Heterozygous GAT-HRA |
|---|---|---|---|
| Untreated | | 76.4 | 98.8 |
| Imidazolinone | 200 g/ha Imazamethabenz-methyl | 66.9 | 95.0 |
| | 200 g/ha Imazethapyr | 6.4 | 93.4 |
| | 200 g/ha Imazamox | 2.2 | 90.9 |
| | 200 g/ha Imazapyr | 2.3 | 97.8 |
| | 200 g/ha Imazaquin | 4.4 | 113.3 |
| Pyrimidinylthiobenzoate | 200 g/ha Pyriminobac-methyl | 7.6 | 95.2 |
| | 200 g/ha Pyrithiobac Na$^+$ | 2.8 | 87.9 |
| Sulfonylaminocarbonyltriazolinone | 200 g/ha Flucarbazone Na$^+$ | 3.1 | 86.0 |
| | 200 g/ha Propoxycarbazone Na$^+$ | 1.9 | 101.2 |
| Sulfonylurea | 200 g/ha Amidosulfuron | 32.0 | 107.4 |
| | 200 g/ha Azimsulfuron | 1.5 | 87.9 |
| | 200 g/ha Bensulfuron-methyl | 9.0 | 103.3 |
| | 200 g/ha Chlorimuron-ethyl | 10.1 | 95.5 |
| | 200 g/ha Chlorsulfuron | 1.7 | 105.2 |
| | 200 g/ha Ethametsulfuron-methyl | 5.6 | 98.0 |
| | 200 g/ha Ethoxysulfuron | 24.3 | 79.3 |
| | 200 g/ha Flupyrsulfuron-methyl | 5.2 | 95.5 |

TABLE 5-continued

Postemergence Effect of 34 ALS Herbicides on Fresh Weight of GAT-HRA and Parent Inbred Corn

| ALS Class | Herbicide Treatment* | Parent elite stiff stalk inbred Fresh Weight (g) | Heterozygous GAT-HRA Fresh Weight (g) |
|---|---|---|---|
| | 200 g/ha Foramsulfuron Na$^+$ | 62.5 | 80.6 |
| | 200 g/ha Halosulfuron-methyl | 58.1 | 94.5 |
| | 200 g/ha Iodosulfuron-methyl Na$^+$ | 3.5 | 95.0 |
| | 200 g/ha Metsulfuron-methyl | 1.9 | 75.5 |
| | 200 g/ha Nicosulfuron | 62.7 | 94.7 |
| | 200 g/ha Primisulfuron-methyl | 16.6 | 101.0 |
| | 200 g/ha Prosulfuron | 53.6 | 91.3 |
| | 200 g/ha Rimsulfuron | 12.6 | 99.2 |
| | 200 g/ha Sulfometuron-methyl | 2.0 | 104.5 |
| | 200 g/ha Sulfosulfuron | 4.0 | 105.5 |
| | 200 g/ha Thifensulfuron-methyl | 4.2 | 86.6 |
| | 200 g/ha Triasulfuron | 6.4 | 90.3 |
| | 200 g/ha Tribenuron-methyl | 1.8 | 90.8 |
| | 200 g/ha Trifloxysulfuron Na$^+$ | 1.0 | 86.6 |
| | 200 g/ha Triflusulfuron-methyl | 2.1 | 110.9 |
| Triazolopyrimidine | 200 g/ha Chloransulam-methyl | 6.8 | 104.4 |
| | 200 g/ha Flumetsulam | 12.8 | 103.8 |
| Glycine | 3472 g ae/ha Glyphosate | 1.0 | 97.4 |
| Phosphinic Acid | 1870 g/ha Glufosinate ammonium | 2.4 | 112.3 |

TABLE 6

Postemergence Effect of 34 ALS Herbicides on GAT-HRA and Parent Inbred Corn

| ALS Class | Herbicide Treatment* | Parent elite stiff stalk inbred % Visual Injury | Heterozygous GAT-HRA % Visual Injury |
|---|---|---|---|
| Imidazolinone | 200 g/ha Imazamethabenz-methyl | 11 | 16 |
| | 200 g/ha Imazethapyr | 97 | 9 |
| | 200 g/ha Imazamox | 100 | 4 |
| | 200 g/ha Imazapyr | 100 | 1 |
| | 200 g/ha Imazaquin | 100 | 2 |
| Pyrimidinylthiobenzoate | 200 g/ha Pyriminobac-methyl | 93 | 4 |
| | 200 g/ha Pyrithiobac Na$^+$ | 100 | 9 |
| Sulfonylaminocarbonyltriazolinone | 200 g/ha Flucarbazone Na$^+$ | 100 | 14 |
| | 200 g/ha Propoxycarbazone Na$^+$ | 100 | 9 |
| Sulfonylurea | 200 g/ha Amidosulfuron | 71 | 8 |
| | 200 g/ha Azimsulfuron | 100 | 20 |
| | 200 g/ha Bensulfuron-methyl | 93 | 14 |
| | 200 g/ha Chlorimuron-ethyl | 93 | 15 |
| | 200 g/ha Chlorsulfuron | 100 | 13 |
| | 200 g/ha Ethametsulfuron-methyl | 96 | 6 |
| | 200 g/ha Ethoxysulfuron | 88 | 15 |
| | 200 g/ha Flupyrsulfuron-methyl Na$^+$ | 95 | 4 |
| | 200 g/ha Foramsulfuron | 28 | 8 |
| | 200 g/ha Halosulfuron-methyl | 14 | 8 |
| | 200 g/ha Iodosulfuron-methyl Na$^+$ | 100 | 1 |
| | 200 g/ha Metsulfuron-methyl | 100 | 14 |
| | 200 g/ha Nicosulfuron | 24 | 0 |
| | 200 g/ha Primisulfuron-methyl | 75 | 5 |
| | 200 g/ha Prosulfuron | 25 | 29 |
| | 200 g/ha Rimsulfuron | 91 | 10 |
| | 200 g/ha Sulfometuron-methyl | 100 | 2 |
| | 200 g/ha Sulfosulfuron | 97 | 3 |
| | 200 g/ha Thifensulfuron-methyl | 98 | 10 |
| | 200 g/ha Triasulfuron | 97 | 6 |
| | 200 g/ha Tribenuron-methyl | 100 | 8 |
| | 200 g/ha Trifloxysulfuron Na$^+$ | 100 | 29 |
| | 200 g/ha Triflusulfuron-methyl | 100 | 8 |

TABLE 6-continued

Postemergence Effect of 34 ALS Herbicides
on GAT-HRA and Parent Inbred Corn

| ALS Class | Herbicide Treatment* | Parent elite stiff stalk inbred % Visual Injury | Heterozygous GAT-HRA % Visual Injury |
|---|---|---|---|
| Triazolopyrimidine | 200 g/ha Chloransulam-methyl | 96 | 3 |
|  | 200 g/ha Flumetsulam | 85 | 3 |
| Glycine | 3472 g ae/ha Glyphosate | 100 | 10 |
| Phosphinic Acid | 1870 g/ha Glufosinate ammonium | 99 | 1 |

Additional Tests Including Other Agricultural Chemicals

Other protocols were used to evaluate whether GAT-HRA plants, in addition to being more tolerant to various herbicides than control plants, were also more tolerant to other agricultural chemicals than control plants. For example, one protocol included treatment of GAT-HRA maize with the sulfonylurea herbicides rimsulfuron and thifensulfuron-methyl in addition to treatment with the organophosphate insecticide chlorpyrifos (Lorsban®). In this test, plants were evaluated 14 days after treatment, and all 20 GAT-HRA transgenic plants showed good to excellent tolerance to these chemicals while the control plants showed significant damage as a result of the treatments (see Table 8). Herbicide injury scores (also called tolerance scores) were assigned on a plot basis on a 1 to 9 scale with a rating of 9 indicating that plants exhibited no injury symptoms and a rating of 1 indicating complete plant death. A rating of 5 indicates moderate leaf injury. The scale used here is further explained in Table 7 below.

TABLE 7

Herbicide injury scale (1 to 9 scale scoring system) for maize

| Rating | Main categories | Detailed description |
|---|---|---|
| 9 | No Effect | No crop reduction or injury |
| 8 | Slight | Slight crop discoloration or stunting |
| 7 | Effect | Some crop discoloration, stunting, or stunt loss |
| 6 |  | Crop injury more pronounced, but not lasting |
| 5 | Moderate | Moderate injury, crop usually recovers |
| 4 | Effect | Crop injury more lasting, recovery doubtful |
| 3 |  | Lasting crop injury, no recovery |
| 2 | Severe | Heavy crop injury and stand loss |
| 1 | Effect | Crop nearly destroyed - A few surviving plants |

TABLE 8

GAT HRA Transgenic Maize Plants
Show Excellent Tolerance to an Herbicide
as Measured by Tolerance Scores V4 Tolerance Scores

| Transgenic Event | Expression cassette | Basis ® (rimsulfuron and thifensulfuron-methyl), 1.0 oz ai/ac (73.9 ml ai/ha); WeatherMax ® (glyphosate) 10.7 oz ai/ac (790 ml ai/ha) | Basis ® (rimsulfuron and thifensulfuron-methyl), 1.0 oz ai/ac (73.9 ml ai/ha); Lorsban ® (chlorpyrifos), 14.4 oz ai/ac (1.06 L ai/ha); WeatherMax ® (glyphosate) 10.7 oz ai/ac (790 ml ai/ha) | WeatherMax ® (glyphosate) 10.7 oz ai/ac (790 ml ai/ha) | WeatherMax ® (glyphosate) 42.9 oz ai/ac (3.17 L ai/ha) |
|---|---|---|---|---|---|
| 2 | 4 | 9 | 9 | 9 | 7 |
| 4 | 3 | 9 | 9 | 9 | 9 |
| 3 | 3 | 9 | 9 | 9 | 5 |
| 10 | 3 | 8 | 9 | 9 | 7 |
| Glyphosate tolerant non-GAT HRA Control |  | 5.5 | 2.5 | 9 | 8.5 |

Fourteen days after the spray application, the 20 transgenic plants were also measured for plant height on a plot basis. Plant heights of the same four most tolerant GAT HRA events along with the non-GAT HRA control were collected. The four transgenic events showed uniform plant growth on all the herbicide treatments. The non-GAT HRA control showed a reduction in plant growth with the sulfonylurea treatments. The average plot height results from these measurements are shown in Table 9.

TABLE 9

GAT HRA Transgenic Maize Plants Show Excellent Tolerance to an Insecticide as Measured by Average Plant Height V4 Average Plant Heights (inches)

| Transgenic Event | Expression cassette | Basis ® (rimsulfuron and thifensulfuron-methyl), 1.0 oz ai/ac (73.9 ml ai/ha); WeatherMax ® (glyphosate) 10.7 oz ai/ac (790 ml ai/ha) | Basis ® (rimsulfuron and thifensulfuron-methyl), 1.0 oz ai/ac (73.9 ml ai/ha); Lorsban ® (chlorpyrifos), 14.4 oz ai/ac (1.06 L ai/ha); WeatherMax ® (glyphosate) 10.7 oz ai/ac (790 ml ai/ha) | WeatherMax ® (glyphosate) 10.7 oz ai/ac (790 ml ai/ha) | WeatherMax ® (glyphosate) 42.9 oz ai/ac (3.17 L ai/ha) |
|---|---|---|---|---|---|
| 2 | 4 | 16 | 14 | 14 | 13 |
| 4 | 3 | 15 | 14 | 15 | 14 |
| 3 | 3 | 15 | 14 | 14 | 14 |
| 10 | 3 | 15 | 15 | 15 | 14 |
| Glyphosate tolerant non-GAT HRA Control | | 10 | 7.5 | 14.5 | 14 |

Comparison of Response of GAT-HRA Plants to a Range of Herbicide Doses

GAT-HRA maize plants were produced using various expression cassettes and assayed as described above for tolerance to multiple sulfonylurea chemistries in combination with glyphosate (see Table 10).

TABLE 10

GAT HRA Maize Produced Using Various Expression Cassettes Is Tolerant to Multiple Sulfonylurea Chemistries

| Spray Treatment | Expression cassette | Percentage of highly tolerant events | Average growth of sprayed plants (inches) | Average growth of non-sprayed plants (inches) | Average number inserts integrated in highly tolerant events | Total number of events evaluated | Number of events with no injury |
|---|---|---|---|---|---|---|---|
| Matrix ® (rimsulfuron) 1.9 oz ai/ac (140 ml ai/ha), WeatherMax ® (glyphosate) 64.4 oz ai/ac (4.7 L ai/ha) | 3 | 25% | 5.2 | 5.1 | 2.0 | 56 | 14 |
| Matrix ® (rimsulfuron) 1.9 oz ai/ac (140 ml ai/ha), WeatherMax ® (glyphosate) 64.4 oz ai/ac (4.7 L ai/ha) | 4 | 31% | 5.2 | 5.1 | 1.6 | 51 | 16 |
| Matrix ® (rimsulfuron) | 5 | 27% | 4.8 | 5.3 | 1.7 | 63 | 17 |

TABLE 10-continued

GAT HRA Maize Produced Using Various Expression Cassettes Is Tolerant to Multiple Sulfonylurea Chemistries

| Spray Treatment | Expression cassette | Percentage of highly tolerant events | Average growth of sprayed plants (inches) | Average growth of non-sprayed plants (inches) | Average number inserts integrated in highly tolerant events | Total number of events evaluated | Number of events with no injury |
|---|---|---|---|---|---|---|---|
| 1.9 oz ai/ac (140 ml ai/ha), WeatherMax ® (glyphosate) 64.4 oz ai/ac (4.7 L ai/ha) | | | | | | | |
| Matrix ® (rimsulfuron) 1.9 oz ai/ac (140 ml ai/ha), WeatherMax ® (glyphosate) 64.4 oz ai/ac (4.7 L ai/ha) | 6 | 41% | 4.5 | 5.0 | 1.4 | 182 | 75 |
| Basis ® (rimsulfuron and thifensulfuron-methyl) 1.4 oz ai/ac (103 ml ai/ha), Lorsban ® (chlorpyrifos) 14.4 oz ai/ac (1.06 L ai/ha), WeatherMax ® (glyphosate) 64.4 oz ai/ac (4.7 L ai/ha) | 9 | 59% | 2.6 | 3.1 | 1.4 | 27 | 16 |
| Oust ® (sulfometuron-methly) 4.5 oz ai/ac (322 ml ai/ac), WeatherMax ® (glyphosate) 64.4 oz ai/ac (4.7 L ai/ha) | 9 | 71% | 4.2 | 4.8 | 1.1 | 146 | 104 |

Example 2

GAT-HRA Soybean Plants are Tolerant of Various Herbicides and Agricultural Chemicals Transformation and Regeneration of Transgenic Plants Soybean embryos were bombarded with an expression cassette containing GAT (SEQ ID NO:68) and HRA polynucleotides (SEQ ID NO:65) operably linked to a constitutive promoter, as follows. The promoter used for the GAT sequence is the SCP1 promoter, and the promoter used for the HRA sequence is the SAMS promoter. The 2 promoter/gene combinations are arranged in a tandem orientation with the HRA promoter/gene downstream of the GAT promoter/gene. To induce somatic embryos, cotyledons less than 4 mm in length dissected from surface-sterilized, immature seeds of the soybean variety Jack were cultured in the light or dark at 26° C. on an appropriate agar medium for six to ten weeks. Somatic embryos producing secondary embryos were then excised and placed into a suitable liquid medium. After repeated selection for clusters of somatic embryos that multiplied as early, globular-staged embryos, the suspensions were maintained as described below. Here, the herbicide-tolerance traits that should be possessed by the transformed plants were used as selectable markers.

Soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of liquid medium.

Soybean embryogenic suspension cultures were then transformed by the method of particle gun bombardment (Klein et al. (1987) Nature (London) 327: 70-73, U.S. Pat. No. 4,945,050).

To 50 µl of a 60 mg/ml 1 µm gold particle suspension was added (in order): 5 µl DNA (1 µg/µl), 20 µl spermidine (0.1 M), and 50 µl $CaCl_2$ (2.5 M). The particle preparation was then agitated for three minutes, spun in a microfuge for 10 seconds and the supernatant removed. The DNA-coated particles were then washed once in 400 µl 70% ethanol and resuspended in 40 µl of anhydrous ethanol. The DNA/particle suspension were sonicated three times for one second each. Five microliters of the DNA-coated gold particles were then loaded on each macro carrier disk.

Approximately 150-200 mg of a two-week-old suspension culture was placed in an empty 60×15 mm Petri dish and the residual liquid removed from the tissue with a pipette. For each transformation experiment, approximately 5-10 plates of tissue were normally bombarded. Membrane rupture pressure was set at 1100 psi (77.356 kg/cm), and the chamber was evacuated to a vacuum of 28 inches mercury. The tissue was placed approximately 8.89 cm away from the retaining screen and bombarded three times. Following bombardment, the tissue was divided in half and placed back into liquid and cultured as described above.

Five to seven days post bombardment, the liquid media was exchanged with fresh media, and eleven to twelve days post-bombardment with fresh media containing 30-50 mg/L hygromycin and 100 ng/ml chlorsulfuron was used as a selection agent. This selective media was refreshed weekly. Seven to eight weeks post-bombardment, green, transformed tissue was observed growing from untransformed, necrotic embryogenic clusters. Isolated green tissue was removed and inoculated into individual flasks to generate new, clonally propagated, transformed embryogenic suspension cultures. Each new culture derived from a separate area of transformed tissue was treated as an independent transformation event; the individual culture as well as the initial (T0) plant(s) derived from a single area of transformed tissue as well as its descendants were generally to represent a single "event." These suspensions were then subcultured and maintained as clusters of immature embryos or regenerated into whole plants by maturation and germination of individual somatic embryos.

Herbicide Treatments

Young regenerated transgenic plants were sprayed with 1× glyphosate (1× rate of glyphosate is 1120 g/ha of glyphosate isopropylamine) to cull segregants. Four replications were performed for each treatment. Plants were then treated with various herbicides, including glyphosate and ALS-inhibitor herbicides. When treated with tribenuron-methyl herbicide, the GAT- and HRA-containing transgenic soybeans treated at 0 and 35 g/ha showed no significant damage, while herbicide-treated non-transgenic control soybeans were killed by the treatment. Plants were then treated with glyphosate at 8× and tribenuron-methyl at 35 g/ha as well as rimsulfuron at 35 g/ha, and similar results were obtained.

Six soybean seeds from each variety to be assayed were planted 1 cm deep in 5.5 (13.97 cm) inch square plastic container of a synthetic growth medium. Very young transgenic seedlings were pretreated with glyphosate to eliminate segregants that were not tolerant to glyphosate; plants injured by this treatment were removed. When possible, containers were thinned to two uniform plants. Non-transgenic lines were thinned to two uniform plants per container. Soybean seedlings were watered and fertilized for rapid growth. The plants were grown with a 16-h light photoperiod, and when natural light intensity fell below 500 µE/m$^2$/s it was supplemented with metal halide lights with 160 µE/m$^2$/s photosynthetically active radiation. Temperature was maintained at 28±2° C. during the day and 22±2° C. at night. Relative humidity generally ranged from 50 to 90%.

These postemergence studies used commercial herbicide formulations and were applied approximately two weeks after planting. Spray mixtures were made using deionized water at room temperature and were stirred for at least 15 minutes. Treatments were sprayed 1 to 2 h after preparation. The 35 g/ha rimsulfuron and tribenuron-methyl herbicide treatments were applied in a spray volume of 374 L/ha with a flat fan nozzle at 51 cm with spray pressure set at 138 kPa and included a high pH, basic blend adjuvant to ensure solubilization and foliar penetration. The commercial formulation of glyphosate treatment was also applied in a spray volume of 374 L/ha with a flat fan nozzle at 51 cm with spray pressure set at 138 kPa. Plants were visually evaluated for injury on a scale of 0% being no injury and 100% being plant death. Results are expressed below in Table 11 as the mean of four replications.

TABLE 11

Postemergence Effect of Glyphosate and Two Sulfonylurea Herbicides on GAT-HRA Soybeans

| Event # | Line # (and mean) | Glyphosate (8960 g/ha) | Tribenuron-methyl (35 g/ha) % Visual Injury | Rimsulfuron (35 g/ha) |
|---|---|---|---|---|
| 64 | Mean | 14 | 43 | 73 |
|  | 47 | 10 | 34 | 73 |
|  | 41 | 20 | 55 | 73 |
| 60 | Mean | 15 | 55 | 83 |
|  | 41 | 13 | 38 | 80 |
|  | 70 | 9 | 40 | 80 |
|  | 35 | 9 | 49 | 85 |
|  | 11 | 11 | 71 | 83 |
|  | 22 | 11 | 45 | 76 |
|  | 75 | 14 | 69 | 86 |
|  | 79 | 18 | 69 | 86 |
|  | 07 | 19 | 46 | 84 |
|  | 77 | 19 | 56 | 90 |
|  | 46 | 20 | 49 | 78 |
|  | 82 | 20 | 61 | 90 |
|  | 84 | 22 | 71 | 83 |
| 61 | Mean | 20 | 54 | 82 |
|  | 99 | 10 | 34 | 79 |
|  | 47 | 15 | 36 | 78 |
|  | 62 | 6 | 43 | 71 |
|  | 49 | 9 | 54 | 84 |
|  | 02 | 10 | 41 | 80 |
|  | 14 | 10 | 65 | 90 |
|  | 18 | 10 | 69 | 89 |
|  | 51 | 10 | 60 | 83 |
|  | 02B | 10 | 40 | 70 |
|  | 05 | 11 | 55 | 78 |
|  | 60 | 16 | 45 | 73 |
|  | 34 | 23 | 76 | 90 |
|  | 24 | 60 | 63 | 90 |
|  | 33 | 84 | 80 | 95 |
| 59 | Mean | 38 | 59 | 87 |
|  | 28 | 37 | 60 | 86 |
|  | 21 | 40 | 58 | 88 |
| STS ® | Mean | 100 | 87 | 97 |
|  | 25 | 100 | 87 | 97 |
|  | 46 | 100 | 88 | 97 |
| Wild Type | Mean | 100 | 97 | 97 |
|  | 82 | 100 | 97 | 97 |
|  | Jack | 100 | 97 | 97 |

Example 3

Transgenic GAT-HRA Cotton is Tolerant of Several Herbicides

Cotton (*Gossypium hirsutum*) Coker 312 was transformed with a GAT polynucleotide (gat 4621) together with an Hra polynucleotide (SEQ ID NO:86) both operably linked to strong, constitutive plant viral promoters. The promoter linked to gat4621 contains a duplicated portion of the Strawberry Vein Banding Virus transcript promoter (Wang et al. Virus Genes 20: 11-17, 2000; Genbank X97304). The Hra gene was driven by a duplicated portion of the Mirabilis Mosaic Caulimovirus full-length transcript promoter (U.S. Pat. No. 6,420,547; Dey and Maiti, Transgenics 3:61-70, 1999). The transformation procedure used *Agrobacterium*

*tumefaciens* containing an expression cassette with the genes to be transferred and cotyledon explant derived callus with some capacity to undergo embryogenesis. The callus was exposed to *Agrobacterium* for 48-72 hours. The callus was then exposed to selection for transformed cells on 50-200 µg/l chlorosulfuron and/or 50-450 µM glyphosate in solid medium. Glyphosate can also be used in a concentration range of about 5 to about 450 µM. Selection was applied until somatic embryos formed, and selection was again applied at the embryo germination step, and optionally during rooting of plantlets. Over 450 GAT-HRA transformation events were produced using selection with both chlorsulfuron and glyphosate.

Transformed cotton plants were rooted and then transferred to soil for further growth. Plants were then subjected to herbicide spray treatments in a greenhouse. In one treatment, glyphosate was sprayed over the top of plants at the 4-6 leaf stage of development at an application rate of 1.5 lb acid equivalent per acre (2.58 Kg acid equivalent per hectare). Untransformed Coker 312 control plants were dead 2 weeks after glyphosate application. In contrast, approximately 50% of the GAT-HRA transgenic plants (each corresponding to a separate transformation event) showed no deleterious symptoms from the glyphosate treatment 14 days after application. Plants transformed with both GAT and HRA were further subjected to an "over the top" application of the sulfonylurea herbicide rimsulfuron at a rate of 16 g active ingredient/ hectare. Again, approximately 35% of the transgenic plants showed no deleterious symptoms from the dual herbicide application 14 days after the rimsulfuron application and 28 days after the glyphosate application. Untransformed Coker 312 plants showed severe damage from the rimsulfuron application, even in the absence of any glyphosate application. In further experiments 32 g ai/ha rimsulfuron were applied to the cotton.

The presence of each of the GAT and HRA polynucleotides was further confirmed in the herbicide-resistant transgenic plants using polymerase chain reaction ("PCR") assays and using Western blot analysis to detect the expressed GAT and HRA polypeptides.

Example 4

Formulation of Homogenous Granule Blends

A herbicidal composition useful for the present invention may be formulated in any suitable manner, for example, as a "homogeneous granule blend" (see, e.g., U.S. Pat. No. 6,022, 552, entitled "Uniform Mixtures of Pesticide Granules"). A herbicidal composition formulated as a homogeneous granule blend according to U.S. Pat. No. 6,022,552 can be prepared by shaking or otherwise mixing two or more groups of substantially cylindrical granules typically made by extrusion or pelletization, wherein one group has an active ingredient content comprising at least one herbicide, and one or more other groups have a different active ingredient content or inert content, the granules within each group having substantially uniform diameters and longitudinal lengths of from 1 to 8 times the diameter with the average length of the granules being from 1.5 to 4 times the diameter, and the average diameter of each group differing from another group by no more than 30%. In some embodiments, each granule group comprises a registered formulation product containing a single active ingredient, which is for example, a herbicide, fungicide, and/or an insecticide. "Substantially cylindrical" is rod like or tubular wherein the cross-sectional shape may be circular, octagonal, rectangular, or any other conceivable shape and wherein the longitudinal surface is spiral, curved, or straight. The difference in average diameter is calculated by subtracting the average diameter of the granules in the group having the smaller diameter from the average diameter of the granules in the group having the larger diameter, then dividing the calculated difference by the average diameter of the granules in the group having the smaller diameter, and finally multiplying the calculated quotient by 100%.

The uniformity of a "homogenous granule blend" can be optimized by controlling the relative sizes and size distributions of the granules used in the blend. Density differences are comparatively unimportant (see, e.g., Rhodes (1990) *Principles of Powder Technology*, pp. 71-76 (John Wiley & Sons)). The diameter of extruded granules is controlled by the size of the holes in the extruder die, and a centrifugal sifting process may be used to obtain a population of extruded granules with a desired length distribution (see, e.g., U.S. Pat. No. 6,270,025). Preferably the average diameter of each granule group differs from another group by no more than 20%, more preferably by no more than 10%. Also preferably the longitudinal length of each group is form 1.5 to 4 times the diameter of the granules.

The active ingredient in each formulation has an associated tolerance for variability based on guidelines of the Food and Agriculture Organization of the United Nations (FAO), as shown below in Table 12.

TABLE 12

| FAO Nominal Concentration Guidelines for Active Ingredient in a Formulation | |
|---|---|
| Nominal Concentration (= N) | FAO Range (as % of Nominal) |
| N ≦ 2.5% | ±25% |
| 2.5% ≦ N ≦ 10% | ±10% |
| 10% ≦ N ≦ 25% | ±6% |
| 25% ≦ N ≦ 50% | ±5% |
| N > 50% | ±25 g/kg |

The active ingredient content in a homogenous granule blend is determined based on the active ingredient content of the component granules and the ratio in which the component granules are mixed. Homogenous granule blends are manufactured assuming that the nominal values of active ingredients of the blend components are correct. Because of the real-life variability associated with assays of active ingredients as well as variability in mixing and sampling, procedures were developed to calculate ranges for the active ingredient content in a homogenous granule blend, as follows.

1. Define the registered FAO specifications for each of the blend components ("% AI in Component").
2. Apply the FAO tolerance to establish manufacturing limits for the amount of each component in the blend ("% Component in Blend").
3. Calculate the maximum limit for the active ingredient in the blend ("% AI in the Blend") by multiplying the maximum limit for "% AI in Component" with the maximum limit for "% Component in Blend." The minimum and nominal calculations are similarly done.

Examples of the calculations for several homogenous granule blend products follow. The last column in each example table shows the standard FAO assay range that would apply to a traditional premix product containing the same active ingredient content as the homogenous granule blend in the example. The broader range for the homogenous granule blend product ("% AI in Blend") allows for the variability introduced by using a registered product with an associated range of active ingredient content as a component in the product.

TABLE 13

Calculations for product "DPX-CDQ73 39.1WG" Homogenous Granule Blend*

| % Al in Components (A) | % Component in Blend (B) | % Al in Blend (A × B) | Compare to FAO tolerance for a premix |
|---|---|---|---|
| % metsulfuro-methyl in Ally 20PX | % Ally 20 PX in DPX-CDQ73 Blend | % metsulfuron-methyl in DPX-CDQ73 Blend | % metsulfuron-methyl in traditional premix |
| 21.2 max | 66.7 max | 14.4 max | 13.8 max |
| 20.0 ± 6% | 65.2 ± 25 g/kg | 13.0 nominal | 13.0 nominal |
| 18.8 min | 62.7 min | 11.8 min | 12.3 min |
| % tribenuron-methyl in Quantum 75PX | % Quantum 75PX in DPX-CDQ73 Blend | % tribenuron-methyl in DPX-CDQ73 Blend | % tribenuron-methyl in traditional premix |
| 77.5 max | 36.5 max | 28.3 max | 27.4 max |
| 75 ± 25 g/kg | 34.8 ± 5% | 26.1 nominal | 26.1 nominal |
| 72.5 min | 33.1 min | 24.0 min | 24.8 min |

*A blend of 65.2% Ally 20PX and 34.8% Quantum 75PX. This blend is sold commercially as BiPlay and DP911.

TABLE 14

Calculations for "DPX-CDQ74 51.5WG" Homogenous Granule Blend**

| % Al in Components (A) | % Component in Blend (B) | % Al in Blend (A × B) | Compare to FAO tolerance for a premix |
|---|---|---|---|
| % metsulfuron-methyl in Ally 20PX | % Ally 20 PX in DPX-CDQ73 Blend | % metsulfuron-methyl in DPX-CDQ73 Blend | % metsulfuron-methyl in traditional premix |
| 21.2 max | 44.9 max | 9.5 max | 9.4 max |
| 20.0 ± 6% | 42.8 ± 5% | 8.6 nominal | 8.6 nominal |
| 18.8 min | 40.7 min | 7.7 min | 7.7 min |
| % thifensulfuron-methyl in Harmony 75PX | % Harmony 75PX in DPX-CDQ74 Blend | % thifensulfuron-methyl in DPX-CDQ74 Blend | % thifensulfuron-methyl in traditional premix |
| 77.5 max | 59.7 max | 46.3 max | 45.0 max |
| 75 ± 25 g/kg | 57.2 ± 25 g/kg | 42.9 nominal | 42.9 nominal |
| 72.5 min | 54.7 min | 39.7 min | 40.8 min |

**A blend of 42.8% Ally 20PX and 57.2% Harmony 75PX. This blend is sold commercially as Finish and DP928.

TABLE 15

"DPX-FKU22 60WG" Homogenous Granule Blend***

| % Al in Components (A) | % Component in Blend (B) | % Al in Blend (A × B) | Compare to FAO tolerance for a premix |
|---|---|---|---|
| % flupyrsulfuron methyl in Lexus 50PX | % Lexus 50PX in DPX-FKU22 Blend | % flupyrsulfuron methyl in DPX-FKU22 Blend | % flupyrsulfuron methyl in traditional premix |
| 52.5 max | 62.5 max | 32.8 max | 31.5 max |
| 50.0 ± 5% | 60.0 ± 25 g/kg | 30.0 nominal | 30.0 nominal |
| 47.5 min | 57.5 min | 27.3 min | 28.5 min |
| % tribenuron-methyl in Quantum 75PX | % Quantum 75PX in DPX-FKU22 Blend | % tribenuron-methyl in DPX-FKU22 Blend | % tribenuron-methyl in traditional premix |
| 77.5 max | 42.0 max | 32.6 max | 31.5 max |
| 75 ± 25 g/kg | 40.0 ± 5% | 30.0 nominal | 30.0 nominal |
| 72.5 min | 38.0 min | 27.6 min | 28.5 min |

***A blend of 60% Lexus 50PX and 40% Quantum 75PX. This blend is sold commercially as DP953.

Procedures were also developed to determine whether a particular homogenous granule blend falls within the desired ranges. Homogenous granule blends are random mixtures of granules; therefore, in order to accurately represent the composition, a certain number of granules must be evaluated. The minimum number of granules for the sample can be estimated using a statistical equation (see Rhodes (1990), *Principles of Powder Technology* (John Wiley & Sons), pp. 71-76), $$s^2 = P(100-P)/n$$

where s=standard deviation for the component proportion in the blend, P=weight percent of the component, and n=number of granules in the sample (~400 1-mm diameter granules=1 gram). The sample size required to represent the blend composition for a particular chosen level of variability can be obtained by solving for n and converting this value to grams by dividing 'n' by the average number of 1-mm paste extruded granules in a 1-gram sample (e.g., 400).

If the standard deviation in this calculation is based on the FAO tolerance for the amount of a component in a particular granule blend, a minimum sample size for that granule blend can be calculated. For 95% confidence, the tolerance around the "% component in the blend" is set as 2 standard deviations. It is understood that this is a theoretical statistical estimate.

For a granule blend to be a feasible commercial product, the statistical sample size must be equivalent to or smaller than the smallest amount that would be measured by a farmer or applicator, typically a hectare dose. Examples of a sample size calculation for the granule blends discussed above is shown below.

TABLE 16

Minimum statistical sample size calculation for DPX-CDQ73 39.1WG Blend

| Blend Component | P (% componen tin Blend) | FOA tolerance for % component | Statistical Minimum Sample Size |
|---|---|---|---|
| Ally 20PX | 65.2 | ±25 g/kg (±3.8% relative) | 4 grams |
| Quantum 75PX | 34.8 | ±5% relative | 8 grams |

Detailed Calculation for Minimum Sample Size for DPX-CDQ73 39.1 WG Blend:

For the minor blend component (Quantum 75PX) the FAO tolerance of ±5% relative gives a range of: 5%×34.8=1.7

For 95% confidence, 2 standard deviations are set at=1.7 giving a standard deviation of s=0.85 for the calculation:

$$s^2 P(1-P)/n = (0.85)2 = (65.2 \times 34.8)/n$$

n=3140 granules=7.8 grams (based on 400 granules/gram)

The calculated minimum statistical sample size of about 8 grams is less than the product use rate of 38 g/ha.

A homogenous granule blend is considered to be "homogenous" when it can be subsampled into appropriately sized aliquots and the composition of each aliquot will meet the required assay specifications. To demonstrate homogeneity, a large sample of the homogenous granule blend is prepared and is then subsampled into aliquots of greater than the minimum statistical sample size. A second sample of the blend is prepared and subjected to a simulated transportation test (ASTM D 4728-87, Standard Method for Random Vibration Testing of Shipping Containers) and then subsampled into aliquots. The aliquots are analyzed for active ingredient using liquid chromatography. The simulated transportation test shakes the bottle at specific frequencies for a standard amount of time, giving the granules an opportunity to move about. When the granule blend components are not appropriately sized, segregation occurs and the aliquot compositions vary unacceptably.

Aliquot analysis data from the homogeneity tests for DPX-CDQ73 39.1WG Blend are shown below in Table 17. All data points tested in the granule blend aliquots fell within their respective calculated specification ranges, indicating that the blend was homogenous.

TABLE 17

Analysis of DPX-CDQ73 39.1WG Blend as made after simulated shipment.

| Aliquot (20 grams) | % metsulfuron-methyl in DPX-CDQ73 Blend | % tribenuron-methyl in DPX-CDQ73 Blend | % metsulfuron-methyl in DPX-CDQ73 Blend after simulated shipment | % tribenuron-methyl in DPX-CDQ73 Blend after simulated shipment |
|---|---|---|---|---|
| Proposed assay range | 11.8-14.4 | 24.0-28.3 | 11.8-14.4 | 24.0-28.3 |
| 1 | 13.43 | 25.95 | 13.83 | 26.84 |
| 2 | 13.87 | 25.05 | 13.84 | 24.43 |
| 3 | 13.79 | 25.88 | 13.28 | 27.2 |
| 4 | 13.36 | 26.8 | 13.67 | 26.25 |
| 5 | 13.49 | 27.37 | 13.57 | 27.33 |

Homogenous granule blends have been manufactured in a batch process using a roll-type mixer. Once mixed, the granule blend is dispensed into appropriate containers (bottles, bags, etc.) for commercial sale. Testing of the manufactured homogenous granule blend DPX-CDQ73 WG showed that all data for the different batches of blend were within the respective proposed assay ranges for active ingredient.

Example 5

Evaluation of Levels of Glyphosate and ALS Inhibitor Herbicide Efficacy Among Soybean Plants Carrying Different GAT and HRA Sequences Three GAT7 events in soybean were compared to four selected GAT11 soybean events to determine if differences could be detected for tolerance to high rates of glyphosate+sulfonylurea treatments. Across the treatment combinations, the GAT7 construct had significantly less spray response compared to the GAT11 constructs at 7, 14, and 28 DAS. Within the 8× Touchdown®+1× Resolve®+2× Express® treatment, and the 8× Touchdown®+2× Resolve®+4× Express® treatment, GAT7 event EAFS 3560.4.3 had the lowest spray response scores compared to all other events at 7, 14, and 28 DAS.

Materials and Methods

For each treatment, three replications of two 12 foot plots of three selected GAT7 events and four selected GAT11 events were grown in a RCB design (blocked by treatment) at two locations in Hawaii. Individual lines, events, and construct tested are listed below in Table 18.

TABLE 18

| Entry Name | GAT | Event | Construct | Construct Description |
|---|---|---|---|---|
| JH12862353 | GAT11 | EAFS 3861.2.3 | PHP22021A | H2B:GAT4618::3(35Senh) + :SCP:HRA (DV) |
| JH12862357 | GAT11 | EAFS 3862.2.5 | PHP22021A | H2B:GAT4618::3(35Senh) + :SCP:HRA (DV) |
| JH12862359 | GAT11 | EAFS 3862.2.5 | PHP22021A | H2B:GAT4618::3(35Senh) + :SCP:HRA (DV) |
| JH12862360 | GAT11 | EAFS 3862.2.5 | PHP22021A | H2B:GAT4618::3(35Senh) + :SCP:HRA (DV) |
| JH12862361 | GAT11 | EAFS 3862.2.5 | PHP22021A | H2B:GAT4618::3(35Senh) + :SCP:HRA (DV) |
| JH12862364 | GAT11 | EAFS 3862.4.2 | PHP22021A | H2B:GAT4618::3(35Senh) + :SCP:HRA (DV) |
| JH12862365 | GAT11 | EAFS 3862.4.2 | PHP22021A | H2B:GAT4618::3(35Senh) + :SCP:HRA (DV) |
| JH12862405 | GAT11 | EAFS 3876.8.15 | PHP22117A | H2B:GAT4621::3(35Senh) + :SCP:HRA (DV) |
| JH12862406 | GAT11 | EAFS 3876.8.15 | PHP22117A | H2B:GAT4621::3(35Senh) + :SCP:HRA (DV) |
| JH12862528 | GAT7 | EAFS 3560.4.3 | PHP20163A | SCP:GAT4601::SAMS:HRA |
| JH12862529 | GAT7 | EAFS 3559.2.1 | PHP20163A | SCP:GAT4601::SAMS:HRA |
| JH12862531 | GAT7 | EAFS 3561.1.1 | PHP20163A | SCP:GAT4601::SAMS:HRA |

The three different treatments applied at the V3 growth stage were; 1.8× Touchdown® Hi-Tech (8630.55 g/ha a.i. glyphosate)+1× Resolve® (35.0 g/ha a.i. rimsulfuron)+2× Express® (17.5 g/ha tribenuron), 2.8× Touchdown® Hi-Tech (8630.55 g/ha a.i. glyphosate)+2× Resolve® (70.0 g/ha a.i. rimsulfuron)+4× Express® (35.0 g/ha tribenuron), and 3. Unsprayed Control. All spray treatments also contained a 1× non-ionic surfactant and ammonium sulfate. At 7, 14, and 28 days after spraying, plots were given a visual spray damage rating based upon observed chlorosis, necrosis, and/or plant stunting (0%=no observed effect to 100%=entire plot deceased). Visual rating data were subject to ANOVA and mean separation using SAS.

Results and Discussion

Across the three treatments, the round of GAT (7 vs. 11), DNA construct, event, treatment, GAT*treatment, construct*treatment, and event*treatment were significantly different at 7 DAS and 14 DAS (data not shown). At 28 DAS, the GAT round, construct, event, treatment, GAT*treatment, and event*treatment effects were significantly different (data not shown). The GAT7 lines had significantly less response noted across the three treatments at 7, 14, and 28 DAS (data not shown).

Within the 8× Touchdown®+1× Resolve®+2× Express® treatment, the GAT7 construct PHP20163A had significantly lower spray response ratings compared to GAT11 construct PHP22021A at 7, 14, and 28 DAS (data not shown). PHP20163A had significantly more tolerance to this treatment compared to PHP22117A only at 28 DAS (data not shown). Among the events compared, GAT7 event EAFS 3560.4.3 had the most initial tolerance observed at 7 and 14 DAS, and had the best recovery score at 28 DAS (data not shown). In examining the differences between least squares means (LSMeans), each of the three GAT7 events had significantly less spray response at 7 DAS compared to GAT11 EAFS 3861.2.3 and GAT11 EAFS 3862.2.5, and were rated statistically similar to GAT11 EAFS 3862.2.5 and GAT11 EAFS 3876.8.1 (data not shown). At 14 DAS, the 3 GAT7 events had significantly less response scores compared to GAT11 EAFS 3862.4.2, but only GAT7 EAFS 3560.4.3 had significantly less response compared to EAFS 3861.2.3 and EAFS 3862.2.5 (data not shown). At 28 DAS, all three GAT7 events had significantly better recovery compared to GAT11 events EAFS 3861.2.3, EAFS 3862.4.2, and EAFS 3876.8.1 (data not shown). In addition, GAT7 event EAFS 3560.4.3 had significantly less spray response compared to GAT11 event EAFS 3862.2.5 at 28 DAS (data not shown).

In examining the 8× Touchdown®+2× Resolve®+4× Express® treatment, GAT7 PHP20163A had significantly less response compared to GAT11 PHP22021 at 7, 14, and 28 DAS, and PHP20163A had significantly less response compared to GAT11 PHP22117A at 28 DAS (data not shown). Among the events, GAT7 EAFS 3560.4.3 had significantly better tolerance compared to all other events at 7 and 14 DAS, and GAT7 EAFS 3559.2.1 and EAFS 3560.4.3 had significantly lower spray response compared to all other events at 28 DAS (data not shown). Comparing the differences in LSMeans, at 7 DAS and 14 DAS, GAT7 EAFS 3560.4.3 had significantly less response compared to all the GAT 11 events (data not shown). The other 2 GAT7 events were significantly lower in response compared to GAT 11 event EAFS 3862.4.2 at 7 and 14 DAS (data not shown). At 28 DAS, GAT7 events EAPS 3559.2.1 and EAFS 3560.4.3 had significantly better recovery compared to all the GAT11 events (data not shown). GAT7 event EAFS 3561.1.1 was only significantly better than GAT11 event EAFS 3862.4.2 (data not shown).

Example 6

Robustness Trial Data Analysis in Soybean

The interactions between sulfonylurea and imidazolinone under field trial conditions have been studied. Antagonism between the sulfonylurea and imidazolinone chemistries has been seen in the past on commercial STS® soybean varieties. An SU like thifensulfuron on STS® soy is normally safe. Add an IMI like imazethapyr (Pursuit) and the mixture becomes less safe (antagonized the crop safety). In the case of GAT Rd7, rimsulfuron causes crop phyto. Add an IMI like Pursuit and the mixture became more safe (antagonized the crop injury). The filed trials described below show there is an increased crop safety when normally injurious amounts of, for example, rimsulfuron were mixed with, for example, imazethapyr, a normally "safe" imidazolinone herbicide. Example 6A comprises a field trial that demonstrates this effect. Example 6B provides greenhouse data that confirms the field trial data.

Example 6A

The T6 generation of soybean of the lead GAT7 event (SEQ ID NO:68) also having HRA (SEQ ID NO:65) [SCP:GAT7:: SAMS:ALS] was compared to 92B25 to determine levels of robustness when sprayed with different combinations and rates of sulfonylurea, chlorpyrifos, and/or imazethapyr chemistries. Across all the treatment combinations except 16× Harmony® (no significance detected), GAT7 had significantly lower spray response compared to STS® at 7, 14, and 28 days after spraying (DAS). Application of 1× Resolve® with and without Lorsban® created a large response from GAT7 and STS® at 7 DAS. The GAT7 was able to significantly recover from these treatments at 14 and 28 DAS, while the STS® line remained heavily damaged. The GAT7 line had significantly less spray response to 4× Pursuit® compared to the STS® line at 7 DAS, while both lines were not statistically different at 14 and 28 DAS. When 1× Resolve®+4× Pursuit® was applied, the GAT7 line had significantly higher tolerance compared to the STS® line at 7, 14, and 28 DAS. At 7, 14, and 28 DAS 16× Harmony®, there was not a large response observed from either the GAT7 or STS® line. Data from the treatments combining 16× Harmony® with 4× Pursuit® or 16× Harmony® with 4× Express® indicated GAT7 had significantly lower spray response compared to the STS® line at 7, 14, and 28 DAS. In addition, the 7, 14, and 28 DAS data from 0.25× Resolve®+1.5× Express® treatment showed GAT7 had significantly higher tolerance compared to STS®. In general, the data from this study indicate GAT7 provides significantly higher tolerance compared to STS® across multiple herbicide and insecticide chemistries.

Materials and Methods

For each treatment, three replications of two 12 foot plots of the lead GAT7 event (EAFS 3560.4.3; GEID=JH12862528) and 92B25 (STS®) were grown in a RCB design (blocked by treatment) at two locations in Hawaii. The nine different treatments applied at the V3 growth stage were; 1.1× Resolve® (2 oz) (35.0 g/ha a.i. rimsulfuron), 2.1× Resolve® (35.0 g/ha a.i. rimsulfuron)+1× Lorsban® 4E (560.0 g/ha a.i. chlorpyrifos), 3. 4× Pursuit® (211.8 g/ha a.i. imazethapyr), 4.1× Resolve® (35.0 g/ha a.i. rimsulfuron)+4× Pursuit® (211.8 g/ha a.i. imazethapyr), 5.16× Harmony® GT (70.0 gms/ha a.i. thifensulfuron), 6.16× Harmony® (70.0 gms/ha a.i. thifensulfuron)+4× Pursuit® (211.8 g/ha a.i. imazethapyr), 7.16× Harmony® (70.0 gms/ha a.i. thifensulfuron)+4× Express® (35.0 g/ha a.i. tribenuron) 8.0.25× Resolve® (2,157 g/ha a.i. glyphosate)+1.5× Express® (13.1 g/ha a.i. tribenuron) 9. Unsprayed Control. All spray treatments also contained a 1× non-ionic surfactant and ammonium sulfide. At 7, 14, and 28 days after spraying, plots were given a visual spray damage rating based upon observed chlorosis, necrosis, and/or plant stunting (0%=no observed effect to 100%=entire plot deceased). Visual rating data were subject to ANOVA and mean separation using SAS.

Results and Discussion

Across all treatments at 7 and 14 DAS, the location, GEID, treatments, and GEID*treatment effects were significantly different (data not shown). The GAT7 line was scored significantly lower than the STS® line across all treatments at 7 and 14 DAS (data not shown). At 28 DAS, the GEID, loc*GEID, treatments, and GEID*treatment effects were significantly different (data not shown). Over all the treatments, the GAT7 line was scored with significantly less spray damage compared to the STS® line at 28 DAS (data not shown).

The 1× Resolve® (rimsulfuron) treatment created a large response from both the GAT7 (70%); and STS® (83%) lines at 7 DAS (data not shown). At 14 DAS, the GAT7 line (74%) had significantly less response compared to the STS® line (93%) (data not shown). By 28 DAS, the GAT7 was able to recover and was scored with significantly less damage compared to the STS® line (32% vs. 93%) (data not shown).

When date from the Lorsban® (chlorpyrifos)+1× Resolve® treatment are examined, the GAT7 line did not have significantly less response compared to the response of the STS® line until 14 and 28 DAS (data not shown). At 28 DAS, the GAT7 line sprayed with Lorsban® and Resolve® (56%) did not recover as quickly compared to only the 1× Resolve® (32%) treatment on the GAT7 line (data not shown).

Application of 4× Pursuit® (imazethapyr) provided a large response from the STS® line (72%) at 7 DAS, while the GAT7 line (29%) had significantly less response (data not shown). At 14 DAS and 28 DAS, the difference between GAT7 and STS® was not significant (data not shown).

A tank mix of 1× Resolve®+4× Pursuit® resulted in significantly less spray response for the GAT7 line compared to the STS® line at 7, 14, and 28 DAS (data not shown). The 1× Resolve®+4× Pursuit® treatment on GAT7 was scored with less damage overall at 7, 14, and 28 DAS compared to the 1× Resolve® only and 1× Resolve®+Lorsban® treatment (data not shown). Using a pairwise comparison of these treatments on only the GAT7 line, the 1× Resolve®+4× Pursuit® treatment was scored significantly less than the 1× Resolve®+Lorsban® treatment at 14 and 28 DAS. In addition, a pairwise comparison of the 1× Resolve®+4× Pursuit® treatment compared to the 1× Resolve® treatment on GAT7 was only significantly less at 14 DAS.

Application of 16× Harmony® did not create a large response from the GAT7 or STS® lines at the three rating dates (data not shown). GAT7 was not significantly different from STS® for all the 16× Harmony® scores (data not shown). The treatment applying 4× Pursuit® mixed with 16× Harmony® did create significantly lower response scores for the GAT7 line compared to the STS® line at 7, 14, and 28 DAS (data not shown). The mixture of 4× Express® with 16× Harmony® was scored significantly lower for the GAT7 line compared to the STS® line at 7, 14, and 28 DAS (data not shown). In general, the GAT7 line provided excellent overall tolerance to the 16× Harmony®, 16× Harmony®+4× Pursuit®, and 16× Harmony®+4× Express® treatments at all the scoring dates.

A mixture of 0.25× Resolve®+1.5× Express® created a crop response from the GAT7 line at 7 DAS (53%) and 14 DAS (47%) that was not as evident at 28 DAS (12%) (data not shown). The STS® line had significantly higher response compared to GAT7 at 7 DAS (79%) and 14 DAS (90%) (data not shown). The STS® line did not recover at 28 DAS (87%) and had significantly more response compared to the GAT7 line (data not shown). Examining only the GAT7 line, a pairwise comparison of the 0.25× Resolves+1.5× Express® treatment had significantly less response observed compared to the 1× Resolve® treatment at 7, 14, and 28 DAS.

TABLE 19

Summary of Treatment Protocols

| TRT | TREATMENT COMPONENT | FORMULATION | RATE | UNIT | TIMING |
|---|---|---|---|---|---|
| 1 | Resolve 2 oz | | | | |
| | A >DPX-E9636 (WG 25.00 PC) | WG 25.00 PC | 2.00 | OMA | 01 POSPOS |
| | B SURFACTANT - NON-IONIC (SL) | SL 1.00 PR | 0.25 | PMV | 01 POSPOS |
| | C >AMSUL (GR 100 PC) | GR 100.00 PC | 2.00 | LMA | 01 POSPOS |
| 2 | Resolve + Lorsban | | | | |
| | A >DPX-E9636 (WG 25.00 PC) | WG 25.00 PC | 2.00 | OMA | 01 POSPOS |
| | B LORSBAN 4E (EC) | EC 4.00 LG | 1.00 | PMA | 01 POSPOS |
| | C SURFACTANT - NON-IONIC (SL) | SL 1.00 PR | 0.25 | PMV | 01 POSPOS |
| | D >AMSUL (GR 100 PC) | GR 100.00 PC | 2.00 | LMA | 01 POSPOS |
| 3 | Pursuit | | | | |
| | A PURSUIT DG (70WG) | WG 70.00 PC | 4.32 | OMA | 01 POSPOS |
| | B SURFACTANT - NON-IONIC (SL) | SL 1.00 PR | 0.25 | PMV | 01 POSPOS |
| | C >AMSUL (GR 100 PC) | GR 100.00 PC | 2.00 | LMA | 01 POSPOS |
| 4 | Resolve + Pursuit | | | | |
| | A >DPX-E9636 (WG 25.00 PC) | WG 25.00 PC | 2.00 | OMA | 01 POSPOS |
| | B PURSUIT DG (70WG) | WG 70.00 PC | 4.32 | OMA | 01 POSPOS |
| | C SURFACTANT - NON-IONIC (SL) | SL 1.00 PR | 0.25 | PMV | 01 POSPOS |
| | D >AMSUL (GR 100 PC) | GR 100.00 PC | 2.00 | LMA | 01 POSPOS |
| 5 | Harmony GT 1.33 oz | | | | |
| | A >HARMONY GT PX (75% EXTRUDED WG) | WG 75.00 PC | 1.33 | OMA | 01 POSPOS |
| | B SURFACTANT - NON-IONIC (SL) | SL 1.00 PR | 0.25 | PMV | 01 POSPOS |
| | C >AMSUL (GR 100 PC) | GR 100.00 PC | 2.00 | LMA | 01 POSPOS |
| 6 | GT + Pursuit | | | | |
| | A >HARMONY GT PX (75% EXTRUDED | WG 75.00 PC | 1.33 | OMA | 01 POSPOS |

TABLE 19-continued

Summary of Treatment Protocols

| TRT | | TREATMENT COMPONENT | FORMULATION | RATE | UNIT | TIMING |
|---|---|---|---|---|---|---|
| | | WG) | | | | |
| | B | PURSUIT DG (70WG) | WG 70.00 PC | 2.16 | OMA | 01 POSPOS |
| | C | SURFACTANT - NON-IONIC (SL) | SL 1.00 PR | 0.25 | PMV | 01 POSPOS |
| | D | >AMSUL (GR 100 PC) | GR 100.00 PC | 2.00 | LMA | 01 POSPOS |
| 7 | | Harmony GT 1.33 + EX 0.67 | | | | |
| | A | >HARMONY GT PX (75% EXTRUDED WG) | WG 75.00 PC | 1.33 | OMA | 01 POSPOS |
| | B | >EXPRESS PX (75% EXTRUDED WG) | WG 75.00 PC | 0.67 | OMA | 01 POSPOS |
| | C | SURFACTANT - NON-IONIC (SL) | SL 1.00 PR | 0.25 | PMV | 01 POSPOS |
| | D | >AMSUL (GR 100 PC) | GR 100.00 PC | 2.00 | LMA | 01 POSPOS |
| 8 | | Resolve 0.5 + Express 0.25 | | | | |
| | A | >DPX-E9636 (WG 25.00 PC) | WG 25.00 PC | 0.50 | OMA | 01 POSPOS |
| | B | >EXPRESS PX (75% EXTRUDED WG) | WG 75.00 PC | 0.25 | OMA | 01 POSPOS |
| | C | SURFACTANT - NON-IONIC (SL) | SL 1.00 PR | 0.25 | PMV | 01 POSPOS |
| | D | >AMSUL (GR 100 PC) | GR 100.00 PC | 2.00 | LMA | 01 POSPOS |
| 999 | | UNTREATED CHECK | | | | |
| | A | UNTREATED CHECK | NA 0.00 NA | 0.00 | NA | 00 UNTRCHK |

> = SUPPLEMENTAL CHEMICAL
RATE UNITS:
LMA = POUNDS MATERIAL/ACRE
NA = NOT APPLICABLE
OMA = OZ (DRY) MATERIAL/ACRE
PMA = PINTS MATERIAL/ACRE
PMV = % MATERIAL VOL TO VOL
DESIGN: RANDOMIZED COMPLETE BLOCK DESIGN
NO. REPS: 3
PLOT SIZE: 5 × 10 FEET
PLOT AREA: 50 SQUARE FEET
OBSERVATIONS/RATING:
Crop Response 7, 14 & 28 DAT
TIMINGS:
00 = UNTRCHK, UNTREATED TIMING
01 = POSPOS, POSTEMERGENCE V2-3

Example 6B

Example 6B provides greenhouse data that confirms the field trial data provided above in Example 6A. Soybeans comprising the lead GAT7 event and also having HRA were used in the studies.

TABLE 20

Summary of treatment conditions

| Test Plant | Rimsulfuron Rate (g ai/ha) | Imazethapyr Rate (g ai/ha) | Treatment # | Replicates | | | | |
|---|---|---|---|---|---|---|---|---|
| | | | | A | B | C | D | Mean |
| GAT/HRA Soybeans | 0 | 0 | 1 | 53.91 | | 53.16 | 59.21 | 55.43 |
| | | 140 | 2 | 48.8 | 52.97 | 54.45 | 61.67 | 54.47 |
| | | 280 | 3 | 49.06 | 53.65 | 39.74 | 61.06 | 50.88 |
| | | 560 | 4 | 56.46 | 52.98 | 57.76 | 55.76 | 55.74 |
| | | 1024 | 5 | 51.34 | 53.89 | 45.64 | 51.47 | 50.59 |
| | 35 | 0 | 6 | 21.09 | 20.45 | 27.11 | 20.83 | 22.37 |
| | | 140 | 7 | 18.18 | 18.79 | 26.03 | 22.15 | 21.29 |
| | | 280 | 8 | 26.45 | 15.59 | 14.53 | 26.5 | 20.77 |
| | | 560 | 9 | 22.2 | 22.97 | 26.8 | 20.65 | 23.16 |
| | | 1024 | 10 | 24.56 | 30.53 | 28.04 | 19.95 | 25.77 |
| | 70 | 0 | 11 | 18.33 | 24.56 | 15.83 | 19.75 | 19.62 |
| | | 140 | 12 | 16.71 | 23.1 | 27.27 | 21.44 | 22.13 |
| | | 280 | 13 | 27.43 | 34.8 | 32.26 | 21.65 | 29.04 |
| | | 560 | 14 | 28.84 | 26.17 | 28.12 | 31.95 | 28.77 |
| | | 1024 | 15 | 32.51 | 25.19 | 34.18 | 29.96 | 30.46 |
| | 140 | 0 | 16 | 20.09 | 12.5 | 13.96 | 23.32 | 17.47 |
| | | 140 | 17 | 21.69 | 24.38 | 16.15 | 17.27 | 19.87 |
| | | 280 | 18 | 23.77 | 21.72 | 27.16 | 26.22 | 24.72 |
| | | 560 | 19 | 30.39 | 34.67 | 21.46 | 28.41 | 28.73 |

TABLE 20-continued

Summary of treatment conditions

| Test Plant | Rimsulfuron Rate (g ai/ha) | Imazethapyr Rate (g ai/ha) | Treatment # | A | B | C | D | Mean |
|---|---|---|---|---|---|---|---|---|
|  |  | 1024 | 20 | 35.19 | 30.68 | 26 | 35.19 | 31.77 |
|  | 280 | 0 | 21 | 18.14 | 17.76 | 20.01 | 14.3 | 17.55 |
|  |  | 140 | 22 | 15.67 | 16.62 | 18.29 | 15.91 | 16.62 |
|  |  | 280 | 23 | 15.83 | 21.36 | 20.3 | 24.67 | 20.52 |
|  |  | 560 | 24 | 23.9 | 19.22 | 28.67 | 24.7 | 24.12 |
|  |  | 1024 | 25 | 30.93 | 28.76 | 24.69 | 36.65 | 30.26 |
| Jack Soybeans | 0 | 0 | 1 | 50.93 | 60.34 | 53.87 | 46.89 | 53.01 |
|  |  | 70 | 2 | 45.88 | 42.49 | 41.6 | 37.47 | 41.86 |
|  |  | 140 | 3 | 38.09 | 38.57 | 28.06 | 42.33 | 36.76 |
|  |  | 280 | 4 | 35.25 | 33.01 | 42.97 | 41.4 | 38.16 |
|  |  | 560 | 5 | 39.2 | 37.15 | 38.6 | 29.67 | 36.16 |
|  | 0.5 | 0 | 6 | 26.27 | 18.24 | 21.48 | 16.09 | 20.52 |
|  |  | 70 | 7 | 15.12 | 13.93 | 11.01 | 7.12 | 11.80 |
|  |  | 140 | 8 | 12.68 | 6.92 | 10.82 | 12.51 | 10.73 |
|  |  | 280 | 9 | 12.86 | 7.14 | 12.16 | 9.61 | 10.44 |
|  |  | 560 | 10 | 12.74 | 10.68 | 12.71 | 11.06 | 11.80 |
|  | 1 | 0 | 11 | 5.8 | 7.64 | 7.13 | 9.21 | 7.45 |
|  |  | 70 | 12 | 8.05 | 6.76 | 8.42 | 7.48 | 7.68 |
|  |  | 140 | 13 | 7.57 | 6.54 | 7.49 | 10 | 7.90 |
|  |  | 280 | 14 | 6.84 | 7.92 | 7.25 | 8.37 | 7.60 |
|  |  | 560 | 15 | 12.51 | 10.59 | 9.57 | 7.16 | 9.96 |
|  | 2 | 0 | 16 | 4.09 | 5.37 | 4.3 | 11.58 | 6.34 |
|  |  | 70 | 17 | 3.36 | 6.57 | 4.83 | 7.67 | 5.61 |
|  |  | 140 | 18 | 6.12 | 6.55 | 5.59 | 6.09 | 6.09 |
|  |  | 280 | 19 | 5.87 | 4.89 | 5.48 | 6.24 | 5.62 |
|  |  | 560 | 20 | 5.35 | 7.73 | 8.9 | 5.48 | 6.87 |
|  | 4 | 0 | 21 | 4.12 | 4.48 | 2.93 | 3.46 | 3.75 |
|  |  | 70 | 22 | 2.75 | 2.94 | 11.64 | 4.21 | 5.39 |
|  |  | 140 | 23 | 3.29 | 3.23 | 4.24 |  | 3.59 |
|  |  | 280 | 24 | 4.46 | 5.9 | 3.92 | 3.65 | 4.48 |
|  |  | 560 | 25 | 4.67 | 5.01 | 2.77 | 4.1 | 4.14 |

TABLE 21

Summary of greenhouse results.

| Test Plant | Rimsulfuron Rate (g ai/ha) | Imazethapyr Rate (g ai/ha) | Treatment # | A | B | C | D | Mean | Standard Deviation | Mean-Initial Weight | % Growth Reduction |
|---|---|---|---|---|---|---|---|---|---|---|---|
| GAT/HRA Soybeans | 0 | 0 | 1 | 53.91 | 53.16 | 59.21 | 55.43 | 55.43 | 3.30 | 49.28 | 0 |
|  |  | 140 | 2 | 48.8 | 52.97 | 54.45 | 61.67 | 54.47 | 5.36 | 48.33 | 2 |
|  |  | 280 | 3 | 49.06 | 53.65 | 39.74 | 61.06 | 50.88 | 8.92 | 44.73 | 9 |
|  |  | 560 | 4 | 56.46 | 52.98 | 57.76 | 55.76 | 55.74 | 2.02 | 49.60 | −1 |
|  |  | 1024 | 5 | 51.34 | 53.89 | 45.64 | 51.47 | 50.59 | 3.50 | 44.44 | 10 |
|  | 35 | 0 | 6 | 21.09 | 20.45 | 27.11 | 20.83 | 22.37 | 3.17 | 16.23 | 67 |
|  |  | 140 | 7 | 18.18 | 18.30 | 26.03 | 22.15 | 21.29 | 3.61 | 15.14 | 69 |
|  |  | 280 | 8 | 26.45 | 15.59 | 14.53 | 26.5 | 20.77 | 6.60 | 14.62 | 70 |
|  |  | 560 | 9 | 22.2 | 22.97 | 26.8 | 20.65 | 23.16 | 2.61 | 17.01 | 65 |
|  |  | 1024 | 10 | 24.56 | 30.53 | 28.04 | 19.95 | 25.77 | 4.59 | 19.63 | 60 |
|  | 70 | 0 | 11 | 18.33 | 24.56 | 15.83 | 19.75 | 19.62 | 3.67 | 13.47 | 73 |
|  |  | 140 | 12 | 16.71 | 23.1 | 27.27 | 21.44 | 22.13 | 4.37 | 15.99 | 68 |
|  |  | 280 | 13 | 27.43 | 34.85 | 32.26 | 21.65 | 29.04 | 5.80 | 22.89 | 54 |
|  |  | 560 | 14 | 28.84 | 26.17 | 28.12 | 31.95 | 28.77 | 2.40 | 22.63 | 54 |
|  |  | 1024 | 15 | 32.51 | 25.19 | 34.18 | 29.96 | 30.46 | 3.92 | 24.32 | 51 |
|  | 140 | 0 | 16 | 20.09 | 12.5 | 13.96 | 23.32 | 17.47 | 5.10 | 11.32 | 77 |
|  |  | 140 | 17 | 21.69 | 24.38 | 16.15 | 17.27 | 19.87 | 3.84 | 13.73 | 72 |
|  |  | 280 | 18 | 23.77 | 21.72 | 27.16 | 26.22 | 24.72 | 2.46 | 18.57 | 62 |
|  |  | 560 | 19 | 30.39 | 34.60 | 21.46 | 28.41 | 28.73 | 5.51 | 22.59 | 54 |
|  |  | 1024 | 20 | 35.19 | 30.68 | 26 | 35.19 | 31.77 | 4.39 | 25.62 | 48 |
|  | 280 | 0 | 21 | 18.14 | 17.76 | 20.01 | 14.3 | 17.55 | 2.38 | 11.41 | 77 |
|  |  | 140 | 22 | 15.67 | 16.62 | 18.29 | 15.91 | 16.62 | 1.18 | 10.48 | 79 |
|  |  | 280 | 23 | 15.83 | 21.36 | 20.3 | 24.57 | 20.52 | 3.61 | 14.37 | 71 |
|  |  | 560 | 24 | 23.9 | 19.22 | 28.67 | 24.7 | 24.12 | 3.88 | 17.98 | 64 |
|  |  | 1024 | 25 | 30.93 | 28.95 | 24.69 | 36.65 | 30.26 | 4.99 | 24.11 | 51 |

Example 7

Methods of Transformation Employing a GAT Sequence in Maize

I. Preparation of *Agrobacterium* Master Plate

1. Obtain engineered *Agrobacterium tumefaciens* strain with GAT components (SEQ ID NO: 70 or SEQ ID NO:55) and stored in −80° C. degree freezer as a 50% glycerol stock. The transcriptional control region used was the 3×35S ENH (−) operably linked to the ZmUbi PRO-5UTR-ZmUbi intron 1 promoter (SEQ ID NO:78). This transcriptional control region (SEQ ID NO:78) is set forth below denoting the location of the various regions of the regulatory region: a) the 35S enhancer (3×) in the reverse direction has a single underline; b) the UBI promoter has a double underline, and c) the UBI intron is in italics.

```
                                          (SEQ ID NO:78)
atcacatcaatccacttgctttgaagacgtggttggaacgtcttcttttt ccacgatgctcctcgtgggtggggtccatctttgggaccactgtcggca gaggcatcttcaacgatggcctttcctttatcgcaatgatggcatttgta ggagccaccttcctttccactatcttcacaataaagtgacagatagctg ggcaatggaatccgaggaggtttccggatattacccttgttgaaaagtc tcaattgccctttggtcttctgagactgtatctttgatattttggagta gacaagcgtgtcgtgctccaccatgttgacgaagattttcttcttgtcat tgagtcgtaagagactctgtatgaactgttcgccagtctttacggcgagt tctgttaggtcctctatttgaatctttgactccatggacggtatcgataa gctagcttgatatcacatcaatccacttgctttgaagacgtggttggaac gtcttcttttccacgatgctcctcgtgggtggggtccatctttgggac cactgtcggcagaggcatcttcaacgatggcctttcctttatcgcaatga tggcatttgtaggagccaccttcctttccactatcttcacaataaagtg acagatagctgggcaatggaatccgaggaggtttccggatattacccttt gttgaaaagtctcaattgccctttggtcttctgagactgtatctttgata ttttggagtagacaagcgtgtcgtgctccaccatgttgacgaagattttc ttcttgtcattgagtcgtaagagactctgtatgaactgttcgccagtct ttacggcgagttctgttaggtcctctatttgaatctttgactccatgatc gaattatcacatcaatccacttgctttgaagacgtggttggaacgtcttc ttttccacgatgctcctcgtgggtggggtccatctttgggaccactgt cggcagaggcatcttcaacgatggcctttcctttatcgcaatgatggcat ttgtaggagccaccttcctttccactatcttcacaataaagtgacagat agctgggcaatggaatccgaggaggtttccggatattacccttgttgaa aagtctcaattgccctttggtcttctgagactgtatctttgatattttg gagtagacaagcgtgtcgtgctccaccatgttgacgaagattttcttctt gtcattgagtcgtaagagactctgtatgaactgttcgccagtctttacgg cgagttctgttaggtcctctatttgaatctttgactccatgggaattcct gcagcccagcttgcatgcctgcagtgcagcgtgacccggtcgtgcccct -continued
ctctagagataatgagcattgcatgtctaagttataaaaaattaccacat attttttttgtcacacttgtttgaagtgcagtttatctatcttatacat atatttaaactttactctacgaataatataatctatagtactacaataat atcagtgttttagagaatcatatatataaatgaacagttagacatggtctaaag gacaattgagtatttttgacaacaggactctacagttttatcttttagtg tgcatgtgttctccttttttttgcaaatagcttcacctatataatactt catccatttttattagtacatccatttagggtttagggttaatggtttta tagactaatttttttagtacatctattttattctattttagcctctaaat taagaaactaaaactcctatttttagttttttttatttaataatttagata taaaatagaataaaataaagtgactaaaaattaaacaaatacccttaag aaattaaaaaaactaaggaaacattttcttgtttcgagtagataatgcc agcctgttaaacgccgtcgacgagtctaacggacaccaaccagcgaacca gcagcgtcgcgtcgggccaagcgaagcagacggcacggcatctctgtcgc tgcctctgacccctctcgagagttccgctccaccgttggacttgctccg ctgtcggcatccagaaattgcgtggcggagcggcagacgtgagccggcac ggcaggcggcctcctcctcctctcacggcaccggcagctacgggggattc ctttccaccgctccttcgctttcccttcctcgcccgccgtaataaatag acacccctccacaccctctttccccaacctcgtgttgttcggagcgcac acacacacaaccagatctcccccaaatccacccgtcggcacctccgcttc aaggtacgccgctcgtcctccccccccccctctctaccttctctagatc ggcgttccggtccatggttagggccccggtagttctacttctgttcatgtt tgtgttagatccgtgtttgtgttagatccgtgctgctagcgttcgtacac ggatgcgacctgtacgtcagacacgttctgattgctaacttgccagtgtt tctctttggggaatcctgggatggctctagccgttccgcagacgggatcg atttcatgatttttttttgtttcgttgcatagggtttggtttgccctttttc ctttatttcaatatatgccgtgcacttgtttgtcgggtcatcttttcatg ctttttttgtcttggttgtgatgatgtggtctggttgggcggtcgttct agatcggagtagaattctgtttcaaactacctggtggatttattaatttt ggatctgtatgtgtgtgccatacatattcatagttacgaattgaagatga tggatggaaatatcgatctaggataggtatacatgttgatgcgggtttta ctgatgcatatacagagatgcttttgttcgcttggttgtgatgatgtgg tgtggttgggcggtcgttcattcgttctagatcggagtagaatactgttt caaactacctggtgtatttattaatttggaactgtatgtgtgtgtcata catcttcatagttacgagtttaagatggatggaaatatcgatctaggata ggtatacatgttgatgtgggttttactgatgcatatacatgatggcatat gcagcatctattcatatgctctaaccttgagtacctatctattataataa acaagtatgttttataattatttttgatcttgatatacttggatgatggca tatgcagcagctatatgtggattttttagccctgccttcatacgctatt tatttgcttggtactgtttcttttgtcgatgctcaccctgttgtttggtg ttacttctgca
```

2. Prepare master plate from a glycerol stock by streaking the bacteria to produce single colonies on #800 medium and incubate the bacteria at 28° C. in the dark for 3-4 days.

3. Prepare a working plate by streaking 1 colony from the master plate across #810 media. Incubate bacteria at 28° C. in the dark for 1-2 days.

II. Preparation of Bacteria for Embryo Infection

1. Prepare liquid culture of *Agrobacterium* 1 day prior to embryo isolation. Set up a flask with 30 mls of 557 A medium, 30 µl of 2% acetosyringone and 30 µl of 5% spectinomycin.
2. Inoculate with 1 loopful of *Agrobacterium* from 810 medium and place on shaker (200 rpm) in dark room at 28° C. overnight.
3. On morning of infection, take samples of the liquid culture of *Agrobacterium* and make a ¼ dilution with 557 A. Use the diluted liquid culture to take OD reading using visible light at 550 nm.
4. Make dilutions to *Agrobacterium* culture as appropriate according the OD reading to maintain OD reading between 0.2-0.8 during embryo isolation.
5. When preparing *Agrobacterium* for infection, repeat OD reading of liquid culture. Using the OD reading calculate the number of mls required to obtain 5 E10 cfu/ml (cfu=colony forming unit) by using the formula EXPONENT (1.755*(lnOD)+21.77) as derived from a standard curve. Pipet the calculated amount of *Agrobacterium* liquid culture into 14 ml tube and centrifuge at 4500 rpm at 4-20° C. for ten minutes. Remove the supernatant and resuspend *Agrobacterium* in appropriate amount of 100 uM acetosyringone solution in 561Q.

III. Immature Embryo Isolation

1. Harvest GS3 ears at 9-11 days after pollination with embryo size of 1-2 mm in length.
2. Sterilize ear in 50% bleach and 1 drop Tween for 20-30 minutes. Rinse 3-5 times in sterile water
3. Isolate embryos from kernels and place in microtube containing 2 mls 561Q.

VI. *Agrobacterium* Infection of Embryos

1. Remove 561Q with pipette from the microtube with isolated embryos and add 1 ml of *Agrobacterium* suspension at OD described above.
2. Mix by vortexing for about 30 seconds.
3. Allow 5 minutes for infection at room temperature.

V. Co-Cultivation

1. After removing liquid medium, transfer embryos and orient the embryos with embryonic axis down on the surface of 562P co-cultivation medium.
2. Place embryos in 20° C. incubator for 3 days. Transfer to 28° C. for 3 additional days.

VI. Selection of Transgenic Putative Callus Events

1. After co-cultivation, transfer embryos to 563I selection medium containing 1 mM glyphosate. Culture the embryos at 28° C. in dark.
2. Every 14-21 days transfer embryos to fresh 563I medium. The selection process may last about 2 months until actively growing putative callus events can be identified. Maintain putative callus events on 563I medium and sample callus for PCR.

VII. Regeneration of T0 Plants

1. Transfer callus events to 287I medium containing 0.1 mM Glyphosate until somatic embryos mature. Culture the callus at 28° C. in dark.

2. Transfer mature embryos to 273I embryo germination medium containing 0.1 mM glyphosate in plates. Culture the plates at 28° C. in light.
3. When shoots and roots emerge, transfer individual plants to 273I containing 0.1 mM Glyphosate in tubes. Culture the tubes at 28° C. in light.
4. Plantlets with established shoots and roots shall be transferred to greenhouse for further growth and production of T1 seed.

Example 8

Effect of 35S Enhancer on Transformation Efficiency and Efficacy of GAT and ALS in Maize Materials and Methods Four 35S enhancer constructs (PHP20118, PHP20120, PHP20122, PHP20124) and one non-35S construct (PHP19288) were used to produce events to evaluate the effect of 35S enhancer on transformation efficiency and efficacy of GAT (SEQ ID NO:70) (FIG. 1). The differences between the four 35S enhancer constructs are the copy numbers of the 35S enhancer and the orientations of the 35S enhancer in the constructs. A summary of each 35S enhancer construct is provided below.

PHP20118 comprises 35S ENH(+):ZmUBI PRO-5UTR-UBI INTRON1 (+denotes forward direction of 35S enhancer). This transcriptional control region (SEQ ID NO:80) is set forth below denoting the location of the various regions of the regulatory region: a) the 35S enhancer in the forward direction has a single underline; b) the UBI promoter has a double underline, and c) the UBI intron is in italics.

```
                                              (SEQ ID NO:80)
cccatggagtcaaagattcaaatagaggacctaacagaactcgccgtaaa gactggcgaacagttcatacagagtctcttacgactcaatgacaagaaga aaatcttcgtcaacatggtggagcacgacacgcttgtctactccaaaata tcaaagatacagtctcagaagaccaaagggcaattgagacttttcaacaa agggtaatatccggaaacctcctcggattccattgcccagctatctgtca ctttattgtgaagatagtggaaaaggaaggtggctcctacaaatgccatc attgcgataaaggaaaggccatcgttgaagatgcctctgccgacagtggt cccaaagatggaccccacccacgaggagcatcgtggaaaaagaagacgt tccaaccacgtcttcaaagcaagtggattgatgtgatatcaagcttatcg ataccgtcgacctcgaggggggggcccagcttgcatgcctgcagtgcagcg tgacccggtcgtgcccctctctagagataatgagcattgcatgtctaagt tataaaaaattaccacatattttttttgtcacacttgtttgaagtgcagt ttatctatctttatacatatatttaaactttactctacgaataatataat ctatagtactacaataatatcagtgtttagagaatcatataaatgaaca gttagacatggtctaaaggacaattgagtatttttgacaacaggactctac agttttatcttttagtgtgcatgtgtttctccttttttttttgcaaaata gcttcacctatataatacttcatccattttattagtacatccatttaggg tttaggggtaatggttttttatagactaatttttttagtacatctattta ttctattttagcctctaaattaagaaaactaaaactctattttagttttt
``` ttatttaataatttagatataaaatagaataaaataaagtgactaaaaat
taaacaaataccctttaagaaattaaaaaaactaaggaaacattttttctt
gtttcgagtagataatgccagcctgttaaacgccgtcgacgagtctaacg
gacaccaaccagcgaaccagcagcgtcgcgtcgggccaagcgaagcagac
ggcacggcatctctgtcgctgcctctggacccctctcgagagttccgctc
caccgttggacttgctccgctgtcggcatccagaaattgcgtggcggagc
ggcagacgtgagccggcacggcaggcggcctcctcctcctctcacggcac
cggcagctacggggattcctttcccaccgctccttcgctttcccttcct
cgcccgccgtaataaatagacaccccctccacaccctctttccccaacct
cgtgttgttcgagcgcacacacacaaccagatctcccccaaatccac
ccgtcggcacctccgcttcaaggtacgccgctcgtcctccccccccccc
tctctaccttctctagatcggcgttccggtccatggttagggccggtag
ttctacttctgttcatgtttgtgttagatccgtgtttgtgttagatccgt
gctgctagcgttcgtacacggatgcgacctgtacgtcagacacgttctga
ttgctaacttgccagtgtttctctttggggaatcctgggatggctctagc
cgttccgcagacgggatcgatttcatgatttttttttgtttcgttgcatag
ggtttggtttgccctttttcctttatttcaatatatgccgtgcacttgttt
gtcgggtcatcttttcatgctttttttttgtcttggttgtgatgatgtggt
ctggttgggcggtcgttctagatcggagtagaattctgtttcaaactacc
tggtggatttattaattttggatctgtatgtgtgtgccatacatattcat
agttacgaattgaagatgatggatggaaatatcgatctaggataggtata
catgttgatgcgggttttactgatgcatatacagagatgcttttgttcg
cttggttgtgatgatgtggtgtggttgggcggtcgttcattcgttctaga
tcggagtagaatactgtttcaaactacctggtgtatttattaattttgga
actgtatgtgtgtgtcatacatcttcatagttacgagtttaagatggatg
gaaatatcgatctaggataggtatacatgttgatgtgggttttactgatg
catatacatgatggcatatgcagcatctattcatatgctctaaccttgag
tacctatctattataataaacaagtatgttttataattattttgatcttg
atatacttggatgatggcatatgcagcagctatatgtggattttttagc
cctgccttcatacgctatttatttgcttggtactgtttcttttgtcgatg
ctcaccctgttgtttggtgttacttctgca PHP20122 comprises 3×35S ENH (+):ZmUBI PRO-5UTR-UBI INTRON1 (+denotes forward direction of 35S enhancer). This transcriptional control region (SEQ ID NO:81) is set forth below denoting the location of the various regions of the regulatory region: a) the 35S enhancer in the forward direction has a single underline; b) the UBI promoter has a double underline, and c) the UBI intron is in italics.

(SEQ ID NO: 81)
cccatggagtcaaagattcaaatagaggacctaacagaactcgccgtaaa
gactggcgaacagttcatacagagtctcttacgactcaatgacaagaaga
aaatcttcgtcaacatggtggagcacgacacgcttgtctactccaaaaat
atcaaagatacagtctcagaagaccaaagggcaattgagacttttcaaca
aagggtaatatccggaaacctcctcggattccattgcccagctatctgtc
actttattgtgaagatagtggaaaaggaaggtggctcctacaaatgccat
cattgcgataaaggaaaggccatcgttgaagatgcctctgccgacagtgg
tcccaaagatggaccccacccacgaggagcatcgtggaaaaagaagacg
ttccaaccacgtcttcaaagcaagtggattgatgtgataattcgatcatg
gagtcaaagattcaaatagaggacctaacagaactcgccgtaaagactgg
cgaacagttcatacagagtctcttacgactcaatgacaagaagaaaatct
tcgtcaacatggtggagcacgacacgcttgtctactccaaaaatatcaaa
gatacagtctcagaagaccaaagggcaattgagacttttcaacaaaggt
aatatccggaaacctcctcggattccattgcccagctatctgtcactta
ttgtgaagatagtggaaaaggaaggtggctcctacaaatgccatcattgc
gataaaggaaaggccatcgttgaagatgcctctgccgacagtggtcccaa
agatggaccccacccacgaggagcatcgtggaaaaagaagacgttccaa
ccacgtcttcaaagcaagtggattgatgtgatatcaagcttatcgatacc
gccatggagtcaaagattcaaatagaggacctaacagaactcgccgtaaa
gactggcgaacagttcatacagagtctcttacgactcaatgacaagaaga
aaatcttcgtcaacatggtggagcacgacacgcttgtctactccaaaaat
atcaaagatacagtctcagaagaccaaagggcaattgagacttttcaaca
aagggtaatatccggaaacctcctcggattccattgcccagctatctgtc
actttattgtgaagatagtggaaaaggaaggtggctcctacaaatgccat
cattgcgataaaggaaaggccatcgttgaagatgcctctgccgacagtgg
tcccaaagatggaccccacccacgaggagcatcgtggaaaaagaagacg
ttccaaccacgtcttcaaagcaagtggattgatgtgatgtctgcagtgca
gcgtgacccggtcgtgcccctctagagataatgagcattgcatgtcta
agttataaaaaattaccacatatttttttgtcacacttgtttgaagtgc
agtttatctatctttatacatatatttaaactttactctacgaataatat
aatctatgtactacaataatatcagtgttttagagaatcatataaatga
acagttagacatggtctaaaggacaattgagtattttgacaacaggactc
tacagttttatcttttagtgtgcatgtgttctccttttttttttgcaaat
agcttcacctatataatacttcatccatttattagtacatccatttagg
gttagggttaatggttttatagactaattttttagtacatctattt
attctattttagcctctaaattaagaaaactaaaactctattttagtttt
tttatttaataatttagatataaaatagaataaaataaagtgactaaaaa
ttaaacaaatacccttaagaaattaaaaaaactaaggaaacattttcct
tgtttcgagtagataatgccagcctgttaaacgccgtcgacgagtctaac
ggacaccaaccagcgaaccagcagcgtcgcgtcgggccaagcgaagcaga
cggcacggcatctctgtcgctgcctctggacccctctcgagagttccgct
ccaccgttggacttgctccgctgtcggcatccagaaattgcgtggcggag
cggcagacgtgagccggcacggcaggcggcctcctcctcctctcacggca -continued ccggcagctacgggggattcctttcccaccgctcctTcgctttcccttcc tcgcccgccgtaataaatagacaccccctccacaccctctttccccaacc tcgtgttgttcggagcgcacacacacaaccagatctcccccaaatcca cccgtcggcacctccgcttcaaggtacgccgctcgtcctccccccccc ctctctaccttctctagatcggcgttccggtccatggttagggcccggta gttctacttctgttcatgtttgtgttagatccgtgtttgtgttagatccg tgctgctagcgttcgtacacggatgcgacctgtacgtcagacacgttctg attgctaacttgccagtgtttctctttggggaatcctgggatggctctag ccgttccgcagacgggatcgatttcatgattttttttgtttcgttgcata gggtttggtttgcccttttcctttatttcaatatatgccgtgcacttgtt tgtcgggtcatcttttcatgcttttttttgtcttggttgtgatgatgtgg tctggttgggcggtcgtctagatcggagtagaattctgtttcaaactac ctggtggatttattaattttggatctgtatgtgtgtgccatacatattca tagttacgaattgaagatgatggatgaaatatcgatctaggataggtat acatgttgatgcgggttttactgatgcatatacagagatgcttttgttc gcttggttgtgatgatgtggtgtggttgggcggtcgttcattcgttctag atcggagtagaatactgtttcaaactacctggtgtatttattaattttgg aactgtatgtgtgtcatacatcttcatagttacgagtttaagatggat ggaaatatcgatctaggataggtatacatgttgatgtgggttttactgat gcatatacatgatggcatatgcagcatctattcatatgctctaaccttga gtacctatctattataataaacaagtatgttttataattattttgatctt gatatacttggatgatggcatatgcagcagctatatgtggatttttttag ccctgccttcatacgctatttatttgcttggtactgtttcttttgtcgat

*gctcaccctgttgtttggtgttacttctgca*

PHP20120 comprises 35S ENH (−):ZmUBI PRO-5UTR-UBI INTRON1 (−denotes reverse direction of 35S enhancer). This transcriptional control region (SEQ ID NO:82) is set forth below denoting the location of the various regions of the regulatory region: a) the 35S enhancer in the reverse direction has a single underline; b) the UBI promoter has a double underline, and c) the UBI intron is in italics.

(SEQ ID NO:82)
atcacatcaatccacttgctttgaagacgtggttggaacgtcttcttttc cacgatgctcctcgtgggtgggggtccatctttgggaccactgtcggcag aggcatcttcaacgatggcctttccttatcgcaatgatggcatttgtag gagccaccttccttttccactatcttcacaataaagtgacagatagctgg gcaatggaatccgaggaggtttccggatattacccttgttgaaaagtct caattgccctttggtcttctgagactgtatctttgatattttggagtag acaagctgtcgtgctccaccatgttgacgaagattttcttcttgtcatt gagtcgtaagagactctgtatgaactgttcgccagtctttacggcgagtt ctgttaggtcctctatttgaatctttgactccatgggaattcctgcagcc cagcttgcatgcctgcagtgcagcgtgacccggtcgtgcccctctctaga -continued gataatgagcattgcatgtctaagttataaaaaattaccacatattttt ttgtcacacttgtttgaagtgcagtttatctatctttatacatatattta aactttactctacgaataatataatctatagtactacaataatatcagtg ttttagagaatcatataaatgaacagttagacatggtctaaaggacaatt gagtattttgacaacaggactctacagtttatcttttagtgtgcatgt gttctccttttttttttgcaaatagcttcacctatataatacttcatccat tttattagtacatccatttagggtttagggttaatggtttttatagacta attttttagtacatctattttattctattttagcctctaaattaagaaa actaaaactctattttagtttttttattaataatttagatataaaatag aataaaataaagtgactaaaaattaaacaaataccctttaagaaattaaa aaaactaaggaaacattttcttgtttcgagtagataatgccagcctgtt aaacgccgtcgacgagtctaacgacaccaaccagcgaaccagcagcgtc gcgtcgggccaagcgaagcagacggcacggcatctctgtcgctgcctctg gaccctctcgagagttcgcctcctcctcctctcacggcaccggcagcta cggggggattcctttcccaccgctcctTcgctttcccttcctcgcccgccg taataaatagacaccccctccacaccctctttccccaacctcgtgttgtt cggagcgcacacacacaaccagatctcccccaaatccaccgtcggca cctccgcttcaaggtacgccgctcgtcctccccccccccctctctacct tctctagatcggcgttccggtccatggttagggcccggtagttctacttc tgttcatgtttgtgttagatccgtgtttgtgttagatccgtgctgctagc gttcgtacacggatgcgacctgtacgtcagacacgttctgattgctaact tgccagtgtttctctttggggaatcctgggatggctctagccgttccgca gacgggatcgatttcatgattttttttgtttcgttgcatagggtttggtt tgccttttcctttatttcaatatatgccgtgcacttgtttgtcgggtca cttttcatgctttttttgtcttggttgtgatgatgtggtctggttgggc ggtcgttctagatcggagtagaattctgtttcaaactacctggtggattt attaattttggatctgtatgtgtgtgccatacatattcatagttacgaat tgaagatgatggatgaaatatcgatctaggataggtatacatgttgatg cgggttttactgatgcatatacagagatgcttttgttcgcttggttgtg

*atgatgtggtgtggttgggcggtcgttcattcgttctagatcggagtaga*

*atactgtttcaaactacctggtgtatttattaattttggaactgtatgtg*

*tgtgtcatacatcttcatagttacgagtttaagatggatggaaatatcga*

*tctaggataggtatacatgttgatgtgggttttactgatgcatatacatg*

*atggcatatgcagcatctattcatatgctctaaccttgagtacctatcta*

*ttataaacaagtatgttttataattattttgatcttgatatacttgg*

*atgatggcatatgcagcagctatatgtggatttttttagccctgccttca*

*tacgctatttatttgcttggtactgtttcttttgtcgatgctcaccctgt*

*tgtttggtgttacttctgca*

PHP20124 comprises 3×35S ENH (−): ZmUBI PRO-5UTR-UBI INTRON1 (−denotes reverse direction of 35S enhancer). This transcriptional control region (SEQ ID NO:83) is set forth below denoting the location of the various regions of the regulatory region: a) the 35S enhancer in the reverse direction has a single underline; b) the UBI promoter has a double underline, and c) the UBI intron is in italics.

(SEQ ID NO:83)
<u>atcacatcaatccacttgctttgaagacgtggttggaacgtcttcttttt</u>

<u>ccacgatgctcctcgtgggtgggggtccatctttgggaccactgtcggca</u>

<u>gaggcatcttcaacgatggcctttcctttatcgcaatgatggcatttgta</u>

<u>ggagccaccttccttttccactatcttcacaataaagtgacagatagctg</u>

<u>ggcaatggaatccgaggaggtttccggatattacccttgttgaaaagtc</u>

<u>tcaattgcctttggtcttctgagactgtatctttgatattttggagta</u>

<u>gacaagcgtgtcgtgctccaccatgttgacgaagattttcttcttgtcat</u>

<u>tgagtcgtaagagactctgtatgaactgttcgccagtctttacggcgagt</u>

<u>tctgttaggtcctgtatttgaatctttgactccatgacggtatcgataa</u>

<u>gctagcttgatatcacatcaatccacttgctttgaagacgtggttggaac</u>

<u>gtcttcttttccacgatgctcctcgtgggtgggggtccatctttgggac</u>

<u>cactgtcggcagaggcatcttcaacgatggcctttcctttatcgcaatga</u>

<u>tggcatttgtaggagccaccttccttttccactatcttcacaataaagtg</u>

<u>acagatagctgggcaatggaatccgaggaggtttccggatattaccctt</u>

<u>gttgaaaagtctcaattgcctttggtcttctgagactgtatctttgata</u>

<u>ttttggagtagacaagcgtgtcgtgctccaccatgttgacgaagatttt</u>

<u>cttcttgtcattgagtcgtaagagactctgtatgaactgttcgccagtct</u>

<u>ttacggcgagttctgttaggtcctctatttgaatctttgactccatgatc</u>

<u>gaattatcacatcaatccacttgctttgaagacgtggttggaacgtcttc</u>

<u>ttttccacgatgctcctcgtgggtgggggtccatctttgggaccactgt</u>

<u>cggcagaggcatcttcaacgatggcctttcctttatcgcaatgatggcat</u>

<u>ttgtaggagccaccttccttttccactatcttcacaataaatgacagata</u>

<u>gctgggcaatggaatccgaggaggtttccggatattacccttgttgaaa</u>

<u>agtctcaattgcctttggtcttctgagactgtatctttgatattttgg</u>

<u>agtagacaagcgtgtcgtgctccaccatgttgacgaagattttcttcttg</u>

<u>tcattgagtcgtaagagactctgtatgaactgttcgccagtctttacggc</u>

<u>gagttctgttaggtcctctatttgaatctttgactccatgggaattcctg</u> cagcccagcttgcatgc<u>ctgcagtgcagcgtgacccggtcgtgccctct</u>

<u>ctagagataatgagcattgcatgtctaagttataaaaattaccacatat</u>

<u>ttttttgtcacacttgtttgaagtgcagtttatctatctttatacatat</u>

<u>atttaaactttactctacgaataatataatctatagtactacaataatat</u>

<u>cagtgttttagagaatcatataaatgaacagttagacatggtctaaagga</u>

<u>caattgagtattttgacaacaggactctacagttttatcttttagtgtg</u>

<u>catgtgttctccttttttttgcaaatagcttcacctatataatacttca</u>

<u>tccattttattagtacatccatttagggtttagggttaatggttttata</u>

<u>gactaatttttttagtacatctattttattctattttagcctctaaatta</u>

<u>agaaaactaaaactctattttagtttttttatttaataatttagatataa</u>

-continued
<u>atagaataaaataaagtgactaaaaattaaacaaataccctttaagaaat</u>

<u>taaaaaaactaaggaaacattttcttgtttcgagtagataatgccagcc</u>

<u>tgttaaacgccgtcgacgagtctaacggacaccaaccagcgaaccagcag</u>

<u>cgtcgcgtcgggccaagcgaagcagacggcacggcatctctgtcgctgcc</u>

<u>tctggacccgcacggcaggcggcctcctcctcctctcacggcaccggcag</u>

<u>ctacgggggattccttcccaccgctccttcgctttcccttcctcgcccgc</u>

<u>cgtaataaatagacacccctccacaccctctttccccaacctcgtgttg</u> ttcggagcgcacacacacacaaccagatctcccccaaatccaccccgtcgg cacctccgcttcaag*gtacgccgctcgtcctccccccccccctctctac*

*cttctctagatcggcgttccggtccatggttagggcccggtagttctact*

*tctgttcatgtttgtgttagatccgtgtttgtgttagatccgtgctgcta*

*gcgttcgtacacggatgcgacctgtacgtcagacacgttctgattgctaa*

*cttgccagtgtttctctttggggaatcctgggatggctctagccgttccg*

*cagacgggatcgatttcatgattttttttgtttcgttgcatagggtttgg*

*tttgcccttttcctttatttcaatatatgccgtgcacttgtttgtcgggt*

*catcttttcatgcttttttttgtcttggttgtgatgatgtggtctggttg*

*ggcggtcgttctagatcggagtagaattctgtttcaaactacctggtgga*

*tttattaattttggatctgtatgtcgtgtgccatacatattcatagttac*

*gaattgaagatgatggatggaaatatcgatctaggataggtatacatgtt*

*gatgcgggttttactgatgcatatacagagatgcttttttgttcgcttggt*

*tgtgatgatgtggtgtggttgggcggtcgttcattcgttctagatcggag*

*tagaatactgtttcaaactacctggtgtatttattaattttggaactgta*

*tgtgtgtgtcatacatcttcatagttacgagtttaagatggatggaaata*

*tcgatctaggataggtatacatgttgatgtgggttttactgatgcatata*

*catgatggcatatgcagcatctattcatatgctctaaccttgagtaccta*

*tctattataataaacaagtatgttttataattattttgatcttgatatac*

*ttggatgatggcatatgcagcagctatatgtggatttttttagccctgcc*

*ttcatacgctatttatttgcttggtactgtttcttttgtcgatgctcacc*

*ctgttgtttggtgttacttctgca*

Figure 3:
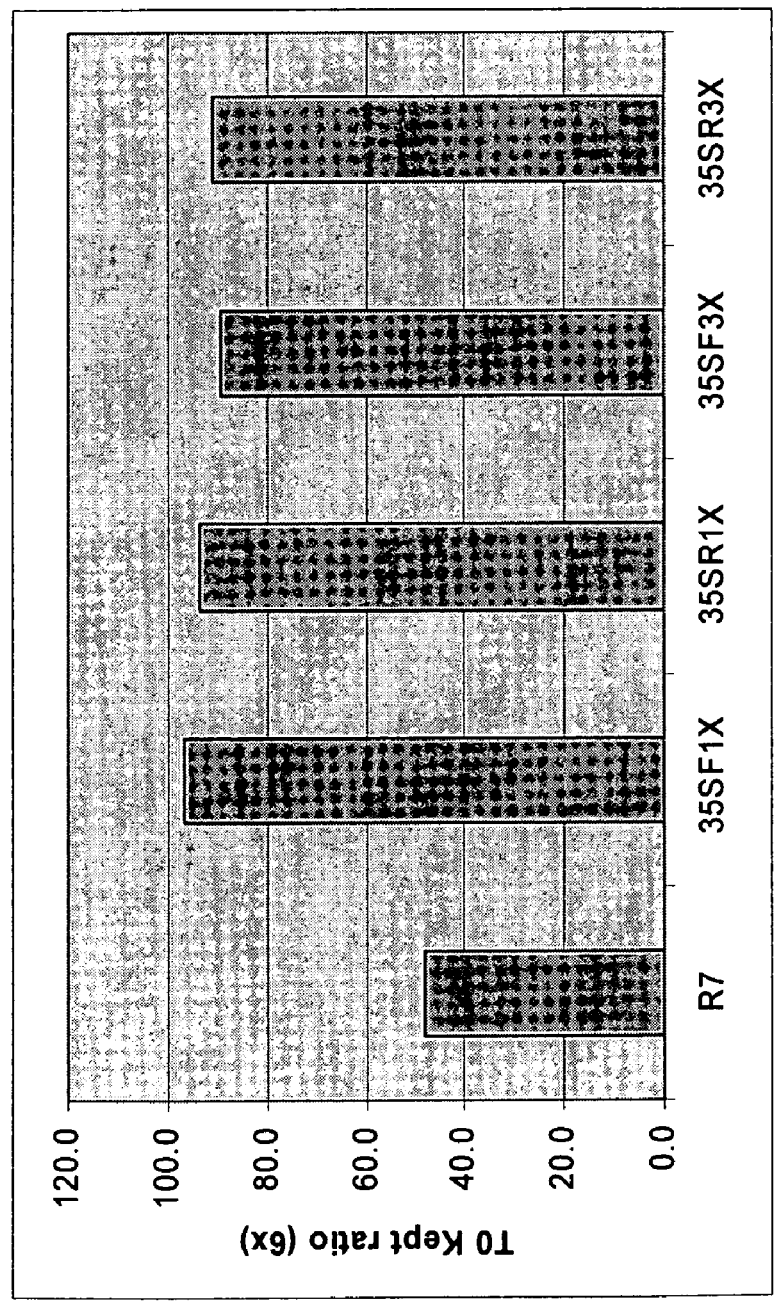
FIG. 3 provides a schematic demonstrating the effect of 35S enhancers on T0 efficiency.

The transformation experiments were conducted side-by-side using the same embryos from the same ears. Immature embryos of GS3 line were aseptically removed from each ear and divided into five portions. Each portion of the embryos was then infected with *A. tumefaciens* strain LBA4404 containing the expression cassettes from each of the five constructs, respectively. After 6 days co-cultivation, the embryos were transferred to fresh selection medium containing glyphosate. The transformed cells, which survived the glyphosate selection, proliferated and produced somatic embryogenic calli. After about two months subculture, the calli were then manipulated to regenerate whole transgenic plants with glyphosate presence and were transferred to the greenhouse. T0 plants were then subjected to glyphosate spray at 6× (156 oz/ac) Roundup Ready UltraMax™ at V3 or V4 stage in the greenhouse. Positive plants were sampled for quantitative PCR for copy number and western for expression. T0 plants were then crossed with inbred lines to obtain seeds for further evaluation. Results Transformation efficiency was measured as the percentage of the infected embryos that produced resistant calli after selection. The average transformation efficiencies for PHP19288, PHP20118, PHP20120, PHP20122, and PHP20124 were 58%, 63%, 59%, 57%, and 51%, respectively. The data indicated that all constructs had quite high and similar transformation efficiencies, although PHP20118 showed a slight increase (FIG. 3).

Figure 4:
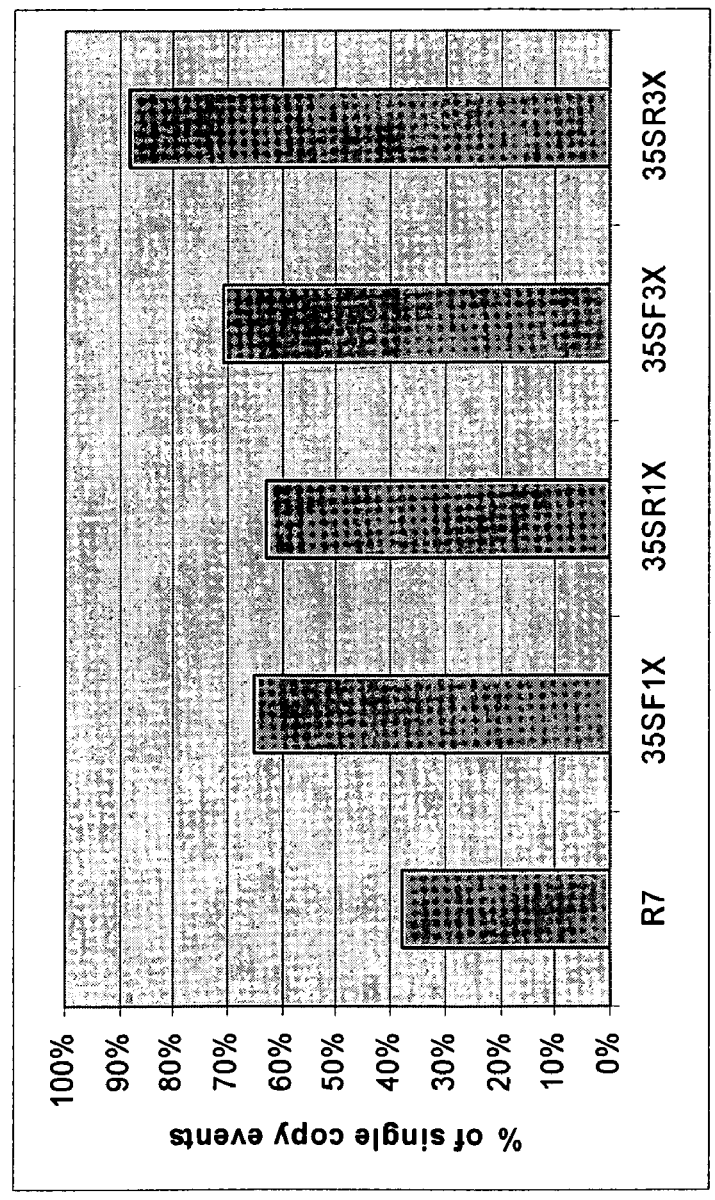
FIG. 4 provides a schematic demonstrating the effect of 35S enhancers on event copy number.

T0 plant efficacy was defined as the percentage of the T0 events that were completely resistant to the 6× glyphosate spray. The efficacy of the non-35S construct (PHP19288) was 48.1%. In contrast, the efficacies of the 35S enhancer constructs (PHP20118, PHP20120, PHP20122, and PHP20124) were 96.6%, 93.5%, 89.1%, and 91.1%, respectively (FIG. 4). The data showed that all 35S enhancer constructs significantly increased the plant efficacy against glyphosate.

Another significant improvement of using 35S enhancer was in integration pattern of the transgene. The percentage of the tested events that were single copy for the non-35S enhancer construct was only 38%, but for the four 35S enhancer constructs (PHP20118, PHP20120, PHP20122, and PHP20124) single copy events represented 65%, 63%, 71%, and 88% of the events, respectively (FIG. 4).

Figure 5:
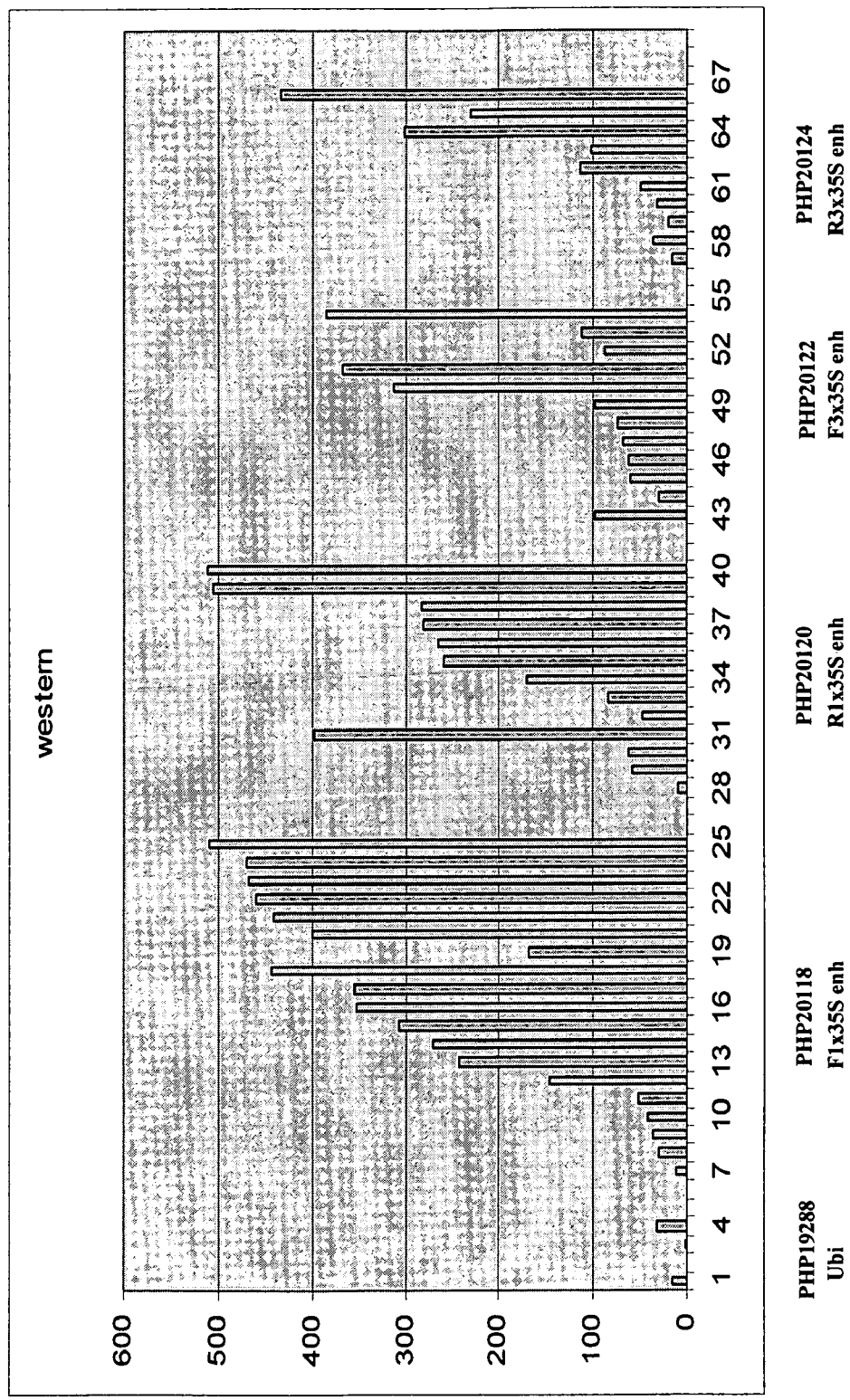
FIG. 5 provides a table showing the effect of the 35S enhancers on T2 efficiency.

A subset of events from all five constructs were sampled by Western analysis to look any comparative differences in GAT expression between non 35S and 35S events. This analysis showed that events from the non-35S enhancer construct had very low levels of GAT expression whereas the majority of the events from the 35S enhancer constructs showed very high levels of GAT expression (FIG. 5).

Example 9

Figure 6:
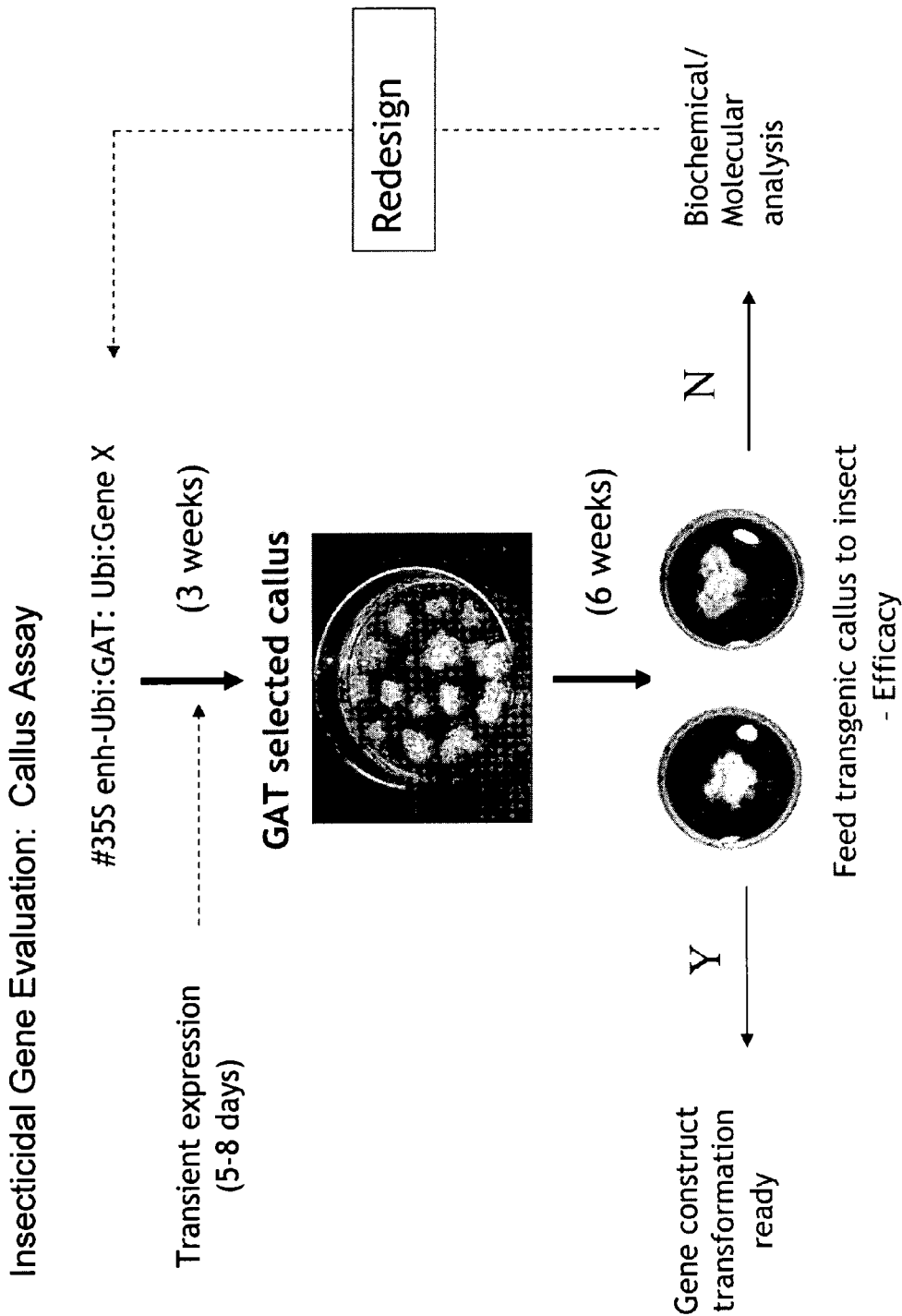
FIG. 6 provides an insecticidal gene evaluation assay.

Using 35S Enhancer GAT in Developing a Novel Callus-Based Gene/Construct Evaluation System Materials and Methods This assay is being developed to improve the evaluation of expression of an insecticidal gene at a very early stage in the transformation process in order to identify potential problems with expression. The basis of this assay is the use of the glyphosate acetyl transferase (GAT) gene (SEQ ID NO:55) as a selectable marker. Both GAT and the insecticidal test gene will be driven by a strong constitutive promoter and linked in the same construct. The promoter employed comprised the ZmUBI PRO-5UTR-UBI INTRON1 with the 3×35S enhancer as described above in Example 7. As a result it is expected that selection on high levels of glyphosate will identify high insecticidal test gene expressors. The callus tissue from these putative high expressors will then be used in insect bioassays to determine whether the gene product is functional. Those constructs showing efficacy can be advanced into transformation. If the construct does not show efficacy then follow up biochemical and molecular analyses can be conducted to identify the problem and the gene will be redesigned and retested in the system (FIG. 6).

Results

The assay is currently under development. Preliminary data has shown that the activity of an efficacious insect control gene can be detected at the callus stage. The correlation between the callus activity and the plant efficacy is currently being evaluated.

Example 10

GAT as a Selectable Marker

Materials and Method

Agrobacterium mediated transformation was used to introduce the GA T (SEQ ID NO:55) expression cassette into the corn genome. The GAT expression cassette comprises, promoter comprising ZmUBI PRO-5UTR-UBI INTRON1 with the 3×35S enhancer (as described above in Example 1) operably linked to the gat gene, and pinII terminator. *Agrobacterium tumefaciens*, strain LBA4404, was pathogenically disarmed by removing its native T-DNA. Instead, the T-DNA site on the Ti plasmid contained the GAT expression cassette.

Immature embryos of maize were aseptically removed from the developing caryopsis and treated with *A. tumefaciens* strain LBA4404 containing GAT expression cassettes. After a period of embryo and *Agrobacterium* co-cultivation on solid culture medium without glyphosate presence, the embryos were transferred to fresh selection medium that contained antibiotics and glyphosate. The antibiotics kill any remaining *Agrobacterium*. The selection medium is stimulatory to maize somatic embryogenesis and selective for those cells that contain an integrated gat gene. Therefore, callus that survives glyphosate to proliferate and produce embryogenic tissue is presumably genetically transformed. Callus samples were taken for molecular analysis to verify the presence of the transgene by PCR. The embryonic tissue is then manipulated to regenerate transgenic plants in the presence of glyphosate that are then transferred to the greenhouse. T0 plants are sprayed with glyphosate at different concentrations. Positive plants are sampled for molecular analysis for transgene copy number and crossed with inbred lines to obtain seeds from the initially transformed plants.

Figure 7:
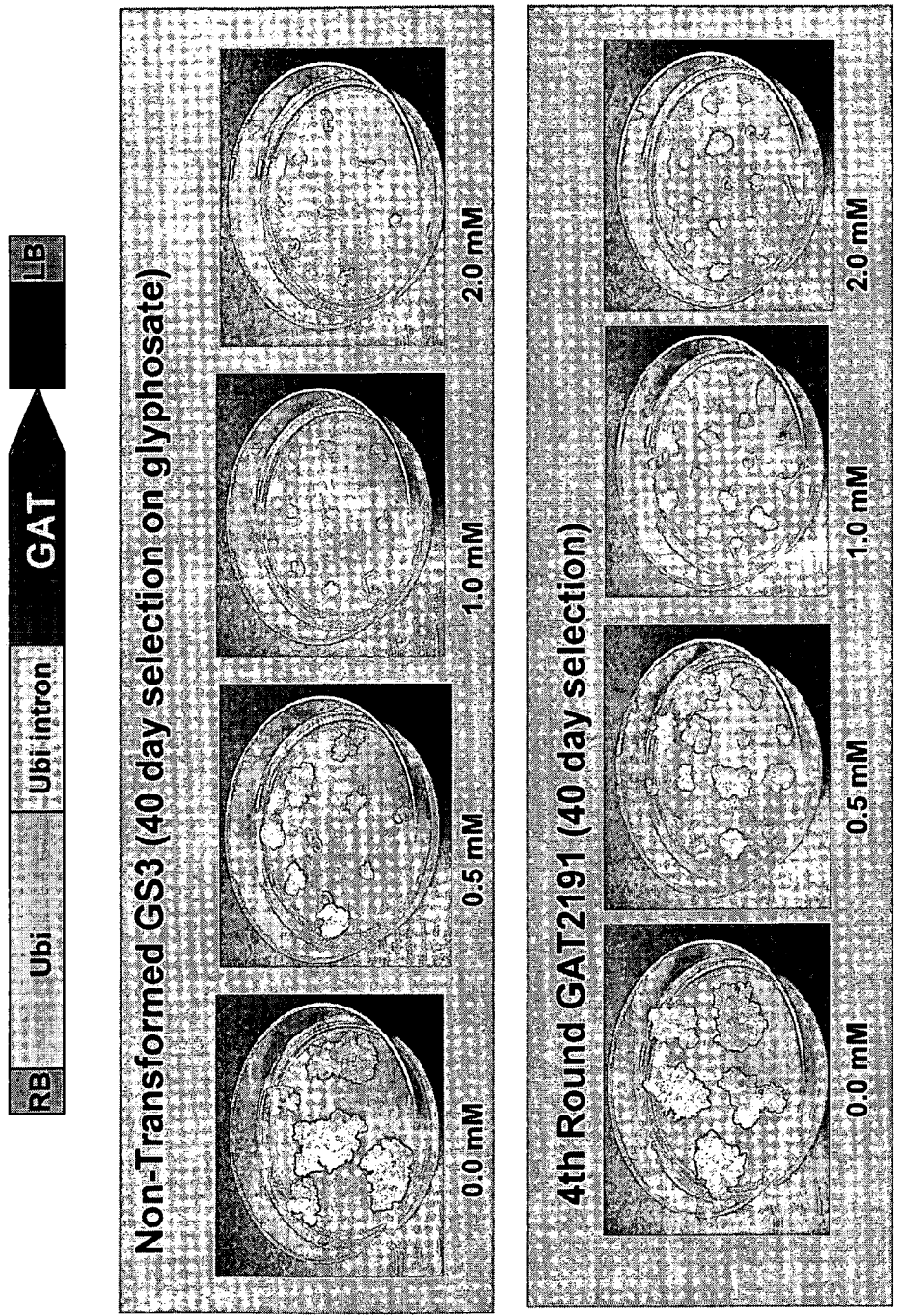
FIG. 7 provides a schematic showing the development of a GAT selection scheme.

A glyphosate kill curve was established by testing non-transformed embryos response on media with different levels of glyphosate. GS3 embryos were isolated from an immature ear and placed onto media containing glyphosate at 0.0, 0.5, 1.0, and 2.0 mM. After about 40 days culture, the response of the embryos were observed and recorded. Similarly, infected GS3 embryos with the GAT construct were placed onto media containing glyphosate at 0.0, 0.5, 1.0, and 2.0 mM. After about 40 days culture, the response of the infected embryos were observed and recorded (FIG. 7).

A side-by-side experiment was conducted to compare the transformation efficiencies of GAT, bar and mopat. Immature embryos of GS3 line were aseptically removed from each ear and divided into three portions. Each portion of the embryos was then infected with *A. tumefaciens* strain LBA4404 containing the expression cassettes of GAT, bar, or mopat respectively. After co-cultivation, the embryos infected with GAT construct were selected on routine glyphosate medium and the embryos infected with bar or mopat constructs were selected on routine glufosinate medium. The subcultures were done every 2 weeks. At about 50 days selection the responses of the embryos were observed and recorded.

Results

From the glyphosate kill curve experiment, all embryos on medium with 0.0 mM glyphosate initiated healthy callus, while about half of the embryos on medium with 0.5 mM glyphosate showed callus initiation. There was very little callus growth with embryos on media containing 1.0 and 2.0 mm glyphosate. This indicated that 0.5 mM is not enough to inhibit all embryos growth, but 1 mM or 2 mM is strong enough to kill the non-transformed embryos. In the infected embryo experiment, more callus was grown on media with 0.0 and 0.5 mM glyphosate, but some embryos initiated resistant callus on media with 1.0 mM or 2.0 mM glyphosate. Western or PCR analysis has confirmed that these resistant calli were transformed. Currently, GAT has performed consistently as an effective selectable marker with excellent transformation efficiency in both GS3 and introEF09B genotypes (FIG. 10 and Table 45).

TABLE 22

GAT transformation efficiency in introEF09B

| genotype | construct | selectable marker | # infected embryos | # events to GH | txn % based on # events to GH |
|---|---|---|---|---|---|
| EFWWBTX | GATHRA | GAT | 1332 | 354 | 27% |
| EFWWCTX | GATHRA | GAT | 136 | 47 | 35% |
| EFWWETX | GATHRA | GAT | 1109 | 158 | 14% |
| EFWWZTX | GATHRA | GAT | 1790 | 502 | 28% |
| | | | 4367 | 1061 | 24% |

Figure 8:
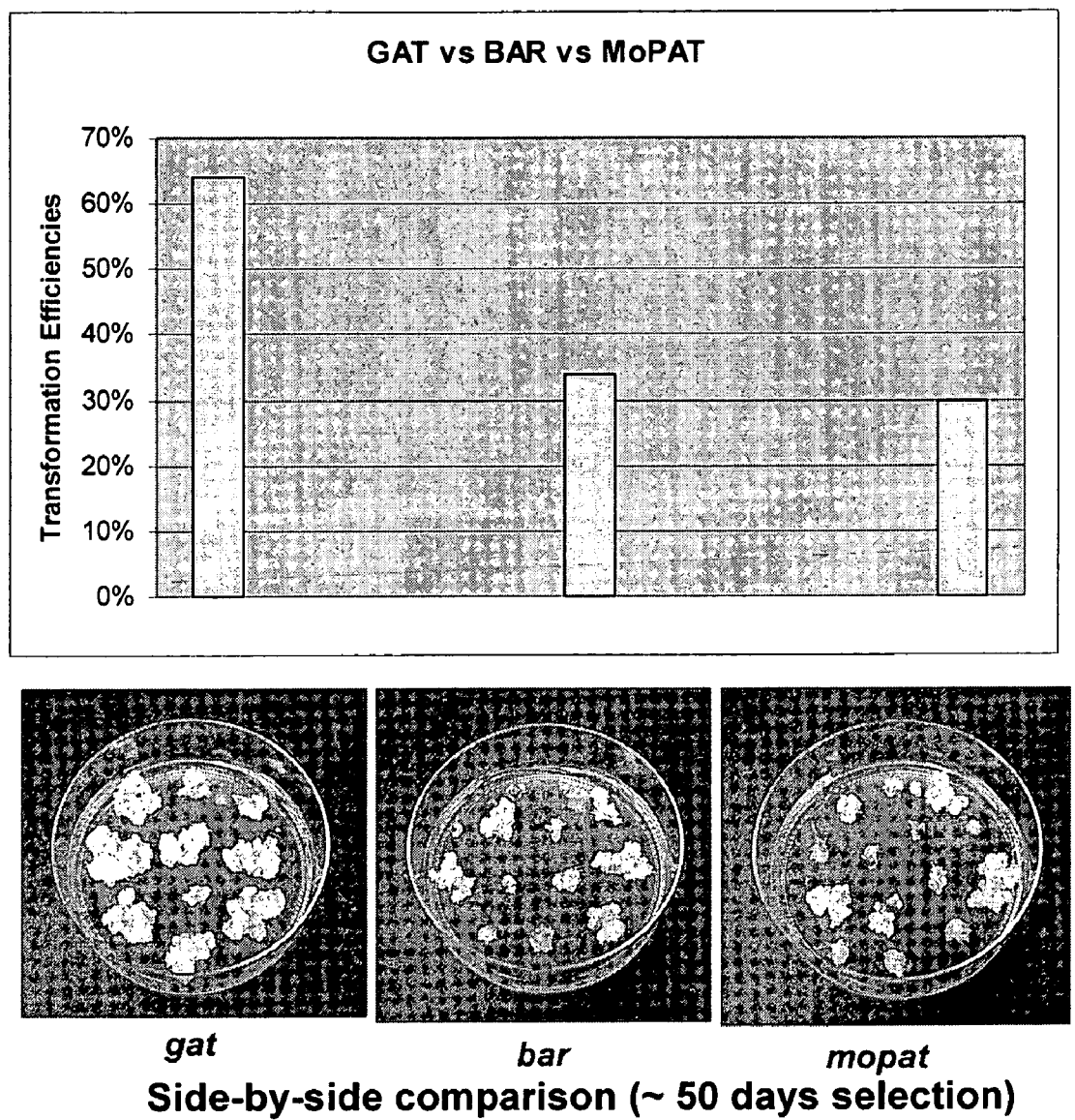
FIG. 8 demonstrates that GAT can be used as a selectable marker.
Figure 9:
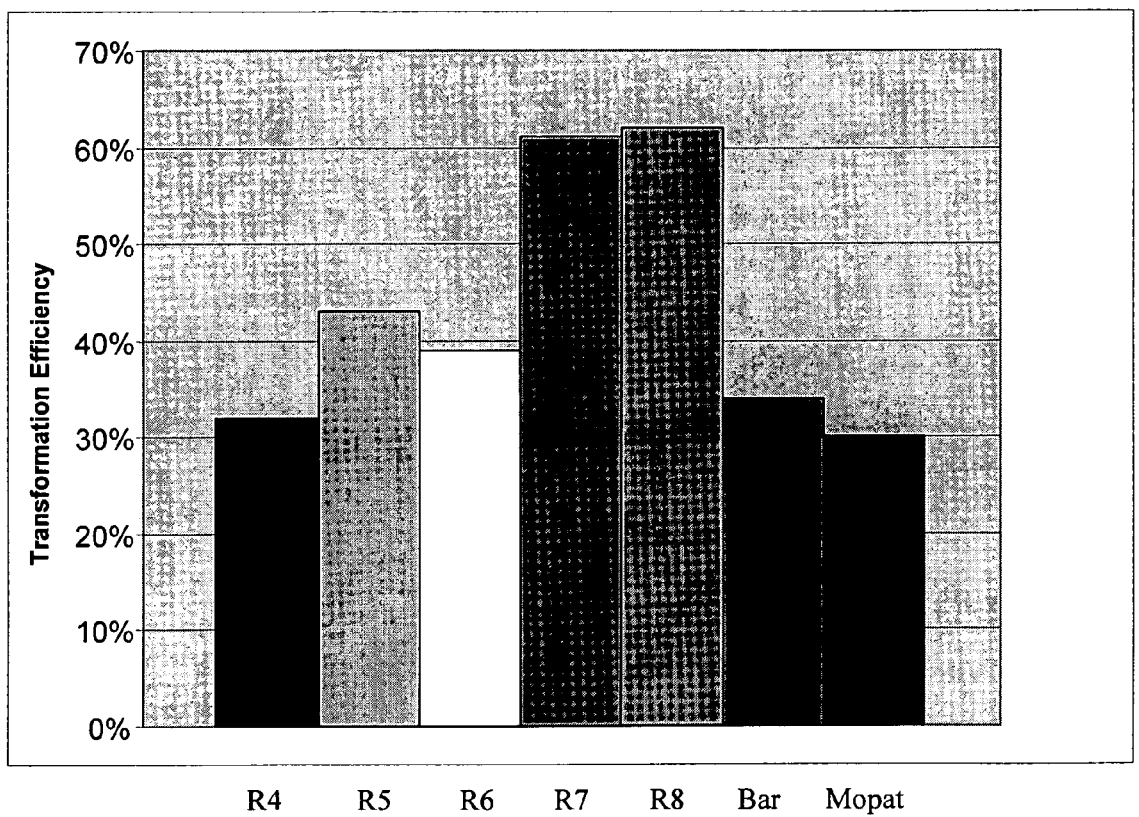
FIG. 9 provides a schematic demonstrating GAT transformation efficiencies.

In the side-by-side experiment to compare GAT, bar and mopat, GAT gave the best transformation efficiency at about 64%, bar at 34%, and mopat at 30%. Calli with GAT selection seem to grow faster that those selected on glufosinate (FIG. 8).

Example 11

Interaction Between Glyphosate, Metsulfuron-Methyl and Two Additives on the Control of Ryegrass The example was conducted on non-glyphosate resistant ryegrass. As provided in Table 23, all treatments that included glyphosate [180 g a.i. L ha$^{-1}$ (0.5 L glyphosate (SCAT®))] plus metsulfuron-methyl (BRUSH-OFF®) (5 and 10 g ha$^{-1}$) gave 100% control of the ryegrass. Metsulfuron-methyl (BRUSH-OFF®) on its own did nothing accept stunt the ryegrass plants slightly. Although 15 of the 16 plants (12%) in the 0.5 L ha$^{-1}$ glyphosate (SCAT®) treatment eventually died, they took much longer to die. These results indicate that there was possible synergism between glyphosate (SCAT®) and metsulfuron-methyl (BRUSH-OFF®). The two additives, e.g., ADD-UP and VELOCITY, made no difference in the degree of control with any of the treatments.

TABLE 23

Interaction Between Glyphosate, metsulfuron-methyl and Two Additives on the Control of Ryegrass

| Trial | Treatment/ha$^{-1}$ | Control (%) |
|---|---|---|
| 1 | glyphosate (SCAT ®) 0.5 L | 94 |
| 2 | Metsulfuron-methyl (BRUSH-OFF ®) 5 g | 0 |
| 3 | Metsulfuron-methyl (BRUSH-OFF ®) 10 g | 0 |
| 4 | glyphosate (SCAT ®) 0.5 L + metsulfuron-methyl (BRUSH-OFF ®) 5 g | 100 |
| 5 | glyphosate (SCAT ®) 0.5 L + metsulfuron-methyl (BRUSH-OFF ®) 10 g | 100 |
| 6 | glyphosate (SCAT ®) 0.5 L + metsulfuron-methyl (BRUSH-OFF ®) 5 g + ammonium sulfate-based adjuvant (ADD-UP ®) 1% | 100 |
| 7 | glyphosate (SCAT ®) 0.5 L + metsulfuron-methyl (BRUSH-OFF ®) 10 g + ammonium sulfate-based adjuvant (ADD-UP ®) 1% | 100 |
| 8 | glyphosate (SCAT ®) 0.5 L + metsulfuron-methyl (BRUSH-OFF ®) 5 g + bispyribac-sodium (VELOCITY ®) 1% | 100 |
| 9 | glyphosate (SCAT ®) 0.5 L + metsulfuron-methyl (BRUSH-OFF ®) 10 g + bispyribac-sodium (VELOCITY ®) 1% | 100 |
| 10 | Control | 0 |

Biotype: non-glyphosate resistant ryegrass (70-04)
Population profile: Rup 0.25 control (%) 6.25
Rup 0.5 control (%) 81.25
Rup 1.0 control (%) 93.75
Growth Stage: 5-6 leaf stage
Conditions: hot and sunny
Volume rate: 200 L ha$^{-1}$ Example 12

Interaction Between Glyphosate, Metsulfuron-Methyl and Two Additives on the Control of Hairy Fleabane (Conyza bonariensis)

This example included the same treatments as used in Example 11, except the treatments were carried out on a glyphosate sensitive biotype of Kleinskraalhans (Conyza bonariensis). Glyphosate on its own gave poor control, killing only 1 out of 16 plants (12%). In this example, however, ammonium sulfate-based adjuvant (ADD-UP®) performed better than bispyribac-sodium (VELOCITY®) with the mixture.

TABLE 24

Interaction Between Glyphosate, metsulfuron-methyl and Two Additives on the Control of Hairy Fleabane (Conyza bonariensis)

| Trial | Treatment/ha$^{-1}$ | Control (%) |
|---|---|---|
| 1 | glyphosate (ROUNDUP ®) 0.5 L | 12 |
| 2 | Metsulfuron-methyl (BRUSH-OFF ®) 5 g | 100 |
| 3 | Metsulfuron-methyl (BRUSH-OFF ®) 10 g | 100 |

TABLE 24-continued

Interaction Between Glyphosate, metsulfuron-methyl and Two Additives on the Control of Hairy Fleabane (*Conyza bonariensis*)

| Trial | Treatment/ha$^{-1}$ | Control (%) |
|---|---|---|
| 4 | glyphosate (ROUNDUP ®) 0.5 L + metsulfuron-methyl (BRUSH-OFF ®) 5 g | 100 |
| 5 | glyphosate (ROUNDUP ®) 0.5 L + metsulfuron-methyl (BRUSH-OFF ®) 10 g | 100 |
| 6 | glyphosate (ROUNDUP ®) 0.5 L + metsulfuron-methyl (BRUSH-OFF ®) 5 g + ammonium sulfate-based adjuvant (ADD-UP ®) 1% | 100 |
| 7 | glyphosate (ROUNDUP ®) 0.5 L + metsulfuron-methyl (BRUSH-OFF ®) 10 g + ammonium sulfate-based adjuvant (ADD-UP ®) 1% | 100 |
| 8 | glyphosate (ROUNDUP ®) 0.5 L + metsulfuron-methyl (BRUSH-OFF ®) 5 g + bispyribac-sodium (VELOCITY ®) 1% | 75 |
| 9 | glyphosate (ROUNDUP ®) 0.5 L + metsulfuron-methyl (BRUSH-OFF ®) 10 g + bispyribac-sodium (VELOCITY ®) 1% | 100 |
| 10 | Control | 0 |

Biotype: Non-glyphosate resistant *Conyza* (Welgevallen-paraquat resistant)
Growth Stage: 10–15 leaf stage
Conditions: Cool and sunny
Volume rate: 200 L ha$^{-1}$
glyphosate (ROUNDUP): 360 g a.i. L$^{-1}$ Example 13

Interaction Between Glyphosate, Metsulfuron-Methyl and Two Additives on the Control of Glyphosate, Paraquat, and ACCase-Inhibitor Resistant Ryegrass This example was conducted on one of the most resistant ryegrass types in the world, ryegrass resistant to non-selective herbicides, e.g., Fairview (Tulbagh), which is resistant to glyphosate, paraquat, and ACCase-inhibitors. In this example, the addition of metsulfuron-methyl (BRUSH-OFF®) at 5 and 10 g ha$^{-1}$, with 1% ammonium sulfate-based adjuvant (ADD-UP®) to 0.5 L Roundup improved control by 44% (e.g., 50% to 94%). Further, ammonium sulfate-based adjuvant (ADD-UP®) was superior to bispyribac-sodium (VELOCITY®) as an additive.

Example 14

Interaction Between Glyphosate and Representative SU's on the Control of Glyphosate Paraquat and ACCase-Inhibitor Resistant Ryegrass In this example, four different SU's were applied together with glyphosate (SCAT®) on the resistant ryegrass. The results as to the best SU partner for glyphosate were inconclusive, but the average benefit of applying an SU with glyphosate on herbicide resistant ryegrass was 39% (e.g., 34% control with glyphosate (SCAT®) only and 57-83% control with glyphosate (SCAT®) plus metsulfuron-methyl (BRUSH-OFF®), chlorsulfuron (GLEAN®), or triasulfuron (LOGRAN®).

TABLE 25

Interaction Between Glyphosate, metsulfuron-methyl and Two Additives on the Control of Glyphosate, Paraquat, and ACCase-Inhibitor Resistant Ryegrass

| Trial | Treatment/ha$^{-1}$ | Control (%) |
|---|---|---|
| 1 | glyphosate (ROUNDUP ®) 0.5 L | 50 |
| 2 | glyphosate (ROUNDUP ®) 0.5 L + metsulfuron-methyl (BRUSH-OFF ®) 5 g | 69 |
| 3 | glyphosate (ROUNDUP ®) 0.5 L + metsulfuron-methyl (BRUSH-OFF ®) 10 g | 88 |
| 4 | glyphosate (ROUNDUP ®) 0.5 L + metsulfuron-methyl (BRUSH-OFF ®) 5 g + ammonium sulfate-based adjuvant (ADD-UP ®) 1% | 94 |
| 5 | glyphosate (ROUNDUP ®) 0.5 L + metsulfuron-methyl (BRUSH-OFF ®) 10 g + ammonium sulfate-based adjuvant (ADD-UP ®) 1% | 94 |
| 6 | glyphosate (ROUNDUP ®) 0.5 L + metsulfuron-methyl (BRUSH-OFF ®) 5 g + bispyribac-sodium (VELOCITY ®) 1% | 69 |
| 7 | glyphosate (ROUNDUP ®) 0.5 L + metsulfuron-methyl (BRUSH-OFF ®) 10 g + bispyribac-sodium (VELOCITY ®) 1% | 75 |

Biotype: Fairview (Tulbagh) resistant to glyphosate, paraquat, and ACCase-inhibitors.
Growth Stage: 10–15 leaf stage
Conditions: Cool and sunny
Volume rate: 200 L ha$^{-1}$
glyphosate (ROUNDUP): 360 g ai L$^{-1}$

TABLE 26

Interaction Between Glyphosate and Representative
SU's on the Control of Glyphosate, Paraquat, and
ACCase-Inhibitor Resistant Ryegrass

| Trial | Treatment/ha$^{-1}$ | Control (%) |
|---|---|---|
| 1 | Control | 0 |
| 2 | glyphosate (SCAT ®) 6 L | 34 |
| 3 | glyphosate (SCAT ®) 6 L + metsulfuron-methyl (BRUSH-OFF ®) 10 g | 67 |
| 4 | glyphosate (SCAT ®) 6 L + chlorsulfuron (GLEAN ®) 15 g | 75 |
| 5 | glyphosate (SCAT ®) 6 L + triasulfuron (LOGRAN ®) 7½ g | 83 |
| 6 | glyphosate (SCAT ®) 6 L + triasulfuron (LOGRAN ®) 15 g | 67 |

Biotype: Fairview (Tulbagh) resistant to glyphosate, paraquat, and ACCase-inhibitors.
Growth Stage: 4 leaf stage
Conditions: Cool and sunny
Volume rate: 200 L ha$^{-1}$
All treatments sprayed with 1% ADD-UP Example 15

GAT Has No Yield Impact on Soybean Isolines

Abstract

Isolines from twelve selected SCP:GAT7::SAMS:ALS events were yield tested in 3 Iowa environments in 2004 and 6 midwest environments in 2005. When yield data for these environments is combined together, there is no significant yield difference between GAT7 positive lines and GAT7 negative lines across the construct, and within a specific event. For the three lead events (EAFS 3559.2.1, EAFS 3560.4.3, EAFS 3561.1.1), there were no statistical yield differences detected when GAT7 positive lines were compared to GAT7 negative sister lines. Overall, the data for the lines tested indicate that presence of the GAT7 transgene does not appear to impact final yield.

Materials and Methods

2004 D Test Materials and Methods:

The variety Jack was transformed with the constituative promoter (SCP1) driving expression of glyphosate acetyl transferase round 7 (GAT7), linked to the selectable marker insert SAMS:ALS. Forty initial events of SCP:GAT7::SAMS:ALS were advanced to the T2 generation. Zygosity of the advanced T2 lines was initially determined by screening 12 random plants per line for PCR amplification of the GAT insert. 454 lines were tentatively selected to be either homozygous positive or homozygous negative for GAT. Selected lines were blocked by event and grown in D level yield tests (1 replication of two 10 foot rows) at Cedar Falls (planted Jun. 5, 2004), Dallas Center (planted Jun. 4, 2004), and Johnston, Iowa (planted Jun. 9, 2004) during 2004. Twelve remnant T3 seed of each line was screened using either glyphosate spray at the V3 growth stage, or soaking remnant seed in sulfonylurea solution. Based upon the glyphosate treatment or SU seed soak, 342 SCP:GAT7::ALS lines from 30 events were confirmed to be homozygous positive or homozygous negative. Maturity scores were collected for all entries at the Dallas Center and Johnston locations. Yield data was collected and subject to multiple regression, ANOVA, and mean separation using SAS.

2005 C Test Materials and Methods

Based upon yield performance and herbicide efficacy scores in 2004, 12 GAT7 events were advanced for C level yield testing in 2005. From these selected twelve events, 28 positive and 23 negative isolines were selected. 2005 C tests were designed as a randomized complete block (by event) and grown at Cedar Falls, Iowa; Johnston, Iowa; Stuart, Iowa; Monmouth, Ill.; Princeton, Ill.; and Napoleon, Ohio. Maturity scores and yield data were collected and subject to multiple regression, ANOVA and mean separation using PRISM and/or SAS.

Results and Discussion

When 2004 yield data for the selected lines tested was subject to ANOVA, the location, events, location*event, and GAT (positive or negative) variables were significantly different (data not shown). A mean of all positive lines was not significantly lower for yield compared to a mean of all negative lines tested in 2004. In 2005, the location, event, location*event, GAT, and GAT*location variables were significantly different (data not shown). A mean of all positive lines tested was not significantly different from a mean of all negative lines tested in 2005 (data not shown). When the 2004 and 2005 data are combined, the year, location, event, year*event, location*event, year*GAT, and location*GAT variables are significantly different (data not shown). A mean of all GAT positive lines was not significantly different from a mean of all GAT negative lines tested across the 9 midwest environments (data not shown).

Based upon 2004 yield, herbicide efficacy, and molecular analyses, 3 lead GAT7 events were selected for potential regulatory and product development experiments. When the 2005 isoline yield data is combined with 2004 data, the locations were significantly different within EAFS 3559.2.1 (data not shown). Positive GAT lines within EAFS 3559.2.1 were not significantly different for yield compared to negative sister isolines (data not shown). Within EAFS 3560.4.3, the 9 locations and location*GAT interaction were significantly different. However, GAT positive isolines were not significantly different for yield when compared to GAT negative isolines within the same event (data not shown). Within event EAFS 3561.1.1, the locations were significantly different, while the GAT score and location*GAT interaction were not significantly different (data not shown). Within EAFS 3561.1.1, GAT positive lines were not significantly different for yield compared to GAT negative sister lines (data not shown).

Multiple regression of yield×maturity for the 6 environments tested in 2005 was performed on the 3 lead events to determine overall yield potential. In general, GAT positive and GAT negative lines within each of the 3 lead events appear to be random (data not shown). This suggests that yield does not appear to be significantly altered when the GAT7 transgene is present.

A modified t-test was completed to compare the GAT7 positive lines to a mean of the GAT7 negative lines within each specific event at each location tested (data not shown). Across the 9 locations tested, there is no apparent yield disadvantage for GAT7 positive lines compared to GAT7 negative sister lines within the same event. For the 3 lead events, GAT positive lines are within 2.6% of the negative mean, indicating overall yield parity exists in all environments tested (data not shown). ANOVA and LSD analyses performed on the individual lines indicate no distinct differences among lines tested in each event, except for EAFS 3560.3.2

(data not shown). Overall, there does not appear to be a yield difference between GAT7 positive lines and GAT7 negative lines.

Example 16

GAT Soybeans Have Tolerance to Glyphosate and Glyphosate+SU Treatments

The objectives of this experiment was to evaluate the sulfonylurea (SU) herbicide tolerance of the lead GAT7 events in direct comparison to the tolerance of STS, and to determine if differences in tolerance could be detected among the lead GAT7 events across different glyphosate (Gly), Gly+SU and SU treatments. Across all the treatments, the four lead GAT7 events were rated with significantly less crop damage response compared to untransformed Jack and STS at 7 days after spraying, and again at 14 days after spraying. Among the 4 lead GAT7 events, there were some response differences detected, with EAFS 3560.4.3 performing the best over all the treatments, and EAFS 3560.3.2 showing the most herbicide response. In general, it appears there is a significantly better tolerance to several SU chemistries for the SAMS:ALS construct compared to STS. In addition, the GAT7 events tested had good tolerance to variable rates of glyphosate, sulfonylurea, and glyphosate plus sulfonylurea chemistry treatments.

Materials and Methods

GAT round 7 (GAT7) transgenic events from construct PHP20163A were evaluated in 2004 for herbicide efficacy (JHM464TGATEFF) and yield potential (JHD4_GAT7 tests). Based upon these preliminary results and commercialization potential, four lead events were selected for additional efficacy testing in 2005 experiment JHM5G030.92M90 was selected as a STS variety to compare directly with the SAMS:ALS construct in the GAT7 events. Variety Jack was utilized as an untransformed negative control.

Selected lines were grown in experiment JHM5G030 in two replications of paired twelve foot rows, with eleven different treatments applied. Lines were blocked by event and treatment to provide side-by-side comparison of the eleven different spray treatments, with a 2 row border between each treatment to catch any spray drift. Spray treatments (at V3 unless specified) were 0× (control), 35.03 g/ha ai Synchrony, 140.11 g/ha ai Synchrony, 8.75 g/ha ai tribenuron, 35.0 g/ha ai tribenuron, 8.75 g/ha ai rimsulfuron, 35.0 g/ha ai rimsulfuron, 3360.0 g/ha ai glyphosate, 3360.0 g/ha ai glyphosate at V3 followed by 3360.0 g/ha ai glyphosate at R1, 3360.0 g/ha ai glyphosate plus 35.0 g/ha ai tribenuron (tank mix) and 3360.0 g/ha ai glyphosate plus 70.0 g/ha ai rimsulfuron (tank mix). Lines were given a 100 (complete susceptibility, 100% damage) to 0 (complete tolerance, 0% damage) visual rating at 7 days after treatment and again at 14 days after treatment. Visual ratings were based upon overall degree of chlorosis, necrosis, and plant stunting (if evident) in the treated rows compared to the respective unsprayed control rows. Rating data at 7 and 14 days after spraying were subject to ANOVA and mean separation using SAS.

Results and Discussion

When all spray rating data for the different treatments at 7 and 14 days after application were subject to ANOVA, the events and treatments were significantly different, while the replication was not significantly different (data not shown). Jack had significantly higher spray response (damage scores) compared to STS and the GAT events at 7 and 14 days after spraying (DAS) (data not shown). The 4 GAT lines were scored with significantly less damage than Jack and STS for all the treatments at both 7 and 14 days after spray application (data not shown).

In examining individual treatments, the control plot appeared to have some spray drift evident, as both the Jack plot and STS plot were rated with significantly higher spray damage scores compared to the 4 GAT events at 7 DAS (data not shown) and 14 DAS (data not shown). Spray drift would potentially confound the results of the other plots, but was hopefully somewhat minimized by the use of a 2 row border between treatments.

Within the 8.75 g/ha ai rimsulfuron treatment, the 4 GAT events were scored with significantly less spray damage compared to Jack and STS at both 7 DAS (data not shown) and 14 DAS (data not shown). Among the 4 GAT events, there was no statistical difference noted at both rating times (data not shown). Examining the 35.0 g/ha ai rimsulfuron treatment, the 4 GAT events were scored with significantly less spray damage compared to Jack and STS at both 7 DAS (data not shown) and 14 DAS (data not shown). GAT7 Event EAFS 3560.4.3 was scored with less damage compared to GAT7 events EAFS 3559.2.1 and EAFS 3561.1.1 at both 7 DAS (data not shown) and 14 DAS (v).

After the 35.03 g/ha ai Synchrony treatment, the 4 GAT events were scored with significantly less spray damage compared to Jack and STS at both 7 DAS (data not shown) and 14 DAS (data not shown). Among the 4 GAT events, there was no statistical difference noted at both 7 DAS (data not shown) and 14 DAS (data not shown). In examining the 140.11 g/ha ai Synchrony treatment, the 4 GAT events were scored with significantly less spray damage compared to Jack and STS at both 7 DAS (data not shown) and 14 DAS (data not shown). GAT7 events EAFS 3560.4.3 and EAFS 3561.1.1 were scored with less damage compared to GAT7 events EAFS 3559.2.1 and EAFS 3560.3.2 at 7 DAS (data not shown). At 14 DAS the 140.11 g/ha ai Synchrony treatment, GAT7 events EAFS 3560.4.2, EAFS 3559.2.1, and EAFS 3561.1.1 were rated with no damage, while EAFS 3560.3.2 was scored similar to STS (data not shown).

In examining the 8.75 g/ha ai tribenuron treatment, the 4 GAT7 events had significantly less visual damage compared to STS and Jack at 7 DAS (data not shown) and 14 DAS (data not shown). The GAT7 events were not statistically different at 7 DAS (data not shown), but Evens EAFS 3560.4.3 and EAFS 3559.2.1 had significantly lower damage compared to EAFS 3560.3.2 at 14 DAS (data not shown). For the 35.0 g/ha ai tribenuron treatment, the 4 GAT7 events were rated with significantly less spray response compared to Jack and STS at 7 DAS (data not shown) and 14 DAS (data not shown). The 4 GAT events were not statistically different from each other at 7 DAS (data not shown), but the EAFS 3560.3.2 was rated with significantly more spray damage than the other 3 GAT7 events at 14 DAS (data not shown).

For the 3360.0 g/ha ai glyphosate and 3360.0 g/ha ai glyphosate at V3 followed by 3360.0 g/ha ai glyphosate at R1 treatments, the Jack and STS varieties were destroyed after 7 days, as expected (data not shown). The 4 GAT7 events did not have any observed spray damage for the 3360.0 g/ha ai glyphosate treatment at 7 DAS (data not shown) and 14 DAS (data not shown). Minimal spray damage was recorded for the 4 GAT7 events at 7 DAS for the treatment (data not shown), and events EAFS 3560.4.3 and EAFS 3559.2.1 were rated significantly better than EAFS 3560.3.2 at 14 DAS (data not shown).

Two tank-mix treatments of glyphosate plus a sulfonylurea herbicide provided similar results at 7 DAS and 14 DAS. For the 3360.0 g/ha ai glyphosate plus 70.0 g/ha ai rimsulfuron treatment, the 4 GAT events had a similar herbicide response at 7 DAS of about 40% damage (data not shown), and approximately 35% damage at 14 DAS (data not shown). Less of an overall crop response was observed for the 3360.0 g/ha ai glyphosate plus 35.0 g/ha ai tribenuron treatment, and the 4 GAT events were not statistically different at 7 DAS (data not shown), and 14 DAS (data not shown).

The mean of visual ratings at 7 DAS and 14 DAS were graphed for the four lead GAT events, Jack, and the STS line to allow visual interpretation of the data (data not shown). For the Rimsulfuron treatments, there was a crop response observed with the 4 lead GAT events, with EAFS 3560.4.3 having the most tolerance noted (data not shown). The response of the GAT7 events was significantly less than the STS and Jack controls for both Rimsulfuron treatments at 7 DAS and 14 DAS (data not shown).

In examining the mean response scores to the 1× and 140.11 g/ha ai Synchrony treatments, there was no apparent damage for GAT7 events EAFS 3560.4.3 and EAFS 3561.1.1, and minimal response of GAT 7 events EAFS 3559.2.1 and EAFS 3560.3.2 (data not shown). All GAT events had significantly less crop response compared to Jack and the STS line (data not shown).

The four GAT7 events had significantly less crop response to 1× and 35.0 g/ha ai tribenuron applications at 7 DAS and 14 DAS when compared to Jack and STS (data not shown). Among the GAT7 events, EAFS 3560.4.3 performed the best, while EAFS 3560.3.2 appeared to show the most response overall (data not shown).

For the 3360.0 g/ha ai glyphosate application, there was no apparent crop response for all 4 GAT7 events at 7 DAS and 14 DAS (data not shown). For the 3360.0 g/ha ai glyphosate at V3 followed by 3360.0 g/ha ai glyphosate at R1, there were no statistical differences noted among the four GAT7 events at 7 DAS, but EAFS 3560.4.3 and EAFS 3559.2.1 appeared to have less response compared to EAFS 3561.1.1 and EAFS 3560.3.2 at 14 DAS (data not shown).

Of the two tank mix treatments, the 70.0 g/ha ai rimsulfuron plus 3360.0 g/ha ai glyphosate caused a higher level of crop damage response compared to the 35.0 g/ha ai tribenuron plus 3360.0 g/ha ai glyphosate treatment (data not shown). Among the four lead GAT7 events, there were no statistical differences observed for the visual ratings at 7 DAS and 14 DAS (data not shown).

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for controlling weeds in an area of cultivation comprising
   a) planting the area with crop seeds or plants which comprise
      i) a first polynucleotide encoding a polypeptide that can confer tolerance to glyphosate operably linked to a promoter active in a plant; and,
      ii) a second polynucleotide encoding an ALS inhibitor-tolerant polypeptide operably linked to a promoter active in a plant;
   b) applying to the crop, crop part, weed or area of cultivation thereof a combination of herbicides comprising at least an effective amount of a first and a second ALS inhibitor, wherein
      i) the effective amount of the combination of herbicides controls weeds;
      ii) the effective amount of the first ALS inhibitor is not tolerated by the crop when applied alone when compared to a control crop that has not been exposed to the first ALS inhibitor; and,
      iii) the effective amount of the second ALS inhibitor is sufficient to produce a safening effect, wherein said safening effect provides an increase in crop tolerance upon the application of the first and the second ALS inhibitor when compared to the crop tolerance when the first ALS inhibitor is applied alone.

2. The method of claim 1, wherein at least said first or said second ALS inhibitor comprises a sulfonylurea or an imidazolinone.

3. The method of claim 1, wherein said first ALS inhibitor comprises a sulfonylurea and the second ALS inhibitor comprises an imidazolinone.

4. The method of claim 3, wherein said sulfonylurea comprises rimsalfuron and said imidazolinone comprises imazethapyr.

5. The method of claim 1, wherein said combination of herbicides further comprises glyphosate.

6. The method of claim 1, wherein said first polynucleotide encodes a glyphosate-N-acetyltransferase.

7. The method of claim 1, wherein said first polynucleotide encodes a glyphosate-tolerant 5-enolpyruvylshikimate-3-phosphate synthase or a glyphosate-tolerant glyphosate oxido-reductase.

8. The method of claim 1, wherein said ALS inhibitor-tolerant polypeptide comprises a mutated acetolactate synthase polypeptide.

9. The method of claim 8, wherein said mutated acetolactate synthase polypeptide comprises HRA.

10. The method of claim 1, wherein said first and said second ALS inhibitor are in a homogeneous granule blend.

11. The method claim 1, wherein at least one of said first or said second polynucleotides is operably linked to at least one copy of the enhancer sequence set forth in SEQ ID NO: 1, 72, 85, 88, or 89, or an enhancer sequence having at least 90% sequence identity to SEQ ID NO: 1, 72, 85, 88, or 89, wherein said enhancer sequence modulates transcription.

12. The method of claim 1, wherein said crop is a dicot.

13. The method of claim 12, wherein said dicot is soybean, canola, sunflower, cotton, alfalfa, an ornamental, a fruit, a vegetable, a sugar beet, or an *Arabidopsis*.

14. The method of claim 1, wherein said plant is a monocot.

15. The method of claim 14, wherein said monocot is maize, wheat, rice, barley, sorghum, sugar cane, Switchgrass, or rye.

16. The method of claim 1, wherein step (b) is performed at least once prior to step (a).

* * * * *

UNITED STATES PATENT AND TRADEMARK OFFICE
CERTIFICATE OF CORRECTION

PATENT NO. : 7,622,641 B2  Page 1 of 1
APPLICATION NO. : 11/507866
DATED : November 24, 2009
INVENTOR(S) : McCutchen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 519 days.

Signed and Sealed this

Twenty-sixth Day of October, 2010

David J. Kappos
*Director of the United States Patent and Trademark Office*

SEQUENCE LISTING

<160> NUMBER OF SEQ ID NOS: 89

<210> SEQ ID NO 1
<211> LENGTH: 534
<212> TYPE: DNA
<213> ORGANISM: Cauliflower mosaic virus
<220> FEATURE:
<221> NAME/KEY: enhancer
<222> LOCATION: (0)...(0)
<223> OTHER INFORMATION: enhancer element of 35S promoter

<400> SEQUENCE: 1

```
ccctgtcctc tccaaatgaa atgaacttcc ttatatagag gaagggtctt gcgaagctta      60
gtgggattgt gcgtcatccc ttacgtcagt ggagatatca catcaatcca cttgctttga     120
agacgtggtt ggaacgtctt cttttccac gatgctcctc gtgggtgggg gtccatcttt      180
gggaccactg tcggcagagg catcttcaac gatggccttt cctttatcgc aatgatggca     240
tttgtaggag ccaccttcct tttccactat cttcacaata aagtgacaga tagctgggca     300
atggaatccg aggaggtttc cggatattac cctttgttga aaagtctcaa ttgccctttg     360
gtcttctgag actgtatctt tgatatttt ggagtagaca agcgtgtcgt gctccaccat     420
gttgacgaag attttcttct tgtcattgag tcgtaagaga ctctgtatga actgttcgcc     480
agtctttacg gcgagttctg ttaggtcctc tatttgaatc tttgactcca tggg           534
```

<210> SEQ ID NO 2
<211> LENGTH: 7565
<212> TYPE: DNA
<213> ORGANISM: Cauliflower mosaic virus
<220> FEATURE:
<221> NAME/KEY: promoter
<222> LOCATION: (0)...(0)

<223> OTHER INFORMATION: S35 promoter: PHP24279 from left boarder to right boarder

<400> SEQUENCE: 2

```
tttacccgcc aatatatcct gtcaaacact gatagtttaa actgaaggcg ggaaacgaca      60
atctgatcat gagcggagaa ttaagggagt cacgttatga cccccgccga tgacgcggga     120
caagccgttt tacgtttgga actgacagaa ccgcaacgtt gaaggagcca ctcagcaagc     180
tgggcccccc ctcgaggtcg gccgcattcg caaaacacac ctagactaga tttgttttgc     240
taacccaatt gatattaatt atatatgatt aatatttata tgtatatgga tttggttaat     300
gaaatgcatc tggttcatca agaattata aagacacgtg acattcattt aggataagaa      360
atatggatga tctctttctc ttttattcag ataactagta attacacata acacacaact     420
ttgatgccca cattatagtg attagcatgt cactatgtgt gcatccttt atttcataca      480
ttaattaagt tggccaatcc agaagatgga caagtctagg ttaactgact agctagtcag     540
tacacagtcc tgccatcacc atccaggatc atatccttga aagccccacc actagggatc     600
ataggcaaca catgctcctg gtgtgggacg attatatcca agaggtacgg ccctggagtc     660
tcgagcatct tctttatcgc tgcgcggact tcgttcttct ttgtcacacg gaccgctgga     720
atgttgaacc ctttggcgat cgtcacgaaa tctggatata tctcactttc attctctggg     780
tttcccaagt atgtgtgcgc tctgttggcc ttatagaacc tgtcctccaa ctgcaccacc     840
atccccaggt gctggttgtt tagcacaaag accttcactg ggaggttctc aattcggatc     900
atagctagct cctgaacgtt catgagaaag ctaccatctc catcgatgtc aacaacagtg     960
acacctgggt tgccacagaa gcaccagca gcagccggca aaccaaatcc catagcccca    1020
agaccagctg aagacaacca ctgccttggc cgcttgtaag tgtagtactg tgccgcccac    1080
atctggtgct gcccaacacc tgtgccgatg atggcctcgc ctttcgtcag ctcatcaaga    1140
acctgaatag catattgtgg ctggatctcc tcattagatg ttttataccc aaggggggaat   1200
tccctcttct gctgatccaa ctcatcgttc catgagccaa agtcaaagct cttctttgat    1260
gtgcttcctt caagaagagc attcatgccc tgcaaagcaa gcttaacatc tgcacagatg    1320
gacacatgtg gctgcttgtt cttgccaatc tcagccggat caatatcaac gtgcacaatc    1380
ttagccctgc ttgcaaaagc ctcaatcttc cctgtcacgc gatcatcaaa ccgcacacca    1440
agtgcaagca acagatcggc cttatccact gcataatttg catacaccgt cccatgcata    1500
cctagcatgc gcagagacag tgggtcgtcg ctggggaagt tgccgaggcc cataagagta    1560
gttgtgaccg ggattccagt cagctccaca aagcgtcgca actcctcacc agatgctgcg    1620
cagccaccgc ccacataaag aacagggcgc gcgattcac caacaagacg cagcacctgc     1680
tcaagcaact cagtcgcagg gggcttggga aggcgcgcaa tgtacccagg cagactcatg    1740
ggcttgtccc agacaggcac cgccatctgc tgctggatgt ccttgggat gtcgacaagc     1800
accggccctg gtcgaccaga ggaggcgagg aagaaagcct cctgcacgac gcggggatg     1860
tcgtcgacgt cgaggaccag gtagttgtgc ttggtgatgg agcgggtgac ctcgacgatg    1920
ggcgtctcct ggaaggcgtc ggtgccaatc atgcgtcgcg ccacctgtcc cgtgatggcg    1980
accatgggga cggaatcgag cagcgcgtcg gcgagcgcgg agactaggtt ggtgcgccgg    2040
gggccggagg tggcgatgca gacgccgacg cggcccgagg agcgcgcgta gccggaggcg    2100
gcaaaggcct cccctggctc gtggcggaag aggtggttgg cgatgacggg ggagcgggtg    2160
agtgcctggt ggatctccat ggacgcgccg ccggggtagg cgaagacgtc gcggacgccg    2220
```

```
cagcgctcga gggactcgac gaggatgtca gcacccttgc ggggctcggt ggggcccccac    2280 ggccggagcg gggtggccgg gggagccatc ggcatggcgg gtgacgccgc tgagcacctg    2340
atgggcgcgg cgagggcgcg gcgggtggcc aggaggtgcg cccggcgcct cgccttgggc    2400
gcagcggtag tggcgccagt gagcgcggta gacgcggcg cggcggtggc catggttgcg     2460
gcggctgtct cggaggcggc gcgagggttt ggggtgggtg ccacggacac ggagtgggag    2520 aaaggggat gtgcgtggag gcctccctgc ttttgttcag aggatgtgtg gctcagatgg     2580
tgatgggaat gggactcgca agacgacgac gacacgtccg tcgcccgaat acgtacacgc    2640
tacagaccgg acgtggggc ctgtcgacgt gggaccgacg tgtcggcctg gattacaaac     2700
gtggtgtcca ccgagtgctg gtacacgaca gcgtgcgtca aggaggtttt gaactgttcc    2760
gttaaaaaaa gaggggagat tttggacttg actgtggacg acggtgcatg tcatcggagt    2820
acagacggta ctgacacaag gggcccagac aagggaatcc aaacgggtcg cacccacctg    2880
ccaggctgcc acccgcaatc cgcaacaggg aaaccgggca cagcccacaa ccacaagatg    2940
agcagctgcg gcgacagcgt caggcccggt gtcggtgtta gggatggcac cctttggctc    3000
cccgtatccg tccccgcgac aaaaaaattt cccgcgggga ttcccacgaa ctcttgcgag    3060
agacatttct tccccatccc cgttccccac ggggataaat cccatcggg gatcctctag      3120 agtcgacctg caggcatgca agcttcggtc cgcggccagc ttgctaaccc gggcccccc      3180 tcgaggtcat cacatcaatc cacttgcttt gaagacgtgg ttggaacgtc ttcttttcc     3240 acgatgctcc tcgtgggtgg gggtccatct ttgggaccac tgtcggcaga ggcatcttca    3300
acgatggcct ttccttatc gcaatgatgg catttgtagg agccaccttc cttttccact      3360
atcttcacaa taaagtgaca gatagctggg caatggaatc cgaggaggtt tccggatatt    3420 acccttgtt gaaaagtctc aattgcccct tggtcttctg agactgtatc tttgatattt      3480
ttggagtaga caagcgtgtc gtgctccacc atgttgacga agattttctt cttgtcattg    3540
agtcgtaaga gactctgtat gaactgttcg ccagtcttta cggcgagttc tgttaggtcc    3600
tctatttgaa tctttgactc catggacggt atcgataagc tagcttgata tcacatcaat   3660
ccacttgctt tgaagacgtg gttggaacgt cttcttttc cacgatgctc ctcgtgggtg    3720
ggggtccatc tttgggacca ctgtcggcag aggcatcttc aacgatggcc tttccttat    3780 cgcaatgatg gcatttgtag agccaccctt ccttttccac tatcttcaca ataaagtgac    3840
agatagctgg gcaatggaat ccgaggaggt ttccggatat tacccttgt tgaaaagtct     3900 caattgccct ttggtcttct gagactgtat ctttgatatt tttggagtag acaagcgtgt    3960
cgtgctccac catgttgacg aagattttct tcttgtcatt gagtcgtaag agactctgta    4020
tgaactgttc gccagtcttt acggcgagtt ctgttaggtc ctctatttga atctttgact    4080
ccatgatcga attatcacat caatccactt gctttgaaga cgtggttgga acgtcttctt    4140
tttccacgat gctcctcgtg ggtggggtc catctttggg accactgtcg gcagaggcat    4200
cttcaacgat ggccttcct ttatcgcaat gatggcattt gtaggagcca cttcctttt     4260 ccactatctt cacaataaag tgacagatag ctgggcaatg gaatccgagg aggtttccgg    4320 atattccct tgttgaaaa gtctcaattg cccttggtc ttctgagact gtatctttga       4380 tattttgga gtagacaagc gtgtcgtgct ccaccatgtt gacgaagatt tcttcttgt     4440 cattgagtcg taagagactc tgtatgaact gttcgccagt ctttacggcg agttctgtta    4500
ggtcctctat ttgaatcttt gactccatgg gaattcctgc agcccgggat ctaggagctt    4560
gcatgcctgc agtgcagcgt gacccggtcg tgcccctctc tagagataat gagcattgca    4620
```

```
tgtctaagtt ataaaaaatt accacatatt tttttttgtca cacttgtttg aagtgcagtt    4680
tatctatctt tatacatata tttaaacttt actctacgaa taatataatc tatagtacta    4740
caataatatc agtgttttag agaatcatat aaatgaacag ttagacatgg tctaaaggac    4800
aattgagtat tttgacaaca ggactctaca gttttatctt tttagtgtgc atgtgttctc    4860
cttttttttt gcaaatagct tcacctatat aatacttcat ccattttatt agtacatcca    4920
tttagggttt agggttaatg gttttatag actaattttt ttagtacatc tattttattc    4980
tattttagcc tctaaattaa gaaaactaaa actctatttt agttttttta tttaataatt    5040
tagatataaa atagaataaa ataaagtgac taaaaattaa acaaataccc tttaagaaat    5100
taaaaaaact aaggaaacat ttttcttgtt tcgagtagat aatgccagcc tgttaaacgc    5160
cgtcgacgag tctaacggac accaaccagc gaaccagcag cgtcgcgtcg ggccaagcga    5220
agcagacggc acggcatctc tgtcgctgcc tctggacccc tctcgagagt tccgctccac    5280
cgttggactt gctccgctgt cggcatccag aaattgcgtg gcggagcggc agacgtgagc    5340
cggcacggca ggcggcctcc tcctcctctc acggcaccgg cagctacggg ggattccttt    5400
cccaccgctc cttcgctttc ccttcctcgc ccgccgtaat aaatagacac cccctccaca    5460
ccctctttcc ccaacctcgt gttgttcgga gcgcacacac acacaaccag atctccccca    5520
aatccacccg tcggcacctc cgcttcaagg tacgccgctc gtcctccccc cccccctct    5580 ctaccttctc tagatcggcg ttccggtcca tggttagggc ccggtagttc tacttctgtt    5640
catgtttgtg ttagatccgt gtttgtgtta gatccgtgct gctagcgttc gtacacggat    5700
gcgacctgta cgtcagacac gttctgattg ctaacttgcc agtgtttctc tttggggaat    5760
cctgggatgg ctctagccgt tccgcagacg ggatcgattt catgattttt tttgtttcgt    5820
tgcatagggt ttggtttgcc cttttccttt atttcaatat atgccgtgca cttgtttgtc    5880
gggtcatctt ttcatgcttt tttttgtctt ggttgtgatg atgtggtctg gttgggcggt    5940
cgttctagat cggagtagaa ttctgtttca aactacctgg tggatttatt aattttggat    6000
ctgtatgtgt gtgccataca tattcatagt tacgaattga agatgatgga tggaaatatc    6060
gatctaggat aggtatacat gttgatgcgg gttttactga tgcatataca gagatgcttt    6120
ttgttcgctt ggttgtgatg atgtggtgtg gttgggcggt cgttcattcg ttctagatcg    6180
gagtagaata ctgtttcaaa ctacctggtg tatttattaa ttttggaact gtatgtgtgt    6240
gtcatacatc ttcatagtta cgagtttaag atggatggaa atatcgatct aggataggta    6300
tacatgttga tgtgggtttt actgatgcat atacatgatg gcatatgcag catctattca    6360
tatgctctaa ccttgagtac ctatctatta aataaacaa gtatgtttta taattattttt    6420 gatcttgata tacttggatg atggcatatg cagcagctat atgtggattt ttttagccct    6480
gccttcatac gctatttatt tgcttggtac tgtttctttt gtcgatgctc acctgttgt    6540 ttggtgttac ttctgcaggt cgaccgccgg ggatccacac gacaccatgg ctattgaggt    6600
taagcctatc aacgcagagg ataccttatga cttaggcat agagtgctca gaccaaacca    6660
gcctatcgaa gcctgcatgt ttgagtctga ccttactagg agtgcatttc accttggtgg    6720
attctacgga ggtaaactga tttccgtggc ttcattccac caagctgagc actctgaact    6780
tcaaggtaag aagcagtacc agcttagagg tgtggctacc ttggaaggtt atagagagca    6840
gaaggctggt tccagtctcg tgaaacacgc tgaagagatt ctcagaaaga gaggtgctga    6900
catgatctgg tgtaatgcca ggacatctgc ttcaggatac tacaggaagt tgggattcag    6960
```

```
tgagcaagga gaggtgttcg atactcctcc agttggacct cacatcctga tgtataagag    7020
gatcacataa ctagctagtc agttaaccta gacttgtcca tcttctggat tggccaactt    7080
aattaatgta tgaaataaaa ggatgcacac atagtgacat gctaatcact ataatgtggg    7140
catcaaagtt gtgtgttatg tgtaattact agttatctga ataaaagaga aagagatcat    7200
ccatatttct tatcctaaat gaatgtcacg tgtctttata attctttgat gaaccagatg    7260
catttcatta accaaatcca tatacatata aatattaatc atatataatt aatatcaatt    7320
gggttagcaa acaaatcta gtctaggtgt gttttgcgaa ttcagtacat taaaaacgtc     7380
cgcaatgtgt tattaagttg tctaagcgtc aatttgttta caccacaata tatcctgcca    7440
ccagccagcc aacagctccc cgaccggcag ctcggcacaa aatcaccact cgatacaggc    7500
agcccatcag tccgggacgg cgtcagcggg agagccgttg taaggcggca gactttgctc    7560
atgtt                                                                7565
```

<210> SEQ ID NO 3
<211> LENGTH: 441
<212> TYPE: DNA
<213> ORGANISM: Artificial Sequence
<220> FEATURE:
<223> OTHER INFORMATION: Optimized GAT sequence-- D_S00341806_GAT20-8H12
<220> FEATURE:
<221> NAME/KEY: CDS
<222> LOCATION: (1)...(441)

<400> SEQUENCE: 3

```
atg ata gag gta aaa ccg att aac gca gag gat acc tat gaa cta agg     48
Met Ile Glu Val Lys Pro Ile Asn Ala Glu Asp Thr Tyr Glu Leu Arg
 1               5                  10                  15 cat aga gtc ctc aga cca aac cag ccg ata gaa gcg tgt atc ttt gaa     96
His Arg Val Leu Arg Pro Asn Gln Pro Ile Glu Ala Cys Ile Phe Glu
             20                  25                  30 agc gat tta atg cgt ggt gca ttt cac tta ggc ggc ttc tac ggg ggc    144
Ser Asp Leu Met Arg Gly Ala Phe His Leu Gly Gly Phe Tyr Gly Gly
         35                  40                  45 aga ctg att tcc gtc gct tca ttc cac cag gcc gag cac tcg gaa ctt    192
Arg Leu Ile Ser Val Ala Ser Phe His Gln Ala Glu His Ser Glu Leu
     50                  55                  60 caa ggc cag aaa cag tac cag ctt cga ggt atg gct acc ttg gaa ggt    240
Gln Gly Gln Lys Gln Tyr Gln Leu Arg Gly Met Ala Thr Leu Glu Gly
 65                  70                  75                  80 tat cgt gag cag aag gcg gga tcc agt cta gtt aaa cac gct gaa gaa    288
Tyr Arg Glu Gln Lys Ala Gly Ser Ser Leu Val Lys His Ala Glu Glu
                 85                  90                  95 att cta cgt aag agg ggg gcg gac cta ctt tgg tgt aat gcg cgg aca    336
Ile Leu Arg Lys Arg Gly Ala Asp Leu Leu Trp Cys Asn Ala Arg Thr
            100                 105                 110 tcc gcc tca ggc tac tac aaa aag tta ggc ttc agc gag cag gga gag    384
Ser Ala Ser Gly Tyr Tyr Lys Lys Leu Gly Phe Ser Glu Gln Gly Glu
        115                 120                 125 gta ttc gac acg ccg cca gta gga cct cac atc ctg atg tat aaa agg    432
Val Phe Asp Thr Pro Pro Val Gly Pro His Ile Leu Met Tyr Lys Arg
    130                 135                 140 atc aca taa                                                        441
Ile Thr *
145
```

<210> SEQ ID NO 4
<211> LENGTH: 441
<212> TYPE: DNA

<210> SEQ ID NO 4
<211> LENGTH: 441
<212> TYPE: DNA
<213> ORGANISM: Artificial Sequence
<220> FEATURE:
<223> OTHER INFORMATION: Optimized GAT sequence-- GAT4604SR
<220> FEATURE:
<221> NAME/KEY: CDS
<222> LOCATION: (1)...(441)
<223> OTHER INFORMATION: encodes 20-H812

<400> SEQUENCE: 4

```
atg ata gag gtg aaa ccg att aac gca gag gat acc tat gaa cta agg        48
Met Ile Glu Val Lys Pro Ile Asn Ala Glu Asp Thr Tyr Glu Leu Arg
1               5                   10                  15 cat aga gtc ctc aga cca aac cag ccg ata gaa gcg tgt atc ttt gaa        96
His Arg Val Leu Arg Pro Asn Gln Pro Ile Glu Ala Cys Ile Phe Glu
                20                  25                  30 agc gat tta atg cgt ggt gca ttt cac tta ggc ggc ttc tac ggg ggc       144
Ser Asp Leu Met Arg Gly Ala Phe His Leu Gly Gly Phe Tyr Gly Gly
            35                  40                  45 aga ctg att tcc gtc gct tca ttc cac cag gcc gag cac tct gaa ctt       192
Arg Leu Ile Ser Val Ala Ser Phe His Gln Ala Glu His Ser Glu Leu
        50                  55                  60 caa ggc cag aaa cag tac cag ctt cga ggt atg gct acc ttg gaa ggt       240
Gln Gly Gln Lys Gln Tyr Gln Leu Arg Gly Met Ala Thr Leu Glu Gly
65                  70                  75                  80 tat cgt gag cag aag gcg ggt tcc agt cta gtt aaa cac gct gaa gaa       288
Tyr Arg Glu Gln Lys Ala Gly Ser Ser Leu Val Lys His Ala Glu Glu
                85                  90                  95 att cta cgt aag agg ggg gcg gac cta ctt tgg tgt aat gcg agg aca       336
Ile Leu Arg Lys Arg Gly Ala Asp Leu Leu Trp Cys Asn Ala Arg Thr
            100                 105                 110 tcc gcc tca ggc tac tac aaa aag tta ggc ttc agc gag cag gga gag       384
Ser Ala Ser Gly Tyr Tyr Lys Lys Leu Gly Phe Ser Glu Gln Gly Glu
        115                 120                 125 gta ttc gac acg ccg cca gta gga cct cac atc ctg atg tat aaa agg       432
Val Phe Asp Thr Pro Pro Val Gly Pro His Ile Leu Met Tyr Lys Arg
    130                 135                 140 atc aca taa                                                           441
Ile Thr *
145
```

<210> SEQ ID NO 5
<211> LENGTH: 146
<212> TYPE: PRT
<213> ORGANISM: Artificial Sequence
<220> FEATURE:
<223> OTHER INFORMATION: Optimized GAT sequence --
    D_S00341806_GAT20-8H12

<400> SEQUENCE: 5

```
Met Ile Glu Val Lys Pro Ile Asn Ala Glu Asp Thr Tyr Glu Leu Arg
1               5                   10                  15

His Arg Val Leu Arg Pro Asn Gln Pro Ile Glu Ala Cys Ile Phe Glu
                20                  25                  30

Ser Asp Leu Met Arg Gly Ala Phe His Leu Gly Gly Phe Tyr Gly Gly
            35                  40                  45

Arg Leu Ile Ser Val Ala Ser Phe His Gln Ala Glu His Ser Glu Leu
        50                  55                  60

Gln Gly Gln Lys Gln Tyr Gln Leu Arg Gly Met Ala Thr Leu Glu Gly
65                  70                  75                  80

Tyr Arg Glu Gln Lys Ala Gly Ser Ser Leu Val Lys His Ala Glu Glu
                85                  90                  95
```

```
Ile Leu Arg Lys Arg Gly Ala Asp Leu Leu Trp Cys Asn Ala Arg Thr
            100                 105                 110

Ser Ala Ser Gly Tyr Tyr Lys Leu Gly Phe Ser Glu Gln Gly Glu
        115                 120                 125

Val Phe Asp Thr Pro Pro Val Gly Pro His Ile Leu Met Tyr Lys Arg
    130                 135                 140

Ile Thr
145

<210> SEQ ID NO 6
<211> LENGTH: 441
<212> TYPE: DNA
<213> ORGANISM: Artificial Sequence
<220> FEATURE:
<223> OTHER INFORMATION: Optimized GAT sequence-- D_S00398097_GAT22-18C5
<220> FEATURE:
<221> NAME/KEY: CDS
<222> LOCATION: (1)...(441)

<400> SEQUENCE: 6 atg ata gag gta aaa ccg att aac gca gag gat acc tat gac cta agg         48
Met Ile Glu Val Lys Pro Ile Asn Ala Glu Asp Thr Tyr Asp Leu Arg
 1               5                  10                  15 cat aga gtc ctc aga cca aac cag ccg ata gaa gcg tgt atg ttt gaa         96
His Arg Val Leu Arg Pro Asn Gln Pro Ile Glu Ala Cys Met Phe Glu
             20                  25                  30 agc gat tta acg cgt ggt gca ttt cac tta ggc ggc ttc tac ggg ggc        144
Ser Asp Leu Thr Arg Gly Ala Phe His Leu Gly Gly Phe Tyr Gly Gly
         35                  40                  45 aaa ctg att tcc gtc gct tca ttc cac cag gcc gag cac tcg gaa ctt        192
Lys Leu Ile Ser Val Ala Ser Phe His Gln Ala Glu His Ser Glu Leu
     50                  55                  60 caa ggc cag aaa cag tat cag ctt cga ggt gtg gct acc ttg gaa ggt        240
Gln Gly Gln Lys Gln Tyr Gln Leu Arg Gly Val Ala Thr Leu Glu Gly
 65                  70                  75                  80 tat cgt gag cag aag gcg gga acc agt cta gtt aaa cac gct gaa gaa        288
Tyr Arg Glu Gln Lys Ala Gly Thr Ser Leu Val Lys His Ala Glu Glu
                 85                  90                  95 att cta cgt aag agg ggg gtg gac cta ctt tgg tgt aat gcg cgg aca        336
Ile Leu Arg Lys Arg Gly Val Asp Leu Leu Trp Cys Asn Ala Arg Thr
            100                 105                 110 tcc gcc tca ggc tac tac aga aag tta ggc ttc agc gag cag gga gag        384
Ser Ala Ser Gly Tyr Tyr Arg Lys Leu Gly Phe Ser Glu Gln Gly Glu
        115                 120                 125 gta ttc gac acg ccg cca gta gga cct cac atc ctg atg tat aaa agg        432
Val Phe Asp Thr Pro Pro Val Gly Pro His Ile Leu Met Tyr Lys Arg
    130                 135                 140 atc aca taa                                                            441
Ile Thr *
145

<210> SEQ ID NO 7
<211> LENGTH: 449
<212> TYPE: DNA
<213> ORGANISM: Artificial Sequence
<220> FEATURE:
<223> OTHER INFORMATION: Optimized GAT sequence-- GAT4609SR
<220> FEATURE:
<221> NAME/KEY: CDS
<222> LOCATION: (1)...(441)
<223> OTHER INFORMATION: encodes 22-18C5

<400> SEQUENCE: 7
```

```
atg ata gag gta aaa ccg att aac gca gag gat acc tat gac cta agg          48
Met Ile Glu Val Lys Pro Ile Asn Ala Glu Asp Thr Tyr Asp Leu Arg
 1               5                  10                  15 cat aga gtc ctc aga cca aac cag ccg ata gaa gcg tgt atg ttt gaa          96
His Arg Val Leu Arg Pro Asn Gln Pro Ile Glu Ala Cys Met Phe Glu
                20                  25                  30 agc gat tta acg cgt ggt gca ttt cac tta ggc ggc ttc tac ggg ggc         144
Ser Asp Leu Thr Arg Gly Ala Phe His Leu Gly Gly Phe Tyr Gly Gly
            35                  40                  45 aaa ctg att tcc gtc gct tca ttc cac cag gcc gag cac tct gaa ctt         192
Lys Leu Ile Ser Val Ala Ser Phe His Gln Ala Glu His Ser Glu Leu
     50                  55                  60 caa ggc cag aaa cag tat cag ctt cga ggt gtg gct acc ttg gaa ggt         240
Gln Gly Gln Lys Gln Tyr Gln Leu Arg Gly Val Ala Thr Leu Glu Gly
 65                  70                  75                  80 tat cgt gag cag aag gcg gga acc agt cta gtt aaa cac gct gaa gaa         288
Tyr Arg Glu Gln Lys Ala Gly Thr Ser Leu Val Lys His Ala Glu Glu
                 85                  90                  95 att cta cgt aag agg ggg gtg gac cta ctt tgg tgt aat gcg agg aca         336
Ile Leu Arg Lys Arg Gly Val Asp Leu Leu Trp Cys Asn Ala Arg Thr
            100                 105                 110 tcc gcc tca ggc tac tac aga aag tta ggc ttc agc gag cag gga gag         384
Ser Ala Ser Gly Tyr Tyr Arg Lys Leu Gly Phe Ser Glu Gln Gly Glu
        115                 120                 125 gta ttc gac acg ccg cca gta gga cct cac atc ctg atg tat aaa agg         432
Val Phe Asp Thr Pro Pro Val Gly Pro His Ile Leu Met Tyr Lys Arg
    130                 135                 140 atc aca taa ggcgcgcc                                                    449
Ile Thr *
145
```

<210> SEQ ID NO 8
<211> LENGTH: 146
<212> TYPE: PRT
<213> ORGANISM: Artificial Sequence
<220> FEATURE:
<223> OTHER INFORMATION: Optimized GAT sequence --
    D_S00398097_GAT22-18C5

<400> SEQUENCE: 8

```
Met Ile Glu Val Lys Pro Ile Asn Ala Glu Asp Thr Tyr Asp Leu Arg
 1               5                  10                  15

His Arg Val Leu Arg Pro Asn Gln Pro Ile Glu Ala Cys Met Phe Glu
                20                  25                  30

Ser Asp Leu Thr Arg Gly Ala Phe His Leu Gly Gly Phe Tyr Gly Gly
            35                  40                  45

Lys Leu Ile Ser Val Ala Ser Phe His Gln Ala Glu His Ser Glu Leu
     50                  55                  60

Gln Gly Gln Lys Gln Tyr Gln Leu Arg Gly Val Ala Thr Leu Glu Gly
 65                  70                  75                  80

Tyr Arg Glu Gln Lys Ala Gly Thr Ser Leu Val Lys His Ala Glu Glu
                 85                  90                  95

Ile Leu Arg Lys Arg Gly Val Asp Leu Leu Trp Cys Asn Ala Arg Thr
            100                 105                 110

Ser Ala Ser Gly Tyr Tyr Arg Lys Leu Gly Phe Ser Glu Gln Gly Glu
        115                 120                 125

Val Phe Asp Thr Pro Pro Val Gly Pro His Ile Leu Met Tyr Lys Arg
    130                 135                 140

Ile Thr
145
```

-continued

```
<210> SEQ ID NO 9
<211> LENGTH: 441
<212> TYPE: DNA
<213> ORGANISM: Artificial Sequence
<220> FEATURE:
<223> OTHER INFORMATION: Optimized GAT sequence-- D_S00397944_22-16D8
<220> FEATURE:
<221> NAME/KEY: CDS
<222> LOCATION: (1)...(441)

<400> SEQUENCE: 9 atg ata gag gta aaa ccg att aac gca gag gat acc tat gaa cta agg      48
Met Ile Glu Val Lys Pro Ile Asn Ala Glu Asp Thr Tyr Glu Leu Arg
 1               5                  10                  15 cat aga gtc ctc aga cca aac cag ccg ata gaa gcg tgt atg ttt gaa      96
His Arg Val Leu Arg Pro Asn Gln Pro Ile Glu Ala Cys Met Phe Glu
            20                  25                  30 agc gat tta ctg cgt ggt gca ttt cac tta ggc ggc ttc tac ggg ggc     144
Ser Asp Leu Leu Arg Gly Ala Phe His Leu Gly Gly Phe Tyr Gly Gly
        35                  40                  45 aaa ctg att tcc gtc gct tca ttc cac cag gcc gag cac acg gaa ctt     192
Lys Leu Ile Ser Val Ala Ser Phe His Gln Ala Glu His Thr Glu Leu
    50                  55                  60 caa ggc cag aaa cag tac cag ctt cga ggt gtg gct acc ttg gaa ggt     240
Gln Gly Gln Lys Gln Tyr Gln Leu Arg Gly Val Ala Thr Leu Glu Gly
65                  70                  75                  80 tat cgt gag cag aag gcg gga acc agt cta gtt aaa cac gct gaa gaa     288
Tyr Arg Glu Gln Lys Ala Gly Thr Ser Leu Val Lys His Ala Glu Glu
                85                  90                  95 att cta cgt aag agg ggg gcg gac atg ctt tgg tgt aat gcg cgg aca     336
Ile Leu Arg Lys Arg Gly Ala Asp Met Leu Trp Cys Asn Ala Arg Thr
            100                 105                 110 tcc gcc tca ggc tac tac aga aag tta ggc ttt agc gag cag gga gag     384
Ser Ala Ser Gly Tyr Tyr Arg Lys Leu Gly Phe Ser Glu Gln Gly Glu
        115                 120                 125 gta ttc gac acg ccg cca gta gga cct cac atc ctg atg tat aaa agg     432
Val Phe Asp Thr Pro Pro Val Gly Pro His Ile Leu Met Tyr Lys Arg
    130                 135                 140 atc aca taa                                                         441
Ile Thr *
145

<210> SEQ ID NO 10
<211> LENGTH: 449
<212> TYPE: DNA
<213> ORGANISM: Artificial Sequence
<220> FEATURE:
<223> OTHER INFORMATION: Optimized GAT sequence -- GAT4610R
<220> FEATURE:
<221> NAME/KEY: CDS
<222> LOCATION: (1)...(441)
<223> OTHER INFORMATION: encodes 22-16D8

<400> SEQUENCE: 10 atg ata gag gta aaa ccg att aac gca gag gat acc tat gaa cta agg      48
Met Ile Glu Val Lys Pro Ile Asn Ala Glu Asp Thr Tyr Glu Leu Arg
 1               5                  10                  15 cat aga gtc ctc aga cca aac cag ccg ata gaa gcg tgt atg ttt gaa      96
His Arg Val Leu Arg Pro Asn Gln Pro Ile Glu Ala Cys Met Phe Glu
            20                  25                  30 agc gat tta ctg cgt ggt gca ttt cac tta ggc ggc ttc tac ggg ggc     144
Ser Asp Leu Leu Arg Gly Ala Phe His Leu Gly Gly Phe Tyr Gly Gly
```

```
                  35                  40                  45
aaa ctg att tcc gtc gct tca ttc cac cag gcc gag cac acg gaa ctt       192
Lys Leu Ile Ser Val Ala Ser Phe His Gln Ala Glu His Thr Glu Leu
         50                  55                  60 caa ggc cag aaa cag tac cag ctt cga ggt gtg gct acc ttg gaa ggt       240
Gln Gly Gln Lys Gln Tyr Gln Leu Arg Gly Val Ala Thr Leu Glu Gly
 65                  70                  75                  80 tat cgt gag cag aag gcg gga acc agt cta gtt aaa cac gct gaa gaa       288
Tyr Arg Glu Gln Lys Ala Gly Thr Ser Leu Val Lys His Ala Glu Glu
                 85                  90                  95 att cta cgt aag agg ggg gcg gac atg ctt tgg tgt aat gcg agg aca       336
Ile Leu Arg Lys Arg Gly Ala Asp Met Leu Trp Cys Asn Ala Arg Thr
            100                 105                 110 tcc gcc tca ggc tac tac aga aag tta ggc ttt agc gag cag gga gag       384
Ser Ala Ser Gly Tyr Tyr Arg Lys Leu Gly Phe Ser Glu Gln Gly Glu
        115                 120                 125 gta ttc gac acg ccg cca gta gga cct cac atc ctg atg tat aaa agg       432
Val Phe Asp Thr Pro Pro Val Gly Pro His Ile Leu Met Tyr Lys Arg
    130                 135                 140 atc aca taa ggcgcgcc                                                  449
Ile Thr *
145

<210> SEQ ID NO 11
<211> LENGTH: 146
<212> TYPE: PRT
<213> ORGANISM: Artificial Sequence
<220> FEATURE:
<223> OTHER INFORMATION: Optimized GAT sequence-- D_S00397944_22-16D8

<400> SEQUENCE: 11

Met Ile Glu Val Lys Pro Ile Asn Ala Glu Asp Thr Tyr Glu Leu Arg
 1               5                  10                  15

His Arg Val Leu Arg Pro Asn Gln Pro Ile Glu Ala Cys Met Phe Glu
                20                  25                  30

Ser Asp Leu Leu Arg Gly Ala Phe His Leu Gly Gly Phe Tyr Gly Gly
            35                  40                  45

Lys Leu Ile Ser Val Ala Ser Phe His Gln Ala Glu His Thr Glu Leu
        50                  55                  60

Gln Gly Gln Lys Gln Tyr Gln Leu Arg Gly Val Ala Thr Leu Glu Gly
 65                  70                  75                  80

Tyr Arg Glu Gln Lys Ala Gly Thr Ser Leu Val Lys His Ala Glu Glu
                 85                  90                  95

Ile Leu Arg Lys Arg Gly Ala Asp Met Leu Trp Cys Asn Ala Arg Thr
            100                 105                 110

Ser Ala Ser Gly Tyr Tyr Arg Lys Leu Gly Phe Ser Glu Gln Gly Glu
        115                 120                 125

Val Phe Asp Thr Pro Pro Val Gly Pro His Ile Leu Met Tyr Lys Arg
    130                 135                 140

Ile Thr
145

<210> SEQ ID NO 12
<211> LENGTH: 441
<212> TYPE: DNA
<213> ORGANISM: Artificial Sequence
<220> FEATURE:
<223> OTHER INFORMATION: Optimized GAT sequence--D_S00397832_GAT22-15B4
<220> FEATURE:
<221> NAME/KEY: CDS
```

<222> LOCATION: (1)...(441)

<400> SEQUENCE: 12

```
atg ata gag gta aaa ccg att aac gca gaa gat acc tat gac cta agg       48
Met Ile Glu Val Lys Pro Ile Asn Ala Glu Asp Thr Tyr Asp Leu Arg
1               5                   10                  15 cat aga gtc ctc aga cca aac cag ccg ata gaa gcg tgt atg ttt gat       96
His Arg Val Leu Arg Pro Asn Gln Pro Ile Glu Ala Cys Met Phe Asp
                20                  25                  30 agc gat tta atg cgt agt gca ttt cac tta ggc ggc ttc tac ggg ggc      144
Ser Asp Leu Met Arg Ser Ala Phe His Leu Gly Gly Phe Tyr Gly Gly
            35                  40                  45 aaa ctg att tcc gtc gct tca ttc cac cag gcc gag cac acg gaa ctt      192
Lys Leu Ile Ser Val Ala Ser Phe His Gln Ala Glu His Thr Glu Leu
        50                  55                  60 caa ggc cag aaa cag tac cag ctt cga ggt gtg gct acc ttg gaa ggt      240
Gln Gly Gln Lys Gln Tyr Gln Leu Arg Gly Val Ala Thr Leu Glu Gly
65                  70                  75                  80 tat cgt gag cag aag gcg ggt tcc agt cta gtt aaa cac gct gaa gaa      288
Tyr Arg Glu Gln Lys Ala Gly Ser Ser Leu Val Lys His Ala Glu Glu
                85                  90                  95 att cta cgt aag agg ggg gtg gac cta ctt tgg tgt aat gcg cgg aca      336
Ile Leu Arg Lys Arg Gly Val Asp Leu Leu Trp Cys Asn Ala Arg Thr
                100                 105                 110 tcc gcc tca ggc tac tac aaa aag tta ggc ttc agc gag cag gga gag      384
Ser Ala Ser Gly Tyr Tyr Lys Lys Leu Gly Phe Ser Glu Gln Gly Glu
            115                 120                 125 gta ttc gac acg ccg cca gta gga cct cac atc ctg atg tat aaa agg      432
Val Phe Asp Thr Pro Pro Val Gly Pro His Ile Leu Met Tyr Lys Arg
        130                 135                 140 atc aca taa                                                          441
Ile Thr *
145
```

<210> SEQ ID NO 13
<211> LENGTH: 449
<212> TYPE: DNA
<213> ORGANISM: Artificial Sequence
<220> FEATURE:
<223> OTHER INFORMATION: Optimized GAT sequence -- GAT4611R
<220> FEATURE:
<221> NAME/KEY: CDS
<222> LOCATION: (1)...(441)
<223> OTHER INFORMATION: encodes 22-15B4

<400> SEQUENCE: 13

```
atg ata gag gta aaa ccg att aac gca gaa gat acc tat gac cta agg       48
Met Ile Glu Val Lys Pro Ile Asn Ala Glu Asp Thr Tyr Asp Leu Arg
1               5                   10                  15 cat aga gtc ctc aga cca aac cag ccg ata gaa gcg tgt atg ttt gat       96
His Arg Val Leu Arg Pro Asn Gln Pro Ile Glu Ala Cys Met Phe Asp
                20                  25                  30 agc gat tta atg cgt agt gca ttt cac tta ggc ggc ttc tac ggg ggc      144
Ser Asp Leu Met Arg Ser Ala Phe His Leu Gly Gly Phe Tyr Gly Gly
            35                  40                  45 aaa ctg att tcc gtc gct tca ttc cac cag gcc gag cac acg gaa ctt      192
Lys Leu Ile Ser Val Ala Ser Phe His Gln Ala Glu His Thr Glu Leu
        50                  55                  60 caa ggc cag aaa cag tac cag ctt cga ggt gtg gct acc ttg gaa ggt      240
Gln Gly Gln Lys Gln Tyr Gln Leu Arg Gly Val Ala Thr Leu Glu Gly
65                  70                  75                  80 tat cgt gag cag aag gcg ggt tcc agt cta gtt aaa cac gct gaa gaa      288
```

```
Tyr Arg Glu Gln Lys Ala Gly Ser Ser Leu Val Lys His Ala Glu Glu
             85                  90                  95 att cta cgt aag agg ggg gtg gac cta ctt tgg tgt aat gcg agg aca      336
Ile Leu Arg Lys Arg Gly Val Asp Leu Leu Trp Cys Asn Ala Arg Thr
            100                 105                 110 tcc gcc tca ggc tac tac aaa aag tta ggc ttc agc gag cag gga gag      384
Ser Ala Ser Gly Tyr Tyr Lys Lys Leu Gly Phe Ser Glu Gln Gly Glu
        115                 120                 125 gta ttc gac acg ccg cca gta gga cct cac atc ctg atg tat aaa agg      432
Val Phe Asp Thr Pro Pro Val Gly Pro His Ile Leu Met Tyr Lys Arg
    130                 135                 140 atc aca taa ggcgcgcc                                                 449
Ile Thr *
145

<210> SEQ ID NO 14
<211> LENGTH: 146
<212> TYPE: PRT
<213> ORGANISM: Artificial Sequence
<220> FEATURE:
<223> OTHER INFORMATION: Optimized GAT sequence --
      D_S00397832_GAT22-15B4

<400> SEQUENCE: 14

Met Ile Glu Val Lys Pro Ile Asn Ala Glu Asp Thr Tyr Asp Leu Arg
1               5                   10                  15

His Arg Val Leu Arg Pro Asn Gln Pro Ile Glu Ala Cys Met Phe Asp
            20                  25                  30

Ser Asp Leu Met Arg Ser Ala Phe His Leu Gly Gly Phe Gly Gly
        35                  40                  45

Lys Leu Ile Ser Val Ala Ser Phe His Gln Ala Glu His Thr Glu Leu
    50                  55                  60

Gln Gly Gln Lys Gln Tyr Gln Leu Arg Gly Val Ala Thr Leu Glu Gly
65                  70                  75                  80

Tyr Arg Glu Gln Lys Ala Gly Ser Ser Leu Val Lys His Ala Glu Glu
                85                  90                  95

Ile Leu Arg Lys Arg Gly Val Asp Leu Leu Trp Cys Asn Ala Arg Thr
            100                 105                 110

Ser Ala Ser Gly Tyr Tyr Lys Lys Leu Gly Phe Ser Glu Gln Gly Glu
        115                 120                 125

Val Phe Asp Thr Pro Pro Val Gly Pro His Ile Leu Met Tyr Lys Arg
    130                 135                 140

Ile Thr
145

<210> SEQ ID NO 15
<211> LENGTH: 441
<212> TYPE: DNA
<213> ORGANISM: Artificial Sequence
<220> FEATURE:
<223> OTHER INFORMATION: Optimized GAT sequence -- GAT24-5H5
<220> FEATURE:
<221> NAME/KEY: CDS
<222> LOCATION: (1)...(441)

<400> SEQUENCE: 15 atg ata gag gta aaa ccg att aac gca gaa gat acc tat gac cta agg       48
Met Ile Glu Val Lys Pro Ile Asn Ala Glu Asp Thr Tyr Asp Leu Arg
1               5                   10                  15 cat aga gtc ctc aga cca aac cag ccg ata gaa gcg tgt atg ttt gat       96
His Arg Val Leu Arg Pro Asn Gln Pro Ile Glu Ala Cys Met Phe Asp
```

-continued

```
                    20                  25                  30
aac gat tta atg cgt agt gca ttt cac tta ggc ggc ttc cac ggg ggc         144
Asn Asp Leu Met Arg Ser Ala Phe His Leu Gly Gly Phe His Gly Gly
            35                  40                  45 aaa ctg att tcc gtc gct tca ttc cac cag gcc gag cac tcg gaa ctt         192
Lys Leu Ile Ser Val Ala Ser Phe His Gln Ala Glu His Ser Glu Leu
    50                  55                  60 caa ggc cag aaa cag tat cag ctt cga ggt gtg gct acc ttg gaa ggt         240
Gln Gly Gln Lys Gln Tyr Gln Leu Arg Gly Val Ala Thr Leu Glu Gly
65                  70                  75                  80 tat cgt gag cag aag gcg ggt tcc agt cta gtt aaa cac gct gaa gaa         288
Tyr Arg Glu Gln Lys Ala Gly Ser Ser Leu Val Lys His Ala Glu Glu
                85                  90                  95 att cta cgt aag agg ggg gcg gac atg ctt tgg tgt aat gcg cgg aca         336
Ile Leu Arg Lys Arg Gly Ala Asp Met Leu Trp Cys Asn Ala Arg Thr
            100                 105                 110 tcc gcc tca ggc tac tac aga aag ttg ggc ttc agc gag cag gga gag         384
Ser Ala Ser Gly Tyr Tyr Arg Lys Leu Gly Phe Ser Glu Gln Gly Glu
        115                 120                 125 gta ttc gac acg ccg ccg gta gga cct cac atc ctg atg tat aaa agg         432
Val Phe Asp Thr Pro Pro Val Gly Pro His Ile Leu Met Tyr Lys Arg
    130                 135                 140 atc aca taa                                                             441
Ile Thr *
145

<210> SEQ ID NO 16
<211> LENGTH: 441
<212> TYPE: DNA
<213> ORGANISM: Artificial Sequence
<220> FEATURE:
<223> OTHER INFORMATION: Optimized GAT sequence  -- GAT4614SR
<220> FEATURE:
<221> NAME/KEY: CDS
<222> LOCATION: (1)...(441)
<223> OTHER INFORMATION: encodes 24-5H5

<400> SEQUENCE: 16 atg ata gag gta aaa ccg att aac gca gaa gat acc tat gac cta agg         48
Met Ile Glu Val Lys Pro Ile Asn Ala Glu Asp Thr Tyr Asp Leu Arg
1               5                   10                  15 cat aga gtc ctc aga cca aac cag ccg ata gaa gcg tgt atg ttt gat         96
His Arg Val Leu Arg Pro Asn Gln Pro Ile Glu Ala Cys Met Phe Asp
                20                  25                  30 aac gat tta atg cgt agt gca ttt cac tta ggc ggc ttc cac ggg ggc         144
Asn Asp Leu Met Arg Ser Ala Phe His Leu Gly Gly Phe His Gly Gly
            35                  40                  45 aaa ctg att tcc gtc gct tca ttc cac cag gcc gag cac tct gaa ctt         192
Lys Leu Ile Ser Val Ala Ser Phe His Gln Ala Glu His Ser Glu Leu
    50                  55                  60 caa ggc cag aaa cag tat cag ctt cga ggt gtg gct acc ttg gaa ggt         240
Gln Gly Gln Lys Gln Tyr Gln Leu Arg Gly Val Ala Thr Leu Glu Gly
65                  70                  75                  80 tat cgt gag cag aag gcg ggt tcc agt cta gtt aaa cac gct gaa gaa         288
Tyr Arg Glu Gln Lys Ala Gly Ser Ser Leu Val Lys His Ala Glu Glu
                85                  90                  95 att cta cgt aag agg ggg gcg gac atg ctt tgg tgt aat gcg agg aca         336
Ile Leu Arg Lys Arg Gly Ala Asp Met Leu Trp Cys Asn Ala Arg Thr
            100                 105                 110 tcc gcc tca ggc tac tac aga aag ttg ggc ttc agc gag cag gga gag         384
Ser Ala Ser Gly Tyr Tyr Arg Lys Leu Gly Phe Ser Glu Gln Gly Glu
        115                 120                 125
```

```
gta ttc gac acg ccg ccg gta gga cct cac atc ctg atg tat aaa agg      432
Val Phe Asp Thr Pro Pro Val Gly Pro His Ile Leu Met Tyr Lys Arg
    130                 135                 140 atc aca taa                                                           441
Ile Thr *
145

<210> SEQ ID NO 17
<211> LENGTH: 146
<212> TYPE: PRT
<213> ORGANISM: Artificial Sequence
<220> FEATURE:
<223> OTHER INFORMATION: Optimized GAT sequence -- 24-5H5

<400> SEQUENCE: 17

Met Ile Glu Val Lys Pro Ile Asn Ala Glu Asp Thr Tyr Asp Leu Arg
1               5                   10                  15

His Arg Val Leu Arg Pro Asn Gln Pro Ile Glu Ala Cys Met Phe Asp
            20                  25                  30

Asn Asp Leu Met Arg Ser Ala Phe His Leu Gly Gly Phe His Gly Gly
        35                  40                  45

Lys Leu Ile Ser Val Ala Ser Phe His Gln Ala Glu His Ser Glu Leu
    50                  55                  60

Gln Gly Gln Lys Gln Tyr Gln Leu Arg Gly Val Ala Thr Leu Glu Gly
65                  70                  75                  80

Tyr Arg Glu Gln Lys Ala Gly Ser Ser Leu Val Lys His Ala Glu Glu
                85                  90                  95

Ile Leu Arg Lys Arg Gly Ala Asp Met Leu Trp Cys Asn Ala Arg Thr
            100                 105                 110

Ser Ala Ser Gly Tyr Tyr Arg Lys Leu Gly Phe Ser Glu Gln Gly Glu
        115                 120                 125

Val Phe Asp Thr Pro Pro Val Gly Pro His Ile Leu Met Tyr Lys Arg
    130                 135                 140

Ile Thr
145

<210> SEQ ID NO 18
<211> LENGTH: 441
<212> TYPE: DNA
<213> ORGANISM: Artificial Sequence
<220> FEATURE:
<223> OTHER INFORMATION: Optimized GAT sequence -- GAT4614VSR
<220> FEATURE:
<221> NAME/KEY: CDS
<222> LOCATION: (1)...(441)
<223> OTHER INFORMATION: encodes 24-5H5

<400> SEQUENCE: 18 atg ata gag gtg aaa ccg att aac gca gaa gat acc tat gac cta agg       48
Met Ile Glu Val Lys Pro Ile Asn Ala Glu Asp Thr Tyr Asp Leu Arg
1               5                   10                  15 cat aga gtc ctc aga cca aac cag ccg ata gaa gcg tgt atg ttt gat       96
His Arg Val Leu Arg Pro Asn Gln Pro Ile Glu Ala Cys Met Phe Asp
            20                  25                  30 aac gat tta atg cgt agt gca ttt cac tta ggc ggc ttc cac ggg ggc      144
Asn Asp Leu Met Arg Ser Ala Phe His Leu Gly Gly Phe His Gly Gly
        35                  40                  45 aaa ctg att tcc gtc gct tca ttc cac cag gcc gag cac tct gaa ctt      192
Lys Leu Ile Ser Val Ala Ser Phe His Gln Ala Glu His Ser Glu Leu
    50                  55                  60
```

```
caa ggc cag aaa cag tat cag ctt cga ggt gtg gct acc ttg gaa ggt       240
Gln Gly Gln Lys Gln Tyr Gln Leu Arg Gly Val Ala Thr Leu Glu Gly
 65                  70                  75                  80 tat cgt gag cag aag gcg ggt tcc agt cta gtt aaa cac gct gaa gaa       288
Tyr Arg Glu Gln Lys Ala Gly Ser Ser Leu Val Lys His Ala Glu Glu
                 85                  90                  95 att cta cgt aag agg ggg gcg gac atg ctt tgg tgt aat gcg agg aca       336
Ile Leu Arg Lys Arg Gly Ala Asp Met Leu Trp Cys Asn Ala Arg Thr
            100                 105                 110 tcc gcc tca ggc tac tac aga aag ttg ggc ttc agc gag cag gga gag       384
Ser Ala Ser Gly Tyr Tyr Arg Lys Leu Gly Phe Ser Glu Gln Gly Glu
        115                 120                 125 gta ttc gac acg ccg ccg gta gga cct cac atc ctg atg tat aaa agg       432
Val Phe Asp Thr Pro Pro Val Gly Pro His Ile Leu Met Tyr Lys Arg
130                 135                 140 atc aca taa                                                           441
Ile Thr *
145

<210> SEQ ID NO 19
<211> LENGTH: 441
<212> TYPE: DNA
<213> ORGANISM: Artificial Sequence
<220> FEATURE:
<223> OTHER INFORMATION: Optimized GAT sequence  -- GAT23-2H11
<220> FEATURE:
<221> NAME/KEY: CDS
<222> LOCATION: (1)...(441)

<400> SEQUENCE: 19 atg ata gag gta aaa ccg att aac gca gag gat acc tat gac cta agg        48
Met Ile Glu Val Lys Pro Ile Asn Ala Glu Asp Thr Tyr Asp Leu Arg
  1               5                  10                  15 cat aga gtc ctc aga cca aac cag ccg ata gaa gcg tgt atg ttt gaa        96
His Arg Val Leu Arg Pro Asn Gln Pro Ile Glu Ala Cys Met Phe Glu
             20                  25                  30 ggc gat tta atg cgt ggt gca ttt cac tta ggc ggc ttc tac ggg ggc       144
Gly Asp Leu Met Arg Gly Ala Phe His Leu Gly Gly Phe Tyr Gly Gly
         35                  40                  45 aaa ctg att tcc gtc gct tca ttc cac cag gcc gag cac tcg gaa ctt       192
Lys Leu Ile Ser Val Ala Ser Phe His Gln Ala Glu His Ser Glu Leu
     50                  55                  60 caa ggc cag aaa cag tac cag ctt cga ggt gtg gct acc ttg gaa ggt       240
Gln Gly Gln Lys Gln Tyr Gln Leu Arg Gly Val Ala Thr Leu Glu Gly
 65                  70                  75                  80 tat cgt gag cag aag gcg ggt tcc agt cta gtt aaa cat gct gaa gaa       288
Tyr Arg Glu Gln Lys Ala Gly Ser Ser Leu Val Lys His Ala Glu Glu
                 85                  90                  95 att cta cgc aag agg ggg gcg gac cta ctt tgg tgt aat gcg cgg aca       336
Ile Leu Arg Lys Arg Gly Ala Asp Leu Leu Trp Cys Asn Ala Arg Thr
            100                 105                 110 tcc gcc tca ggc tac tac aga aag tta ggc ttc agc gag cag gga gag       384
Ser Ala Ser Gly Tyr Tyr Arg Lys Leu Gly Phe Ser Glu Gln Gly Glu
        115                 120                 125 gta ttc gac acg ccg cca gta gga cct cac atc ctg atg tat aaa agg       432
Val Phe Asp Thr Pro Pro Val Gly Pro His Ile Leu Met Tyr Lys Arg
130                 135                 140 atc aca taa                                                           441
Ile Thr *
145

<210> SEQ ID NO 20
```

```
<211> LENGTH: 441
<212> TYPE: DNA
<213> ORGANISM: Artificial Sequence
<220> FEATURE:
<223> OTHER INFORMATION: Optimized GAT sequence  -- GAT4615R
<220> FEATURE:
<221> NAME/KEY: CDS
<222> LOCATION: (1)...(441)
<223> OTHER INFORMATION: encodes 23-2H11

<400> SEQUENCE: 20 atg ata gag gta aaa ccg att aac gca gag gat acc tat gac cta agg      48
Met Ile Glu Val Lys Pro Ile Asn Ala Glu Asp Thr Tyr Asp Leu Arg
 1               5                  10                  15 cat aga gtc ctc aga cca aac cag ccg ata gaa gcg tgt atg ttt gaa      96
His Arg Val Leu Arg Pro Asn Gln Pro Ile Glu Ala Cys Met Phe Glu
             20                  25                  30 ggc gat tta atg cgt ggt gca ttt cac tta ggc ggc ttc tac ggg ggc     144
Gly Asp Leu Met Arg Gly Ala Phe His Leu Gly Gly Phe Tyr Gly Gly
         35                  40                  45 aaa ctg att tcc gtc gct tca ttc cac cag gcc gag cac tcg gaa ctt     192
Lys Leu Ile Ser Val Ala Ser Phe His Gln Ala Glu His Ser Glu Leu
     50                  55                  60 caa ggc cag aaa cag tac cag ctt cga ggt gtg gct acc ttg gaa ggt     240
Gln Gly Gln Lys Gln Tyr Gln Leu Arg Gly Val Ala Thr Leu Glu Gly
 65                  70                  75                  80 tat cgt gag cag aag gcg ggt tcc agt cta gtt aaa cat gct gaa gaa     288
Tyr Arg Glu Gln Lys Ala Gly Ser Ser Leu Val Lys His Ala Glu Glu
                 85                  90                  95 att cta cgc aag agg ggg gcg gac cta ctt tgg tgt aat gcg agg aca     336
Ile Leu Arg Lys Arg Gly Ala Asp Leu Leu Trp Cys Asn Ala Arg Thr
            100                 105                 110 tcc gcc tca ggc tac tac aga aag tta ggc ttc agc gag cag gga gag     384
Ser Ala Ser Gly Tyr Tyr Arg Lys Leu Gly Phe Ser Glu Gln Gly Glu
        115                 120                 125 gta ttc gac acg ccg cca gta gga cct cac atc ctg atg tat aaa agg     432
Val Phe Asp Thr Pro Pro Val Gly Pro His Ile Leu Met Tyr Lys Arg
    130                 135                 140 atc aca taa                                                         441
Ile Thr  *
145

<210> SEQ ID NO 21
<211> LENGTH: 146
<212> TYPE: PRT
<213> ORGANISM: Artificial Sequence
<220> FEATURE:
<223> OTHER INFORMATION: Optimized GAT sequence  --  23-2H11

<400> SEQUENCE: 21

Met Ile Glu Val Lys Pro Ile Asn Ala Glu Asp Thr Tyr Asp Leu Arg
 1               5                  10                  15

His Arg Val Leu Arg Pro Asn Gln Pro Ile Glu Ala Cys Met Phe Glu
             20                  25                  30

Gly Asp Leu Met Arg Gly Ala Phe His Leu Gly Gly Phe Tyr Gly Gly
         35                  40                  45

Lys Leu Ile Ser Val Ala Ser Phe His Gln Ala Glu His Ser Glu Leu
     50                  55                  60

Gln Gly Gln Lys Gln Tyr Gln Leu Arg Gly Val Ala Thr Leu Glu Gly
 65                  70                  75                  80

Tyr Arg Glu Gln Lys Ala Gly Ser Ser Leu Val Lys His Ala Glu Glu
                 85                  90                  95
```

```
Ile Leu Arg Lys Arg Gly Ala Asp Leu Leu Trp Cys Asn Ala Arg Thr
            100                 105                 110

Ser Ala Ser Gly Tyr Tyr Arg Lys Leu Gly Phe Ser Glu Gln Gly Glu
        115                 120                 125

Val Phe Asp Thr Pro Pro Val Gly Pro His Ile Leu Met Tyr Lys Arg
    130                 135                 140

Ile Thr
145

<210> SEQ ID NO 22
<211> LENGTH: 441
<212> TYPE: DNA
<213> ORGANISM: Artificial Sequence
<220> FEATURE:
<223> OTHER INFORMATION: Optimized GAT sequence  -- GAT24-15C3
<220> FEATURE:
<221> NAME/KEY: CDS
<222> LOCATION: (1)...(441)

<400> SEQUENCE: 22 atg ata gag gta aaa ccg att aac gca gag gat acc tat gac cta agg      48
Met Ile Glu Val Lys Pro Ile Asn Ala Glu Asp Thr Tyr Asp Leu Arg
 1               5                  10                  15 cat aga gtc ctc aga cca aac cag ccg ata gaa gcg tgt atg ttt gaa      96
His Arg Val Leu Arg Pro Asn Gln Pro Ile Glu Ala Cys Met Phe Glu
                20                  25                  30 agc gat tta acg cgt agt gca ttt cac tta ggc ggc ttc tac ggg ggc     144
Ser Asp Leu Thr Arg Ser Ala Phe His Leu Gly Gly Phe Tyr Gly Gly
            35                  40                  45 aaa ctg att tcc gtc gct tca ttc cac cag gcc gag cac tcg gaa ctt     192
Lys Leu Ile Ser Val Ala Ser Phe His Gln Ala Glu His Ser Glu Leu
        50                  55                  60 cag ggc cag aaa cag tac cag ctt cga ggt gtg gct acc ttg gaa ggt     240
Gln Gly Gln Lys Gln Tyr Gln Leu Arg Gly Val Ala Thr Leu Glu Gly
 65                  70                  75                  80 tat cgt gag cag aag gcg gga acc agt cta gtt aaa cac gct gaa gaa     288
Tyr Arg Glu Gln Lys Ala Gly Thr Ser Leu Val Lys His Ala Glu Glu
                85                  90                  95 att cta cgt aag agg ggg gcg gac cta ctt tgg tgt aat gcg cgg aca     336
Ile Leu Arg Lys Arg Gly Ala Asp Leu Leu Trp Cys Asn Ala Arg Thr
            100                 105                 110 tcc gcc tca ggc tac tac aga aag tta ggc ttc agc gag cag gga gag     384
Ser Ala Ser Gly Tyr Tyr Arg Lys Leu Gly Phe Ser Glu Gln Gly Glu
        115                 120                 125 gta ttc gac acg ccg cca gta gga cct cac atc ctg atg tat aaa agg     432
Val Phe Asp Thr Pro Pro Val Gly Pro His Ile Leu Met Tyr Lys Arg
    130                 135                 140 atc aca taa                                                          441
Ile Thr *
145

<210> SEQ ID NO 23
<211> LENGTH: 441
<212> TYPE: DNA
<213> ORGANISM: Artificial Sequence
<220> FEATURE:
<223> OTHER INFORMATION: Optimized GAT sequence  -- GAT4616R
<220> FEATURE:
<221> NAME/KEY: CDS
<222> LOCATION: (1)...(441)
<223> OTHER INFORMATION: encodes 24-15C3

<400> SEQUENCE: 23
```

```
atg ata gag gta aaa ccg att aac gca gag gat acc tat gac cta agg      48
Met Ile Glu Val Lys Pro Ile Asn Ala Glu Asp Thr Tyr Asp Leu Arg
 1               5                  10                  15 cat aga gtc ctc aga cca aac cag ccg ata gaa gcg tgt atg ttt gaa      96
His Arg Val Leu Arg Pro Asn Gln Pro Ile Glu Ala Cys Met Phe Glu
                20                  25                  30 agc gat tta acg cgt agt gca ttt cac tta ggc ggc ttc tac ggg ggc     144
Ser Asp Leu Thr Arg Ser Ala Phe His Leu Gly Gly Phe Tyr Gly Gly
         35                  40                  45 aaa ctg att tcc gtc gct tca ttc cac cag gcc gag cac tcg gaa ctt     192
Lys Leu Ile Ser Val Ala Ser Phe His Gln Ala Glu His Ser Glu Leu
 50                  55                  60 cag ggc cag aaa cag tac cag ctt cga ggt gtg gct acc ttg gaa ggt     240
Gln Gly Gln Lys Gln Tyr Gln Leu Arg Gly Val Ala Thr Leu Glu Gly
 65                  70                  75                  80 tat cgt gag cag aag gcg gga acc agt cta gtt aaa cac gct gaa gaa     288
Tyr Arg Glu Gln Lys Ala Gly Thr Ser Leu Val Lys His Ala Glu Glu
                 85                  90                  95 att cta cgt aag agg ggg gcg gac cta ctt tgg tgt aat gcg agg aca     336
Ile Leu Arg Lys Arg Gly Ala Asp Leu Leu Trp Cys Asn Ala Arg Thr
            100                 105                 110 tcc gcc tca ggc tac tac aga aag tta ggc ttc agc gag cag gga gag     384
Ser Ala Ser Gly Tyr Tyr Arg Lys Leu Gly Phe Ser Glu Gln Gly Glu
        115                 120                 125 gta ttc gac acg ccg cca gta gga cct cac atc ctg atg tat aaa agg     432
Val Phe Asp Thr Pro Pro Val Gly Pro His Ile Leu Met Tyr Lys Arg
130                 135                 140 atc aca taa                                                         441
Ile Thr *
145
```

<210> SEQ ID NO 24
<211> LENGTH: 146
<212> TYPE: PRT
<213> ORGANISM: Artificial Sequence
<220> FEATURE:
<223> OTHER INFORMATION: Optimized GAT sequence -- 24-15C3

<400> SEQUENCE: 24

```
Met Ile Glu Val Lys Pro Ile Asn Ala Glu Asp Thr Tyr Asp Leu Arg
 1               5                  10                  15

His Arg Val Leu Arg Pro Asn Gln Pro Ile Glu Ala Cys Met Phe Glu
                20                  25                  30

Ser Asp Leu Thr Arg Ser Ala Phe His Leu Gly Gly Phe Tyr Gly Gly
         35                  40                  45

Lys Leu Ile Ser Val Ala Ser Phe His Gln Ala Glu His Ser Glu Leu
 50                  55                  60

Gln Gly Gln Lys Gln Tyr Gln Leu Arg Gly Val Ala Thr Leu Glu Gly
 65                  70                  75                  80

Tyr Arg Glu Gln Lys Ala Gly Thr Ser Leu Val Lys His Ala Glu Glu
                 85                  90                  95

Ile Leu Arg Lys Arg Gly Ala Asp Leu Leu Trp Cys Asn Ala Arg Thr
            100                 105                 110

Ser Ala Ser Gly Tyr Tyr Arg Lys Leu Gly Phe Ser Glu Gln Gly Glu
        115                 120                 125

Val Phe Asp Thr Pro Pro Val Gly Pro His Ile Leu Met Tyr Lys Arg
130                 135                 140

Ile Thr
```

-continued

```
<210> SEQ ID NO 25
<211> LENGTH: 441
<212> TYPE: DNA
<213> ORGANISM: Artificial Sequence
<220> FEATURE:
<223> OTHER INFORMATION: Optimized GAT sequence  - GAT23-6H10
<220> FEATURE:
<221> NAME/KEY: CDS
<222> LOCATION: (1)...(441)

<400> SEQUENCE: 25 atg ata gag gta aaa ccg att aac gca gag gat acc tat gaa cta agg      48
Met Ile Glu Val Lys Pro Ile Asn Ala Glu Asp Thr Tyr Glu Leu Arg
 1               5                  10                  15 cat aga gtc ctc aga cca aac cag ccg ata gaa gcg tgt atg ttt gaa      96
His Arg Val Leu Arg Pro Asn Gln Pro Ile Glu Ala Cys Met Phe Glu
            20                  25                  30 agc gat tta acg cgt ggt gca ttt cac cta ggc ggc ttc tac ggg ggc     144
Ser Asp Leu Thr Arg Gly Ala Phe His Leu Gly Gly Phe Tyr Gly Gly
        35                  40                  45 aaa ctg att tcc gtc gct tca ttc cac cag gcc gag cac acg gaa ctt     192
Lys Leu Ile Ser Val Ala Ser Phe His Gln Ala Glu His Thr Glu Leu
    50                  55                  60 caa ggc cag aaa cag tac cag ctt cga ggt gtg gct acc ttg gaa ggt     240
Gln Gly Gln Lys Gln Tyr Gln Leu Arg Gly Val Ala Thr Leu Glu Gly
 65                  70                  75                  80 tat cgt gag cag aag gcg ggt tcc agt cta gtt aaa cac gct gaa gaa     288
Tyr Arg Glu Gln Lys Ala Gly Ser Ser Leu Val Lys His Ala Glu Glu
                85                  90                  95 att cta cgt aag agg ggg gcg gac cta ctt tgg tgt aat gcg cgg aca     336
Ile Leu Arg Lys Arg Gly Ala Asp Leu Leu Trp Cys Asn Ala Arg Thr
            100                 105                 110 tcc gcc tca ggc tac tac aga aag tta ggc ttc agc gag cag ggg gag     384
Ser Ala Ser Gly Tyr Tyr Arg Lys Leu Gly Phe Ser Glu Gln Gly Glu
        115                 120                 125 gta ttc gac acg ccg cca gta gga cct cac atc ctg atg tat aaa agg     432
Val Phe Asp Thr Pro Pro Val Gly Pro His Ile Leu Met Tyr Lys Arg
    130                 135                 140 atc aca taa                                                          441
Ile Thr *
145

<210> SEQ ID NO 26
<211> LENGTH: 441
<212> TYPE: DNA
<213> ORGANISM: Artificial Sequence
<220> FEATURE:
<223> OTHER INFORMATION: Optimized GAT sequence  -- GAT4617R
<220> FEATURE:
<221> NAME/KEY: CDS
<222> LOCATION: (1)...(440)
<223> OTHER INFORMATION: encodes 23-6H10

<400> SEQUENCE: 26 atg ata gag gta aaa ccg att aac gca gag gat acc tat gaa cta agg      48
Met Ile Glu Val Lys Pro Ile Asn Ala Glu Asp Thr Tyr Glu Leu Arg
 1               5                  10                  15 cat aga gtc ctc aga cca aac cag ccg ata gaa gcg tgt atg ttt gaa      96
His Arg Val Leu Arg Pro Asn Gln Pro Ile Glu Ala Cys Met Phe Glu
            20                  25                  30 agc gat tta acg cgt ggt gca ttt cac cta ggc ggc ttc tac ggg ggc     144
Ser Asp Leu Thr Arg Gly Ala Phe His Leu Gly Gly Phe Tyr Gly Gly
```

```
              35                  40                  45
aaa ctg att tcc gtc gct tca ttc cac cag gcc gag cac acg gaa ctt      192
Lys Leu Ile Ser Val Ala Ser Phe His Gln Ala Glu His Thr Glu Leu
         50                  55                  60 caa ggc cag aaa cag tac cag ctt cga ggt gtg gct acc ttg gaa ggt      240
Gln Gly Gln Lys Gln Tyr Gln Leu Arg Gly Val Ala Thr Leu Glu Gly
 65                  70                  75                  80 tat cgt gag cag aag gcg ggt tcc agt cta gtt aaa cac gct gaa gaa      288
Tyr Arg Glu Gln Lys Ala Gly Ser Ser Leu Val Lys His Ala Glu Glu
                 85                  90                  95 att cta cgt aag agg ggg gcg gac cta ctt tgg tgt aat gcg agg aca      336
Ile Leu Arg Lys Arg Gly Ala Asp Leu Leu Trp Cys Asn Ala Arg Thr
            100                 105                 110 tcc gcc tca ggc tac tac aga aag tta ggc ttc agc gag cag ggg gag      384
Ser Ala Ser Gly Tyr Tyr Arg Lys Leu Gly Phe Ser Glu Gln Gly Glu
        115                 120                 125 gta ttc gac acg ccg cca gta gga cct cac atc ctg atg tat aaa agg      432
Val Phe Asp Thr Pro Pro Val Gly Pro His Ile Leu Met Tyr Lys Arg
    130                 135                 140 atc aca ta a                                                         441
Ile Thr
145

<210> SEQ ID NO 27
<211> LENGTH: 146
<212> TYPE: PRT
<213> ORGANISM: Artificial Sequence
<220> FEATURE:
<223> OTHER INFORMATION: Optimized GAT sequence  -- 23-6H10

<400> SEQUENCE: 27

Met Ile Glu Val Lys Pro Ile Asn Ala Glu Asp Thr Tyr Glu Leu Arg
 1               5                  10                  15

His Arg Val Leu Arg Pro Asn Gln Pro Ile Glu Ala Cys Met Phe Glu
                20                  25                  30

Ser Asp Leu Thr Arg Gly Ala Phe His Leu Gly Gly Phe Tyr Gly Gly
            35                  40                  45

Lys Leu Ile Ser Val Ala Ser Phe His Gln Ala Glu His Thr Glu Leu
         50                  55                  60

Gln Gly Gln Lys Gln Tyr Gln Leu Arg Gly Val Ala Thr Leu Glu Gly
 65                  70                  75                  80

Tyr Arg Glu Gln Lys Ala Gly Ser Ser Leu Val Lys His Ala Glu Glu
                 85                  90                  95

Ile Leu Arg Lys Arg Gly Ala Asp Leu Leu Trp Cys Asn Ala Arg Thr
            100                 105                 110

Ser Ala Ser Gly Tyr Tyr Arg Lys Leu Gly Phe Ser Glu Gln Gly Glu
        115                 120                 125

Val Phe Asp Thr Pro Pro Val Gly Pro His Ile Leu Met Tyr Lys Arg
    130                 135                 140

Ile Thr
145

<210> SEQ ID NO 28
<211> LENGTH: 441
<212> TYPE: DNA
<213> ORGANISM: Artificial Sequence
<220> FEATURE:
<223> OTHER INFORMATION: Optimized GAT sequence--GAT25-8H7
<220> FEATURE:
<221> NAME/KEY: CDS
```

-continued

```
<222> LOCATION: (1)...(441)

<400> SEQUENCE: 28 atg ata gag gta aaa ccg att aac gca gag gat acc tat gac cta agg       48
Met Ile Glu Val Lys Pro Ile Asn Ala Glu Asp Thr Tyr Asp Leu Arg
 1               5                  10                  15 cat aga gtc ctc aga cca aac cag ccg ata gaa gcg tgt atg ttt gaa       96
His Arg Val Leu Arg Pro Asn Gln Pro Ile Glu Ala Cys Met Phe Glu
             20                  25                  30 agc gat tta acg cgt agt gca ttt cac tta ggc ggc ttc tac ggg ggc      144
Ser Asp Leu Thr Arg Ser Ala Phe His Leu Gly Gly Phe Tyr Gly Gly
         35                  40                  45 aaa ctg att tcc gtc gct tca ttc cac cag gcc gag cac tcg gaa ctt      192
Lys Leu Ile Ser Val Ala Ser Phe His Gln Ala Glu His Ser Glu Leu
     50                  55                  60 caa ggc aag aaa cag tac cag ctt cga ggt gtg gct acc ttg gaa ggt      240
Gln Gly Lys Lys Gln Tyr Gln Leu Arg Gly Val Ala Thr Leu Glu Gly
 65                  70                  75                  80 tat cgt gag cag aag gcg ggt tcc agt cta gtt aaa cac gct gaa gaa      288
Tyr Arg Glu Gln Lys Ala Gly Ser Ser Leu Val Lys His Ala Glu Glu
                 85                  90                  95 att cta cgt aag agg ggg gcg gac atg att tgg tgt aat gcg cgg aca      336
Ile Leu Arg Lys Arg Gly Ala Asp Met Ile Trp Cys Asn Ala Arg Thr
            100                 105                 110 tct gcc tca ggc tac tac aga aag tta ggc ttc agc gag cag gga gag      384
Ser Ala Ser Gly Tyr Tyr Arg Lys Leu Gly Phe Ser Glu Gln Gly Glu
        115                 120                 125 gta ttc gac acg ccg cca gta gga cct cac atc ctg atg tat aaa agg      432
Val Phe Asp Thr Pro Pro Val Gly Pro His Ile Leu Met Tyr Lys Arg
    130                 135                 140 atc aca taa                                                          441
Ile Thr  *
145

<210> SEQ ID NO 29
<211> LENGTH: 441
<212> TYPE: DNA
<213> ORGANISM: Artificial Sequence
<220> FEATURE:
<223> OTHER INFORMATION: Optimized GAT sequence--GAT4618SR
<220> FEATURE:
<221> NAME/KEY: CDS
<222> LOCATION: (1)...(441)
<223> OTHER INFORMATION: encodes 25-8H7

<400> SEQUENCE: 29 atg ata gag gta aaa ccg att aac gca gag gat acc tat gac cta agg       48
Met Ile Glu Val Lys Pro Ile Asn Ala Glu Asp Thr Tyr Asp Leu Arg
 1               5                  10                  15 cat aga gtc ctc aga cca aac cag ccg ata gaa gcg tgt atg ttt gaa       96
His Arg Val Leu Arg Pro Asn Gln Pro Ile Glu Ala Cys Met Phe Glu
             20                  25                  30 agc gat tta acg cgt agt gca ttt cac tta ggc ggc ttc tac ggg ggc      144
Ser Asp Leu Thr Arg Ser Ala Phe His Leu Gly Gly Phe Tyr Gly Gly
         35                  40                  45 aaa ctg att tcc gtc gct tca ttc cac cag gcc gag cac tct gaa ctt      192
Lys Leu Ile Ser Val Ala Ser Phe His Gln Ala Glu His Ser Glu Leu
     50                  55                  60 caa ggc aag aaa cag tac cag ctt cga ggt gtg gct acc ttg gaa ggt      240
Gln Gly Lys Lys Gln Tyr Gln Leu Arg Gly Val Ala Thr Leu Glu Gly
 65                  70                  75                  80 tat cgt gag cag aag gcg ggt tcc agt cta gtt aaa cac gct gaa gaa      288
```

```
Tyr Arg Glu Gln Lys Ala Gly Ser Ser Leu Val Lys His Ala Glu Glu
            85                  90                  95 att cta cgt aag agg ggg gcg gac atg att tgg tgt aat gcg agg aca      336
Ile Leu Arg Lys Arg Gly Ala Asp Met Ile Trp Cys Asn Ala Arg Thr
            100                 105                 110 tct gcc tca ggc tac tac aga aag tta ggc ttc agc gag cag gga gag      384
Ser Ala Ser Gly Tyr Tyr Arg Lys Leu Gly Phe Ser Glu Gln Gly Glu
        115                 120                 125 gta ttc gac acg ccg cca gta gga cct cac atc ctg atg tat aaa agg      432
Val Phe Asp Thr Pro Pro Val Gly Pro His Ile Leu Met Tyr Lys Arg
    130                 135                 140 atc aca taa                                                          441
Ile Thr *
145

<210> SEQ ID NO 30
<211> LENGTH: 146
<212> TYPE: PRT
<213> ORGANISM: Artificial Sequence
<220> FEATURE:
<223> OTHER INFORMATION: Optimized GAT sequence -- encodes 25-8H7

<400> SEQUENCE: 30

Met Ile Glu Val Lys Pro Ile Asn Ala Glu Asp Thr Tyr Asp Leu Arg
1               5                   10                  15

His Arg Val Leu Arg Pro Asn Gln Pro Ile Glu Ala Cys Met Phe Glu
            20                  25                  30

Ser Asp Leu Thr Arg Ser Ala Phe His Leu Gly Gly Phe Gly Gly
        35                  40                  45

Lys Leu Ile Ser Val Ala Ser Phe His Gln Ala Glu His Ser Glu Leu
50                  55                  60

Gln Gly Lys Lys Gln Tyr Gln Leu Arg Gly Val Ala Thr Leu Glu Gly
65                  70                  75                  80

Tyr Arg Glu Gln Lys Ala Gly Ser Ser Leu Val Lys His Ala Glu Glu
            85                  90                  95

Ile Leu Arg Lys Arg Gly Ala Asp Met Ile Trp Cys Asn Ala Arg Thr
            100                 105                 110

Ser Ala Ser Gly Tyr Tyr Arg Lys Leu Gly Phe Ser Glu Gln Gly Glu
        115                 120                 125

Val Phe Asp Thr Pro Pro Val Gly Pro His Ile Leu Met Tyr Lys Arg
    130                 135                 140

Ile Thr
145

<210> SEQ ID NO 31
<211> LENGTH: 146
<212> TYPE: PRT
<213> ORGANISM: Artificial Sequence
<220> FEATURE:
<223> OTHER INFORMATION: Optimized GAT sequence --con alt e
<220> FEATURE:
<221> NAME/KEY: VARIANT
<222> LOCATION: 14
<223> OTHER INFORMATION: Asp or Glu
<220> FEATURE:
<221> NAME/KEY: VARIANT
<222> LOCATION: 33
<223> OTHER INFORMATION: Gly or Ser or Asn
<220> FEATURE:
<221> NAME/KEY: VARIANT
<222> LOCATION: 38
<223> OTHER INFORMATION: Gly or Ser
<220> FEATURE:
```

```
<221> NAME/KEY: VARIANT
<222> LOCATION: 46
<223> OTHER INFORMATION: His or Tyr
<220> FEATURE:
<221> NAME/KEY: VARIANT
<222> LOCATION: 51
<223> OTHER INFORMATION: Ile or Val
<220> FEATURE:
<221> NAME/KEY: VARIANT
<222> LOCATION: (58)...(58)
<223> OTHER INFORMATION: Gln or Arg
<220> FEATURE:
<221> NAME/KEY: VARIANT
<222> LOCATION: (60)...(60)
<223> OTHER INFORMATION: Glu or Gly
<220> FEATURE:
<221> NAME/KEY: VARIANT
<222> LOCATION: (62)...(62)
<223> OTHER INFORMATION: Ser or Thr
<220> FEATURE:
<221> NAME/KEY: VARIANT
<222> LOCATION: (67)...(67)
<223> OTHER INFORMATION: Gln or Lys or Arg
<220> FEATURE:
<221> NAME/KEY: VARIANT
<222> LOCATION: (88)...(88)
<223> OTHER INFORMATION: Ser or Thr
<220> FEATURE:
<221> NAME/KEY: VARIANT
<222> LOCATION: (103)...(103)
<223> OTHER INFORMATION: Ala or Val
<220> FEATURE:
<221> NAME/KEY: VARIANT
<222> LOCATION: (105)...(105)
<223> OTHER INFORMATION: Leu or Met
<220> FEATURE:
<221> NAME/KEY: VARIANT
<222> LOCATION: (106)...(106)
<223> OTHER INFORMATION: Ile or Leu
<220> FEATURE:
<221> NAME/KEY: VARIANT
<222> LOCATION: (119)...(119)
<223> OTHER INFORMATION: Arg or Lys
<220> FEATURE:
<221> NAME/KEY: VARIANT
<222> LOCATION: (139)...(139)
<223> OTHER INFORMATION: Ile or Val

<400> SEQUENCE: 31

Met Ile Glu Val Lys Pro Ile Asn Ala Glu Asp Thr Tyr Xaa Leu Arg
 1               5                  10                  15

His Arg Val Leu Arg Pro Asn Gln Pro Ile Glu Ala Cys Met Phe Asp
                20                  25                  30

Xaa Asp Leu Thr Arg Xaa Ala Phe His Leu Gly Gly Phe Xaa Gly Gly
            35                  40                  45

Lys Leu Xaa Ser Val Ala Ser Phe His Xaa Ala Xaa His Xaa Glu Leu
    50                  55                  60

Gln Gly Xaa Lys Gln Tyr Gln Leu Arg Gly Val Ala Thr Leu Glu Gly
65                  70                  75                  80

Tyr Arg Glu Gln Lys Ala Gly Xaa Ser Leu Val Lys His Ala Glu Glu
                85                  90                  95

Ile Leu Arg Lys Arg Gly Xaa Asp Xaa Xaa Trp Cys Asn Ala Arg Thr
            100                 105                 110

Ser Ala Ser Gly Tyr Tyr Xaa Lys Leu Gly Phe Ser Glu Gln Gly Glu
        115                 120                 125

Val Phe Asp Thr Pro Pro Val Gly Pro His Xaa Leu Met Tyr Lys Arg
    130                 135                 140

Ile Thr
145
```

<210> SEQ ID NO 32
<211> LENGTH: 441
<212> TYPE: DNA
<213> ORGANISM: Artificial Sequence
<220> FEATURE:
<223> OTHER INFORMATION: Optimized GAT sequence--GAT4618VSR
<220> FEATURE:
<221> NAME/KEY: CDS
<222> LOCATION: (1)...(441)
<223> OTHER INFORMATION: encodes 25-8H7

<400> SEQUENCE: 32

| | | | | | | | | | | | | | | | | |
|---|---|---|---|---|---|---|---|---|---|---|---|---|---|---|---|---|
| atg | ata | gag | gtg | aaa | ccg | att | aac | gca | gag | gat | acc | tat | gac | cta | agg | 48 |
| Met | Ile | Glu | Val | Lys | Pro | Ile | Asn | Ala | Glu | Asp | Thr | Tyr | Asp | Leu | Arg | |
| 1 | | | | 5 | | | | | 10 | | | | | 15 | | |

| cat | aga | gtc | ctc | aga | cca | aac | cag | ccg | ata | gaa | gcg | tgt | atg | ttt | gaa | 96 |
|---|---|---|---|---|---|---|---|---|---|---|---|---|---|---|---|---|
| His | Arg | Val | Leu | Arg | Pro | Asn | Gln | Pro | Ile | Glu | Ala | Cys | Met | Phe | Glu | |
| | | | 20 | | | | | 25 | | | | | 30 | | | |

| agc | gat | tta | acg | cgt | agt | gca | ttt | cac | tta | ggc | ggc | ttc | tac | ggg | ggc | 144 |
|---|---|---|---|---|---|---|---|---|---|---|---|---|---|---|---|---|
| Ser | Asp | Leu | Thr | Arg | Ser | Ala | Phe | His | Leu | Gly | Gly | Phe | Tyr | Gly | Gly | |
| | | 35 | | | | | 40 | | | | | 45 | | | | |

| aaa | ctg | att | tcc | gtc | gct | tca | ttc | cac | cag | gcc | gag | cac | tct | gaa | ctt | 192 |
|---|---|---|---|---|---|---|---|---|---|---|---|---|---|---|---|---|
| Lys | Leu | Ile | Ser | Val | Ala | Ser | Phe | His | Gln | Ala | Glu | His | Ser | Glu | Leu | |
| | 50 | | | | | 55 | | | | | 60 | | | | | |

| caa | ggc | aag | aaa | cag | tac | cag | ctt | cga | ggt | gtg | gct | acc | ttg | gaa | ggt | 240 |
|---|---|---|---|---|---|---|---|---|---|---|---|---|---|---|---|---|
| Gln | Gly | Lys | Lys | Gln | Tyr | Gln | Leu | Arg | Gly | Val | Ala | Thr | Leu | Glu | Gly | |
| 65 | | | | | 70 | | | | | 75 | | | | | 80 | |

| tat | cgt | gag | cag | aag | gcg | ggt | tcc | agt | cta | gtt | aaa | cac | gct | gaa | gaa | 288 |
|---|---|---|---|---|---|---|---|---|---|---|---|---|---|---|---|---|
| Tyr | Arg | Glu | Gln | Lys | Ala | Gly | Ser | Ser | Leu | Val | Lys | His | Ala | Glu | Glu | |
| | | | | 85 | | | | | 90 | | | | | 95 | | |

| att | cta | cgt | aag | agg | ggg | gcg | gac | atg | att | tgg | tgt | aat | gcg | agg | aca | 336 |
|---|---|---|---|---|---|---|---|---|---|---|---|---|---|---|---|---|
| Ile | Leu | Arg | Lys | Arg | Gly | Ala | Asp | Met | Ile | Trp | Cys | Asn | Ala | Arg | Thr | |
| | | | 100 | | | | | 105 | | | | | 110 | | | |

| tct | gcc | tca | ggc | tac | tac | aga | aag | tta | ggc | ttc | agc | gag | cag | gga | gag | 384 |
|---|---|---|---|---|---|---|---|---|---|---|---|---|---|---|---|---|
| Ser | Ala | Ser | Gly | Tyr | Tyr | Arg | Lys | Leu | Gly | Phe | Ser | Glu | Gln | Gly | Glu | |
| | | 115 | | | | | 120 | | | | | 125 | | | | |

| gta | ttc | gac | acg | ccg | cca | gta | gga | cct | cac | atc | ctg | atg | tat | aaa | agg | 432 |
|---|---|---|---|---|---|---|---|---|---|---|---|---|---|---|---|---|
| Val | Phe | Asp | Thr | Pro | Pro | Val | Gly | Pro | His | Ile | Leu | Met | Tyr | Lys | Arg | |
| | 130 | | | | | 135 | | | | | 140 | | | | | |

| atc | aca | taa | | | | | | | | | | | | | | 441 |
|---|---|---|---|---|---|---|---|---|---|---|---|---|---|---|---|---|
| Ile | Thr | * | | | | | | | | | | | | | | |
| 145 | | | | | | | | | | | | | | | | |

<210> SEQ ID NO 33
<211> LENGTH: 441
<212> TYPE: DNA
<213> ORGANISM: Artificial Sequence
<220> FEATURE:
<223> OTHER INFORMATION: Optimized GAT sequence
<220> FEATURE:
<221> NAME/KEY: CDS
<222> LOCATION: (1)...(441)
<223> OTHER INFORMATION: GAT25-19C8

<400> SEQUENCE: 33

| atg | ata | gag | gta | aaa | ccg | att | aac | gca | gaa | gat | acc | tat | gac | cta | agg | 48 |
|---|---|---|---|---|---|---|---|---|---|---|---|---|---|---|---|---|
| Met | Ile | Glu | Val | Lys | Pro | Ile | Asn | Ala | Glu | Asp | Thr | Tyr | Asp | Leu | Arg | |
| 1 | | | | 5 | | | | | 10 | | | | | 15 | | |

| cat | aga | gtc | ctc | aga | cca | aac | cag | ccg | ata | gaa | gcg | tgt | atg | ttt | gaa | 96 |
|---|---|---|---|---|---|---|---|---|---|---|---|---|---|---|---|---|
| His | Arg | Val | Leu | Arg | Pro | Asn | Gln | Pro | Ile | Glu | Ala | Cys | Met | Phe | Glu | |
| | | | 20 | | | | | 25 | | | | | 30 | | | |

| agc | gat | tta | acg | cgt | agt | gca | ttt | cac | tta | ggc | ggc | ttc | tac | ggg | ggc | 144 |
|---|---|---|---|---|---|---|---|---|---|---|---|---|---|---|---|---|
| Ser | Asp | Leu | Thr | Arg | Ser | Ala | Phe | His | Leu | Gly | Gly | Phe | Tyr | Gly | Gly | |

-continued

```
                    35                  40                  45
aaa ctg att tcc gtc gct tca ttc cac cag gcc gag cac tcg gaa ctt        192
Lys Leu Ile Ser Val Ala Ser Phe His Gln Ala Glu His Ser Glu Leu
         50                  55                  60 caa ggc cag aaa cag tat cag ctt cga ggc gtg gct acc ttg gaa ggt        240
Gln Gly Gln Lys Gln Tyr Gln Leu Arg Gly Val Ala Thr Leu Glu Gly
 65                  70                  75                  80 tat cgt gag cag aag gcg ggt tcc agt cta gtc aaa cac gct gaa gaa        288
Tyr Arg Glu Gln Lys Ala Gly Ser Ser Leu Val Lys His Ala Glu Glu
                 85                  90                  95 att cta cgt aag agg ggg gtg gac cta ctt tgg tgt aat gcg cgg aca        336
Ile Leu Arg Lys Arg Gly Val Asp Leu Leu Trp Cys Asn Ala Arg Thr
            100                 105                 110 tcc gcc tca ggc tac tac aga aag tta ggc ttc agc gag cag gga gag        384
Ser Ala Ser Gly Tyr Tyr Arg Lys Leu Gly Phe Ser Glu Gln Gly Glu
        115                 120                 125 gta ttc gac acg ccg cca gta ggt cct cac atc ctg atg tat aaa agg        432
Val Phe Asp Thr Pro Pro Val Gly Pro His Ile Leu Met Tyr Lys Arg
    130                 135                 140 atc aca taa                                                            441
Ile Thr *
145

<210> SEQ ID NO 34
<211> LENGTH: 441
<212> TYPE: DNA
<213> ORGANISM: Artificial Sequence
<220> FEATURE:
<223> OTHER INFORMATION: Optimized GAT sequence--GAT4619SR
<220> FEATURE:
<221> NAME/KEY: CDS
<222> LOCATION: (1)...(441)
<223> OTHER INFORMATION: encodes 25-19C8

<400> SEQUENCE: 34 atg ata gag gta aaa ccg att aac gca gaa gat acc tat gac cta agg         48
Met Ile Glu Val Lys Pro Ile Asn Ala Glu Asp Thr Tyr Asp Leu Arg
  1               5                  10                  15 cat aga gtc ctc aga cca aac cag ccg ata gaa gcg tgt atg ttt gaa         96
His Arg Val Leu Arg Pro Asn Gln Pro Ile Glu Ala Cys Met Phe Glu
             20                  25                  30 agc gat tta acg cgt agt gca ttt cac tta ggc ggc ttc tac ggg ggc        144
Ser Asp Leu Thr Arg Ser Ala Phe His Leu Gly Gly Phe Tyr Gly Gly
         35                  40                  45 aaa ctg att tcc gtc gct tca ttc cac cag gcc gag cac tct gaa ctt        192
Lys Leu Ile Ser Val Ala Ser Phe His Gln Ala Glu His Ser Glu Leu
     50                  55                  60 caa ggc cag aaa cag tat cag ctt cga ggc gtg gct acc ttg gaa ggt        240
Gln Gly Gln Lys Gln Tyr Gln Leu Arg Gly Val Ala Thr Leu Glu Gly
 65                  70                  75                  80 tat cgt gag cag aag gcg ggt tcc agt cta gtc aaa cac gct gaa gaa        288
Tyr Arg Glu Gln Lys Ala Gly Ser Ser Leu Val Lys His Ala Glu Glu
                 85                  90                  95 att cta cgt aag agg ggg gtg gac cta ctt tgg tgt aat gcg agg aca        336
Ile Leu Arg Lys Arg Gly Val Asp Leu Leu Trp Cys Asn Ala Arg Thr
            100                 105                 110 tcc gcc tca ggc tac tac aga aag tta ggc ttc agc gag cag gga gag        384
Ser Ala Ser Gly Tyr Tyr Arg Lys Leu Gly Phe Ser Glu Gln Gly Glu
        115                 120                 125 gta ttc gac acg ccg cca gta ggt cct cac atc ctg atg tat aaa agg        432
Val Phe Asp Thr Pro Pro Val Gly Pro His Ile Leu Met Tyr Lys Arg
    130                 135                 140
```

```
atc aca taa                                                           441
Ile Thr *
145

<210> SEQ ID NO 35
<211> LENGTH: 146
<212> TYPE: PRT
<213> ORGANISM: Artificial Sequence
<220> FEATURE:
<223> OTHER INFORMATION: Optimized GAT sequence encoding 25-19C8

<400> SEQUENCE: 35

Met Ile Glu Val Lys Pro Ile Asn Ala Glu Asp Thr Tyr Asp Leu Arg
 1               5                  10                  15

His Arg Val Leu Arg Pro Asn Gln Pro Ile Glu Ala Cys Met Phe Glu
            20                  25                  30

Ser Asp Leu Thr Arg Ser Ala Phe His Leu Gly Gly Phe Tyr Gly Gly
        35                  40                  45

Lys Leu Ile Ser Val Ala Ser Phe His Gln Ala Glu His Ser Glu Leu
    50                  55                  60

Gln Gly Gln Lys Gln Tyr Gln Leu Arg Gly Val Ala Thr Leu Glu Gly
65                  70                  75                  80

Tyr Arg Glu Gln Lys Ala Gly Ser Ser Leu Val Lys His Ala Glu Glu
                85                  90                  95

Ile Leu Arg Lys Arg Gly Val Asp Leu Leu Trp Cys Asn Ala Arg Thr
            100                 105                 110

Ser Ala Ser Gly Tyr Tyr Arg Lys Leu Gly Phe Ser Glu Gln Gly Glu
        115                 120                 125

Val Phe Asp Thr Pro Pro Val Gly Pro His Ile Leu Met Tyr Lys Arg
    130                 135                 140

Ile Thr
145

<210> SEQ ID NO 36
<211> LENGTH: 441
<212> TYPE: DNA
<213> ORGANISM: Artificial Sequence
<220> FEATURE:
<223> OTHER INFORMATION: Optimized GAT sequence--GAT4619VSR
<220> FEATURE:
<221> NAME/KEY: CDS
<222> LOCATION: (1)...(441)
<223> OTHER INFORMATION: encodes 25-19C8

<400> SEQUENCE: 36 atg ata gag gtg aaa ccg att aac gca gaa gat acc tat gac cta agg    48
Met Ile Glu Val Lys Pro Ile Asn Ala Glu Asp Thr Tyr Asp Leu Arg
 1               5                  10                  15 cat aga gtc ctc aga cca aac cag ccg ata gaa gcg tgt atg ttt gaa    96
His Arg Val Leu Arg Pro Asn Gln Pro Ile Glu Ala Cys Met Phe Glu
            20                  25                  30 agc gat tta acg cgt agt gca ttt cac tta ggc ggc ttc tac ggg ggc   144
Ser Asp Leu Thr Arg Ser Ala Phe His Leu Gly Gly Phe Tyr Gly Gly
        35                  40                  45 aaa ctg att tcc gtc gct tca ttc cac cag gcc gag cac tct gaa ctt   192
Lys Leu Ile Ser Val Ala Ser Phe His Gln Ala Glu His Ser Glu Leu
    50                  55                  60 caa ggc cag aaa cag tat cag ctt cga ggc gtg gct acc ttg gaa ggt   240
Gln Gly Gln Lys Gln Tyr Gln Leu Arg Gly Val Ala Thr Leu Glu Gly
65                  70                  75                  80
```

```
tat cgt gag cag aag gcg ggt tcc agt cta gtc aaa cac gct gaa gaa    288
Tyr Arg Glu Gln Lys Ala Gly Ser Ser Leu Val Lys His Ala Glu Glu
            85                  90                  95 att cta cgt aag agg ggg gtg gac cta ctt tgg tgt aat gcg agg aca    336
Ile Leu Arg Lys Arg Gly Val Asp Leu Leu Trp Cys Asn Ala Arg Thr
        100                 105                 110 tcc gcc tca ggc tac tac aga aag tta ggc ttc agc gag cag gga gag    384
Ser Ala Ser Gly Tyr Tyr Arg Lys Leu Gly Phe Ser Glu Gln Gly Glu
    115                 120                 125 gta ttc gac acg ccg cca gta ggt cct cac atc ctg atg tat aaa agg    432
Val Phe Asp Thr Pro Pro Val Gly Pro His Ile Leu Met Tyr Lys Arg
130                 135                 140 atc aca taa                                                         441
Ile Thr *
145

<210> SEQ ID NO 37
<211> LENGTH: 441
<212> TYPE: DNA
<213> ORGANISM: Artificial Sequence
<220> FEATURE:
<223> OTHER INFORMATION: Optimized GAT sequence--D_S00397832_GAT22-15B4
<220> FEATURE:
<221> NAME/KEY: CDS
<222> LOCATION: (1)...(441)

<400> SEQUENCE: 37 atg ata gag gta aaa ccg att aac gca gaa gat acc tat gac cta agg    48
Met Ile Glu Val Lys Pro Ile Asn Ala Glu Asp Thr Tyr Asp Leu Arg
1               5                   10                  15 cat aga gtc ctc aga cca aac cag ccg ata gaa gcg tgt atg ttt gat    96
His Arg Val Leu Arg Pro Asn Gln Pro Ile Glu Ala Cys Met Phe Asp
            20                  25                  30 agc gat tta atg cgt agt gca ttt cac tta ggc ggc ttc tac ggg ggc    144
Ser Asp Leu Met Arg Ser Ala Phe His Leu Gly Gly Phe Tyr Gly Gly
        35                  40                  45 aaa ctg att tcc gtc gct tca ttc cac cag gcc gag cac acg gaa ctt    192
Lys Leu Ile Ser Val Ala Ser Phe His Gln Ala Glu His Thr Glu Leu
    50                  55                  60 caa ggc cag aaa cag tac cag ctt cga ggt gtg gct acc ttg gaa ggt    240
Gln Gly Gln Lys Gln Tyr Gln Leu Arg Gly Val Ala Thr Leu Glu Gly
65                  70                  75                  80 tat cgt gag cag aag gcg ggt tcc agt cta gtt aaa cac gct gaa gaa    288
Tyr Arg Glu Gln Lys Ala Gly Ser Ser Leu Val Lys His Ala Glu Glu
            85                  90                  95 att cta cgt aag agg ggg gtg gac cta ctt tgg tgt aat gcg cgg aca    336
Ile Leu Arg Lys Arg Gly Val Asp Leu Leu Trp Cys Asn Ala Arg Thr
        100                 105                 110 tcc gcc tca ggc tac tac aaa aag tta ggc ttc agc gag cag gga gag    384
Ser Ala Ser Gly Tyr Tyr Lys Lys Leu Gly Phe Ser Glu Gln Gly Glu
    115                 120                 125 gta ttc gac acg ccg cca gta gga cct cac atc ctg atg tat aaa agg    432
Val Phe Asp Thr Pro Pro Val Gly Pro His Ile Leu Met Tyr Lys Arg
130                 135                 140 atc aca taa                                                         441
Ile Thr *
145

<210> SEQ ID NO 38
<211> LENGTH: 452
<212> TYPE: DNA
<213> ORGANISM: Artificial Sequence
<220> FEATURE:
```

```
<223> OTHER INFORMATION: Optimized GAT sequence--GAT4611A
<220> FEATURE:
<221> NAME/KEY: CDS
<222> LOCATION: (1)...(441)
<223> OTHER INFORMATION: encodes 22-15B4 M1MA

<400> SEQUENCE: 38 atg gcg ata gag gta aaa ccg att aac gca gaa gat acc tat gac cta      48
Met Ala Ile Glu Val Lys Pro Ile Asn Ala Glu Asp Thr Tyr Asp Leu
 1               5                  10                  15 agg cat aga gtc ctc aga cca aac cag ccg ata gaa gcg tgt atg ttt      96
Arg His Arg Val Leu Arg Pro Asn Gln Pro Ile Glu Ala Cys Met Phe
             20                  25                  30 gat agc gat tta atg cgt agt gca ttt cac tta ggc ggc ttc tac ggg     144
Asp Ser Asp Leu Met Arg Ser Ala Phe His Leu Gly Gly Phe Tyr Gly
         35                  40                  45 ggc aaa ctg att tcc gtc gct tca ttc cac cag gcc gag cac acg gaa     192
Gly Lys Leu Ile Ser Val Ala Ser Phe His Gln Ala Glu His Thr Glu
     50                  55                  60 ctt caa ggc cag aaa cag tac cag ctt cga ggt gtg gct acc ttg gaa     240
Leu Gln Gly Gln Lys Gln Tyr Gln Leu Arg Gly Val Ala Thr Leu Glu
 65                  70                  75                  80 ggt tat cgt gag cag aag gcg ggt tcc agt cta gtt aaa cac gct gaa     288
Gly Tyr Arg Glu Gln Lys Ala Gly Ser Ser Leu Val Lys His Ala Glu
                 85                  90                  95 gaa att cta cgt aag agg ggg gtg gac cta ctt tgg tgt aat gcg cgg     336
Glu Ile Leu Arg Lys Arg Gly Val Asp Leu Leu Trp Cys Asn Ala Arg
            100                 105                 110 aca tcc gcc tca ggc tac tac aaa aag tta ggc ttc agc gag cag gga     384
Thr Ser Ala Ser Gly Tyr Tyr Lys Lys Leu Gly Phe Ser Glu Gln Gly
        115                 120                 125 gag gta ttc gac acg ccg cca gta gga cct cac atc ctg atg tat aaa     432
Glu Val Phe Asp Thr Pro Pro Val Gly Pro His Ile Leu Met Tyr Lys
    130                 135                 140 agg atc aca taaggcgcgc c                                            452
Arg Ile Thr
145

<210> SEQ ID NO 39
<211> LENGTH: 147
<212> TYPE: PRT
<213> ORGANISM: Artificial Sequence
<220> FEATURE:
<223> OTHER INFORMATION: Optimized GAT sequence--22-15B4 M1MA

<400> SEQUENCE: 39

Met Ala Ile Glu Val Lys Pro Ile Asn Ala Glu Asp Thr Tyr Asp Leu
 1               5                  10                  15

Arg His Arg Val Leu Arg Pro Asn Gln Pro Ile Glu Ala Cys Met Phe
             20                  25                  30

Asp Ser Asp Leu Met Arg Ser Ala Phe His Leu Gly Gly Phe Tyr Gly
         35                  40                  45

Gly Lys Leu Ile Ser Val Ala Ser Phe His Gln Ala Glu His Thr Glu
     50                  55                  60

Leu Gln Gly Gln Lys Gln Tyr Gln Leu Arg Gly Val Ala Thr Leu Glu
 65                  70                  75                  80

Gly Tyr Arg Glu Gln Lys Ala Gly Ser Ser Leu Val Lys His Ala Glu
                 85                  90                  95

Glu Ile Leu Arg Lys Arg Gly Val Asp Leu Leu Trp Cys Asn Ala Arg
            100                 105                 110
```

```
Thr Ser Ala Ser Gly Tyr Tyr Lys Lys Leu Gly Phe Ser Glu Gln Gly
        115                 120                 125

Glu Val Phe Asp Thr Pro Pro Val Gly Pro His Ile Leu Met Tyr Lys
    130                 135                 140

Arg Ile Thr
145

<210> SEQ ID NO 40
<211> LENGTH: 441
<212> TYPE: DNA
<213> ORGANISM: Artificial Sequence
<220> FEATURE:
<223> OTHER INFORMATION: Optimized GAT sequence
<220> FEATURE:
<221> NAME/KEY: CDS
<222> LOCATION: (1)...(441)
<223> OTHER INFORMATION: D_S00397832_GAT22-15B4

<400> SEQUENCE: 40 atg ata gag gta aaa ccg att aac gca gaa gat acc tat gac cta agg      48
Met Ile Glu Val Lys Pro Ile Asn Ala Glu Asp Thr Tyr Asp Leu Arg
 1               5                  10                  15 cat aga gtc ctc aga cca aac cag ccg ata gaa gcg tgt atg ttt gat      96
His Arg Val Leu Arg Pro Asn Gln Pro Ile Glu Ala Cys Met Phe Asp
                20                  25                  30 agc gat tta atg cgt agt gca ttt cac tta ggc ggc ttc tac ggg ggc     144
Ser Asp Leu Met Arg Ser Ala Phe His Leu Gly Gly Phe Tyr Gly Gly
            35                  40                  45 aaa ctg att tcc gtc gct tca ttc cac cag gcc gag cac acg gaa ctt     192
Lys Leu Ile Ser Val Ala Ser Phe His Gln Ala Glu His Thr Glu Leu
 50                  55                  60 caa ggc cag aaa cag tac cag ctt cga ggt gtg gct acc ttg gaa ggt     240
Gln Gly Gln Lys Gln Tyr Gln Leu Arg Gly Val Ala Thr Leu Glu Gly
 65                  70                  75                  80 tat cgt gag cag aag gcg ggt tcc agt cta gtt aaa cac gct gaa gaa     288
Tyr Arg Glu Gln Lys Ala Gly Ser Ser Leu Val Lys His Ala Glu Glu
                85                  90                  95 att cta cgt aag agg ggg gtg gac cta ctt tgg tgt aat gcg cgg aca     336
Ile Leu Arg Lys Arg Gly Val Asp Leu Leu Trp Cys Asn Ala Arg Thr
            100                 105                 110 tcc gcc tca ggc tac tac aaa aag tta ggc ttc agc gag cag gga gag     384
Ser Ala Ser Gly Tyr Tyr Lys Lys Leu Gly Phe Ser Glu Gln Gly Glu
        115                 120                 125 gta ttc gac acg ccg cca gta gga cct cac atc ctg atg tat aaa agg     432
Val Phe Asp Thr Pro Pro Val Gly Pro His Ile Leu Met Tyr Lys Arg
    130                 135                 140 atc aca taa                                                          441
Ile Thr  *
145

<210> SEQ ID NO 41
<211> LENGTH: 455
<212> TYPE: DNA
<213> ORGANISM: Artificial Sequence
<220> FEATURE:
<223> OTHER INFORMATION: Optimized GAT sequence--GAT4611AA
<220> FEATURE:
<221> NAME/KEY: CDS
<222> LOCATION: (1)...(447)
<223> OTHER INFORMATION: encodes 22-15B4 M1MAA

<400> SEQUENCE: 41 atg gcg gcc ata gag gta aaa ccg att aac gca gaa gat acc tat gac      48
Met Ala Ala Ile Glu Val Lys Pro Ile Asn Ala Glu Asp Thr Tyr Asp
```

```
                1               5              10              15 cta agg cat aga gtc ctc aga cca aac cag ccg ata gaa gcg tgt atg          96
Leu Arg His Arg Val Leu Arg Pro Asn Gln Pro Ile Glu Ala Cys Met
            20                  25                  30 ttt gat agc gat tta atg cgt agt gca ttt cac tta ggc ggc ttc tac         144
Phe Asp Ser Asp Leu Met Arg Ser Ala Phe His Leu Gly Gly Phe Tyr
        35                  40                  45 ggg ggc aaa ctg att tcc gtc gct tca ttc cac cag gcc gag cac acg         192
Gly Gly Lys Leu Ile Ser Val Ala Ser Phe His Gln Ala Glu His Thr
    50                  55                  60 gaa ctt caa ggc cag aaa cag tac cag ctt cga ggt gtg gct acc ttg         240
Glu Leu Gln Gly Gln Lys Gln Tyr Gln Leu Arg Gly Val Ala Thr Leu
65                  70                  75                  80 gaa ggt tat cgt gag cag aag gcg ggt tcc agt cta gtt aaa cac gct         288
Glu Gly Tyr Arg Glu Gln Lys Ala Gly Ser Ser Leu Val Lys His Ala
                85                  90                  95 gaa gaa att cta cgt aag agg ggg gtg gac cta ctt tgg tgt aat gcg         336
Glu Glu Ile Leu Arg Lys Arg Gly Val Asp Leu Leu Trp Cys Asn Ala
            100                 105                 110 cgg aca tcc gcc tca ggc tac tac aaa aag tta ggc ttc agc gag cag         384
Arg Thr Ser Ala Ser Gly Tyr Tyr Lys Lys Leu Gly Phe Ser Glu Gln
        115                 120                 125 gga gag gta ttc gac acg ccg cca gta gga cct cac atc ctg atg tat         432
Gly Glu Val Phe Asp Thr Pro Pro Val Gly Pro His Ile Leu Met Tyr
    130                 135                 140 aaa agg atc aca taa ggcgcgcc                                            455
Lys Arg Ile Thr *
145

<210> SEQ ID NO 42
<211> LENGTH: 148
<212> TYPE: PRT
<213> ORGANISM: Artificial Sequence
<220> FEATURE:
<223> OTHER INFORMATION: Optimized GAT sequence--22-15B4 M1MAA

<400> SEQUENCE: 42

Met Ala Ala Ile Glu Val Lys Pro Ile Asn Ala Glu Asp Thr Tyr Asp
 1               5                  10                  15

Leu Arg His Arg Val Leu Arg Pro Asn Gln Pro Ile Glu Ala Cys Met
            20                  25                  30

Phe Asp Ser Asp Leu Met Arg Ser Ala Phe His Leu Gly Gly Phe Tyr
        35                  40                  45

Gly Gly Lys Leu Ile Ser Val Ala Ser Phe His Gln Ala Glu His Thr
    50                  55                  60

Glu Leu Gln Gly Gln Lys Gln Tyr Gln Leu Arg Gly Val Ala Thr Leu
65                  70                  75                  80

Glu Gly Tyr Arg Glu Gln Lys Ala Gly Ser Ser Leu Val Lys His Ala
                85                  90                  95

Glu Glu Ile Leu Arg Lys Arg Gly Val Asp Leu Leu Trp Cys Asn Ala
            100                 105                 110

Arg Thr Ser Ala Ser Gly Tyr Tyr Lys Lys Leu Gly Phe Ser Glu Gln
        115                 120                 125

Gly Glu Val Phe Asp Thr Pro Pro Val Gly Pro His Ile Leu Met Tyr
    130                 135                 140

Lys Arg Ile Thr
145
```

<210> SEQ ID NO 43
<211> LENGTH: 444
<212> TYPE: DNA
<213> ORGANISM: Artificial Sequence
<220> FEATURE:
<223> OTHER INFORMATION: Optimized GAT sequence-- GAT4620
<220> FEATURE:
<221> NAME/KEY: CDS
<222> LOCATION: (1)...(444)
<223> OTHER INFORMATION: encodes 25-8H7 M1MA

<400> SEQUENCE: 43

```
atg gct att gag gtt aaa cct att aac gca gag gat acc tat gac cta      48
Met Ala Ile Glu Val Lys Pro Ile Asn Ala Glu Asp Thr Tyr Asp Leu
 1               5                  10                  15 agg cat aga gtc ctc aga cca aac cag ccg ata gaa gcg tgt atg ttt      96
Arg His Arg Val Leu Arg Pro Asn Gln Pro Ile Glu Ala Cys Met Phe
             20                  25                  30 gaa agc gat tta acg cgt agt gca ttt cac tta ggc ggc ttc tac ggg     144
Glu Ser Asp Leu Thr Arg Ser Ala Phe His Leu Gly Gly Phe Tyr Gly
         35                  40                  45 ggc aaa ctg att tcc gtc gct tca ttc cac cag gcc gag cac tct gaa     192
Gly Lys Leu Ile Ser Val Ala Ser Phe His Gln Ala Glu His Ser Glu
     50                  55                  60 ctt caa ggc aag aaa cag tac cag ctt cga ggt gtg gct acc ttg gaa     240
Leu Gln Gly Lys Lys Gln Tyr Gln Leu Arg Gly Val Ala Thr Leu Glu
 65                  70                  75                  80 ggt tat cgt gag cag aag gcg ggt tcc agt cta gtt aaa cac gct gaa     288
Gly Tyr Arg Glu Gln Lys Ala Gly Ser Ser Leu Val Lys His Ala Glu
                 85                  90                  95 gaa att cta cgt aag agg ggg gcg gac atg att tgg tgt aat gcg agg     336
Glu Ile Leu Arg Lys Arg Gly Ala Asp Met Ile Trp Cys Asn Ala Arg
            100                 105                 110 aca tct gcc tca ggc tac tac aga aag tta ggc ttc agc gag cag gga     384
Thr Ser Ala Ser Gly Tyr Tyr Arg Lys Leu Gly Phe Ser Glu Gln Gly
        115                 120                 125 gag gta ttc gac acg ccg cca gta gga cct cac atc ctg atg tat aaa     432
Glu Val Phe Asp Thr Pro Pro Val Gly Pro His Ile Leu Met Tyr Lys
    130                 135                 140 agg atc aca taa                                                     444
Arg Ile Thr *
145
```

<210> SEQ ID NO 44
<211> LENGTH: 444
<212> TYPE: DNA
<213> ORGANISM: Artificial Sequence
<220> FEATURE:
<223> OTHER INFORMATION: Optimized GAT sequence -- GAT4618A
<220> FEATURE:
<221> NAME/KEY: CDS
<222> LOCATION: (1)...(444)
<223> OTHER INFORMATION: encodes 25-8H7 M1MA

<400> SEQUENCE: 44

```
atg gcg ata gag gta aaa ccg att aac gca gag gat acc tat gac cta      48
Met Ala Ile Glu Val Lys Pro Ile Asn Ala Glu Asp Thr Tyr Asp Leu
 1               5                  10                  15 agg cat aga gtc ctc aga cca aac cag ccg ata gaa gcg tgt atg ttt      96
Arg His Arg Val Leu Arg Pro Asn Gln Pro Ile Glu Ala Cys Met Phe
             20                  25                  30 gaa agc gat tta acg cgt agt gca ttt cac tta ggc ggc ttc tac ggg     144
Glu Ser Asp Leu Thr Arg Ser Ala Phe His Leu Gly Gly Phe Tyr Gly
         35                  40                  45
```

```
ggc aaa ctg att tcc gtc gct tca ttc cac cag gcc gag cac tcg gaa      192
Gly Lys Leu Ile Ser Val Ala Ser Phe His Gln Ala Glu His Ser Glu
     50                  55                  60 ctt caa ggc aag aaa cag tac cag ctt cga ggt gtg gct acc ttg gaa      240
Leu Gln Gly Lys Lys Gln Tyr Gln Leu Arg Gly Val Ala Thr Leu Glu
 65                  70                  75                  80 ggt tat cgt gag cag aag gcg ggt tcc agt cta gtt aaa cac gct gaa      288
Gly Tyr Arg Glu Gln Lys Ala Gly Ser Ser Leu Val Lys His Ala Glu
             85                  90                  95 gaa att cta cgt aag agg ggg gcg gac atg att tgg tgt aat gcg cgg      336
Glu Ile Leu Arg Lys Arg Gly Ala Asp Met Ile Trp Cys Asn Ala Arg
            100                 105                 110 aca tct gcc tca ggc tac tac aga aag tta ggc ttc agc gag cag gga      384
Thr Ser Ala Ser Gly Tyr Tyr Arg Lys Leu Gly Phe Ser Glu Gln Gly
        115                 120                 125 gag gta ttc gac acg ccg cca gta gga cct cac atc ctg atg tat aaa      432
Glu Val Phe Asp Thr Pro Pro Val Gly Pro His Ile Leu Met Tyr Lys
    130                 135                 140 agg atc aca taa                                                       444
Arg Ile Thr  *
145
```

<210> SEQ ID NO 45
<211> LENGTH: 147
<212> TYPE: PRT
<213> ORGANISM: Artificial Sequence
<220> FEATURE:
<223> OTHER INFORMATION: Optimized GAT sequence--25-8H7 M1MA

<400> SEQUENCE: 45

```
Met Ala Ile Glu Val Lys Pro Ile Asn Ala Glu Asp Thr Tyr Asp Leu
 1               5                  10                  15

Arg His Arg Val Leu Arg Pro Asn Gln Pro Ile Glu Ala Cys Met Phe
                20                  25                  30

Glu Ser Asp Leu Thr Arg Ser Ala Phe His Leu Gly Phe Tyr Gly
            35                  40                  45

Gly Lys Leu Ile Ser Val Ala Ser Phe His Gln Ala Glu His Ser Glu
     50                  55                  60

Leu Gln Gly Lys Lys Gln Tyr Gln Leu Arg Gly Val Ala Thr Leu Glu
 65                  70                  75                  80

Gly Tyr Arg Glu Gln Lys Ala Gly Ser Ser Leu Val Lys His Ala Glu
             85                  90                  95

Glu Ile Leu Arg Lys Arg Gly Ala Asp Met Ile Trp Cys Asn Ala Arg
            100                 105                 110

Thr Ser Ala Ser Gly Tyr Tyr Arg Lys Leu Gly Phe Ser Glu Gln Gly
        115                 120                 125

Glu Val Phe Asp Thr Pro Pro Val Gly Pro His Ile Leu Met Tyr Lys
    130                 135                 140

Arg Ile Thr
145
```

<210> SEQ ID NO 46
<211> LENGTH: 146
<212> TYPE: PRT
<213> ORGANISM: Artificial Sequence
<220> FEATURE:
<223> OTHER INFORMATION: Optimized GAT sequence -- R12G1

<400> SEQUENCE: 46

Met Ile Glu Val Lys Pro Ile Asn Ala Glu Asp Thr Tyr Asp Leu Arg

```
  1               5                  10                  15

His Arg Val Leu Arg Pro Asn Gln Pro Ile Glu Ala Cys Met Phe Glu
            20                  25                  30

Ser Asp Leu Thr Arg Gly Ala Phe His Leu Gly Gly Phe Tyr Gly Gly
            35                  40                  45

Lys Leu Ile Ser Val Ala Ser Phe His Gln Ala Glu His Thr Glu Leu
 50                  55                  60

Gln Gly Lys Lys Gln Tyr Gln Leu Arg Gly Val Ala Thr Leu Glu Gly
 65                  70                  75                  80

Tyr Arg Glu Gln Lys Ala Gly Ser Ser Leu Val Lys His Ala Glu Glu
                 85                  90                  95

Ile Leu Arg Lys Arg Gly Ala Asp Met Ile Trp Cys Asn Ala Arg Thr
                100                 105                 110

Ser Ala Ser Gly Tyr Tyr Arg Lys Leu Gly Phe Ser Glu Gln Gly Glu
                115                 120                 125

Val Phe Asp Thr Pro Pro Val Gly Pro His Ile Leu Met Tyr Lys Arg
            130                 135                 140

Ile Thr
145

<210> SEQ ID NO 47
<211> LENGTH: 146
<212> TYPE: PRT
<213> ORGANISM: Artificial Sequence
<220> FEATURE:
<223> OTHER INFORMATION: Optimized GAT sequence--R12G2

<400> SEQUENCE: 47

Met Ile Glu Val Lys Pro Ile Asn Ala Glu Asp Thr Tyr Asp Leu Arg
 1               5                  10                  15

His Arg Val Leu Arg Pro Asn Gln Pro Ile Glu Ala Cys Met Phe Glu
            20                  25                  30

Ser Asp Leu Thr Arg Ser Ala Phe His Leu Gly Gly Phe Tyr Gly Gly
            35                  40                  45

Lys Leu Ile Ser Val Ala Ser Phe His Gln Ala Glu His Thr Glu Leu
 50                  55                  60

Gln Gly Lys Lys Gln Tyr Gln Leu Arg Gly Val Ala Thr Leu Glu Gly
 65                  70                  75                  80

Tyr Arg Glu Gln Lys Ala Gly Ser Ser Leu Val Lys His Ala Glu Glu
                 85                  90                  95

Ile Leu Arg Lys Arg Gly Ala Asp Met Ile Trp Cys Asn Ala Arg Thr
                100                 105                 110

Ser Ala Ser Gly Tyr Tyr Arg Lys Leu Gly Phe Ser Glu Gln Gly Glu
                115                 120                 125

Val Phe Asp Thr Pro Pro Val Gly Pro His Ile Leu Met Tyr Lys Arg
            130                 135                 140

Ile Thr
145

<210> SEQ ID NO 48
<211> LENGTH: 146
<212> TYPE: PRT
<213> ORGANISM: Artificial Sequence
<220> FEATURE:
<223> OTHER INFORMATION: Optimized GAT sequence-- R12G3

<400> SEQUENCE: 48
```

Met Ile Glu Val Lys Pro Ile Asn Ala Glu Asp Thr Tyr Asp Leu Arg
1               5                   10                  15

His Arg Val Leu Arg Pro Asn Gln Pro Ile Glu Ala Cys Met Phe Asp
            20                  25                  30

Asn Asp Leu Thr Arg Gly Ala Phe His Leu Gly Gly Phe Tyr Gly Gly
                35                  40                  45

Lys Leu Ile Ser Val Ala Ser Phe His Gln Ala Glu His Ser Glu Leu
50                  55                  60

Gln Gly Lys Lys Gln Tyr Gln Leu Arg Gly Val Ala Thr Leu Glu Gly
65                  70                  75                  80

Tyr Arg Glu Gln Lys Ala Gly Ser Ser Leu Val Lys His Ala Glu Glu
                85                  90                  95

Ile Leu Arg Lys Arg Gly Ala Asp Met Ile Trp Cys Asn Ala Arg Thr
            100                 105                 110

Ser Ala Ser Gly Tyr Tyr Arg Lys Leu Gly Phe Ser Glu Gln Gly Glu
                115                 120                 125

Val Phe Asp Thr Pro Pro Val Gly Pro His Ile Leu Met Tyr Lys Arg
            130                 135                 140

Ile Thr
145

<210> SEQ ID NO 49
<211> LENGTH: 146
<212> TYPE: PRT
<213> ORGANISM: Artificial Sequence
<220> FEATURE:
<223> OTHER INFORMATION: Optimized GAT sequence -- R12G4

<400> SEQUENCE: 49

Met Ile Glu Val Lys Pro Ile Asn Ala Glu Asp Thr Tyr Glu Leu Arg
1               5                   10                  15

His Arg Val Leu Arg Pro Asn Gln Pro Ile Glu Ala Cys Met Phe Asp
            20                  25                  30

Ser Asp Leu Thr Arg Ser Ala Phe His Leu Gly Gly Phe Tyr Gly Gly
                35                  40                  45

Lys Leu Ile Ser Val Ala Ser Phe His Gln Ala Glu His Ser Glu Leu
50                  55                  60

Gln Gly Lys Lys Gln Tyr Gln Leu Arg Gly Val Ala Thr Leu Glu Gly
65                  70                  75                  80

Tyr Arg Glu Gln Lys Ala Gly Ser Ser Leu Val Lys His Ala Glu Glu
                85                  90                  95

Ile Leu Arg Lys Arg Gly Ala Asp Met Ile Trp Cys Asn Ala Arg Thr
            100                 105                 110

Ser Ala Ser Gly Tyr Tyr Arg Lys Leu Gly Phe Ser Glu Gln Gly Glu
                115                 120                 125

Val Phe Asp Thr Pro Pro Val Gly Pro His Ile Leu Met Tyr Lys Arg
            130                 135                 140

Ile Thr
145

<210> SEQ ID NO 50
<211> LENGTH: 146
<212> TYPE: PRT
<213> ORGANISM: Artificial Sequence
<220> FEATURE:
<223> OTHER INFORMATION: Optimized GAT sequence -- R12G5

<400> SEQUENCE: 50

```
Met Ile Glu Val Lys Pro Ile Asn Ala Glu Asp Thr Tyr Glu Leu Arg
1               5                   10                  15

His Arg Val Leu Arg Pro Asn Gln Pro Ile Glu Ala Cys Met Phe Asp
                20                  25                  30

Ser Asp Leu Thr Arg Gly Ala Phe His Leu Gly Gly Phe Tyr Gly Gly
            35                  40                  45

Lys Leu Ile Ser Val Ala Ser Phe His Gln Ala Glu His Ser Glu Leu
    50                  55                  60

Gln Gly Lys Lys Gln Tyr Gln Leu Arg Gly Val Ala Thr Leu Glu Gly
65              70                  75                  80

Tyr Arg Glu Gln Lys Ala Gly Ser Ser Leu Val Lys His Ala Glu Glu
                85                  90                  95

Ile Leu Arg Lys Arg Gly Ala Asp Met Ile Trp Cys Asn Ala Arg Thr
            100                 105                 110

Ser Ala Ser Gly Tyr Tyr Arg Lys Leu Gly Phe Ser Glu Gln Gly Glu
        115                 120                 125

Val Phe Asp Thr Pro Pro Val Gly Pro His Ile Leu Met Tyr Lys Arg
    130                 135                 140

Ile Thr
145

<210> SEQ ID NO 51
<211> LENGTH: 146
<212> TYPE: PRT
<213> ORGANISM: Artificial Sequence
<220> FEATURE:
<223> OTHER INFORMATION: Optimized GAT sequence -- R12G6

<400> SEQUENCE: 51

Met Ile Glu Val Lys Pro Ile Asn Ala Glu Asp Thr Tyr Asp Leu Arg
1               5                   10                  15

His Arg Val Leu Arg Pro Asn Gln Pro Ile Glu Ala Cys Met Phe Asp
                20                  25                  30

Asn Asp Leu Thr Arg Ser Ala Phe His Leu Gly Gly Phe Tyr Gly Gly
            35                  40                  45

Lys Leu Ile Ser Val Ala Ser Phe His Gln Ala Glu His Ser Glu Leu
    50                  55                  60

Gln Gly Lys Lys Gln Tyr Gln Leu Arg Gly Val Ala Thr Leu Glu Gly
65              70                  75                  80

Tyr Arg Glu Gln Lys Ala Gly Ser Ser Leu Val Lys His Ala Glu Glu
                85                  90                  95

Ile Leu Arg Lys Arg Gly Ala Asp Met Ile Trp Cys Asn Ala Arg Thr
            100                 105                 110

Ser Ala Ser Gly Tyr Tyr Arg Lys Leu Gly Phe Ser Glu Gln Gly Glu
        115                 120                 125

Val Phe Asp Thr Pro Pro Val Gly Pro His Ile Leu Met Tyr Lys Arg
    130                 135                 140

Ile Thr
145

<210> SEQ ID NO 52
<211> LENGTH: 146
<212> TYPE: PRT
<213> ORGANISM: Artificial Sequence
<220> FEATURE:
<223> OTHER INFORMATION: Optimized GAT sequence -- R12G7
```

<400> SEQUENCE: 52

Met Ile Glu Val Lys Pro Ile Asn Ala Glu Asp Thr Tyr Asp Leu Arg
1               5                   10                  15

His Arg Val Leu Arg Pro Asn Gln Pro Ile Glu Ala Cys Met Phe Asp
            20                  25                  30

Asn Asp Leu Met Arg Gly Ala Phe His Leu Gly Gly Phe His Gly Gly
        35                  40                  45

Lys Leu Ile Ser Val Ala Ser Phe His Gln Ala Glu His Thr Glu Leu
    50                  55                  60

Gln Gly Gln Lys Gln Tyr Gln Leu Arg Gly Val Ala Thr Leu Glu Gly
65                  70                  75                  80

Tyr Arg Glu Gln Lys Ala Gly Ser Ser Leu Val Lys His Ala Glu Glu
                85                  90                  95

Ile Leu Arg Lys Arg Gly Ala Asp Met Leu Trp Cys Asn Ala Arg Thr
            100                 105                 110

Ser Ala Ser Gly Tyr Tyr Arg Lys Leu Gly Phe Ser Glu Gln Gly Glu
        115                 120                 125

Val Phe Asp Thr Pro Pro Val Gly Pro His Ile Leu Met Tyr Lys Arg
    130                 135                 140

Ile Thr
145

<210> SEQ ID NO 53
<211> LENGTH: 146
<212> TYPE: PRT
<213> ORGANISM: Artificial Sequence
<220> FEATURE:
<223> OTHER INFORMATION: Optimized GAT sequence -- R12G8

<400> SEQUENCE: 53

Met Ile Glu Val Lys Pro Ile Asn Ala Glu Asp Thr Tyr Asp Leu Arg
1               5                   10                  15

His Arg Val Leu Arg Pro Asn Gln Pro Ile Glu Ala Cys Met Phe Asp
            20                  25                  30

Asn Asp Leu Met Arg Ser Ala Phe His Leu Gly Gly Phe His Gly Gly
        35                  40                  45

Lys Leu Ile Ser Val Ala Ser Phe His Gln Ala Glu His Thr Glu Leu
    50                  55                  60

Gln Gly Gln Lys Gln Tyr Gln Leu Arg Gly Val Ala Thr Leu Glu Gly
65                  70                  75                  80

Tyr Arg Glu Gln Lys Ala Gly Ser Ser Leu Val Lys His Ala Glu Glu
                85                  90                  95

Ile Leu Arg Lys Arg Gly Ala Asp Met Leu Trp Cys Asn Ala Arg Thr
            100                 105                 110

Ser Ala Ser Gly Tyr Tyr Arg Lys Leu Gly Phe Ser Glu Gln Gly Glu
        115                 120                 125

Val Phe Asp Thr Pro Pro Val Gly Pro His Ile Leu Met Tyr Lys Arg
    130                 135                 140

Ile Thr
145

<210> SEQ ID NO 54
<211> LENGTH: 146
<212> TYPE: PRT
<213> ORGANISM: Artificial Sequence
<220> FEATURE:
<223> OTHER INFORMATION: Optimized GAT sequence -- con alt e

```
<220> FEATURE:
<221> NAME/KEY: VARIANT
<222> LOCATION: 14
<223> OTHER INFORMATION: Asp or Glu
<220> FEATURE:
<221> NAME/KEY: VARIANT
<222> LOCATION: 33
<223> OTHER INFORMATION: Gly or Ser or Asn
<220> FEATURE:
<221> NAME/KEY: VARIANT
<222> LOCATION: 38
<223> OTHER INFORMATION: Gly or Ser
<220> FEATURE:
<221> NAME/KEY: VARIANT
<222> LOCATION: 46
<223> OTHER INFORMATION: His or Tyr
<220> FEATURE:
<221> NAME/KEY: VARIANT
<222> LOCATION: 51
<223> OTHER INFORMATION: Ile or Val
<220> FEATURE:
<221> NAME/KEY: VARIANT
<222> LOCATION: (58)...(58)
<223> OTHER INFORMATION: Gln or Arg
<220> FEATURE:
<221> NAME/KEY: VARIANT
<222> LOCATION: (60)...(60)
<223> OTHER INFORMATION: Glu or Gly
<220> FEATURE:
<221> NAME/KEY: VARIANT
<222> LOCATION: (62)...(62)
<223> OTHER INFORMATION: Ser or Thr
<220> FEATURE:
<221> NAME/KEY: VARIANT
<222> LOCATION: (67)...(67)
<223> OTHER INFORMATION: Gln or Lys or Arg
<220> FEATURE:
<221> NAME/KEY: VARIANT
<222> LOCATION: (88)...(88)
<223> OTHER INFORMATION: Ser or Thr
<220> FEATURE:
<221> NAME/KEY: VARIANT
<222> LOCATION: (103)...(103)
<223> OTHER INFORMATION: Ala or Val
<220> FEATURE:
<221> NAME/KEY: VARIANT
<222> LOCATION: (105)...(105)
<223> OTHER INFORMATION: Leu or Met
<220> FEATURE:
<221> NAME/KEY: VARIANT
<222> LOCATION: (106)...(106)
<223> OTHER INFORMATION: Ile or Leu
<220> FEATURE:
<221> NAME/KEY: VARIANT
<222> LOCATION: (119)...(119)
<223> OTHER INFORMATION: Arg or Lys
<220> FEATURE:
<221> NAME/KEY: VARIANT
<222> LOCATION: (139)...(139)
<223> OTHER INFORMATION: Ile or Val

<400> SEQUENCE: 54

Met Ile Glu Val Lys Pro Ile Asn Ala Glu Asp Thr Tyr Xaa Leu Arg
 1               5                  10                  15

His Arg Val Leu Arg Pro Asn Gln Pro Ile Glu Ala Cys Met Phe Asp
                20                  25                  30

Xaa Asp Leu Thr Arg Xaa Ala Phe His Leu Gly Gly Phe Xaa Gly Gly
            35                  40                  45

Lys Leu Xaa Ser Val Ala Ser Phe His Xaa Ala Xaa His Xaa Glu Leu
50                  55                  60

Gln Gly Xaa Lys Gln Tyr Gln Leu Arg Gly Val Ala Thr Leu Glu Gly
65                  70                  75                  80

Tyr Arg Glu Gln Lys Ala Gly Xaa Ser Leu Val Lys His Ala Glu Glu
```

-continued

```
                    85                  90                  95
Ile Leu Arg Lys Arg Gly Xaa Asp Xaa Xaa Trp Cys Asn Ala Arg Thr
            100                 105                 110

Ser Ala Ser Gly Tyr Tyr Xaa Lys Leu Gly Phe Ser Glu Gln Gly Glu
        115                 120                 125

Val Phe Asp Thr Pro Pro Val Gly Pro His Xaa Leu Met Tyr Lys Arg
    130                 135                 140

Ile Thr
145

<210> SEQ ID NO 55
<211> LENGTH: 444
<212> TYPE: DNA
<213> ORGANISM: Artificial Sequence
<220> FEATURE:
<223> OTHER INFORMATION: Optimized GAT sequence -- GAT4621
<220> FEATURE:
<221> NAME/KEY: CDS
<222> LOCATION: (1)...(444)
<223> OTHER INFORMATION: encodes 25-8H7 M1MA

<400> SEQUENCE: 55 atg gct att gag gtt aag cct atc aac gca gag gat acc tat gac ctt      48
Met Ala Ile Glu Val Lys Pro Ile Asn Ala Glu Asp Thr Tyr Asp Leu
 1               5                  10                  15 agg cat aga gtg ctc aga cca aac cag cct atc gaa gcc tgc atg ttt      96
Arg His Arg Val Leu Arg Pro Asn Gln Pro Ile Glu Ala Cys Met Phe
                20                  25                  30 gag tct gac ctt act agg agt gca ttt cac ctt ggt gga ttc tac gga     144
Glu Ser Asp Leu Thr Arg Ser Ala Phe His Leu Gly Gly Phe Tyr Gly
            35                  40                  45 ggt aaa ctg att tcc gtg gct tca ttc cac caa gct gag cac tct gaa     192
Gly Lys Leu Ile Ser Val Ala Ser Phe His Gln Ala Glu His Ser Glu
        50                  55                  60 ctt caa ggt aag aag cag tac cag ctt aga ggt gtg gct acc ttg gaa     240
Leu Gln Gly Lys Lys Gln Tyr Gln Leu Arg Gly Val Ala Thr Leu Glu
    65                  70                  75                  80 ggt tat aga gag cag aag gct ggt tcc agt ctc gtg aaa cac gct gaa     288
Gly Tyr Arg Glu Gln Lys Ala Gly Ser Ser Leu Val Lys His Ala Glu
                85                  90                  95 gag att ctc aga aag aga ggt gct gac atg atc tgg tgt aat gcc agg     336
Glu Ile Leu Arg Lys Arg Gly Ala Asp Met Ile Trp Cys Asn Ala Arg
            100                 105                 110 aca tct gct tca gga tac tac agg aag ttg gga ttc agt gag caa gga     384
Thr Ser Ala Ser Gly Tyr Tyr Arg Lys Leu Gly Phe Ser Glu Gln Gly
        115                 120                 125 gag gtg ttc gat act cct cca gtt gga cct cac atc ctg atg tat aag     432
Glu Val Phe Asp Thr Pro Pro Val Gly Pro His Ile Leu Met Tyr Lys
    130                 135                 140 agg atc aca taa                                                      444
Arg Ile Thr *
145

<210> SEQ ID NO 56
<211> LENGTH: 147
<212> TYPE: PRT
<213> ORGANISM: Artificial Sequence
<220> FEATURE:
<223> OTHER INFORMATION: Optimized GAT sequence -- GAT4621, encodes
      25-8H7 M1MA

<400> SEQUENCE: 56
```

```
Met Ala Ile Glu Val Lys Pro Ile Asn Ala Glu Asp Thr Tyr Asp Leu
 1               5                  10                  15

Arg His Arg Val Leu Arg Pro Asn Gln Pro Ile Glu Ala Cys Met Phe
                 20                  25                  30

Glu Ser Asp Leu Thr Arg Ser Ala Phe His Leu Gly Gly Phe Tyr Gly
             35                  40                  45

Gly Lys Leu Ile Ser Val Ala Ser Phe His Gln Ala Glu His Ser Glu
 50                  55                  60

Leu Gln Gly Lys Lys Gln Tyr Gln Leu Arg Gly Val Ala Thr Leu Glu
 65                  70                  75                  80

Gly Tyr Arg Glu Gln Lys Ala Gly Ser Ser Leu Val Lys His Ala Glu
                 85                  90                  95

Glu Ile Leu Arg Lys Arg Gly Ala Asp Met Ile Trp Cys Asn Ala Arg
                100                 105                 110

Thr Ser Ala Ser Gly Tyr Tyr Arg Lys Leu Gly Phe Ser Glu Gln Gly
             115                 120                 125

Glu Val Phe Asp Thr Pro Pro Val Gly Pro His Ile Leu Met Tyr Lys
130                 135                 140

Arg Ile Thr
145

<210> SEQ ID NO 57
<211> LENGTH: 441
<212> TYPE: DNA
<213> ORGANISM: Artificial Sequence
<220> FEATURE:
<223> OTHER INFORMATION: Optimized GAT sequence -- R12G1
<220> FEATURE:
<221> NAME/KEY: CDS
<222> LOCATION: (1)...(441)

<400> SEQUENCE: 57 atg ata gag gta aaa ccg att aac gca gag gat acc tat gac cta agg      48
Met Ile Glu Val Lys Pro Ile Asn Ala Glu Asp Thr Tyr Asp Leu Arg
 1               5                  10                  15 cat aga gtc ctc aga cca aac cag ccg ata gaa gcg tgt atg ttt gaa      96
His Arg Val Leu Arg Pro Asn Gln Pro Ile Glu Ala Cys Met Phe Glu
                 20                  25                  30 agc gat tta acg cgt ggt gca ttt cac tta ggc ggc ttc tac ggg ggc     144
Ser Asp Leu Thr Arg Gly Ala Phe His Leu Gly Gly Phe Tyr Gly Gly
             35                  40                  45 aaa ctg att tcc gtc gct tca ttc cac cag gcc gag cac act gaa ctt     192
Lys Leu Ile Ser Val Ala Ser Phe His Gln Ala Glu His Thr Glu Leu
 50                  55                  60 caa ggc aag aaa cag tac cag ctt cga ggt gtg gct acc ttg gaa ggt     240
Gln Gly Lys Lys Gln Tyr Gln Leu Arg Gly Val Ala Thr Leu Glu Gly
 65                  70                  75                  80 tat cgt gag cag aag gcg ggt tcc agt cta gtt aaa cac gct gaa gaa     288
Tyr Arg Glu Gln Lys Ala Gly Ser Ser Leu Val Lys His Ala Glu Glu
                 85                  90                  95 att cta cgt aag agg ggg gcg gac atg att tgg tgt aat gcg cgg aca     336
Ile Leu Arg Lys Arg Gly Ala Asp Met Ile Trp Cys Asn Ala Arg Thr
                100                 105                 110 tct gcc tca ggc tac tac aga aag tta ggc ttc agc gag cag gga gag     384
Ser Ala Ser Gly Tyr Tyr Arg Lys Leu Gly Phe Ser Glu Gln Gly Glu
             115                 120                 125 gta ttc gac acg ccg cca gta gga cct cac atc ctg atg tat aaa agg     432
Val Phe Asp Thr Pro Pro Val Gly Pro His Ile Leu Met Tyr Lys Arg
130                 135                 140
```

```
atc aca taa                                                          441
Ile Thr  *
145

<210> SEQ ID NO 58
<211> LENGTH: 441
<212> TYPE: DNA
<213> ORGANISM: Artificial Sequence
<220> FEATURE:
<223> OTHER INFORMATION: Optimized GAT sequence -- R12G2

<400> SEQUENCE: 58
atgatagagg taaaaccgat taacgcagag gataccatg acctaaggca tagagtcctc     60
agaccaaacc agccgataga agcgtgtatg tttgaaagcg atttaacgcg tagtgcattt    120
cacttaggcg gcttctacgg gggcaaactg atttccgtcg cttcattcca ccaggccgag    180
cacactgaac ttcaaggcaa gaaacagtac cagcttcgag gtgtggctac cttggaaggt    240
tatcgtgagc agaaggcggg ttccagtcta gttaaacacg ctgaagaaat tctacgtaag    300 agggggggcgg acatgatttg gtgtaatgcg cggacatctg cctcaggcta ctacagaaag    360
ttaggcttca gcgagcaggg agaggtattc gacacgccgc cagtaggacc tcacatcctg    420
atgtataaaa ggatcacata a                                              441

<210> SEQ ID NO 59
<211> LENGTH: 441
<212> TYPE: DNA
<213> ORGANISM: Artificial Sequence
<220> FEATURE:
<223> OTHER INFORMATION: Optimized GAT sequence--R12G3
<220> FEATURE:
<221> NAME/KEY: CDS
<222> LOCATION: (1)...(441)

<400> SEQUENCE: 59 atg ata gag gta aaa ccg att aac gca gag gat acc tat gac cta agg       48
Met Ile Glu Val Lys Pro Ile Asn Ala Glu Asp Thr Tyr Asp Leu Arg
 1               5                  10                  15 cat aga gtc ctc aga cca aac cag ccg ata gaa gcg tgt atg ttt gat       96
His Arg Val Leu Arg Pro Asn Gln Pro Ile Glu Ala Cys Met Phe Asp
             20                  25                  30 aac gat tta acg cgt ggt gca ttt cac tta ggc ggc ttc tac ggg ggc      144
Asn Asp Leu Thr Arg Gly Ala Phe His Leu Gly Gly Phe Tyr Gly Gly
         35                  40                  45 aaa ctg att tcc gtc gct tca ttc cac cag gcc gag cac tcg gaa ctt      192
Lys Leu Ile Ser Val Ala Ser Phe His Gln Ala Glu His Ser Glu Leu
     50                  55                  60 caa ggc aag aaa cag tac cag ctt cga ggt gtg gct acc ttg gaa ggt      240
Gln Gly Lys Lys Gln Tyr Gln Leu Arg Gly Val Ala Thr Leu Glu Gly
 65                  70                  75                  80 tat cgt gag cag aag gcg ggt tcc agt cta gtt aaa cac gct gaa gaa      288
Tyr Arg Glu Gln Lys Ala Gly Ser Ser Leu Val Lys His Ala Glu Glu
                 85                  90                  95 att cta cgt aag agg ggg gcg gac atg att tgg tgt aat gcg cgg aca      336
Ile Leu Arg Lys Arg Gly Ala Asp Met Ile Trp Cys Asn Ala Arg Thr
            100                 105                 110 tct gcc tca ggc tac tac aga aag tta ggc ttc agc gag cag gga gag      384
Ser Ala Ser Gly Tyr Tyr Arg Lys Leu Gly Phe Ser Glu Gln Gly Glu
        115                 120                 125 gta ttc gac acg ccg cca gta gga cct cac atc ctg atg tat aaa agg      432
Val Phe Asp Thr Pro Pro Val Gly Pro His Ile Leu Met Tyr Lys Arg
    130                 135                 140
``` atc aca taa                                                          441
Ile Thr *
145

<210> SEQ ID NO 60
<211> LENGTH: 441
<212> TYPE: DNA
<213> ORGANISM: Artificial Sequence
<220> FEATURE:
<223> OTHER INFORMATION: Optimized GAT sequence -- R12G4

<400> SEQUENCE: 60
atgatagagg taaaaccgat taacgcagag gatacctatg aactaaggca tagagtcctc      60
agaccaaacc agccgataga agcgtgtatg tttgatagcg atttaacgcg tagtgcattt     120
cacttaggcg gcttctacgg gggcaaactg atttccgtcg cttcattcca ccaggccgag     180
cactcggaac ttcaaggcaa gaaacagtac cagcttcgag gtgtggctac cttggaaggt     240
tatcgtgagc agaaggcggg ttccagtcta gttaaacacg ctgaagaaat tctacgtaag     300 agggggggcgg acatgatttg tgtaatgcg cggacatctg cctcaggcta ctacagaaag     360
ttaggcttca gcgagcaggg agaggtattc gacacgccgc cagtaggacc tcacatcctg     420
atgtataaaa ggatcacata a                                              441

<210> SEQ ID NO 61
<211> LENGTH: 441
<212> TYPE: DNA
<213> ORGANISM: Artificial Sequence
<220> FEATURE:
<223> OTHER INFORMATION: Optimized GAT sequence --  R12G5
<220> FEATURE:
<221> NAME/KEY: CDS
<222> LOCATION: (1)...(441)

<400> SEQUENCE: 61 atg ata gag gta aaa ccg att aac gca gag gat acc tat gaa cta agg       48
Met Ile Glu Val Lys Pro Ile Asn Ala Glu Asp Thr Tyr Glu Leu Arg
 1               5                  10                  15 cat aga gtc ctc aga cca aac cag ccg ata gaa gcg tgt atg ttt gat       96
His Arg Val Leu Arg Pro Asn Gln Pro Ile Glu Ala Cys Met Phe Asp
            20                  25                  30 agc gat tta acg cgt ggt gca ttt cac tta ggc ggc ttc tac ggg ggc      144
Ser Asp Leu Thr Arg Gly Ala Phe His Leu Gly Gly Phe Tyr Gly Gly
        35                  40                  45 aaa ctg att tcc gtc gct tca ttc cac cag gcc gag cac tcg gaa ctt      192
Lys Leu Ile Ser Val Ala Ser Phe His Gln Ala Glu His Ser Glu Leu
    50                  55                  60 caa ggc aag aaa cag tac cag ctt cga ggt gtg gct acc ttg gaa ggt      240
Gln Gly Lys Lys Gln Tyr Gln Leu Arg Gly Val Ala Thr Leu Glu Gly
65                  70                  75                  80 tat cgt gag cag aag gcg ggt tcc agt cta gtt aaa cac gct gaa gaa      288
Tyr Arg Glu Gln Lys Ala Gly Ser Ser Leu Val Lys His Ala Glu Glu
                85                  90                  95 att cta cgt aag agg ggg gcg gac atg att tgg tgt aat gcg cgg aca      336
Ile Leu Arg Lys Arg Gly Ala Asp Met Ile Trp Cys Asn Ala Arg Thr
            100                 105                 110 tct gcc tca ggc tac tac aga aag tta ggc ttc agc gag cag gga gag      384
Ser Ala Ser Gly Tyr Tyr Arg Lys Leu Gly Phe Ser Glu Gln Gly Glu
        115                 120                 125 gta ttc gac acg ccg cca gta gga cct cac atc ctg atg tat aaa agg      432
Val Phe Asp Thr Pro Pro Val Gly Pro His Ile Leu Met Tyr Lys Arg
    130                 135                 140

```
atc aca taa                                                              441
Ile Thr  *
145

<210> SEQ ID NO 62
<211> LENGTH: 441
<212> TYPE: DNA
<213> ORGANISM: Artificial Sequence
<220> FEATURE:
<223> OTHER INFORMATION: Optimized GAT sequence -- R12G6
<220> FEATURE:
<221> NAME/KEY: CDS
<222> LOCATION: (1)...(441)

<400> SEQUENCE: 62 atg ata gag gta aaa ccg att aac gca gag gat acc tat gac cta agg        48
Met Ile Glu Val Lys Pro Ile Asn Ala Glu Asp Thr Tyr Asp Leu Arg
1               5                  10                  15 cat aga gtc ctc aga cca aac cag ccg ata gaa gcg tgt atg ttt gat        96
His Arg Val Leu Arg Pro Asn Gln Pro Ile Glu Ala Cys Met Phe Asp
            20                  25                  30 aac gat tta acg cgt agt gca ttt cac tta ggc ggc ttc tac ggg ggc       144
Asn Asp Leu Thr Arg Ser Ala Phe His Leu Gly Gly Phe Tyr Gly Gly
        35                  40                  45 aaa ctg att tcc gtc gct tca ttc cac cag gcc gag cac tcg gaa ctt       192
Lys Leu Ile Ser Val Ala Ser Phe His Gln Ala Glu His Ser Glu Leu
    50                  55                  60 caa ggc aag aaa cag tac cag ctt cga ggt gtg gct acc ttg gaa ggt       240
Gln Gly Lys Lys Gln Tyr Gln Leu Arg Gly Val Ala Thr Leu Glu Gly
65                  70                  75                  80 tat cgt gag cag aag gcg ggt tcc agt cta gtt aaa cac gct gaa gaa       288
Tyr Arg Glu Gln Lys Ala Gly Ser Ser Leu Val Lys His Ala Glu Glu
                85                  90                  95 att cta cgt aag agg ggg gcg gac atg att tgg tgt aat gcg cgg aca       336
Ile Leu Arg Lys Arg Gly Ala Asp Met Ile Trp Cys Asn Ala Arg Thr
            100                 105                 110 tct gcc tca ggc tac tac aga aag tta ggc ttc agc gag cag gga gag       384
Ser Ala Ser Gly Tyr Tyr Arg Lys Leu Gly Phe Ser Glu Gln Gly Glu
        115                 120                 125 gta ttc gac acg ccg cca gta gga cct cac atc ctg atg tat aaa agg       432
Val Phe Asp Thr Pro Pro Val Gly Pro His Ile Leu Met Tyr Lys Arg
    130                 135                 140 atc aca taa                                                            441
Ile Thr  *
145

<210> SEQ ID NO 63
<211> LENGTH: 441
<212> TYPE: DNA
<213> ORGANISM: Artificial Sequence
<220> FEATURE:
<223> OTHER INFORMATION: Optimized GAT sequence -- R12G7
<220> FEATURE:
<221> NAME/KEY: CDS
<222> LOCATION: (1)...(441)

<400> SEQUENCE: 63 atgatagag gta aaa ccg att aac gca gaa gat acc tat gac cta agg cat       51
          Val Lys Pro Ile Asn Ala Glu Asp Thr Tyr Asp Leu Arg His
                1               5                  10 aga gtc ctc aga cca aac cag ccg ata gaa gcg tgt atg ttt gat aac        99
Arg Val Leu Arg Pro Asn Gln Pro Ile Glu Ala Cys Met Phe Asp Asn
15                  20                  25                  30 gat tta atg cgt ggt gca ttt cac tta ggc ggc ttc cac ggg ggc aaa       147
```

| | | |
|---|---|---|
| Asp Leu Met Arg Gly Ala Phe His Leu Gly Gly Phe His Gly Gly Lys<br>35 40 45 | | |
| ctg att tcc gtc gct tca ttc cac cag gcc gag cac act gaa ctt caa<br>Leu Ile Ser Val Ala Ser Phe His Gln Ala Glu His Thr Glu Leu Gln<br>50 55 60 | 195 | |
| ggc cag aaa cag tat cag ctt cga ggt gtg gct acc ttg gaa ggt tat<br>Gly Gln Lys Gln Tyr Gln Leu Arg Gly Val Ala Thr Leu Glu Gly Tyr<br>65 70 75 | 243 | |
| cgt gag cag aag gcg ggt tcc agt cta gtt aaa cac gct gaa gaa att<br>Arg Glu Gln Lys Ala Gly Ser Ser Leu Val Lys His Ala Glu Glu Ile<br>80 85 90 | 291 | |
| cta cgt aag agg ggg gcg gac atg ctt tgg tgt aat gcg cgg aca tcc<br>Leu Arg Lys Arg Gly Ala Asp Met Leu Trp Cys Asn Ala Arg Thr Ser<br>95 100 105 110 | 339 | |
| gcc tca ggc tac tac aga aag ttg ggc ttc agc gag cag gga gag gta<br>Ala Ser Gly Tyr Tyr Arg Lys Leu Gly Phe Ser Glu Gln Gly Glu Val<br>115 120 125 | 387 | |
| ttc gac acg ccg ccg gta gga cct cac atc ctg atg tat aaa agg atc<br>Phe Asp Thr Pro Pro Val Gly Pro His Ile Leu Met Tyr Lys Arg Ile<br>130 135 140 | 435 | |
| aca taa<br>Thr * | 441 | |

```
<210> SEQ ID NO 64
<211> LENGTH: 441
<212> TYPE: DNA
<213> ORGANISM: Artificial Sequence
<220> FEATURE:
<223> OTHER INFORMATION: Optimized GAT sequence -- R12G8

<400> SEQUENCE: 64
```

| | |
|---|---|
| atgatagagg taaaaccgat taacgcagaa gataccctatg acctaaggca tagagtcctc | 60 |
| agaccaaacc agccgataga agcgtgtatg tttgataacg atttaatgcg tagtgcattt | 120 |
| cacttaggcg gcttccacgg gggcaaactg atttccgtcg cttcattcca ccaggccgag | 180 |
| cacactgaac ttcaaggcca gaaacagtat cagcttcgag gtgtggctac cttggaaggt | 240 |
| tatcgtgagc agaaggcggg ttccagtcta gttaaacacg ctgaagaaat tctacgtaag | 300 |
| agggggggcgg acatgctttg tgtaatgcg cggacatccg cctcaggcta ctacagaaag | 360 |
| ttgggcttca gcgagcaggg agaggtattc gacacgccgc cggtaggacc tcacatcctg | 420 |
| atgtataaaa ggatcacata a | 441 |

```
<210> SEQ ID NO 65
<211> LENGTH: 3936
<212> TYPE: DNA
<213> ORGANISM: Glycine max
<220> FEATURE:
<221> NAME/KEY: misc_feature
<222> LOCATION: (0)...(0)
<223> OTHER INFORMATION: HRA sequence

<400> SEQUENCE: 65
```

| | |
|---|---|
| atgctacgca cacaacacaa tggcggccac cgcttccaga accacccgat tctcttcttc | 60 |
| ctcttcacac cccaccttcc ccaaacgcat tactagatcc accctcccgt gtgttgtgtt | 120 |
| accgccggtg gcgaaggtct tggtgggcta agagaagaag gagaagtgtg ggtggaagg | 180 |
| ggtttgcgta atgatctagg tgggagggtc tctctcatca accctcaccc aaacccaacc | 240 |
| acgctctcaa aatcaaatgt tccatctcca aaccccccac ggcggcgccc ttcaccaagg | 300 |
| aagcgccgag agagagtagt ttgggagtgg tttgggttgg tgcgagagtt ttagtttaca | 360 |

```
aggtagaggt tgggggggtg ccgccgcggg aagtggttcc ttcgcggcac cacggagccc      420
ttcgtgtcac ggttcgcctc cggcgaacct cgcaagggcg cggacatcct tgtggaggcg      480
ctggagaggc agggcgtgac gacggtgttg gtgcctcggg aagcacagtg ccaagcggag      540
gccgcttgga gcgttcccgc gcctgtagga acacctccgc gacctctccg tcccgcactg      600
ctgccacatc gcgtaccccg gcggtgcgtc gatggagatc caccaggcgc tcacgcgctc      660
cgccgccatc cgcaacgtgc tcccgcgcca cgagcagggc ggcgtcttag cgcatggggc      720
cgccacgcag ctacctctag gtggtccgcg agtgcgcgag gcggcggtag gcgttgcacg      780
agggcgcggt gctcgtcccg ccgcagaacg ccgccgaagg ctacgcgcgt tcctccggcc      840
tccccggcgt ctgcattgcc acctccggcc ccggcgccac caacctcgtg agcggcctcg      900
ccgacgctgc ggcggcttcc gatgcgcgca aggaggccgg aggggccgca gacgtaacgg      960
tggaggccgg ggccgcggtg gttggagcac tcgccggagc ggctgcgatt aatggacagc     1020
gtcccagtcg tcgccatcac cggccaggtc gcccgccgga tgatcggcac cgacgccttc     1080
caagaaaccc cgatcgtgga ggtgagcaaa ttacctgtcg cagggtcagc agcggtagtg     1140
gccggtccag cgggcggcct actagccgtg gctgcggaag gttctttggg gctagcacct     1200
ccactcgtga tccatcacga agcacaacta cctcatcctc gacgtcgacg acatcccccg     1260
cgtcgtcgcc gaggctttct tcgtcgccac ctccggccgc cccggtccct aggtagtgct     1320
tcgtgttgat ggagtaggag ctgcagctgc tgtaggggc gcagcagcgg ctccgaaaga     1380
agcagcggtg gaggccggcg gggccagggg tcctcatcga cattcccaaa gacgttcagc     1440
agcaactcgc cgtgcctaat tgggacgagc ccgttaacct ccccggttac ctcgccaggc     1500
tgcccaggcc aggagtagct gtaagggttt ctgcaagtcg tcgttgagcg gcacggatta     1560
accctgctcg ggcaattgga ggggccaatg gagcggtccg acgggtcccc cccgccgag      1620 gcccaattgg aacacattgt cagactcatc atggaggccc aaaagcccgt tctctacgtc     1680
ggcggtggca gtttgaattc cagtgctggg ggggcggctc cgggttaacc ttgtgtaaca     1740
gtctgagtag tacctccggg ttttcgggca agagatgcag ccgccaccgt caaacttaag     1800
gtcacgacaa ttgaggcgct ttgttgaact cactggtatt cccgttgcta gcactttaat     1860
gggtcttgga acttttccta ttggtgatga atattcccctt cagatgcttt aactccgcga     1920
aacaacttga gtgaccataa gggcaacgat cgtgaaatta cccagaacct tgaaaaggat     1980
aaccactact tataagggaa gtctacgagg gtatgcatgg tactgtttat gctaactatg     2040
ctgttgacaa tagtgatttg ttgcttgcct ttggggtaag gtttgatgac cgtgttactg     2100
ggaagcttcc catacgtacc atgacaaata cgattgatac gacaactgtt atcactaaac     2160
aacgaacgga aaccccattc caaactactg gcacaatgac ccttcgaaga ggcttttgct     2220
agtagggcta agattgttca cattgatatt gattctgccg agattgggaa gaacaagcag     2280
gcgcacgtgt cggtttgcgc ggatttgact ccgaaaacga tcatcccgat tctaacaagt     2340
gtaactataa ctaagacggc tctaacccctt cttgttcgtc cgcgtgcaca gccaaacgcg     2400
cctaaactag ttggccttga agggaattaa tatgattttg gaggagaaag gagtggaggg     2460
taagtttgat cttggaggtt ggagagaaga gattaatgtg cagaaacatc aaccggaact     2520
tcccttaatt atactaaaac ctcctctttc ctcacctccc attcaaacta gaacctccaa     2580
cctctcttct ctaattacac gtctttgtca agtttccatt gggttacaag acattccagg     2640
acgcgatttc tccgcagcat gctatcgagg ttcttgatga gttgactaat ggagatgcta     2700
```

```
ttgttagtgt tcaaaggtaa cccaatgttc tgtaaggtcc tgcgctaaag aggcgtcgta    2760
cgatagctcc aagaactact caactgatta cctctacgat aacaatcaac tggggttggg    2820
cagcatcaaa tgtgggctgc gcagttttac aagtacaaga gaccgaggca gtggttgacc    2880
tcagggggtc ttggagccat gggttttgtg accccaaccc gtcgtagttt acacccgacg    2940
cgtcaaaatg ttcatgttct ctggctccgt caccaactgg agtccccag aacctcggta     3000 cccaaaacga ttgcctgcgg ctattggtgc tgctgttgct aaccctgggg ctgttgtggt    3060
tgacattgat ggggatggta gtttcatcat gaatgttcag gagttggcct aacggacgcc    3120
gataaccacg acgacaacga ttgggacccc gacaacacca actgtaacta cccctaccat    3180
caaagtagta cttacaagtc ctcaaccgca ctataagagt ggagaatctc ccagttaaga    3240
tattgttgtt gaacaatcag catttgggta tggtggttca gttggaggat aggttctaca    3300
agtccaatgt gatattctca cctcttagag ggtcaattct ataacaacaa cttgttagtc    3360
gtaaacccat accaccaagt caacctccta tccaagatgt tcaggttaag agctcacacc    3420
tatcttggag atccgtctag cgagagcgag atattcccaa acatgctcaa gtttgctgat    3480
gcttgtggga taccggcagc gcgagtgatc tcgagtgtgg atagaacctc taggcagatc    3540
gctctcgctc tataagggtt tgtacgagtt caaacgacta cgaacaccct atggccgtcg    3600
cgctcactcg aagaaggaag agcttagagc ggcaattcag agaatgttgg acaccctgg    3660 cccctacctt cttgatgtca ttgtgcccca tcaggagcat gtgttgccgc ttcttccttc    3720
tcgaatctcg ccgttaagtc tcttacaacc tgtggggacc ggggatggaa gaactacagt    3780
aacacggggt agtcctcgta cacaacggga tgattcccag taatggatcc ttcaaggatg    3840
tgataactga gggtgatggt agaacgaggt acctactaag ggtcattacc taggaagttc    3900
ctacactatt gactcccact accatcttgc tccatg                              3936

<210> SEQ ID NO 66
<211> LENGTH: 3834
<212> TYPE: DNA
<213> ORGANISM: Zea Mays
<220> FEATURE:
<221> NAME/KEY: misc_feature
<222> LOCATION: (0)...(0)
<223> OTHER INFORMATION: HRA sequence

<400> SEQUENCE: 66
cagtacacag tcctgccatc accatccagg atcatatcct tgaaagcccc accactaggg      60
atcataggca acacatgtca tgtgtcagga cggtagtggt aggtcctagt ataggaactt     120
tcggggtggt gatccctagt atccgttgtg tagctcctgg tgtgggacga ttatatccaa     180
gaggtacggc cctggagtct cgagcatctt ctttatcgct gcgcggactt cgttcttctt     240
tgtcacacgg accgaggacc acccctgct aatataggtt ctccatgccg ggacctcaga      300
gctcgtagaa gaaatagcga cgcgcctgaa gcaagaagaa acagtgtgcc tgcgctggaa     360
tgttgaaccc tttggcgatc gtcacgaaat ctggatatat ctcactttca ttctctgggt     420
ttcccaagta tgtgtgcgct ctgttggcct tagcgacctt acaacttggg aaaccgctag     480
cagtgcttta gacctatata gagtgaaagt aagagaccca aagggttcat acacacgcga     540
gacaaccgga attagaacct gtcctccaac tgcaccacca tccccaggtg ctggttgttt     600
agcacaaaga ccttcactgg gaggttctca attcggatca tagctagctc ctatcttgga     660
caggaggttg acgtggtggt aggggtccac gaccaacaaa tcgtgtttct ggaagtgacc     720
ctccaagagt taagcctagt atcgatcgag gagaacgttc atgagaaagc taccatctcc     780
```

-continued

```
atcgatgtca acaacagtga cacctgggtt tgccacagaa gcaccagcag cagccggcaa    840
accaaatccc atcttgcaag tactctttcg atggtagagg tagctacagt tgttgtcact    900
gtggacccaa acggtgtctt cgtggtcgtc gtcggccgtt tggtttaggg taagccccaa    960
gaccagctga agacaaccac tgccttggcc gcttgtaagt gtagtactgt gccgcccaca   1020
tctggtgctg cccaacacct gtgccgatga tgtcggggtt ctggtcgact tctgttggtg   1080
acggaaccgg cgaacattca catcatgaca cggcgggtgt agaccacgac gggttgtgga   1140
cacggctact acgcctcgcc tttcgtcagc tcatcaagaa cctgaatagc atattgtggc   1200
tggatctcct cattagatgt tttatacccca aggggggaatt ccctcttctg ctcggagcgg   1260
aaagcagtcg agtagttctt ggacttatcg tataacaccg acctagagga gtaatctaca   1320
aaatatgggt tccccttaa gggagaagac gagatccaac tcatcgttcc atgagccaaa    1380
gtcaaagctc ttctttgatg tgcttccttc aagaagagca ttcatgccct gcaaagcaag   1440
cttaacatct gcctaggttg agtagcaagg tactcggttt cagtttcgag aagaaactac   1500
acgaaggaag ttcttctcgt aagtacggga cgtttcgttc gaattgtaga cgacagatgg   1560
acacatgtgg ctgcttgttc ttgccaatct cagccggatc aatatcaacg tgcacaatct   1620
tagccctgct tgcaaaagcc tcaatcttcc cttgtctacc tgtgtacacc gacgaacaag   1680
aacggttaga gtcggcctag ttatagttgc acgtgttaga atcgggacga acgttttcgg   1740
agttagaagg gagtcacgcg atcatcaaac cgcacaccaa gtgcaagcaa cagatcggcc   1800
ttatccactg cataatttgc atacaccgtc ccatgcatac ctagcatgcg cacagtcgcg   1860
tagtagtttg gcgtgtggtt cacgttcgtt gtctagccgg aataggtgac gtattaaacg   1920
tatgtggcag ggtacgtatg gatcgtacgc gtgagacagt gggtcgtcgc tggggaagtt   1980
gccgaggccc ataagagtag ttgtgaccgg gattccagtc agctccacaa agcgtcgcaa   2040
ctcctcacca gactctgtca cccagcagcg accccttcaa cggctccggg tattctcatc   2100
aacactggcc ctaaggtcag tcgaggtgtt tcgcagcgtt gaggagtggt cttgctgcgc   2160
agccaccgcc cacataaaga acagggcgcc gcgattcacc aacaagacgc agcacctgct   2220
caagcaactc agtcgcaggg ggcttgggaa ggacgacgcg tcggtggcgg gtgtatttct   2280
tgtcccgcgg cgctaagtgg ttgttctgcg tcgtggacga gttcgttgag tcagcgtccc   2340
ccgaaccctt cccgcgcaat gtacccaggc agactcatgg gcttgtccca gacaggcacc   2400
gccatctgct gctggatgtc cttggggatg tcgacaagca ccggccctgg tcgcgcgtta   2460
catgggtccg tctgagtacc cgaacagggt ctgtccgtgg cggtagacga cgacctacag   2520
gaaccctac agctgttcgt ggccgggacc aggaccagag gaggcgagga agaaagcctc   2580
ctgcacgacg cgggggatgt cgtcgacgtc gaggaccagg tagttgtgct tggtgatgga   2640
gcgggtgacc tcctggtctc ctccgctcct tctttcggag gacgtgctgc gccccctaca   2700
gcagctgcag ctcctggtcc atcaacacga accactacct cgcccactgg aggacgatgg   2760
gcgtctcctg gaaggcgtcg gtgccaatca tgcgtcgcgc cacctgtccc gtgatggcga   2820
ccatggggac ggaatcgagc agcgcgtcgg cgctgctacc cgcagaggac cttccgcagc   2880
cacggttagt acgcagcgcg gtggacaggg cactaccgct ggtacccctg ccttagctcg   2940
tcgcgcagcc gcagcgcgga gactaggttg gtggcgccgg ggccggaggt ggcgatgcag   3000
acgccgacgc ggcccgagga gcgcgcgtag ccggaggcgg caaaggcctc cctcgcgcct   3060
ctgatccaac caccgcggcc ccggcctcca ccgctacgtc tgcggctgcg ccgggctcct   3120
```

```
cgcgcgcatc ggcctccgcc gtttccggag ggcttgctcg tggcggaaga ggtggttggc    3180
gatgacgggg gagcgggtga gtgcctggtg gatctccatg gacgcgccgc cggggtaggc    3240
gaagacgtcg cggaacgagc accgccttct ccaccaaccg ctactgcccc ctcgcccact    3300
cacggaccac ctagaggtac ctgcgcggcg gccccatccg cttctgcagc gcgacgccgc    3360
agcgctcgag ggactcgacg aggatgtcag caccccttgcg gggctcggtg gggcccacg    3420 gccggagcgg ggtggccggg ggagccatcg gcctgcgggc tcgcgagctc cctgagctgc    3480
tcctacagtc gtgggaacgc cccgagccac cccggggtgc cggcctcgcc ccaccggccc    3540
cctcggtagc cgatgcgggg tgacgccgct gagcacctga tgggcgcggc gagggcgcgg    3600
cgggtggcca ggaggtgcgc ccggcgcctc gccttgggcg cagcggtagt ggtaccgccc    3660
actgcggcga ctcgtggact acccgcgccg ctcccgcgcc gcccaccggt cctccacgcg    3720
ggccgcggag cggaacccgc gtcgccatca cccgccagtg agcgcggtag acgcggcggc    3780
ggcggtggcc atggcggtca ctcgcgccat ctgcgccgcc gccgccaccg gtac          3834

<210> SEQ ID NO 67
<211> LENGTH: 4278
<212> TYPE: DNA
<213> ORGANISM: Arabidopsis
<220> FEATURE:
<221> NAME/KEY: misc_feature
<222> LOCATION: (0)...(0)
<223> OTHER INFORMATION: HRA sequence

<400> SEQUENCE: 67
aaatacgttt tatgcaacct acgcaccctg cgctaccatc cctagagctg cagcttattt      60
ttacaacaat taccaacaac aacaaacaac aaacaacatt acaattacta tttacatgga     120
tgcgtgggac gcgatggtag ggatctcgac gtcgaataaa aatgttgtta atggttgttg     180
ttgtttgttg tttgttgtaa tgttaatgat aaatgtatta cagtcgaccc gggatccatg     240
gcggcggcaa caacaacaac aacaacatct tcttcgatct ccttctccac caaaccatct     300
ccttcctcct ccaaattaat gtcagctggg ccctaggtac cgccgccgtt gttgttgttg     360
ttgttgtaga agaagctaga ggaagaggtg gtttggtaga ggaaggagga ggtttacacc     420
attaccaatc tccagattct ccctcccatt tccctaaac cccaacaaat catcctcctc      480
ctcccgccgc cgcggtatca aatccagctc tccctcgtgg taatggttag aggtctaaga     540
gggagggtaa gagggatttg gggttgttta gtaggaggag gagggcggcg cgcgccatagt    600 ttaggtcgag agggagctcc atctccgccg tgctcaacac aaccaccaat gtcacaacca     660
ctccctctcc aaccaaacct accaaacccg aaacattcat ctcccgattc gctccagagg     720
tagaggcgga acgagttgtg ttggtggtta cagtgttggt gagggagagg ttggttggga     780
tggtttgggc tttgtaagta gagggctaag cgaggtgatc aaccccgcaa aggcgctgat     840
atcctcgtcg aagctttaga acgtcaaggc gtagaaaccg tattcgctta ccctggaggt     900
gcatcaatgg agattcctag ttggggcgtt ccgcgactaa taggagcagc ttcgaaatct     960
tgcagttccg catctttggc ataagcgaat gggacctcca cgtagttacc tctaagacca    1020
agccttaacc cgctcttcct caatccgtaa cgtccttcct cgtcacgaac aaggaggtgt    1080
attcgcagca gaaggatacg ctcgatcctc aggtaatggt tcggaattgg gcgagaagga    1140
gttaggcatt gcaggaagga gcagtgcttg ttcctccaca taagcgtcgt cttcctatgc    1200
gagctaggag tccattacca ggtatctgta tagccacttc aggtcccgga gctacaaatc    1260
tcgttagcgg attagccgat gcgttgttag atagtgttcc tcttgtagca atcacatggt    1320
```

```
ccatagacat atcggtgaag tccagggcct cgatgtttag agcaatcgcc taatcggcta    1380
cgcaacaatc tatcacaagg agaacatcgt tagtgtggac aagtcgctcg tcgtatgatt    1440
ggtacagatg cgtttcaaga gactccgatt gttgaggtaa cgcgttcgat tacgaagcat    1500
aactatcttg tgatggcctg ttcagcgagc agcatactaa ccatgtctac gcaaagttct    1560
ctgaggctaa caactccatt gcgcaagcta atgcttcgta ttgatagaac actaccatgt    1620
tgaagatatc cctaggatta ttgaggaagc tttcttttta gctacttctg gtagacctgg    1680
acctgttttg gttgatgttc ctaaagatat tcaacataca acttctatag ggatcctaat    1740
aactccttcg aaagaaaaat cgatgaagac catctggacc tggacaaaac caactacaag    1800
gatttctata agttgtacag cttgcgattc ctaattggga acaggctatg agattacctg    1860
gttatatgtc taggatgcct aaacctccgg aagattctca tttggagcag attgtttgtc    1920
gaacgctaag gattaaccct tgtccgatac tctaatggac caatatacag atcctacgga    1980
tttgaggcc ttctaagagt aaacctcgtc taacaaaggt tgatttctga gtctaagaag    2040
cctgtgttgt atgttggtgg tggttgtttg aattctagcg atgaattggg taggtttgtt    2100
gagcttacgg ggatcctcca actaaagact cagattcttc ggacacaaca tacaaccacc    2160
accaacaaac ttaagatcgc tacttaaccc atccaaacaa ctcgaatgcc cctaggctgt    2220
tgcgagtacg ttgatggggc tgggatctta tccttgtgat gatgagttgt cgttacatat    2280
gcttggaatg catgggactg tgtatgcaaa ttacgcgaca acgctcatgc aactaccccg    2340
accctagaat aggaacacta ctactcaaca gcaatgtata cgaaccttac gtaccctgac    2400
acatacgttt aatgcgtgtg gagcatagtg atttgttgtt ggcgtttggg gtaaggtttg    2460
atgatcgtgt cacgggtaag cttgaggctt ttgctagtag ggctaagatt gttcatacac    2520
ctcgtatcac taaacaacaa ccgcaaaccc cattccaaac tactagcaca gtgcccattc    2580
gaactccgaa aacgatcatc ccgattctaa caagtaattg atattgactc ggctgagatt    2640
gggaagaata agactcctca tgtgtctgtg tgtggtgatg ttaagctggc tttgcaaggg    2700
atgaatatga ttcttgtaac tataactgag ccgactctaa cccttcttat tctgaggagt    2760
acacagacac acaccactac aattcgaccg aaacgttccc tacttatact aagaacagag    2820
ccgagcggag gagcttaagc ttgatttttgg agtttggagg aatgagttga acgtacagaa    2880
acagaagttt ccgttgagct ttaagacgtt tggggatctc ggctcgcctc ctcgaattcg    2940
aactaaaacc tcaaacctcc ttactcaact tgcatgtctt tgtcttcaaa ggcaactcga    3000
aattctgcaa accccctagct attcctccac agtatgcgat taaggtcctt gatgagttga    3060
ctgatggaaa agccataata agtactggtg tcgggcaaca tcaaatgtgg gcggcgtcga    3120
taaggaggtg tcatacgcta attccaggaa ctactcaact gactaccttt tcggtattat    3180
tcatgaccac agcccgttgt agtttacacc cgccgccagt tctacaatta caagaaacca    3240
aggcagtggc tatcatcagg aggccttgga gctatgggat ttggacttcc tgctgcgatt    3300
ggagcgtctg ttgctagtca agatgttaat gttctttggt tccgtcaccg atagtagtcc    3360
tccggaacct cgatacccta aacctgaagg acgacgctaa cctcgcagac aacgataccc    3420
tgatgcgata gttgtggata ttgacggaga tggaagcttt ataatgaatg tgcaagagct    3480
agccactatt cgtgtagaga atcttccagt gaaggttggg actacgctat caacacctat    3540
aactgcctct accttcgaaa tattacttac acgttctcga tcggtgataa gcacatctct    3600
tagaaggtca cttccaactt ttattaaaca accagcatct tggcatggtt atgcaattgg    3660
```

```
aagatcggtt ctacaaagct aaccgagctc acacatttct cggggatccg gctcagtgaa      3720
aataatttgt tggtcgtaga accgtaccaa tacgttaacc ttctagccaa gatgtttcga      3780
ttggctcgag tgtgtaaaga gcccctaggc cgagtcgagg acgagatatt cccgaacatg      3840
ttgctgtttg cagcagcttg cgggattcca gcggcgaggg tgacaaagaa agcagatctc      3900
cgagaagcta ttcagactcc tgctctataa gggcttgtac aacgacaaac gtcgtcgaac      3960
gccctaaggt cgccgctccc actgtttctt tcgtctagag gctcttcgat aagtctcaat      4020
gctggataca ccaggacctt acctgttgga tgtgatttgt ccgcaccaag aacatgtgtt      4080
gccgatgatc ccgagtggtg gcactttcaa cgatgtgtta cgacctatgt ggtcctggaa      4140
tggacaacct acactaaaca ggcgtggttc ttgtacacaa cggctactag ggctcaccac      4200
cgtgaaagtt gctacacata acggaaggag atggccggat taaatacgta ttgccttcct      4260
ctaccggcct aatttatg                                                   4278

<210> SEQ ID NO 68
<211> LENGTH: 442
<212> TYPE: DNA
<213> ORGANISM: Artificial Sequence
<220> FEATURE:
<223> OTHER INFORMATION: optimized GAT sequence (GAT4601)
<220> FEATURE:
<221> NAME/KEY: CDS
<222> LOCATION: (2)...(442)

<400> SEQUENCE: 68 c atg ata gag gtg aaa ccg att aac gca gag gat acc tat gaa cta agg         49
  Met Ile Glu Val Lys Pro Ile Asn Ala Glu Asp Thr Tyr Glu Leu Arg
  1               5                  10                  15 cat aga ata ctc aga cca aac cag ccg ata gaa gcg tgt atg ttt gaa           97
His Arg Ile Leu Arg Pro Asn Gln Pro Ile Glu Ala Cys Met Phe Glu
            20                  25                  30 agc gat tta ctt cgt ggt gca ttt cac tta ggc ggc ttt tac agg ggc          145
Ser Asp Leu Leu Arg Gly Ala Phe His Leu Gly Gly Phe Tyr Arg Gly
        35                  40                  45 aaa ctg att tcc ata gct tca ttc cac cag gcc gag cac tcg gaa ctc          193
Lys Leu Ile Ser Ile Ala Ser Phe His Gln Ala Glu His Ser Glu Leu
    50                  55                  60 caa ggc cag aaa cag tac cag ctc cga ggt atg gct acc ttg gaa ggt          241
Gln Gly Gln Lys Gln Tyr Gln Leu Arg Gly Met Ala Thr Leu Glu Gly
65                  70                  75                  80 tat cgt gag cag aaa gcg gga tca act cta gtt aaa cac gct gaa gaa          289
Tyr Arg Glu Gln Lys Ala Gly Ser Thr Leu Val Lys His Ala Glu Glu
                85                  90                  95 atc ctt cgt aag agg ggg gcg gac atg ctt tgg tgt aat gcg agg aca          337
Ile Leu Arg Lys Arg Gly Ala Asp Met Leu Trp Cys Asn Ala Arg Thr
            100                 105                 110 tcc gcc tca ggc tac tac aaa aag tta ggc ttc agc gag cag gga gag          385
Ser Ala Ser Gly Tyr Tyr Lys Lys Leu Gly Phe Ser Glu Gln Gly Glu
        115                 120                 125 ata ttt gac acg ccg cca gta gga cct cac atc ctg atg tat aaa agg          433
Ile Phe Asp Thr Pro Pro Val Gly Pro His Ile Leu Met Tyr Lys Arg
    130                 135                 140 atc aca taa                                                              442
Ile Thr *
145

<210> SEQ ID NO 69
<211> LENGTH: 146
<212> TYPE: PRT
```

<213> ORGANISM: Artificial Sequence
<220> FEATURE:
<223> OTHER INFORMATION: :

<400> SEQUENCE: 69

```
Met Ile Glu Val Lys Pro Ile Asn Ala Glu Asp Thr Tyr Glu Leu Arg
1               5                   10                  15

His Arg Ile Leu Arg Pro Asn Gln Pro Ile Glu Ala Cys Met Phe Glu
            20                  25                  30

Ser Asp Leu Leu Arg Gly Ala Phe His Leu Gly Gly Phe Tyr Arg Gly
        35                  40                  45

Lys Leu Ile Ser Ile Ala Ser Phe His Gln Ala Glu His Ser Glu Leu
    50                  55                  60

Gln Gly Gln Lys Gln Tyr Gln Leu Arg Gly Met Ala Thr Leu Glu Gly
65                  70                  75                  80

Tyr Arg Glu Gln Lys Ala Gly Ser Thr Leu Val Lys His Ala Glu Glu
                85                  90                  95

Ile Leu Arg Lys Arg Gly Ala Asp Met Leu Trp Cys Asn Ala Arg Thr
            100                 105                 110

Ser Ala Ser Gly Tyr Tyr Lys Lys Leu Gly Phe Ser Glu Gln Gly Glu
        115                 120                 125

Ile Phe Asp Thr Pro Pro Val Gly Pro His Ile Leu Met Tyr Lys Arg
    130                 135                 140

Ile Thr
145
```

<210> SEQ ID NO 70
<211> LENGTH: 441
<212> TYPE: DNA
<213> ORGANISM: Artificial Sequence
<220> FEATURE:
<223> OTHER INFORMATION: optimized GAT sequence (GAT4602)
<220> FEATURE:
<221> NAME/KEY: CDS
<222> LOCATION: (1)...(441)

<400> SEQUENCE: 70

```
atg ata gag gtg aaa ccg att aac gca gag gat acc tat gaa cta agg      48
Met Ile Glu Val Lys Pro Ile Asn Ala Glu Asp Thr Tyr Glu Leu Arg
1               5                   10                  15 cat aga ata ctc aga cca aac cag ccg ata gaa gcg tgt atg ttt gaa      96
His Arg Ile Leu Arg Pro Asn Gln Pro Ile Glu Ala Cys Met Phe Glu
            20                  25                  30 agc gat tta ctt cgt ggt gca ttt cac tta ggc ggc tat tac ggg ggc     144
Ser Asp Leu Leu Arg Gly Ala Phe His Leu Gly Gly Tyr Tyr Gly Gly
        35                  40                  45 aaa ctg att tcc ata gct tca ttc cac cag gcc gag cac tca gaa ctc     192
Lys Leu Ile Ser Ile Ala Ser Phe His Gln Ala Glu His Ser Glu Leu
    50                  55                  60 caa ggc cag aaa cag tac cag ctc cga ggt atg gct acc ttg gaa ggt     240
Gln Gly Gln Lys Gln Tyr Gln Leu Arg Gly Met Ala Thr Leu Glu Gly
65                  70                  75                  80 tat cgt gag cag aag gcg gga tcg agt cta att aaa cac gct gaa gaa     288
Tyr Arg Glu Gln Lys Ala Gly Ser Ser Leu Ile Lys His Ala Glu Glu
                85                  90                  95 att ctt cgt aag agg ggg gcg gac ttg ctt tgg tgt aat gcg cgg aca     336
Ile Leu Arg Lys Arg Gly Ala Asp Leu Leu Trp Cys Asn Ala Arg Thr
            100                 105                 110 tcc gcc tca ggc tac tac aaa aag tta ggc ttc agc gag cag gga gag     384
Ser Ala Ser Gly Tyr Tyr Lys Lys Leu Gly Phe Ser Glu Gln Gly Glu
```

```
                115              120                125
gta ttc gac acg ccg cca gta gga cct cac atc ctg atg tat aaa agg    432
Val Phe Asp Thr Pro Pro Val Gly Pro His Ile Leu Met Tyr Lys Arg
    130                 135                140 atc aca taa                                                        441
Ile Thr *
145

<210> SEQ ID NO 71
<211> LENGTH: 146
<212> TYPE: PRT
<213> ORGANISM: Artificial Sequence
<220> FEATURE:
<223> OTHER INFORMATION: :

<400> SEQUENCE: 71

Met Ile Glu Val Lys Pro Ile Asn Ala Glu Asp Thr Tyr Glu Leu Arg
  1               5                  10                  15

His Arg Ile Leu Arg Pro Asn Gln Pro Ile Glu Ala Cys Met Phe Glu
             20                  25                  30

Ser Asp Leu Leu Arg Gly Ala Phe His Leu Gly Gly Tyr Tyr Gly Gly
         35                  40                  45

Lys Leu Ile Ser Ile Ala Ser Phe His Gln Ala Glu His Ser Glu Leu
     50                  55                  60

Gln Gly Gln Lys Gln Tyr Gln Leu Arg Gly Met Ala Thr Leu Glu Gly
 65                  70                  75                  80

Tyr Arg Glu Gln Lys Ala Gly Ser Ser Leu Ile Lys His Ala Glu Glu
                 85                  90                  95

Ile Leu Arg Lys Arg Gly Ala Asp Leu Leu Trp Cys Asn Ala Arg Thr
            100                 105                 110

Ser Ala Ser Gly Tyr Tyr Lys Lys Leu Gly Phe Ser Glu Gln Gly Glu
        115                 120                 125

Val Phe Asp Thr Pro Pro Val Gly Pro His Ile Leu Met Tyr Lys Arg
    130                 135                 140

Ile Thr
145

<210> SEQ ID NO 72
<211> LENGTH: 438
<212> TYPE: DNA
<213> ORGANISM: cauliflower mosaic virus
<220> FEATURE:
<221> NAME/KEY: enhancer
<222> LOCATION: (0)...(0)
<223> OTHER INFORMATION: 35S enhancer

<400> SEQUENCE: 72
cccatggagt caaagattca aatagaggac ctaacagaac tcgccgtaaa gactggcgaa     60
cagttcatac agagtctctt acgactcaat gacaagaaga aaatcttcgt caacatggtg    120
gagcacgaca cgcttgtcta ctccaaaaat atcaaagata cagtctcaga agaccaaagg    180
gcaattgaga cttttcaaca aagggtaata tccggaaacc tcctcggatt ccattgccca    240
gctatctgtc actttattgt gaagatagtg gaaaaggaag gtggctccta caaatgccat    300
cattgcgata aaggaaaggc catcgttgaa gatgcctctg ccgacagtgg tcccaaagat    360
ggacccccac ccacgaggag catcgtggaa aaagaagacg ttccaaccac gtcttcaaag    420
caagtggatt gatgtgat                                                  438
```

```
<210> SEQ ID NO 73
<211> LENGTH: 534
<212> TYPE: DNA
<213> ORGANISM: cauliflower mosaic virus
<220> FEATURE:
<221> NAME/KEY: promoter
<222> LOCATION: (0)...(0)
<223> OTHER INFORMATION: S35 enhancer with minimial core promoter

<400> SEQUENCE: 73
cccatggagt caaagattca atagaggac ctaacagaac tcgccgtaaa gactggcgaa      60
cagttcatac agagtctctt acgactcaat gacaagaaga aaatcttcgt caacatggtg    120
gagcacgaca cgcttgtcta ctccaaaaat atcaaagata cagtctcaga agaccaaagg    180
gcaattgaga cttttcaaca aagggtaata tccggaaacc tcctcggatt ccattgccca    240
gctatctgtc actttattgt gaagatagtg gaaaggaag gtggctccta caaatgccat    300
cattgcgata aaggaaaggc catcgttgaa gatgcctctg ccgacagtgg tcccaaagat    360
ggacccccac ccacgaggag catcgtggaa aaagaagacg ttccaaccac gtcttcaaag    420
caagtggatt gatgtgatat ctccactgac gtaagggatg acgcacaatc ccactaagct    480
tcgcaagacc cttcctctat ataaggaagt tcatttcatt tggagaggac aggg          534

<210> SEQ ID NO 74
<211> LENGTH: 52
<212> TYPE: DNA
<213> ORGANISM: cauliflower mosaic virus
<220> FEATURE:
<221> NAME/KEY: promoter
<222> LOCATION: (0)...(0)
<223> OTHER INFORMATION: mimimal core promoter

<400> SEQUENCE: 74
gcaagaccct tcctctatat aaggaagttc atttcatttg gagaggacag gg             52

<210> SEQ ID NO 75
<211> LENGTH: 162
<212> TYPE: DNA
<213> ORGANISM: cauliflower mosaic virus

<400> SEQUENCE: 75
catcgttgaa gatgcctctg ccgacagtgg tcccaaagat ggacccccac ccacgaggag     60
catcgtggaa aaagaagacg ttccaaccac gtcttcaaag caagtggatt gatgtgatat    120
ctccactgac gtaagggatg acgcacaatc ccactaagct tc                       162

<210> SEQ ID NO 76
<211> LENGTH: 44
<212> TYPE: DNA
<213> ORGANISM: cauliflower mosaic virus

<400> SEQUENCE: 76
atctccactg acgtaaggga tgacgcacaa tcccactaag cttc                      44

<210> SEQ ID NO 77
<211> LENGTH: 1991
<212> TYPE: DNA
<213> ORGANISM: Artificial Sequence
<220> FEATURE:
<223> OTHER INFORMATION: promoter sequence comprising ZmUBI
      PRO-5'UTR-ZMUBI INTRON 1

<400> SEQUENCE: 77
gcagtgcagc gtgacccggt cgtgcccctc tctagagata atgagcattg catgtctaag     60
```

-continued

| | |
|---|---|
| ttataaaaaa ttaccacata ttttttttgt cacacttgtt tgaagtgcag tttatctatc | 120 |
| tttatacata tatttaaact ttactctacg aataatataa tctatagtac tacaataata | 180 |
| tcagtgtttt agagaatcat ataaatgaac agttagacat ggtctaaagg acaattgagt | 240 |
| attttgacaa caggactcta cagttttatc tttttagtgt gcatgtgttc tccttttttt | 300 |
| ttgcaaatag cttcacctat ataatacttc atccatttta ttagtacatc catttagggt | 360 |
| ttagggttaa tggtttttat agactaattt ttttagtaca tctattttat tctattttag | 420 |
| cctctaaatt aagaaaacta aaactctatt ttagtttttt tatttaataa tttagatata | 480 |
| aaatagaata aaataaagtg actaaaaatt aaacaaatac cctttaagaa attaaaaaaa | 540 |
| ctaaggaaac atttttcttg tttcgagtag ataatgccag cctgttaaac gccgtcgacg | 600 |
| agtctaacgg acaccaacca gcgaaccagc agcgtcgcgt cgggccaagc gaagcagacg | 660 |
| gcacggcatc tctgtcgctg cctctggacc cctctcgaga gttccgctcc accgttggac | 720 |
| ttgctccgct gtcggcatcc agaaattgcg tggcggagcg gcagacgtga gccggcacgg | 780 |
| caggcggcct cctcctcctc tcacggcacc ggcagctacg ggggattcct ttcccaccgc | 840 |
| tccttcgctt tcccttcctc gcccgccgta ataaatagac acccctcca caccctcttt | 900 |
| ccccaacctc gtgttgttcg gagcgcacac acacacaacc agatctcccc caaatccacc | 960 |
| cgtcggcacc tccgcttcaa ggtacgccgc tcgtcctccc ccccccccct ctctaccttc | 1020 |
| tctagatcgg cgttccggtc catggttagg gcccggtagt tctacttctg ttcatgtttg | 1080 |
| tgttagatcc gtgtttgtgt tagatccgtg ctgctagcgt tcgtacacgg atgcgacctg | 1140 |
| tacgtcagac acgttctgat tgctaacttg ccagtgtttc tctttgggga atcctgggat | 1200 |
| ggctctagcc gttccgcaga cgggatcgat ttcatgattt tttttgtttc gttgcatagg | 1260 |
| gtttggtttg ccctttttcct ttatttcaat atatgccgtg cacttgtttg tcgggtcatc | 1320 |
| ttttcatgct ttttttttgtc ttggttgtga tgatgtggtc tggttgggcg gtcgttctag | 1380 |
| atcggagtag aattctgttt caaactacct ggtggattta ttaattttgg atctgtatgt | 1440 |
| gtgtgccata catattcata gttacgaatt gaagatgatg gatggaaata tcgatctagg | 1500 |
| ataggtatac atgttgatgc gggttttact gatgcatata cagagatgct ttttgttcgc | 1560 |
| ttggttgtga tgatgtggtg tggttgggcg gtcgttcatt cgttctagat cggagtagaa | 1620 |
| tactgtttca aactacctgg tgtatttatt aattttggaa ctgtatgtgt gtgtcataca | 1680 |
| tcttcatagt tacgagttta agatggatgg aaatatcgat ctaggatagg tatacatgtt | 1740 |
| gatgtgggtt ttactgatgc atatacatga tggcatatgc agcatctatt catatgctct | 1800 |
| aaccttgagt acctatctat tataataaac aagtatgttt tataattatt ttgatcttga | 1860 |
| tatacttgga tgatggcata tgcagcagct atatgtggat ttttttagcc ctgccttcat | 1920 |
| acgctattta tttgcttggt actgtttctt ttgtcgatgc tcaccctgtt gtttggtgtt | 1980 |
| acttctgcag g | 1991 |

<210> SEQ ID NO 78
<211> LENGTH: 3359
<212> TYPE: DNA
<213> ORGANISM: Artificial Sequence
<220> FEATURE:
<223> OTHER INFORMATION: 3X35S ENH operbably linked to the ZmUbi
    PRO-5UTR-ZmUbi intron 1 promoter ; 35S enhancer in
    the reverse direction

<400> SEQUENCE: 78

```
atcacatcaa tccacttgct ttgaagacgt ggttggaacg tcttctttt ccacgatgct        60
cctcgtgggt gggggtccat ctttgggacc actgtcggca gaggcatctt caacgatggc      120
ctttccttta tcgcaatgat ggcatttgta ggagccacct tccttttcca ctatcttcac      180
aataaagtga cagatagctg ggcaatggaa tccgaggagg tttccggata ttaccctttg      240
ttgaaaagtc tcaattgccc tttggtcttc tgagactgta tctttgatat ttttggagta      300
gacaagcgtg tcgtgctcca ccatgttgac gaagattttc ttcttgtcat tgagtcgtaa      360
gagactctgt atgaactgtt cgccagtctt tacggcgagt tctgttaggt cctctatttg      420
aatctttgac tccatggacg gtatcgataa gctagcttga tatcacatca atccacttgc      480
tttgaagacg tggttggaac gtcttctttt ccacgatgc tcctcgtggg tgggggtcca       540
tctttgggac cactgtcggc agaggcatct tcaacgatgg cctttccttt atcgcaatga      600
tggcatttgt aggagccacc ttccttttcc actatcttca aataaagtg acagatagct       660
gggcaatgga atccgaggag gtttccggat attacccttt gttgaaaagt ctcaattgcc      720
ctttggtctt ctgagactgt atctttgata ttttggagt agacaagcgt gtcgtgctcc       780
accatgttga cgaagatttt cttcttgtca ttgagtcgta agagactctg tatgaactgt      840
tcgccagtct ttacggcgag ttctgttagg tcctctattt gaatctttga ctccatgatc      900
gaattatcac atcaatccac ttgctttgaa gacgtggttg gaacgtcttc ttttccacg       960
atgctcctcg tgggtggggg tccatctttg gaccactgt cggcagaggc atcttcaacg      1020
atggcctttc ctttatcgca atgatggcat ttgtaggagc caccttcctt ttccactatc     1080
ttcacaataa agtgacagat agctgggcaa tggaatccga ggaggtttcc ggatattacc     1140
ctttgttgaa aagtctcaat tgcccttt gg tcttctgaga ctgtatcttt gatattttg     1200
gagtagacaa gcgtgtcgtg ctccaccatg ttgacgaaga ttttcttctt gtcattgagt     1260
cgtaagagac tctgtatgaa ctgttcgcca gtctttacgg cgagttctgt taggtcctct     1320
atttgaatct ttgactccat gggaattcct gcagcccagc ttgcatgcct gcagtgcagc     1380
gtgacccggt cgtgcccctc tctagagata atgagcattg catgtctaag ttataaaaaa     1440
ttaccacata ttttttttgt cacacttgtt tgaagtgcag tttatctatc tttatacata     1500
tatttaaact ttactctacg aataatataa tctatagtac tacaataata tcagtgtttt     1560
agagaatcat ataaatgaac agttagacat ggtctaaagg acaattgagt attttgacaa     1620
caggactcta cagttttatc ttttttagtgt gcatgtgttc tccttttttt ttgcaaatag     1680
cttcacctat ataatacttc atccatttta ttagtacatc catttagggt ttagggttaa     1740
tggttttttat agactaattt ttttagtaca tctattttat tctattttag cctctaaatt     1800
aagaaaacta aaactctatt ttagtttttt tatttaataa tttagatata aaatagaata     1860
aaataaagtg actaaaaatt aaacaaatac cctttaagaa attaaaaaaa ctaaggaaac     1920
attttttcttg tttcgagtag ataatgccag cctgttaaac gccgtcgacg agtctaacgg     1980
acaccaacca gcgaaccagc agcgtcgcgt cgggccaagc gaagcagacg gcacggcatc     2040
tctgtcgctg cctctggacc cctctcgaga gttccgctcc accgttggac ttgctccgct     2100
gtcggcatcc agaaattgcg tggcggagcg gcagacgtga gccggcacgg caggcggcct     2160
cctcctcctc tcacgcacc ggcagctacg ggggattcct ttcccaccgc tccttcgctt      2220
tcccttcctc gcccgccgta taaatagac accccctcca caccctcttt ccccaacctc      2280
gtgttgttcg gagcgcacac acacacaacc agatctcccc caaatccacc cgtcggcacc     2340
tccgcttcaa ggtacgccgc tcgtcctccc ccccccccct ctctaccttc tctagatcgg     2400
```

```
cgttccggtc catggttagg gcccggtagt tctacttctg ttcatgtttg tgttagatcc    2460
gtgtttgtgt tagatccgtg ctgctagcgt tcgtacacgg atgcgacctg tacgtcagac    2520
acgttctgat tgctaacttg ccagtgtttc tctttgggga atcctgggat ggctctagcc    2580
gttccgcaga cgggatcgat ttcatgattt tttttgtttc gttgcatagg gtttggtttg    2640
cccttttcct ttatttcaat atatgccgtg cacttgtttg tcgggtcatc ttttcatgct    2700
tttttttgtc ttggttgtga tgatgtggtc tggttgggcg tcgttctag atcggagtag    2760 aattctgttt caaactacct ggtggattta ttaattttgg atctgtatgt gtgtgccata    2820
catattcata gttacgaatt gaagatgatg gatggaaata tcgatctagg ataggtatac    2880
atgttgatgc gggttttact gatgcatata cagagatgct ttttgttcgc ttggttgtga    2940
tgatgtggtg tggttgggcg tcgttcatt cgttctagat cggagtagaa tactgtttca    3000
aactacctgg tgtatttatt aattttggaa ctgtatgtgt gtgtcataca tcttcatagt    3060
tacgagttta agatggatgg aaatatcgat ctaggatagg tatacatgtt gatgtgggtt    3120
ttactgatgc atatacatga tggcatatgc agcatctatt catatgctct aaccttgagt    3180
acctatctat tataataaac aagtatgttt tataattatt ttgatcttga tatacttgga    3240
tgatggcata tgcagcagct atatgtggat ttttttagcc ctgccttcat acgctattta    3300
tttgcttggt actgtttctt ttgtcgatgc tcaccctgtt gtttggtgtt acttctgca    3359

<210> SEQ ID NO 79
<211> LENGTH: 1343
<212> TYPE: DNA
<213> ORGANISM: cauliflower mosaic virus
<220> FEATURE:
<221> NAME/KEY: enhancer
<222> LOCATION: (0)...(0)
<223> OTHER INFORMATION: 35S ehancer 3X in reverse direction

<400> SEQUENCE: 79
atcacatcaa tccacttgct ttgaagacgt ggttggaacg tcttcttttt ccacgatgct      60
cctcgtgggt gggggtccat ctttgggacc actgtcggca gaggcatctt caacgatggc    120
ctttccttta tcgcaatgat ggcatttgta ggagccacct tccttttcca ctatcttcac    180
aataaagtga cagatagctg gcaatgaa tccgaggagg tttccggata ttacccttg      240 ttgaaaagtc tcaattgccc tttggtcttc tgagactgta tctttgatat ttttggagta    300
gacaagcgtg tcgtgctcca ccatgttgac gaagattttc ttcttgtcat tgagtcgtaa    360
gagactctgt atgaactgtt cgccagtctt tacggcgagt tctgttaggt cctctatttg    420
aatctttgac tccatggacg gtatcgataa gctagcttga tatcacatca atccacttgc    480
tttgaagacg tggttggaac gtcttctttt tccacgatgc tcctcgtggg tgggggtcca    540
tctttgggac cactgtcggc agaggcatct tcaacgatgg cctttccttt atcgcaatga    600
tggcatttgt aggagccacc ttccttttcc actatcttca aataaagtg acagatagct    660 gggcaatgga atccgaggag gtttccggat tacccttt gttgaaaagt ctcaattgcc    720
ctttggtctt ctgagactgt atctttgata ttttggagt agacaagcgt gtcgtgctcc    780
accatgttga cgaagattt cttcttgtca ttgagtcgta agagactctg tatgaactgt    840
tcgccagtct ttacggcgag ttctgttagg tcctctattt gaatctttga ctccatgatc    900
gaattatcac atcaatccac ttgctttgaa gacgtggttg aacgtcttc ttttccacg    960 atgctcctcg tgggtggggg tccatctttg ggaccactgt cggcagaggc atcttcaacg   1020
```

```
atggccttc ctttatcgca atgatggcat ttgtaggagc caccttcctt ttccactatc    1080
ttcacaataa agtgacagat agctgggcaa tggaatccga ggaggtttcc ggatattacc    1140
ctttgttgaa aagtctcaat tgcccttttgg tcttctgaga ctgtatcttt gatatttttg   1200
gagtagacaa gcgtgtcgtg ctccaccatg ttgacgaaga ttttcttctt gtcattgagt    1260
cgtaagagac tctgtatgaa ctgttcgcca gtctttacgg cgagttctgt taggtcctct    1320
atttgaatct ttgactccat ggg                                            1343
```

<210> SEQ ID NO 80  
<211> LENGTH: 2479  
<212> TYPE: DNA  
<213> ORGANISM: Artificial Sequence  
<220> FEATURE:  
<223> OTHER INFORMATION: 35S ENH(+):ZmUBI PRO-5UTR-UBI INTRON1 ; 35S enhancer in the forward direction

<400> SEQUENCE: 80

```
cccatggagt caaagattca aatagaggac ctaacagaac tcgccgtaaa gactggcgaa     60
cagttcatac agagtctctt acgactcaat gacaagaaga aaatcttcgt caacatggtg    120
gagcacgaca cgcttgtcta ctccaaaaat atcaaagata cagtctcaga agaccaaagg    180
gcaattgaga cttttcaaca aagggtaata tccggaaacc cctcggatt ccattgccca     240 gctatctgtc actttattgt gaagatagtg gaaaaggaag gtggctccta caaatgccat    300
cattgcgata aaggaaaggc catcgttgaa gatgcctctg ccgacagtgg tcccaaagat    360
ggacccccac ccacgaggag catcgtggaa aagaagacg ttccaaccac gtcttcaaag     420
caagtggatt gatgtgatat caagcttatc gataccgtcg acctcgaggg ggggcccagc    480
ttgcatgcct gcagtgcagc gtgacccggt cgtgccctc tctagagata atgagcattg     540
catgtctaag ttataaaaaa ttaccacata ttttttttgt cacacttgtt tgaagtgcag    600
tttatctatc tttatacata tatttaaact ttactctacg aataatataa tctatagtac    660
tacaataata tcagtgtttt agagaatcat ataaatgaac agttagacat ggtctaaagg    720
acaattgagt attttgacaa caggactcta cagtttatc tttttagtgt gcatgtgttc     780 tcctttttt ttgcaaatag cttcacctat ataatacttc atccatttta ttagtacatc     840
catttagggt ttagggttaa tggtttttat agactaattt ttttagtaca tctattttat    900 tctatttttag cctctaaatt aagaaaacta aaactctatt ttagtttttt tatttaataa    960
tttagatata aaatagaata aaataaagtg actaaaaatt aaacaaatac cctttaagaa   1020
attaaaaaaa ctaaggaaac attttttcttg tttcgagtag ataatgccag cctgttaaac   1080
gccgtcgacg agtctaacgg acaccaacca gcgaaccagc agcgtcgcgt cgggccaagc   1140
gaagcagacg gcacggcatc tctgtcgctg cctctggacc cctctcgaga gttccgctcc   1200
accgttggac ttgctccgct gtcggcatcc agaaattgcg tggcggagcg cagacgtga    1260 gccggcacgg caggcggcct cctcctcctc tcacggcacc ggcagctacg ggggattcct   1320
ttcccaccgc tccttcgctt tcccttcctc gcccgccgta taaatagac ccccctcca     1380 caccctcttt ccccaacctc gtgttgttcg gagcgcacac acacacaacc agatctcccc   1440
caaatccacc cgtcggcacc tccgcttcaa ggtacgccgc tcgtcctccc cccccccct    1500 ctctaccttc tctagatcgg cgttccggtc catggttagg gccggtagt tctacttctg   1560 ttcatgtttg tgttagatcc gtgtttgtgt tagatccgtg ctgctagcgt tcgtacacgg   1620
atgcgacctg tacgtcagac acgttctgat tgctaacttg ccagtgtttc tctttgggga   1680
```

```
atcctgggat ggctctagcc gttccgcaga cgggatcgat ttcatgattt tttttgtttc    1740
gttgcatagg gtttggtttg ccctttctcc tttatttcaat atatgccgtg cacttgtttg    1800
tcgggtcatc ttttcatgct ttttttttgtc ttggttgtga tgatgtggtc tggttgggcg    1860
gtcgttctag atcggagtag aattctgttt caaactacct ggtggattta ttaattttgg    1920
atctgtatgt gtgtgccata catattcata gttacgaatt gaagatgatg gatggaaata    1980
tcgatctagg ataggtatac atgttgatgc gggttttact gatgcatata cagagatgct    2040
ttttgttcgc ttggttgtga tgatgtggtg tggttgggcg gtcgttcatt cgttctagat    2100
cggagtagaa tactgtttca aactacctgg tgtatttatt aattttggaa ctgtatgtgt    2160
gtgtcataca tcttcatagt tacgagttta agatggatgg aaatatcgat ctaggatagg    2220
tatacatgtt gatgtgggtt ttactgatgc atatacatga tggcatatgc agcatctatt    2280
catatgctct aaccttgagt acctatctat tataataaac aagtatgttt tataattatt    2340
ttgatcttga tacttggaa tgatggcata tgcagcagct atatgtggat tttttagcc    2400 ctgccttcat acgctattta tttgcttggt actgtttctt ttgtcgatgc tcaccctgtt    2460
gtttggtgtt acttctgca                                                  2479
```

<210> SEQ ID NO 81
<211> LENGTH: 3331
<212> TYPE: DNA
<213> ORGANISM: Artificial Sequence
<220> FEATURE:
<223> OTHER INFORMATION: 3X35S ENH (+):ZmUBI PRO-5UTR-UBI INTRON1; 35S enhancer in the forward direction

<400> SEQUENCE: 81

```
cccatggagt caaagattca aatagaggac ctaacagaac tcgccgtaaa gactggcgaa      60
cagttcatac agagtctctt acgactcaat gacaagaaga aaatcttcgt caacatggtg     120
gagcacgaca cgcttgtcta ctccaaaaat atcaaagata cagtctcaga agaccaaagg     180
gcaattgaga cttttcaaca aagggtaata tccggaaacc tcctcggatt ccattgccca     240
gctatctgtc actttattgt gaagatagtg gaaaaggaag gtggctccta caaatgccat     300
cattgcgata aaggaaaggc catcgttgaa gatgcctctg ccgacagtgg tcccaaagat     360
ggacccccac ccacgaggag catcgtggaa aagaagacg ttccaaccac gtcttcaaag     420
caagtggatt gatgtgataa ttcgatcatg gagtcaaaga ttcaaataga ggacctaaca     480
gaactcgccg taaagactgg cgaacagttc atacagagtc tcttacgact caatgacaag     540
aagaaaatct tcgtcaacat ggtggagcac gacacgcttg tctactccaa aaatatcaaa     600
gatacagtct cagaagacca aagggcaatt gagactttc aacaaagggt aatatccgga     660
aacctcctcg gattccattg cccagctatc tgtcacttta ttgtgaagat agtggaaaag     720
gaaggtggct cctacaaatg ccatcattgc gataaaggaa aggccatcgt tgaagatgcc     780
tctgccgaca gtggtcccaa agatggaccc ccacccacga ggagcatcgt ggaaaaagaa     840
gacgttccaa ccacgtcttc aaagcaagtg gattgatgtg atatcaagct tatcgatacc     900
gccatggagt caaagattca aatagaggac ctaacagaac tcgccgtaaa gactggcgaa     960
cagttcatac agagtctctt acgactcaat gacaagaaga aaatcttcgt caacatggtg    1020
gagcacgaca cgcttgtcta ctccaaaaat atcaaagata cagtctcaga agaccaaagg    1080
gcaattgaga cttttcaaca aagggtaata tccggaaacc tcctcggatt ccattgccca    1140
gctatctgtc actttattgt gaagatagtg gaaaaggaag gtggctccta caaatgccat    1200
```

```
cattgcgata aaggaaaggc catcgttgaa gatgcctctg ccgacagtgg tcccaaagat    1260 ggaccccccac ccacgaggag catcgtggaa aaagaagacg ttccaaccac gtcttcaaag   1320
caagtggatt gatgtgatgt ctgcagtgca gcgtgacccg tcgtgcccc tctctagaga    1380 taatgagcat tgcatgtcta agttataaaa aattaccaca tattttttt gtcacacttg    1440 tttgaagtgc agtttatcta tctttataca tatatttaaa ctttactcta cgaataatat   1500
aatctatagt actacaataa tatcagtgtt ttagagaatc atataaatga acagttagac   1560
atggtctaaa ggacaattga gtattttgac aacaggactc tacagtttta tcttttagt   1620 gtgcatgtgt tctccttttt ttttgcaaat agcttcacct atataatact tcatccattt   1680
tattagtaca tccatttagg gtttagggtt aatggttttt atagactaat ttttttagta   1740
catctatttt attctatttt agcctctaaa ttaagaaaac taaaactcta ttttagtttt   1800
tttatttaat aatttagata taaaatagaa taaaataaag tgactaaaaa ttaaacaaat   1860 acccttaag aaattaaaaa aactaaggaa acattttct tgtttcgagt agataatgcc     1920
agcctgttaa acgccgtcga cgagtctaac ggacaccaac cagcgaacca gcagcgtcgc   1980
gtcgggccaa gcgaagcaga cggcacggca tctctgtcgc tgcctctgga cccctctcga   2040
gagttccgct ccaccgttgg acttgctccg ctgtcggcat ccagaaattg cgtggcggag   2100
cggcagacgt gagccggcac ggcaggcggc ctcctcctcc tctcacggca ccggcagcta   2160
cgggggattc ctttcccacc gctccttcgc tttcccttcc tcgcccgccg taataaatag   2220
acaccccctc cacccctct ttccccaacc tcgtgttgtt cggagcgcac acacacacaa    2280
ccagatctcc cccaaatcca cccgtcggca cctccgcttc aaggtacgcc gctcgtcctc   2340
cccccccccc ctctctacct tctctagatc ggcgttccgg tccatggtta gggcccggta   2400
gttctacttc tgttcatgtt tgtgttagat ccgtgtttgt gttagatccg tgctgctagc   2460
gttcgtacac ggatgcgacc tgtacgtcag acacgttctg attgctaact tgccagtgtt   2520
tctctttggg gaatcctggg atggctctag ccgttccgca gacgggatcg atttcatgat   2580 ttttttttgtt tcgttgcata gggtttggtt tgcccttttc ctttatttca atatatgccg   2640
tgcacttgtt tgtcgggtca tcttttcatg cttttttttg tcttggttgt gatgatgtgg   2700
tctggttggg cggtcgttct agatcggagt agaattctgt ttcaaactac ctggtggatt   2760
tattaatttt ggatctgtat gtgtgtgcca tacatattca tagttacgaa ttgaagatga   2820
tggatggaaa tatcgatcta ggataggtat acatgttgat gcgggttta ctgatgcata   2880 tacagagatg cttttttgttc gcttggttgt gatgatgtgg tgtggttggg cggtcgttca   2940
ttcgttctag atcggagtag aatactgttt caaactacct ggtgtattta ttaattttgg   3000
aactgtatgt gtgtgtcata catcttcata gttacgagtt taagatggat ggaaatatcg   3060
atctaggata ggtatacatg ttgatgtggg ttttactgat gcatatacat gatggcatat   3120
gcagcatcta ttcatatgct ctaaccttga gtacctatct attataataa acaagtatgt   3180
tttataatta ttttgatctt gatatacttg gatgatggca tatgcagcag ctatatgtgg   3240 attttttttag ccctgccttc atacgctatt tatttgcttg gtactgtttc ttttgtcgat   3300
gctcaccctg ttgtttggtg ttacttctgc a                                  3331
```

<210> SEQ ID NO 82
<211> LENGTH: 2454
<212> TYPE: DNA
<213> ORGANISM: Artificial Sequence
<220> FEATURE:
<223> OTHER INFORMATION: 35S ENH (-):ZmUBI PRO-5UTR-UBI INTRON1 ; 35S enhancer in the reverse direction

<400> SEQUENCE: 82

```
atcacatcaa tccacttgct ttgaagacgt ggttggaacg tcttcttttt ccacgatgct      60
cctcgtgggt gggggtccat ctttgggacc actgtcggca gaggcatctt caacgatggc     120
ctttcccttta tcgcaatgat ggcatttgta ggagccacct tccttttcca ctatcttcac    180
aataaagtga cagatagctg ggcaatggaa tccgaggagg tttccggata ttaccctttg     240
ttgaaaagtc tcaattgccc tttggtcttc tgagactgta tctttgatat ttttggagta     300
gacaagcgtg tcgtgctcca ccatgttgac gaagattttc ttcttgtcat tgagtcgtaa     360
gagactctgt atgaactgtt cgccagtctt tacggcgagt tctgttaggt cctctatttg     420
aatctttgac tccatgggaa ttcctgcagc ccagcttgca tgcctgcagt gcagcgtgac     480
ccggtcgtgc ccctctctag agataatgag cattgcatgt ctaagttata aaaaattacc     540
acatatttt tttgtcacac ttgtttgaag tgcagtttat ctatctttat acatatattt      600
aaactttact ctacgaataa tataatctat agtactacaa taatatcagt gttttagaga     660
atcatataaa tgaacagtta gacatggtct aaaggacaat tgagtatttt gacaacagga     720
ctctacagtt ttatctttt agtgtgcatg tgttctcctt tttttttgca aatagcttca      780
cctatataat acttcatcca tttttattagt acatccattt aggggtttagg gttaatggtt   840
tttatagact aatttttttta gtacatctat tttattctat tttagcctct aaattaagaa    900
aactaaaact ctattttagt ttttttattt aataatttag atataaaata gaataaaata     960
aagtgactaa aaattaaaca aatacccttt aagaaattaa aaaaactaag gaaacatttt    1020
tcttgtttcg agtagataat gccagcctgt taaacgccgt cgacgagtct aacggacacc    1080
aaccagcgaa ccagcagcgt cgcgtcgggc caagcgaagc agacggcacg gcatctctgt    1140
cgctgcctct ggacccctct cgagagttcc gctccaccgt tggacttgct ccgctgtcgg    1200
catccagaaa ttgcgtggcg gagcggcaga cgtgagccgg cacggcaggc ggcctcctcc    1260
tcctctcacg gcaccggcag ctacggggga ttcctttccc accgctcctt cgctttccct    1320
tcctcgcccg ccgtaataaa tagacacccc ctccacaccc tctttcccca acctcgtgtt    1380
gttcggagcg cacacacaca caaccagatc tcccccaaat ccacccgtcg gcacctccgc    1440
ttcaaggtac gccgctcgtc ctcccccccc cccctctcta ccttctctag atcggcgttc    1500
cggtccatgg ttagggcccg gtagttctac ttctgttcat gtttgtgtta gatccgtgtt    1560
tgtgttagat ccgtgctgct agcgttcgta cacggatgcg acctgtacgt cagacacgtt    1620
ctgattgcta acttgccagt gtttctcttt ggggaatcct gggatggctc tagccgttcc    1680
gcagacggga tcgatttcat gattttttttt gtttcgttgc atagggtttg gtttgccctt    1740
ttcctttatt tcaatatatg ccgtgcactt gtttgtcggg tcatcttttc atgctttttt    1800
ttgtcttggt tgtgatgatg tggtctggtt gggcggtcgt tctagatcgg agtagaattc    1860
tgtttcaaac tacctggtgg atttattaat tttggatctg tatgtgtgtg ccatacatat    1920
tcatagttac gaattgaaga tgatggatgg aaatatcgat ctaggatagg tatacatgtt    1980
gatgcgggtt ttactgatgc atatacagag atgcttttttg ttcgcttggt tgtgatgatg   2040
tggtgtggtt gggcggtcgt tcattcgttc tagatcggag tagaatactg tttcaaacta    2100
cctggtgtat ttattaattt tggaactgta tgtgtgtgtc atacatcttc atagttacga    2160
gtttaagatg gatggaaata tcgatctagg ataggtatac atgttgatgt gggttttact    2220
gatgcatata catgatggca tatgcagcat ctattcatat gctctaacct tgagtaccta    2280
```

-continued

| | |
|---|---|
| tctattataa taaacaagta tgttttataa ttattttgat cttgatatac ttggatgatg | 2340 |
| gcatatgcag cagctatatg tggattttt tagccctgcc ttcatacgct atttatttgc | 2400 |
| ttggtactgt ttcttttgtc gatgctcacc ctgttgtttg gtgttacttc tgca | 2454 |

<210> SEQ ID NO 83
<211> LENGTH: 3359
<212> TYPE: DNA
<213> ORGANISM: Artificial Sequence
<220> FEATURE:
<223> OTHER INFORMATION: 3X35S ENH (-): ZmUBI PRO-5UTR-UBI INTRON1 ; 35S enhancer in the reverse direction

<400> SEQUENCE: 83

| | |
|---|---|
| atcacatcaa tccacttgct ttgaagacgt ggttggaacg tcttcttttt ccacgatgct | 60 |
| cctcgtgggt gggggtccat ctttgggacc actgtcggca gaggcatctt caacgatggc | 120 |
| cttccttta tcgcaatgat ggcatttgta ggagccacct tccttttcca ctatcttcac | 180 |
| aataaagtga cagatagctg gcaatggaa tccgaggagg tttccggata ttacccttg | 240 |
| ttgaaaagtc tcaattgccc tttggtcttc tgagactgta tctttgatat ttttggagta | 300 |
| gacaagcgtg tcgtgctcca ccatgttgac gaagatttc ttcttgtcat tgagtcgtaa | 360 |
| gagactctgt atgaactgtt cgccagtctt tacggcgagt tctgttaggt cctctatttg | 420 |
| aatctttgac tccatggacg gtatcgataa gctagcttga tatcacatca atccacttgc | 480 |
| tttgaagacg tggttggaac gtcttctttt tccacgatgc tcctcgtggg tgggggtcca | 540 |
| tctttgggac cactgtcggc agaggcatct tcaacgatgg cctttccttt atcgcaatga | 600 |
| tggcatttgt aggagccacc ttccttttcc actatcttca aataaagtg acagatagct | 660 |
| gggcaatgga atccgaggag gtttccggat attacccttt gttgaaaagt ctcaattgcc | 720 |
| ctttggtctt ctgagactgt atctttgata ttttggagt agacaagcgt gtcgtgctcc | 780 |
| accatgttga cgaagatttt cttcttgtca ttgagtcgta agagactctg tatgaactgt | 840 |
| tcgccagtct ttacgcgag ttctgttagg tcctctatt gaatctttga ctccatgatc | 900 |
| gaattatcac atcaatccac ttgctttgaa gacgtggttg gaacgtcttc ttttccacg | 960 |
| atgctcctcg tgggtgggg tccatctttg gaccactgt cggcagaggc atcttcaacg | 1020 |
| atggcctttc ctttatcgca atgatggcat ttgtaggagc caccttcctt ttccactatc | 1080 |
| ttcacaataa agtgacagat agctgggcaa tggaatccga ggaggtttcc ggatattacc | 1140 |
| ctttgttgaa aagtctcaat tgcccttgg tcttctgaga ctgtatcttt gatattttg | 1200 |
| gagtagacaa gcgtgtcgtg ctccaccatg ttgacgaaga ttttcttctt gtcattgagt | 1260 |
| cgtaagagac tctgtatgaa ctgttcgcca gtctttacgg cgagttctgt taggtcctct | 1320 |
| atttgaatct ttgactccat gggaattcct gcagcccagc ttgcatgcct gcagtgcagc | 1380 |
| gtgacccggt cgtgccctc tctagagata tgagcattg catgtctaag ttataaaaaa | 1440 |
| ttaccacata tttttttgt cacacttgtt tgaagtgcag tttatctatc tttatacata | 1500 |
| tatttaaact ttactctacg aataatataa tctatagtac tacaataata tcagtgtttt | 1560 |
| agagaatcat ataaatgaac agttagacat ggtctaaagg acaattgagt attttgacaa | 1620 |
| caggactcta cagttttatc ttttagtgt gcatgtgttc tccttttttt ttgcaaatag | 1680 |
| cttcacctat ataatacttc atccatttta ttagtacatc catttagggt ttagggttaa | 1740 |
| tggtttttat agactaattt ttttagtaca tctattttat tctatttag cctctaaatt | 1800 |
| aagaaaacta aaactctatt ttagtttttt tatttaataa tttagatata aaatagaata | 1860 |

```
aaataaagtg actaaaaatt aaacaaatac cctttaagaa attaaaaaaa ctaaggaaac    1920 attttttcttg tttcgagtag ataatgccag cctgttaaac gccgtcgacg agtctaacgg   1980
acaccaacca gcgaaccagc agcgtcgcgt cgggccaagc gaagcagacg gcacggcatc    2040
tctgtcgctg cctctggacc cctctcgaga gttccgctcc accgttggac ttgctccgct    2100
gtcggcatcc agaaattgcg tggcggagcg gcagacgtga gccggcacgg caggcggcct    2160
cctcctcctc tcacggcacc ggcagctacg ggggattcct ttcccaccgc tccttcgctt    2220
tcccttcctc gcccgccgta ataaatagac accccctcca cccctctttt ccccaacctc    2280
gtgttgttcg gagcgcacac acacacaacc agatctcccc caaatccacc cgtcggcacc    2340
tccgcttcaa ggtacgccgc tcgtcctccc cccccccccct ctctaccttc tctagatcgg    2400
cgttccggtc catggttagg gcccggtagt tctacttctg ttcatgtttg tgttagatcc    2460
gtgtttgtgt tagatccgtg ctgctagcgt tcgtacacgg atgcgacctg tacgtcagac    2520
acgttctgat tgctaacttg ccagtgtttc tctttgggga atcctgggat ggctctagcc    2580
gttccgcaga cgggatcgat ttcatgattt ttttttgtttc gttgcatagg gtttggtttg    2640
cccttttcct ttatttcaat atatgccgtg cacttgtttg tcgggtcatc ttttcatgct    2700 ttttttttgtc ttggttgtga tgatgtggtc tggttgggcg gtcgttctag atcggagtag    2760
aattctgttt caaactacct ggtggattta ttaattttgg atctgtatgt gtgtgccata    2820
catattcata gttacgaatt gaagatgatg gatggaaata tcgatctagg ataggtatac    2880
atgttgatgc gggttttact gatgcatata cagagatgct ttttgttcgc ttggttgtga    2940
tgatgtggtg tggttgggcg gtcgttcatt cgttctagat cggagtagaa tactgtttca    3000
aactacctgg tgtatttatt aattttggaa ctgtatgtgt gtgtcataca tcttcatagt    3060
tacgagttta agatggatgg aaatatcgat ctaggatagg tatacatgtt gatgtgggtt    3120
ttactgatgc atatacatga tggcatatgc agcatctatt catatgctct aaccttgagt    3180
acctatctat tataataaac aagtatgttt tataattatt ttgatcttga tatacttgga    3240
tgatggcata tgcagcagct atatgtggat ttttttagcc ctgccttcat acgctattta    3300
tttgcttggt actgtttctt ttgtcgatgc tcaccctgtt gtttggtgtt acttctgca    3359
```

<210> SEQ ID NO 84
<211> LENGTH: 1340
<212> TYPE: DNA
<213> ORGANISM: Artificial Sequence
<220> FEATURE:
<223> OTHER INFORMATION: 3X35S enhancer in the forward direction

<400> SEQUENCE: 84

```
cccatggagt caaagattca aatagaggac ctaacagaac tcgccgtaaa gactggcgaa     60
cagttcatac agagtctctt acgactcaat gacaagaaga aaatcttcgt caacatggtg    120
gagcacgaca cgcttgtcta ctccaaaaat atcaaagata cagtctcaga agaccaaagg    180
gcaattgaga cttttcaaca aagggtaata tccggaaacc tcctcggatt ccattgccca    240
gctatctgtc actttattgt gaagatagtg gaaaggaag gtggctccta caaatgccat    300
cattgcgata aaggaaaggc catcgttgaa gatgcctctg ccgacagtgg tcccaaagat    360
ggacccccac ccacgaggag catcgtggaa aaagaagacg ttccaaccac gtcttcaaag    420
caagtggatt gatgtgataa ttcgatcatg gagtcaaaga ttcaaataga ggacctaaca    480
gaactcgccg taaagactgg cgaacagttc atacagagtc tcttacgact caatgacaag    540
```

```
aagaaaatct tcgtcaacat ggtggagcac gacacgcttg tctactccaa aaatatcaaa      600
gatacagtct cagaagacca aagggcaatt gagactttc aacaagggt aatatccgga       660 aacctcctcg gattccattg cccagctatc tgtcacttta ttgtgaagat agtggaaaag      720
gaaggtggct cctacaaatg ccatcattgc gataaaggaa aggccatcgt tgaagatgcc      780
tctgccgaca gtggtcccaa agatggaccc ccacccacga ggagcatcgt ggaaaagaa       840 gacgttccaa ccacgtcttc aaagcaagtg gattgatgtg atatcaagct tatcgatacc      900
gccatggagt caaagattca atagaggac ctaacagaac tcgccgtaaa gactggcgaa       960
cagttcatac agagtctctt acgactcaat gacaagaaga aaatcttcgt caacatggtg     1020
gagcacgaca cgcttgtcta ctccaaaaat atcaagata cagtctcaga agaccaaagg      1080
gcaattgaga cttttcaaca aagggtaata tccggaaacc tcctcggatt ccattgccca     1140
gctatctgtc actttattgt gaagatagtg gaaaggaag gtggctccta caaatgccat      1200
cattgcgata aaggaaaggc catcgttgaa gatgcctctg ccgacagtgg tcccaaagat     1260 ggaccccca ccacgaggag catcgtggaa aagaagacg ttccaaccac gtcttcaaag      1320
caagtggatt gatgtgatgt                                                 1340

<210> SEQ ID NO 85
<211> LENGTH: 438
<212> TYPE: DNA
<213> ORGANISM: cauliflower mosaic virus

<400> SEQUENCE: 85
atcacatcaa tccacttgct ttgaagacgt ggttggaacg tcttcttttt ccacgatgct       60
cctcgtgggt gggggtccat ctttgggacc actgtcggca gaggcatctt caacgatggc      120
ctttccttta tcgcaatgat ggcatttgta ggagccacct tccttttcca ctatcttcac      180
aataaagtga cagatagctg gcaatggaa tccgaggagg tttccggata ttaccctttg       240
ttgaaaagtc tcaattgccc tttggtcttc tgagactgta tctttgatat ttttggagta      300
gacaagcgtg tcgtgctcca ccatgttgac gaagattttc ttcttgtcat tgagtcgtaa      360
gagactctgt atgaactgtt cgccagtctt tacggcgagt tctgttaggt cctctatttg      420
aatctttgac tccatggg                                                    438

<210> SEQ ID NO 86
<211> LENGTH: 657
<212> TYPE: PRT
<213> ORGANISM: Gossypium hirsutum

<400> SEQUENCE: 86

Met Ala Pro His Asn Thr Met Ala Ala Thr Ala Ser Arg Thr Thr Arg
  1               5                  10                  15

Phe Ser Ser Ser Ser His Pro Thr Phe Pro Lys Arg Ile Thr Arg
                 20                  25                  30

Ser Thr Leu Pro Leu Ser His Gln Thr Leu Thr Lys Pro Asn His Ala
             35                  40                  45

Leu Lys Ile Lys Cys Ser Ile Ser Lys Pro Pro Thr Ala Ala Pro Phe
         50                  55                  60

Thr Lys Glu Ala Pro Thr Thr Glu Pro Phe Val Ser Arg Phe Ala Ser
 65                  70                  75                  80

Gly Glu Pro Arg Lys Gly Ala Asp Ile Leu Val Glu Ala Leu Glu Arg
                 85                  90                  95

Gln Gly Val Thr Thr Val Phe Ala Tyr Pro Gly Gly Ala Ser Met Glu
```

```
              100                 105                 110
Ile His Gln Ala Leu Thr Arg Ser Ala Ala Ile Arg Asn Val Leu Pro
            115                 120                 125
Arg His Glu Gln Gly Gly Val Phe Ala Ala Glu Gly Tyr Ala Arg Ser
            130                 135                 140
Ser Gly Leu Pro Gly Val Cys Ile Ala Thr Ser Gly Pro Gly Ala Thr
145                 150                 155                 160
Asn Leu Val Ser Gly Leu Ala Asp Ala Leu Met Asp Ser Val Pro Val
                165                 170                 175
Val Ala Ile Thr Gly Gln Val Ala Arg Arg Met Ile Gly Thr Asp Ala
            180                 185                 190
Phe Gln Glu Thr Pro Ile Val Glu Val Ser Arg Ser Ile Thr Lys His
            195                 200                 205
Asn Tyr Leu Ile Leu Asp Val Asp Asp Ile Pro Arg Val Val Ala Glu
            210                 215                 220
Ala Phe Phe Val Ala Thr Ser Gly Arg Pro Gly Pro Val Leu Ile Asp
225                 230                 235                 240
Ile Pro Lys Asp Val Gln Gln Gln Leu Ala Val Pro Asn Trp Asp Glu
                245                 250                 255
Pro Val Asn Leu Pro Gly Tyr Leu Ala Arg Leu Pro Arg Pro Pro Ala
            260                 265                 270
Glu Ala Gln Leu Glu His Ile Val Arg Leu Ile Met Glu Ala Gln Lys
            275                 280                 285
Pro Val Leu Tyr Val Gly Gly Gly Ser Phe Asn Ser Ser Ala Glu Leu
            290                 295                 300
Arg Arg Phe Val Glu Leu Thr Gly Ile Pro Val Ala Ser Thr Leu Met
305                 310                 315                 320
Gly Leu Gly Thr Phe Pro Ile Gly Asp Glu Tyr Ser Leu Gln Met Leu
                325                 330                 335
Gly Met His Gly Thr Val Tyr Ala Asn Tyr Ala Val Asp Asn Ser Asp
            340                 345                 350
Leu Leu Leu Ala Phe Gly Val Arg Phe Asp Asp Arg Val Thr Gly Lys
            355                 360                 365
Leu Glu Ala Phe Ala Ser Arg Ala Lys Ile Val His Ile Asp Ile Asp
            370                 375                 380
Ser Ala Glu Ile Gly Lys Asn Lys Gln Ala His Val Ser Val Cys Ala
385                 390                 395                 400
Asp Leu Lys Leu Ala Leu Lys Gly Ile Asn Met Ile Leu Glu Glu Lys
                405                 410                 415
Gly Val Glu Gly Lys Phe Asp Leu Gly Gly Trp Arg Glu Glu Ile Asn
            420                 425                 430
Val Gln Lys His Lys Phe Pro Leu Gly Tyr Lys Thr Phe Gln Asp Ala
            435                 440                 445
Ile Ser Pro Gln His Ala Ile Glu Val Leu Asp Glu Leu Thr Asn Gly
            450                 455                 460
Asp Ala Ile Val Ser Thr Gly Val Gly Gln His Gln Met Trp Ala Ala
465                 470                 475                 480
Gln Phe Tyr Lys Tyr Lys Arg Pro Arg Gln Trp Leu Thr Ser Gly Gly
                485                 490                 495
Leu Gly Ala Met Gly Phe Gly Leu Pro Ala Ala Ile Gly Ala Ala Val
            500                 505                 510
Ala Asn Pro Gly Ala Val Val Asp Ile Asp Gly Asp Gly Ser Phe
            515                 520                 525
```

```
Ile Met Asn Val Gln Glu Leu Ala Thr Ile Arg Val Glu Asn Leu Pro
    530                 535                 540

Val Lys Ile Leu Leu Leu Asn Asn Gln His Leu Gly Met Val Val Gln
545                 550                 555                 560

Leu Glu Asp Arg Phe Tyr Lys Ser Asn Arg Ala His Thr Tyr Leu Gly
                565                 570                 575

Asp Pro Ser Ser Glu Ser Glu Ile Phe Pro Asn Met Leu Lys Phe Ala
            580                 585                 590

Asp Ala Cys Gly Ile Pro Ala Ala Arg Val Thr Lys Lys Glu Glu Leu
        595                 600                 605

Arg Ala Ala Ile Gln Arg Met Leu Asp Thr Pro Gly Pro Tyr Leu Leu
    610                 615                 620

Asp Val Ile Val Pro His Gln Glu His Val Leu Pro Met Ile Pro Ser
625                 630                 635                 640

Asn Gly Ser Phe Lys Asp Val Ile Thr Glu Gly Asp Gly Arg Thr Arg
                645                 650                 655

Tyr

<210> SEQ ID NO 87
<211> LENGTH: 1309
<212> TYPE: DNA
<213> ORGANISM: Glycine max
<220> FEATURE:
<221> NAME/KEY: promoter
<222> LOCATION: (0)...(0)
<223> OTHER INFORMATION: SAM promoter

<400> SEQUENCE: 87
ctagatcaaa ctcacatcca aacataacat ggatatcttc cttaccaatc atactaatta      60
ttttgggtta aatattaatc attattttta agatattaat taagaaatta aaagattttt    120 taaaaaatg tataaaatta tattattcat gattttcat acatttgatt ttgataataa      180 atatatttt tttaatttct taaaaaatgt tgcaagacac ttattagaca tagtcttgtt     240
ctgtttacaa aagcattcat catttaatac attaaaaaat atttaatact aacagtagaa    300
tcttcttgtg agtggtgtgg gagtaggcaa cctggcattg aaacgagaga agagagtca     360 gaaccagaag acaaataaaa agtatgcaac aaacaaatca aaatcaaagg gcaaaggctg    420
gggttggctc aattggttgc tacattcaat tttcaactca gtcaacggtt gagattcact    480
ctgacttccc caatctaagc cgcggatgca aacggttgaa tctaacccac aatccaatct    540
cgttacttag gggctttttcc gtcattaact caccccctgcc acccggtttc cctataaatt    600
ggaactcaat gctcccctct aaactcgtat cgcttcagag ttgagaccaa gacacactcg    660
ttcatatatc tctctgctct tctcttctct tctacctctc aaggtacttt tcttctccct    720
ctaccaaatc ctagattccg tggttcaatt tcggatcttg cacttctggt ttgctttgcc    780 ttgcttttc ctcaactggg tccatctagg atccatgtga aactctactc tttctttaat    840
atctgcggaa tacgcgttgg actttcagat ctagtcgaaa tcatttcata attgcctttc    900 tttctttag cttatgagaa ataaaatcac tttttttta tttcaaaata aaccttgggc    960
cttgtgctga ctgagatggg gtttggtgat tacagaattt tagcgaattt tgtaattgta   1020
cttgtttgtc tgtagttttg ttttgttttc ttgtttctca tacattcctt aggcttcaat   1080
tttattcgag tataggtcac aataggaatt caaactttga gcaggggaat taatcccttc   1140
cttcaaatcc agtttgtttg tatatatgtt taaaaaatga aacttttgct ttaaattcta   1200
```

```
ttataacttt ttttatggct gaaatttttg catgtgtctt tgctctctgt tgtaaattta    1260
ctgtttaggt actaactcta ggcttgttgt gcagtttttg aagtataac                1309

<210> SEQ ID NO 88
<211> LENGTH: 1344
<212> TYPE: DNA
<213> ORGANISM: Artificial Sequence
<220> FEATURE:
<223> OTHER INFORMATION: 3X 35S enhancer in forward direction

<400> SEQUENCE: 88
cccatggagt caaagattca aatagaggac ctaacagaac tcgccgtaaa gactggcgaa      60
cagttcatac agagtctctt acgactcaat gacaagaaga aaatcttcgt caacatggtg    120
gagcacgaca cgcttgtcta ctccaaaaat atcaaagata cagtctcaga agaccaaagg    180
gcaattgaga cttttcaaca aagggtaata tccggaaacc tcctcggatt ccattgccca    240
gctatctgtc actttattgt gaagatagtg gaaaaggaag gtggctccta caaatgccat    300
cattgcgata aggaaaggc catcgttgaa gatgcctctg ccgacagtgg tcccaaagat    360 ggaccccac ccacgaggag catcgtggaa aagaagacg ttccaaccac gtcttcaaag    420
caagtggatt gatgtgataa ttcgatcatg gagtcaaaga ttcaaataga ggacctaaca    480
gaactcgccg taaagactgg cgaacagttc atacagagtc tcttacgact caatgacaag    540
aagaaaatct tcgtcaacat ggtggagcac gacacgcttg tctactccaa aaatatcaaa    600
gatacagtct cagaagacca aagggcaatt gagacttttc aacaaagggt aatatccgga    660
aacctcctcg gattccattg cccagctatc tgtcacttta ttgtgaagat agtggaaaag    720
gaaggtggct cctacaaatg ccatcattgc gataaaggaa aggccatcgt tgaagatgcc    780
tctgccgaca gtggtcccaa agatggaccc ccacccacga ggagcatcgt ggaaaaagaa    840
gacgttccaa ccacgtcttc aaagcaagtg gattgatgtg atatcaagct agcttatcga    900
taccgtccat ggagtcaaag attcaaatag gacctaac agaactcgcc gtaaagactg    960
gcgaacagtt catacagagt ctcttacgac tcaatgacaa gaagaaaatc ttcgtcaaca    1020
tggtggagca cgacacgctt gtctactcca aaaatatcaa agatacagtc tcagaagacc    1080
aaagggcaat tgagactttt caacaaaggg taatatccgg aaacctcctc ggattccatt    1140
gcccagctat ctgtcacttt attgtgaaga gtggaaaa ggaaggtggc tcctacaaat    1200
gccatcattg cgataaagga aaggccatcg ttgaagatgc ctctgccgac agtggtccca    1260
aagatggacc cccacccacg aggagcatcg tggaaaaaga agacgttcca accacgtctt    1320
caaagcaagt ggattgatgt gatg                                          1344

<210> SEQ ID NO 89
<211> LENGTH: 1344
<212> TYPE: DNA
<213> ORGANISM: Artificial Sequence
<220> FEATURE:
<223> OTHER INFORMATION: 3X 35S enhancer in reverse direction

<400> SEQUENCE: 89
catcacatca atccacttgc tttgaagacg tggttggaac gtcttctttt tccacgatgc      60
tcctcgtggg tggggtcca tctttgggac cactgtcggc agaggcatct tcaacgatgg    120
cctttccttt atcgcaatga tggcatttgt aggagccacc ttcctttcc actatcttca    180
```

-continued

```
caataaagtg acagatagct gggcaatgga atccgaggag gtttccggat attacccttt      240
gttgaaaagt ctcaattgcc ctttggtctt ctgagactgt atctttgata ttttggagt       300
agacaagcgt gtcgtgctcc accatgttga cgaagatttt cttcttgtca ttgagtcgta      360
agagactctg tatgaactgt tcgccagtct ttacggcgag ttctgttagg tcctctattt      420
gaatctttga ctccatggac ggtatcgata agctagcttg atatcacatc aatccacttg      480
ctttgaagac gtggttggaa cgtcttcttt ttccacgatg ctcctcgtgg gtggggtcc       540
atctttggga ccactgtcgg cagaggcatc ttcaacgatg gcctttcctt tatcgcaatg      600
atggcatttg taggagccac cttccttttc cactatcttc acaataaagt gacagatagc      660
tgggcaatgg aatccgagga ggtttccgga tattacccttt tgttgaaaag tctcaattgc     720
cctttggtct tctgagactg tatctttgat attttggag tagacaagcg tgtcgtgctc       780
caccatgttg acgaagattt tcttcttgtc attgagtcgt aagagactct gtatgaactg      840
ttcgccagtc tttacggcga gttctgttag gtcctctatt tgaatctttg actccatgat      900
cgaattatca catcaatcca cttgctttga agacgtggtt ggaacgtctt cttttccac      960
gatgctcctc gtgggtgggg gtccatcttt gggaccactg tcggcagagg catcttcaac     1020
gatggccttt cctttatcgc aatgatggca tttgtaggag ccaccttcct tttccactat     1080
cttcacaata aagtgacaga tagctgggca atggaatccg aggagggttc cggatattac     1140
cctttgttga aaagtctcaa ttgccctttg gtcttctgag actgtatctt tgatattttt     1200
ggagtagaca agcgtgtcgt gctccaccat gttgacgaag attttcttct tgtcattgag     1260
tcgtaagaga ctctgtatga actgttcgcc agtctttacg gcgagttctg ttaggtcctc     1320
tatttgaatc tttgactcca tggg                                            1344
```